United States Patent
Limberis et al.

(10) Patent No.: US 10,786,568 B2
(45) Date of Patent: Sep. 29, 2020

(54) AAV MEDIATED INFLUENZA VACCINES

(71) Applicants: The Trustees of the University of Pennsylvania, Philadelphia, PA (US); Janssen Biotech, Inc., Horsham, PA (US)

(72) Inventors: Maria P. Limberis, Philadelphia, PA (US); Anna P. Tretiakova, Woburn, MA (US); James M. Wilson, Philadelphia, PA (US); Michael Naso, Swarthmore, PA (US); Joost Kolkman, Maarn (NL); Robert Friesen, Wassenaar (NL); Qiang Wang, Philadelphia, PA (US)

(73) Assignees: The Trustees of the University of Pennsylvania, Philadelphia, PA (US); Janssen Biotech, Inc., Horsham, PA (US)

(*) Notice: Subject to any disclaimer, the term of this patent is extended or adjusted under 35 U.S.C. 154(b) by 0 days.

(21) Appl. No.: 15/906,887

(22) Filed: Feb. 27, 2018

(65) Prior Publication Data
US 2018/0243416 A1    Aug. 30, 2018

Related U.S. Application Data

(60) Provisional application No. 62/464,753, filed on Feb. 28, 2017, provisional application No. 62/504,293, filed on May 10, 2017, provisional application No. 62/560,834, filed on Sep. 20, 2017, provisional application No. 62/618,443, filed on Jan. 17, 2018.

(51) Int. Cl.
| | |
|---|---|
| *A61K 39/42* | (2006.01) |
| *A61K 39/145* | (2006.01) |
| *C07K 16/10* | (2006.01) |
| *C12N 7/06* | (2006.01) |
| *A61P 31/16* | (2006.01) |
| *C12N 7/00* | (2006.01) |
| *A61K 39/00* | (2006.01) |

(52) U.S. Cl.
CPC .......... *A61K 39/42* (2013.01); *A61K 39/145* (2013.01); *A61P 31/16* (2018.01); *C07K 16/1018* (2013.01); *C12N 7/00* (2013.01); *C12N 7/06* (2013.01); *A61K 2039/505* (2013.01); *A61K 2039/5256* (2013.01); *C07K 2317/31* (2013.01); *C07K 2317/52* (2013.01); *C07K 2317/569* (2013.01); *C12N 2750/14121* (2013.01); *C12N 2750/14143* (2013.01); *C12N 2840/203* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,139,941 A | 8/1992 | Muzycka et al. |
| 5,478,745 A | 12/1995 | Samulski et al. |
| 5,741,683 A | 4/1998 | Zhou et al. |
| 5,811,524 A | 9/1998 | Brams et al. |
| 5,830,462 A | 11/1998 | Crabtree et al. |
| 5,834,266 A | 11/1998 | Crabtree et al. |
| 5,869,337 A | 2/1999 | Crabtree et al. |
| 5,871,753 A | 2/1999 | Crabtree et al. |
| 6,011,018 A | 1/2000 | Crabtree et al. |
| 6,015,709 A | 1/2000 | Natesan |
| 6,043,082 A | 3/2000 | Crabtree et al. |
| 6,046,047 A | 4/2000 | Crabtree et al. |
| 6,057,152 A | 5/2000 | Samulski et al. |
| 6,063,625 A | 5/2000 | Crabtree et al. |
| 6,117,680 A | 9/2000 | Natesan et al. |
| 6,127,521 A | 10/2000 | Berlin et al. |
| 6,133,456 A | 10/2000 | Holt et al. |
| 6,140,120 A | 10/2000 | Crabtree et al. |
| 6,150,137 A | 11/2000 | Berlin et al. |
| 6,150,527 A | 11/2000 | Holt et al. |
| 6,165,787 A | 12/2000 | Crabtree et al. |
| 6,187,757 B1 | 2/2001 | Clackson et al. |

(Continued)

FOREIGN PATENT DOCUMENTS

| | | |
|---|---|---|
| EP | 1310571 | 5/2003 |
| EP | 2296700 A2 | 3/2011 |

(Continued)

OTHER PUBLICATIONS

Adam VS et al., Adeno-associated virus 9-mediated airway expression of antibody protects old and immunodeficient mice against influenza virus. Clin. Vaccine Immunol., 21(11):1528-33, Nov. 2014. (Epub Sep. 10, 2014).

(Continued)

*Primary Examiner* — Stacy B Chen
(74) *Attorney, Agent, or Firm* — Cathy A. Kodroff; Howson & Howson LLP; Cathy Kodroff

(57) ABSTRACT

A non-replicating recombinant adeno-associated associated virus (rAAV) having an AAV capsid having packaged therein a vector genome which comprises AAV inverted terminal repeat sequences and at least one nucleic acid sequence encoding four different immunoglobulin regions (a), (b), (c) and (d) is provided. The rAAV-expressed immunoglobulins are useful for providing passive immunization against influenza A and influenza B. Also described herein are compositions containing the rAAV. Methods of vaccinating patients against influenza are provided.

18 Claims, 25 Drawing Sheets

Figure 1A:
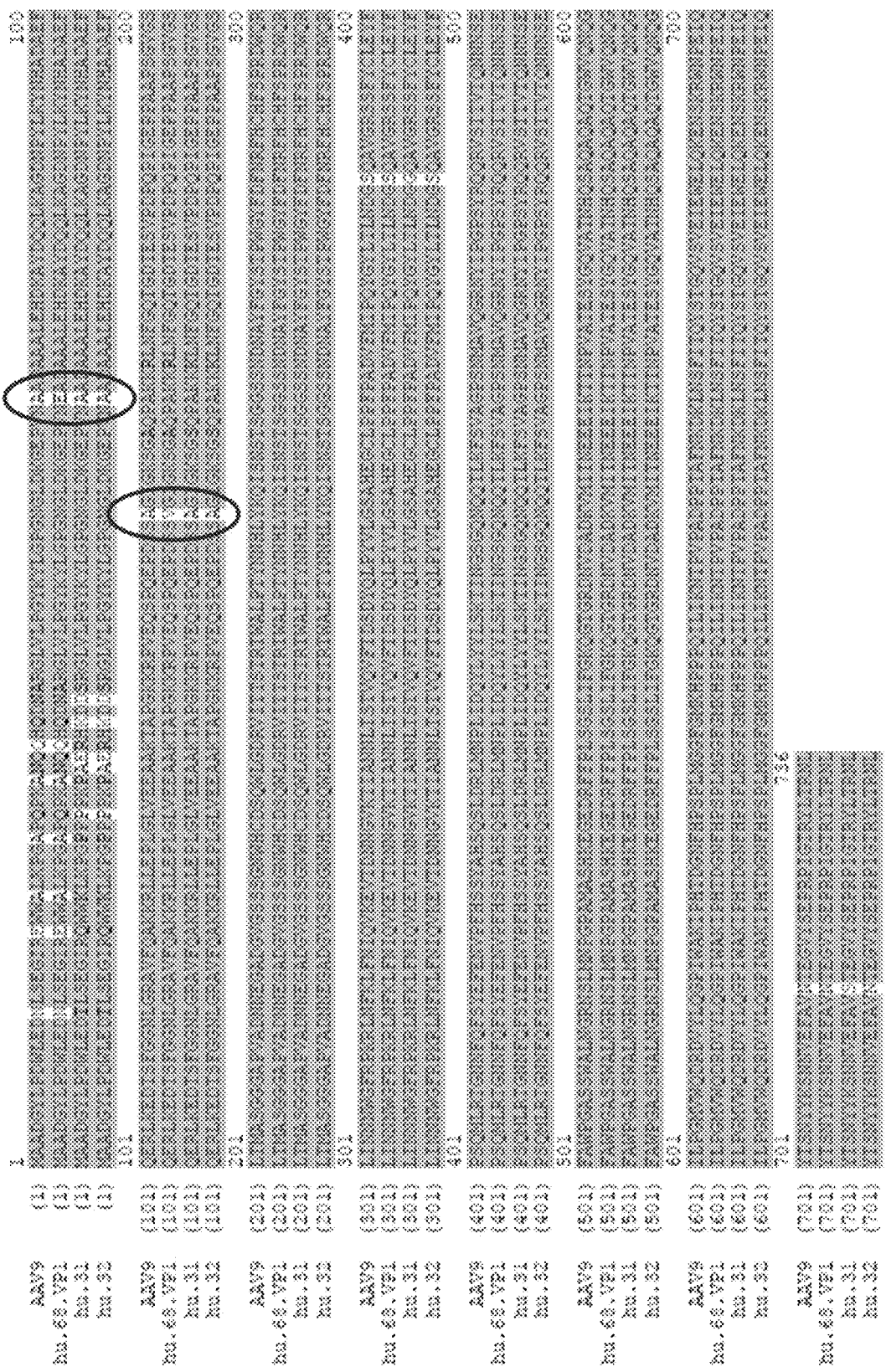

Specification includes a Sequence Listing.

(56) References Cited

U.S. PATENT DOCUMENTS

| | | |
|---|---|---|
| 6,204,059 B1 | 3/2001 | Samulski et al. |
| 6,258,603 B1 | 7/2001 | Carlson et al. |
| 6,258,823 B1 | 7/2001 | Holt et al. |
| 6,268,213 B1 | 7/2001 | Samulski et al. |
| 6,326,166 B1 | 12/2001 | Pomerantz et al. |
| 6,464,374 B2 | 10/2002 | Akiyama et al. |
| 6,464,974 B1 | 10/2002 | Berlin et al. |
| 6,476,200 B1 | 11/2002 | Sabatini et al. |
| 6,479,653 B1 | 11/2002 | Natesan et al. |
| 6,491,907 B1 | 12/2002 | Rabinowitz et al. |
| 6,492,106 B1 | 12/2002 | Sabatini et al. |
| 6,506,379 B1 | 1/2003 | Clackson et al. |
| 6,509,152 B1 | 1/2003 | Berlin et al. |
| 6,596,535 B1 | 7/2003 | Carter |
| 6,649,595 B2 | 11/2003 | Clackson et al. |
| 6,660,514 B1 | 12/2003 | Zolotukhin et al. |
| 6,693,189 B2 | 2/2004 | Holt et al. |
| 6,780,639 B1 | 8/2004 | Chtarto et al. |
| 6,951,753 B2 | 10/2005 | Shenk et al. |
| 6,972,193 B1 | 12/2005 | Crabtree et al. |
| 6,984,635 B1 | 1/2006 | Schreiber et al. |
| 7,008,780 B2 | 3/2006 | Pomerantz et al. |
| 7,045,315 B2 | 5/2006 | Evans et al. |
| 7,067,526 B1 | 6/2006 | Yang et al. |
| 7,091,038 B2 | 8/2006 | Palli et al. |
| 7,094,604 B2 | 8/2006 | Snyder et al. |
| 7,109,317 B1 | 9/2006 | Clemons et al. |
| 7,125,717 B2 | 10/2006 | Carter |
| 7,172,893 B2 | 2/2007 | Rabinowitz et al. |
| 7,196,192 B2 | 3/2007 | Yang et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,442,373 B2 | 10/2008 | Kang et al. |
| 7,456,683 B2 | 11/2008 | Takano et al. |
| 7,485,441 B2 | 2/2009 | Pomerantz et al. |
| 7,588,772 B2 | 9/2009 | Kay et al. |
| 7,785,888 B2 | 8/2010 | Carter |
| 7,790,449 B2 | 9/2010 | Gao et al. |
| 7,846,729 B2 | 12/2010 | Carter |
| 7,906,111 B2 | 3/2011 | Wilson et al. |
| 8,093,054 B2 | 1/2012 | Carter |
| 8,114,402 B2 | 2/2012 | Grandea et al. |
| 8,124,092 B2 | 2/2012 | Lanzavecchia |
| 8,734,809 B2 | 5/2014 | Gao et al. |
| 8,852,595 B2 | 10/2014 | Vogels et al. |
| 8,927,514 B2 | 1/2015 | Chatterjee et al. |
| 8,961,978 B2 | 2/2015 | Kwaks et al. |
| 9,340,603 B2 | 5/2016 | Lanzavecchia |
| 9,719,106 B2 | 8/2017 | Wilson et al. |
| 10,370,435 B2 | 8/2019 | Brandenburg et al. |
| 2002/0110861 A1 | 8/2002 | Dhadialla et al. |
| 2002/0173474 A1 | 11/2002 | Schreiber et al. |
| 2004/0033600 A1 | 2/2004 | Palli et al. |
| 2004/0096942 A1 | 5/2004 | Kapitskaya et al. |
| 2005/0266457 A1 | 12/2005 | Palli et al. |
| 2006/0014711 A1 | 1/2006 | Evans et al. |
| 2006/0100416 A1 | 5/2006 | Palli et al. |
| 2006/0136184 A1 | 6/2006 | Gustafsson et al. |
| 2007/0036760 A1 | 2/2007 | Wilson et al. |
| 2007/0161086 A1 | 7/2007 | Palli et al. |
| 2009/0100535 A1 | 4/2009 | Pomerantz et al. |
| 2009/0104232 A1 | 4/2009 | Crystal et al. |
| 2009/0197338 A1 | 8/2009 | Vandenberghe et al. |
| 2009/0275107 A1 | 11/2009 | Lock et al. |
| 2010/0080813 A1 | 4/2010 | Lanzavecchia |
| 2011/0076265 A1 | 3/2011 | Burioni et al. |
| 2011/0150904 A1* | 6/2011 | Schiltz ............... C07K 16/1081 424/159.1 |
| 2011/0236353 A1 | 9/2011 | Wilson et al. |
| 2011/0274702 A1 | 11/2011 | Lanzavecchia |
| 2012/0232133 A1 | 9/2012 | Balazs et al. |
| 2012/0282695 A1 | 11/2012 | Blain et al. |
| 2013/0045186 A1 | 2/2013 | Gao et al. |
| 2013/0243792 A1 | 9/2013 | Vogels et al. |
| 2014/0032186 A1 | 1/2014 | Gustafsson et al. |
| 2014/0037637 A1 | 2/2014 | McNally et al. |
| 2014/0065666 A1 | 3/2014 | Simpson et al. |
| 2014/0094392 A1 | 4/2014 | Bowers et al. |
| 2014/0127749 A1 | 5/2014 | Mason et al. |
| 2015/0344911 A1 | 12/2015 | Chatterjee et al. |
| 2017/0028082 A1 | 2/2017 | Wilson et al. |
| 2017/0043035 A1 | 2/2017 | Wilson et al. |
| 2017/0081392 A1 | 3/2017 | Wilson et al. |
| 2017/0101458 A1 | 4/2017 | Wilson et al. |
| 2017/0159027 A1 | 6/2017 | Wilson et al. |
| 2017/0292132 A1 | 10/2017 | Wilson et al. |
| 2018/0243416 A1 | 8/2018 | Limberis et al. |
| 2019/0216841 A1 | 7/2019 | Wilson et al. |

FOREIGN PATENT DOCUMENTS

| | | |
|---|---|---|
| WO | WO 1994/18347 | 8/1994 |
| WO | WO 1995/33052 | 12/1995 |
| WO | WO 1996/06097 | 2/1996 |
| WO | WO 1996/009378 | 3/1996 |
| WO | WO 1996/020951 | 7/1996 |
| WO | WO 1996/41865 | 12/1996 |
| WO | WO 1997/31898 | 9/1997 |
| WO | WO 1998/02441 | 1/1998 |
| WO | WO 1999/10508 | 3/1999 |
| WO | WO 1999/10510 | 3/1999 |
| WO | WO 1999/36553 | 7/1999 |
| WO | WO 1999/41258 | 8/1999 |
| WO | WO 2001/114387 | 3/2001 |
| WO | WO 2001/70816 | 9/2001 |
| WO | WO 2002/029075 | 4/2002 |
| WO | WO 2002/066612 | 8/2002 |
| WO | WO 2002/066613 | 8/2002 |
| WO | WO 2002/066614 | 8/2002 |
| WO | WO 2002/066615 | 8/2002 |
| WO | WO 2003/042397 | 5/2003 |
| WO | WO 2005/033321 | 4/2005 |
| WO | WO 2005/108617 | 11/2005 |
| WO | WO 2006/110689 | 10/2006 |
| WO | WO 2008/156763 | 12/2008 |
| WO | WO 2009/079259 A2 | 6/2009 |
| WO | WO 2009/115972 | 9/2009 |
| WO | WO 2009/121004 A2 | 10/2009 |
| WO | WO 2010/010466 | 1/2010 |
| WO | WO 2010/044921 A2 | 4/2010 |
| WO | WO 2010/130636 | 11/2010 |
| WO | WO 2010/140114 | 12/2010 |
| WO | WO 2010/151673 | 12/2010 |
| WO | WO 2011/126808 | 10/2011 |
| WO | WO 2011/126868 | 10/2011 |
| WO | WO 2012/145572 | 10/2012 |
| WO | WO 2013/007770 | 1/2013 |
| WO | WO 2013/049492 | 4/2013 |
| WO | WO 2013/114885 | 8/2013 |
| WO | WO 2013/132007 | 9/2013 |
| WO | WO 2013/155222 | 10/2013 |
| WO | WO 2015/012924 | 1/2015 |
| WO | WO 2015/127136 | 8/2015 |
| WO | WO 2015/175639 A1 | 11/2015 |
| WO | WO 2016/049230 | 3/2016 |
| WO | WO 2016/054598 | 4/2016 |
| WO | WO 2016/124768 | 8/2016 |
| WO | WO 2016/200543 | 12/2016 |
| WO | WO 2017/100674 | 6/2017 |
| WO | WO 2017/100676 | 6/2017 |
| WO | WO 2017/100704 | 6/2017 |
| WO | WO 2017/106244 | 6/2017 |
| WO | WO 2017/106326 | 6/2017 |
| WO | WO 2017/160360 | 9/2017 |
| WO | WO 2018/057916 | 3/2018 |

OTHER PUBLICATIONS

Afonine PV et al., Towards automated crystallographic structure refinement with phenix.refine, Acta Crystallogr. D Biol. Crystallogr., 68(Pt 4):352-67, Apr. 2012. (Epub Mar. 16, 2012).

(56) References Cited

OTHER PUBLICATIONS

Alexander MC et al., Insulin stimulates glyceraldehyde-3-phosphate. dehydrogenase gene expression through cis-acting DNA sequences, Proc Natl Acad Sci U S A, 85(14):5092-6, Jul. 1988.
Ali MY, Histology of the Human Nasopharyngeal Mucosa, J. Anat., 99(3):657-672, 1965.
Almond B. and Schenborn ET, A Comparison of pCI-neo Vector and pcDNA4/HisMax Vector, Promega Corporation Website, Updated 2000, Available from: http://www.promega.com/resources/pubhub/enotes/a-comparison-of-pcineo-vector-and-pcdna4hismax-vector/.
Amara JF et al., A versatile synthetic dimerizer for the regulation of protein-protein interactions, Proc. Natl. Acad. Sci. USA, 94(20):10618-23, Sep. 1997.
An W et al., Active retrotransposition by a synthetic L1 element in mice, Proc Natl Acad Sci U S A, 103(49):18662-7, Dec. 5, 2006. (Epub Nov. 21, 2006).
Andersson R et al, An atlas of active enhancers across human cell types and tissues, Nature, 507(7493):455-61, Mar. 27, 2014.
Aquino TL et al., Influenza Outbreak in a Vaccinated Population—USS Ardent, Feb. 2014. MNWR Morb Mortal Wkly Rep, 63(42):947-9, Oct. 24, 2014.
Ashkenazi A et al., Immunoadhesins, International reviews of immunology, 10(2):219-227, 1993.
Balazs AB et al., Antibody-based protection against HIV infection by vectored immunoprophylaxis, Nature, 481(7379):81-4, Nov. 30, 2011.
Balazs AB et al., Broad protection against influenza infection by vectored immunoprophylaxis in mice, Nat. Biotechnol., 31(7):647-52, Jul. 2013. (Epub Jun. 2, 2013).
Ballay A et al., In vitro and in vivo synthesis of the hepatitis B virus surface antigen and of the receptor for polymerized human serum albumin from recombinant human adenoviruses, EMBO J., 4(13B):3861-5, Dec. 30, 1985.
Bell CL et al, The AAV9 receptor and its modification to improve in vivo lung gene transfer in mice, J Clin. Invest., 121(6):2427-35, Jun. 2011.
Berezov a et al., Disabling erbB receptors with rationally designed exocyclic mimetics of antibodies: structure-function analysis, J. Med. Chem., 44(16):2565-74, Aug. 2001.
Beyer WE et al., Cochrane re-arranged: support for policies to vaccinate elderly people against influenza,Vaccine, 31(50):6030-3, Dec. 2013. (Epub Oct. 3, 2013).
Bouvier NM et al., The biology of influenza viruses, Vaccine, 26 Suppl 4:D49-53, Sep. 2008.
Boyer JL et al., 853. Persistent expression of single chain antibodies mediated by AAV5 and AAVrh.10 vectors, Molecular Therapy, 11(Supp. 1):331-2, May 2005.
Brandenburg B et al., Mechanisms of hemagglutinin targeted influenza virus neutralization, PLoS One, 8(12):e80034, Dec. 11, 2013.
Brinster et al., Regulation of metallothionein-thymidine kinase fusion plasmids injected into mouse eggs, Nature, 296:39-42, Mar. 4, 1982.
Buning H et al., Recent developments in adeno-associated virus vector technology, J. Gene Med., 10:717-33, 2008. (Epub May 2, 2008).
Calcedo R et al., Worldwide Epidemiology of Neutralizing Antibodies to Adeno-Associated Viruses, Journal of Infectious Diseases, 2009, 199(3):381-90.
Carragher B et al., Leginon: an automated system for acquisition of images from vitreous ice specimens, J. Struct. Biol., 132(1):33-45, Oct. 2000.
Carter BJ, Chapter 10: The Growth Cycle of Adeno-associated Virus, in CRC Handbook of Parvoviruses, ed. P. Tijsser, CRC Press, p. 155-68, 1990.
Center for Disease Control and Prevention,"Types of Influenza Viruses" Web page <https://www.cdc.gov/flu/about/viruses/types.htm>, 2 pages, Apr. 4, 2016, page last updated Aug. 19, 2014, retrieved from Internet Archive Wayback Machine <https://web.archive.org/web/20160404144120/https://www.cdc.gov/flu/about/viruses/types.htm> on May 11, 2018.

Chamow SM and Ashkenazi, Immunoadhesins: principles and applications, Trends in biotechnology, 14(2):52-60, Feb. 1996.
Chen H et al., Avian flu: H5N1 virus outbreak in migratory waterfowl. Nature, 436(7048):191-2, Jul. 14, 2005.
Ch'Ng JL et al., Antisense RNA complementary to 3' coding and noncoding sequences of creatine kinase is a potent inhibitor of translation in vivo, Proc. Natl. Acad. Sci. USA, 86(24):10006-10, Dec. 1989.
Corti D et al., A neutralizing antibody selected from plasma cells that binds to group 1 and group 2 influenza A hemagglutinins, Science, 333:850-6, Aug. 12, 2011. (Epub Jul. 28, 2011).
Cox F et al., Protection against H5N1 influenza virus induced by matrix-M adjuvanted seasonal virosomal vaccine in mice requires both antibodies and T cells, PLoS One, 10(12):e0145243, Dec. 22, 2015.
Crosariol M, et al., Effective AAV9 Vector Delivery to Nasal Mucosa for Protection Against Airborne Challenge With Influenza A and B, Abstract 699, Molecular Therapy, 24(Supp. 1):S276, May 2016.
Davidson E et al., Mechanism of Binding to Ebola Virus Glycoprotein by the ZMapp, ZMAb, and MB-003 Cocktail Antibodies, 89(21):10982-92, Nov. 2015. (Epub Aug. 26, 2015).
Dawood FS et al., Estimated global mortality associated with the first 12 months of 2009 pandemic influenza A H1N1 virus circulation: a modelling study, Lancet Infect Dis, 12(9):687-95, Sep. 2012. (Epub Jun. 26, 2012).
De BP et al, Abstract 611—Induction of Persistent Passive Immunity Against Anthrax Toxin by an Adeno-Associated Virus Type rh1O Vector Expressing Anti-Protective Antigene Antibody, Molecular Therapy, 13(Suppl. 1):S236, May 2006.
De BP et al, Rapid/ Sustained Anti-anthrax Passive Immunity Mediated by co-administration od Ad/AAV, Molecular Therapy, 6(1):203-9, Jan. 2008.
De BP et al., High levels of persistent expression of alpha 1antitrypsin mediated by the nonhuman primate serotype rh.10 adeno-associated virus despite preexisting immunity to common human adeno-associated viruses, Mol. Ther., 13(1):67-76, Jan. 2006.
Deuschle U et al., Tetracycline-Reversible Silencing of Eukaryotic Promoters, Mol Cell Biol., 15(4):1907-14, Apr. 1995.
Dhuria SV et al., Intranasal Delivery to the Central Nervous System: Mechanisms and Experimental Considerations, Journal of Pharmaceutical Sciences, 99(4):1654-73, Apr. 2010. (Epub Oct. 29, 2009).
Dilillo DJ et al., Broadly neutralizing anti-influenza antibodies require Fc receptor engagement for in vivo protection, J. Clin. Invest., 126(2):605-10, Feb. 2016. (Epub Jan. 5, 2016).
Dilillo DJ et al., Broadly neutralizing hemagglutinin stalk-specific antibodies require FcγR interactions for protection against influenza virus in vivo, Nat. Med., 20(2):143-51, Feb. 2014. (Epub Jan. 12, 2014).
Djupesland PG, Nasal drug delivery devices: characteristics and performance in a clinical perspective-a review, Drug Deliv Transl Res, 3(1):42-62, Feb. 2013. (Epub Oct. 18, 2012).
Donnelly MLL et al., The cleavage activities of aphthovirus and cardiovirus 2A proteins, J. Gen. Virol., 78(Pt 1):13-21, Jan. 1997.
Dreyfus C et al., Highly conserved protective epitopes on influenza B viruses, Science, 337:1343-8, Sep. 14, 2012. (Epub Aug. 9, 2012).
Du L et al., Intranasal vaccination of recombinant adeno-associated virus encoding receptor-binding domain of severe acute respiratory syndrome coronavirus (SARS-CoV) spike protein induces strong mucosal immune responses and provides long-term protection against SARS-CoV infection, J Immunology,180(2):948-956, Jan. 2008.
Ekiert DC et al., A highly conserved neutralizing epitope on group 2 influenza A viruses, Science, 333(6044):843-50, Aug. 12, 2011. (Epub Jul. 7, 2011).
Ekiert DC et al., Antibody recognition of a highly conserved influenza virus epitope, Science, 324(5924):246-51, Apr. 10, 2009. (Epub Feb. 26, 2009).
Ekiert DC et al., Cross-neutralization of influenza A viruses mediated by a single antibody loop, Nature, 489(7417):526-32, Sep. 27, 2012. (Epub Sep. 16, 2012).
Emsley P et al., Cowtan, Features and development of Coot, Acta Crystallogr. D Biol. Crystallogr., 66(Pt 4):486-501, Apr. 2010. (Epub Mar. 24, 2010).

(56) References Cited

OTHER PUBLICATIONS

Ercolani L et al., Isolation and complete sequence of a functional human glyceraldehyde-3-phosphate dehydrogenase gene, J Biol Chem, 263(30):15335-41, Oct. 25, 1988.

Centers for Disease Control and Prevention, Estimates of deaths associated with seasonal influenza: United States, 1976-2007, available in MMWR Morb. Mortal. Wkly. Rep. 59:1057-1062, Aug. 27, 2010.

European Medicines Agency, Guideline on Development, Production, Characterisation and Specifications for Monoclonal Antibodies and Related Products (EMEA/CHMP/BWP/157653/2007), published Dec. 2008.

Fang J et al., An antibody delivery system for regulated expression of therapeutic levels of monoclonal antibodies in vivo, Mol. Ther., 15(6);1153-9, Jun. 2007. (Epub Mar. 20, 2007).

Fisher K et al., Transduction with recombinant adeno-associated virus for gene therapy is limited by leading-strand synthesis, J. Virol., 70(1):520-32, Jan. 1996.

Flotte TR et al., Stable in vivo expression of the cystic fibrosis transmembrane.conductance regulator with an adeno-associated virus vector. Proc Natl Acad Sci U S A. 90(22):10613-7, Nov. 15, 1993.

Forsman A et al., Llama antibody fragments with cross-subtype human immunodeficiency virus type 1 (HIV-1)-neutralizing properties and high affinity for HIV-1 gp120. J. Virol., 82(24):12069-81, Dec. 2008. (Epub Oct. 8, 2008).

Friesen RH et al., A common solution to group 2 influenza virus neutralization. Proc. Natl. Acad. Sci. U.S.A. 111(1):445-50, Jan. 7, 2014. (Epub Dec. 11, 2013).

Furler S et al., Recombinant AAV vectors containing the foot and mouth disease virus 2A sequence confer efficient bicistronic gene expression in cultured cells and rat substantia nigra neurons, Gene Ther., 8(11):864-73, Jun. 2001.

Gamblin SJ et al., Influenza hemagglutinin and neuraminidase membrane glycoproteins, Journal of Biological Chemistry, 285(37):28403-9, Sep. 10, 2010. (Epub Jun. 10, 2010).

Gao et al, Adeno-associated viruses undergo substantial evolution in primates during natural infections, Proc. Natl. Acad. Sci. U.S.A., 100(10):6081-6, May 13, 2003. (Epub Apr. 25, 2003).

Gao G et al. Purification of recombinant adeno-associated virus vectors by column chromatography and its performance in vivo. Human Gene Therapy, 11(15):2079-91, Oct. 10, 2000.

Gao G et al., Clades of Adeno-associated viruses are widely disseminated in human tissues, J Virol., 78(12):6381-8, Jun. 2004.

Gao GP et al., Novel adeno-associated viruses from rhesus monkeys as vectors for human gene therapy, Proc Natl Acad Sci USA, 99(18):11854-9, Sep. 3, 2002. (Epub Aug. 21, 2002).

Gao R et al., Human infection with a novel avian-origin influenza A (H7N9) virus. N. Engl. J. Med., 368:1888-97, May 16, 2013. (Epub Apr. 11, 2013).

Glaven RH et al., Linking Single Domain Antibodies that Recognize Different Epitopes on the Same Target, Biosensors (Basel), 2(1):43-56, Feb. 1, 2012.

Glezen WP et al., The burden of influenza B: a structured literature review, Am J Public Health, 103(3):e43-51, Mar. 2013. (Epub Jan. 17, 2013).

Gossen M and Bujard H, Tight control of gene expression in mammalian cells by tetracycline-responsive promoters, Proc. Natl. Acad. Sci. USA, 89:5547-51, Jun. 1992.

Gossen M et al., Transcriptional activation by tetracyclines in mammalian cells, Science 268(5218):1766-9, Jun. 23, 1995.

Grieger JC and Samulski RJ, Adeno-associated virus as a gene therapy vector: Vector development, production and clinical applications, Adv. Biochem. Engin/Biotechnol., 99: 119-145, 2005. (Epub Oct. 25, 2005).

Grimm et al., Titration of AAV-2 particles via a novel capsid ELISA: packaging of genomes can limit production of recombinant AAV-2, Gene Therapy, 6(7):1322-30, Jul. 1999.

Gupta P, Preclinical pharmacokinetics of MHAA4549A, a human monoclonal antibody to influenza A virus, and the prediction of its efficacious clinical dose for the treatment of patients hospitalized with influenza A, Mabs, 8(5):991-7, Jul. 2016. (Epub Mar. 31, 2016).

Harris A et al., Influenza virus pleiomorphy characterized by cryoelectron tomograph, Proc. Natl. Acad. Sci. U.S.A., 103(50)19123-7, Dec. 12, 2006. (Epub Dec. 4, 2006).

Hessell AJ et al., Fc receptor but not complement binding is important in antibody protection against HIV, Nature, 449(7158):101-104, Sep. 6, 2007.

Hinderer C et al., Severe Toxicity in Nonhuman Primates and Piglets Following High-Dose Intravenous Administration of an Adeno-Associated Virus Vector Expressing Human SMN, Human Gene Therapy, 29(3):285-298, Mar. 2018. (Epub Feb. 12, 2018).

Hohn M et al., SPARX, a new environment for Cryo-EM image processing, J. Struct. Biol., 157(1):47-55, Jan. 2007. (Epub Jul. 16, 2006).

Hoogenboom HR et al, By-passing immunisation: Human antibodies from synthetic repertoires of germline VH gene segments rearranged in vitro, J. Mil. Biol., 227(2):381-8, Sep. 1992.

Hufton SE et al. The breadth of cross sub-type neutralisation activity of a single domain antibody to influenza hemagglutinin can be increased by antibody valency, PLoS One, 9(8):e103294, Aug. 1, 2014.

Hultberg A et al., Llama-derived single domain antibodies to build multivalent, superpotent and broadened neutralizing anti-viral molecules, PLoS One 6(4):e17665, Apr. 1, 2011.

Hynes et al., Hormone-responsive expression of an endogenous proviral gene of mouse mammary tumor virus after molecular cloning and gene transfer into cultured cells, Proc. Natl. Acad. Sci. USA, 78(4):2038-42, Apr. 1981.

Invivogen, IgG-Fc Engineering for Therapeutic Use, available online at www.invivogen.com/docs/Insight200605.pdf, Apr. 2006.

Irani V et al., Molecular properties of human IgG subclasses and their implications for designing therapeutic monoclonal antibodies against infectious diseases, Molecular immunology, 67(2):171-82, Oct. 2015. (Epub Apr. 18, 2015).

Israel DI and Kaufman RJ, Highly inducible expression from vectors containing multiple GRE's in CHO cells overexpressing the glucocorticoid receptor, Nucl. Acids Res., 17(12):2589-2604, Nov. 12, 1989.

Jegaskanda PC et al., Influenza-specific antibody-dependent cellular cytotoxicity: toward a universal influenza vaccine, J. Immunol. 193(2):469-75, Jul. 15, 2014.

Jin X et al., Direct Liquid Chromatography/Mass Spectrometry Analysis for Complete Characterization of Recombinant Adeno-Associated Virus Capsid Proteins, Hu Gene Therapy Methods, 28(5):255-67, Oct. 2017. (Epub Jun. 16, 2017).

Johnson PR et al., Vector-mediated gene transfer engenders long-lived.neutralizing activity and protection against SIV infection in monkeys, Nat Med., 15(8):901-6, Aug. 2009. (Epub May 17, 2009).

Jones PT et al., Replacing the complementarity-determining regions in a human antibody with those from a mouse, Nature, 321(6069):522-5, May 1986.

Julien JP et al., Structural insights into key sites of vulnerability on HIV-1 Env and influenza HA, Immunol. Rev., 250(1):180-98, Nov. 2012.

Juno J et al., Immunogenetic Factors Associated with Severe Respiratory Illness Caused by Zoonotic H1N1 and H5N1 Influenza Viruses, Clinical and Developmental Immunology, vol. 2012, Article ID 797180, 9 pages. (Epub Nov. 3, 2011).

Kabsch W, XDS, Acta Crystallogr. D Biol. Crystallogr., 66(Pt 2):125-32, Feb. 2010. (Epub Jan. 22, 2010).

Kaplitt MG, et al. Long-term gene expression and phenotypic correction using adeno-associated virus vectors in the mammalian brain. Nat Genet., 8(2):148-54, Oct. 1, 1994.

Kashyap AK et al., Combinatorial antibody libraries from survivors of the Turkish H5N1 avian influenza outbreak reveal virus neutralization strategies, Proc. Natl. Acad. Sci. U.S.A., 105(16):5986-91, Apr. 22, 2008. (Epub Apr. 14, 2008).

Kashyap AK et al., Protection from the 2009 H1N1 Pandemic Influenza by an Antibody from Combinatorial Survivor-Based Libraries, PLoS Pathog., 6(7):e1000990, Jul. 2010.

(56) References Cited

OTHER PUBLICATIONS

Kelly S et al., Splicing of many human genes involves sites embedded within introns, Nucleic Acids Research, 2015) 43(9):4721-32, May 19, 2015. (Epub Apr. 20, 2015).

Klein C et al., Progress in overcoming the chain association issue in bispecific heterodimeric IgG antibodies, mAbs, 4(6):653-63, Nov.-Dec. 2012. (Epub Aug. 27, 2012).

Klock G et al., Oestrogen and glucocorticoid responsive elements are closely related but distinct, Nature, 329(6141):734-6, Oct. 22-28, 1987.

Klump H et al., Retroviral vector-mediated expression of HoxB4 in hematopoietic cells using a novel coexpression strategy, Gene Ther., 8(10):811-7, May 2001.

Kohler et al., Continuous cultures of fused cells secreting antibody of predefined specificity, Nature, 256(5517):495-7, Aug. 1975.

Kortt AA et al., Recombinant anti-sialidase single-chain variable fragment antibody. Characterization, formation of dimer and higher-molecular-mass multimers and the solution of the crystal structure of the single-chain variable fragment/sialidase complex, Eur. J. Biochem., 221(1):151-7, Apr. 1994.

Krah S et al., Single-domain antibodies for biomedical applications, Immunopharmacol. Immunotoxicol., 38(1):2128, 2016. (Epub Nov. 9, 2015).

Kramer RA et al., A novel helper phage that improves phage display selection efficiency by preventing the amplification of phages without recombinant protein. Nucleic Acids Res., 31(11):e59, Jun. 1, 2003.

Kramer RA et al., The human antibody repertoire specific for rabies virus glycoprotein as selected from immune libraries, Eur. J. Immunol., 35(7):2131-45, Jul. 2005.

Krause et al., Human Monoclonal Antibodies to Pandemic 1957 H2N2 and Pandemic 1968 H3N2 Influence Viruses, Journal of Virology, 86(11):6334-6340, Jun. 2012.

Kuo TT et al., Neonatal Fc Receptor and IgG-Based Therapeutics, mAbs, 3(5):422-30, Sep.-Oct. 2011. (Epub Sep. 1, 2011).

Labrijn et al., Efficient generation of stable bispecific IgG1 by controlled Fab-arm exchange, PProc Natl Acad Sci USA, 110(13):5145-50, Mar. 26, 2013. (Epub Mar. 11, 2013).

Lander et al., Appion: an integrated, database-driven pipeline to facilitate EM image processing, J. Struct. Biol., 166(1):95-102, Apr. 2009.

Laursen S and Wilson IA, Broadly neutralizing antibodies against influenza viruses, Antiviral. Res. 98(3):476-83, Jun. 2013. (Epub Apr. 9, 2013).

Lee F et al., Glucocorticoids regulate expression of dihydrofolate reductase cDNA in mouse mammary tumour virus chimaeric plasmids, Nature 294(5838):228-32, Nov. 19, 1981.

Lee PS et al., Heterosubtypic antibody recognition of the influenza virus hemagglutinin receptor binding site enhanced by avidity. Proc. Natl. Acad. Sci. U.S.A. 109(42):17040-5, Oct. 16, 2012. (Epub Oct. 1, 2012).

Levitt N et al., Definition of an efficient synthetic poly(A) site, Genes Dev., 3(7):1019-25, Jul. 1989.

Limberis et al., Vectored expression of the broadly neutralizing antibody FI6 in mouse airway provides partial protection against a new avian influenza A virus, H7N9., Clin Vaccine Immunol, 20(12):1836-7. Dec. 2013. (Epub Oct. 16, 2013).

Limberis MP and Wilson JM, Adeno-associated virus serotype 9 vectors transduce murine alveolar and nasal epithelia and can be readministered 2006, Proc Natl Acad Sci USA, 103(35):12993-8, Aug. 29, 2006. (Epub Aug. 22, 2006).

Limberis MP et al, Establishment of a New AAV Clinical Candidate for Prophylaxis Against Influenza A and B (Abstract 398), Poster presented at American Society of Gene & Cell Therapy 2017 Annual Meeting on May 11, 2017.

Limberis MP et al, Intranasal Antibody Gene Transfer in Mice and Ferrets ElicitsBroad Protection Against Pandemic Influenza, Sci Transl Med., 5(187):187ra72, May 29, 2013.

Limberis MP et al., Adeno-Associated Virus Serotype 9-Expressed ZMapp in Mice Confers Protection Against Systemic and Airway-Acquired Ebola Virus Infection, J Infect Dis., 214(12):1975-79, Dec. 2016. (Epub Sep. 28, 2016).

Limberis MP et al., Transduction efficiencies of novel AAV vectors in mouse airway epithelium in vivo and human ciliated airway epithelium in vitro, Mol. Ther., 17(2):294-301, Feb. 2009. (Epub Dec. 9, 2008).

Limberis MP, AAV Vectors for Rapid and Effective Prophylaxis against Airborne Viruses, presented on Feb. 14, 2018 at 2018 ASM Biothreats meeting in Baltimore, Maryland, pp. 1-34.

Liu J et al., Highly pathogenic H5N1 influenza virus infection in migratory birds, Science, 309(5738):1206m, Aug. 19, 2005. (Epub Jul. 6, 2005).

Ljungman P, Vaccination of immunocompromised patients, Clin Microbiol Infect,18 Suppl 5:93-9, Oct. 2012.

Lobner E et al., Engineered IgG1-Fc—one fragment to bind them all, Immunological reviews, 270(1):113-131, Mar. 2016. (Epub Feb. 10, 2016).

Lock M et al., Rapid, simple, and versatile manufacturing of recombinant adeno-associated viral vectors at scale, Hum Gene Ther. 21(10):1259-71, Oct. 2010. (Published online Sep. 24, 2010).

Lock et al., Absolute determination of single-stranded and self-complementary adeno-associated viral vector genome titers by droplet digital PCR, Hum Gene Ther Methods, 25(2):115-25, Apr. 2014. (Epub Feb. 14, 2014).

Marks JD et al., By-passing immunization. Human antibodies from V-gene libraries displayed on phage, J. Mol. Biol., 222(3):381-97, Dec. 1991.

Mayo KE et al. The mouse metallothionein-I gene is transcriptionally regulated by cadmium following transfection into human or mouse cells, Cell, 29(1):99-108, May 1982.

McBride JM et al. Phase 2 Randomized Trial of the Safety and Efficacy of MHAA4549A, a Broadly Neutralizing Monoclonal Antibody, in a Human Influenza A Virus Challenge Model. Antimicrob Agents Chemother. Oct. 24, 2017;61(11). Pii: e01154-17. Accepted manuscript posted online Aug. 14, 2017.

McCarty DM et al., Self-complementary recombinant adeno-associated virus (scAAV) vectors promote efficient transduction independently of DNA synthesis, Gene Therapy, 8(2):1248-54, Aug. 2001.

McCoy AJ et al., Likelihood-enhanced fast translation functions. Acta Crystallogr. D Biol. Crystallogr. 61(Pt 4):458-64, Apr. 2005. (Epub Mar. 24, 2005).

McLellan JS et al., Structure of respiratory syncytial virus fusion glycoprotein in the postfusion conformation reveals preservation of neutralizing epitopes, J Virol., 85(15):7788-96, Aug. 2011. (Epub May 25, 2011).

Medina RA, Influenza A viruses: new research developments, Nat Rev Microbiol., 9(8):590-603, Jul. 11, 2011.

Melnick JL et al., Association of 20-Millimicron Particles with Adenoviruses, J Bacteriol., 90(1):271-4, Jul. 1965.

Merrifield, Solid Phase Peptide Synthesis I. The Synthesis of a Tetrapepide. J. Am. Chem. Soc., vol. 85, p. 2149, Jan. 1963.

Miller AD et al., Expression of a retrovirus encoding human HPRT in mice, Science, 225(4662):630-2, Aug. 10, 1984.

Miller MA et al. Visualization of murine intranasal dosing efficiency using luminescent Francisella tularensis: effect of instillation volume and form of anesthesia. PLoS One, 7(2):e31359, 2012. (Epub Feb. 24, 2012).

Molinari N-A M et al., The annual impact of seasonal influenza in the US: measuring disease burden and costs, Vaccine, 25(27):5086-96, Jun. 28, 2007. (Epub Apr. 20, 2007).

Mouquet H et al., Enhanced HIV-1 neutralization by antibody heteroligation, Proc. Natl. Acad. Sci. U.S.A., 109(3):875-80, Jan. 17, 2012. (Epub Jan. 4, 2012).

Murshudov GN et al., Refinement of macromolecular structures by the maximum-likelihood method, Acta Crystallogr. D Biol. Crystallogr., 53(Pt 3):240-55, May 1, 1997.

Nakamura G et al., An in vivo human-plasmablast enrichment technique allows rapid identification of therapeutic A antibodies. Cell Host Microbe, 14(1):93-103, Jul. 17, 2013.

Ng S-Y et al., Regulation of the human beta-actin promoter by upstream and intron domains, Nuc. Nucleic Acids Res.,17(2): 601-615, Jan. 25, 1989.

(56) References Cited

OTHER PUBLICATIONS

Nieto K et al., Combined prophylactic and therapeutic intranasal vaccination against human papillomavirus type-16 using different adeno-associated virus serotype vectors, Antiviral Ther., 14(8):1125-37, 2009.
Ogura T et al., Topology representing network enables highly accurate classification of protein images taken by cryo electron-microscope without masking, J. Struct. Biol., 143(3):185-200, Sep. 2003.
Oliveira EC et al., Influenza in the intensive care unit. J Intensive Care Med, 18(2):80-91, Mar.-Apr. 2003. (First Published Mar. 1, 2003 ).
Osterholm MT et al., Efficacy and effectiveness of influenza vaccines: a systematic review and meta-analysis. Lancet Infect Dis. 12(1):36-44, Jan. 2012. (Epub Oct. 25, 2011).
Ostrowski LE et al., Targeting expression of a transgene to the airway surface epithelium using a ciliated cell-specific promoter, Molecular Therapy, 8(4):637-45, Oct. 2003.
Pettersen EF et al., UCSF Chimera—a visualization system for exploratory research and analysis, J. Comput. Chem., 25(13):1605-12, Oct. 2004.
Quitschke WW et al., The beta actin promoter, High levels of transcription depend upon a CCAAT binding factor, 264(16):9539-46, Jun. 5, 1989.
Radcliffe PA et al., Multiple gene products from a single vector: 'self-cleaving' 2A peptides, Gene Therapy, 11(23):1673-4, 2004. (Published Oct. 26, 2004).
Rath T et al., Fc-fusion proteins and FcRn: structural insights for longer-lasting and more effective therapeutics, Critical reviews in biotechnology, 35(2):235-54, Jun. 2015. (Epub Oct. 24, 2013).
Riechmann L et al., Reshaping human antibodies for therapy, Nature, 332(6162):323-7, Mar. 1988.
Roscilli G et al., Long-Term and Tight Control of Gene Expression in Mouse Skeletal Muscle by a New Hybrid Human Transcription Factor, Mol. Ther., 6(5):653-63, Nov. 2002.
Roseman AM, FindEM—a fast, efficient program for automatic selection of particles from electron micrographs, J. Struct. Biol., 145(1-2):91-9, Jan.-Feb. 2004.
Sanner MF et al., Reduced surface: an efficient way to compute molecular surfaces, Biopolymers, 38(3):305-20, Mar. 1996.
Sawada-Hirai R et al., Human anti-anthrax protective antigen neutralizing monoclonal antibodies derived from donors vaccinated with anthrax vaccine adsorbed, J. Immune Based Ther. Vaccines, 2(1):5, May 12, 2004.
Saxena A and Wu D, Advances in therapeutic Fc engineering—modulation of IgG-Associated effector functions and serum half-life, Frontiers in immunology, 7:580, Dec. 12, 2016.
Scharfmann R et al., Long-term in vivo expression of retrovirus-mediated gene transfer in mouse fibroblast implants, Proc. Natl. Acad. Sci. USA, 88(11):4626-30, Jun. 1, 1991.
Scheres SH, A Bayesian view on cryo-EM structure determination, J. Mol. Biol., 415(2):406-18, Jan. 13, 2012. (Epub Nov. 12, 2011).
Schillinger KJ et al., Regulatable atrial natriuretic peptide gene therapy for hypertension, Proc. Natl. Acad. Sci. U S A., 102(39):13789-94, Sep. 27, 2005. (Epub Sep. 14, 2005).
Searle et al., Building a Metal-Responsive Promoter with Synthetic Regulatory Elements, Mol. Cell. Biol., 5(6):1480-9, Jun. 1985.
Shapiro RJ, The potential American market for generic biological treatments and the associated cost savings, Feb. 2008, Available from: http://www.sonecon.com/docs/studies/0208_GenericBiologicsStudy.pdf.
Shapshak P et al., The Influenza Pandemic of 2009: Lessons and Implications, Mol Diagn Ther., 15(2):63-81, Apr. 1, 2011.
Shepelev V and Fedorov A. Advances in the Exon-Intron Database. Briefings in Bioinformatics, 7(2):178-85, Jun. 2006. (Epub Mar. 9, 2006).
Skaricic D et al., Genetic delivery of an anti-RSV antibody to protect against pulmonary infection with RSV, Virology, 378(1):79-85, Aug. 2008.
Sommer JM et al., Quantification of adeno-associated virus particles and empty capsids by optical density measurement, Molec. Ther., 7(1):122-8, Jan. 2003.
Stratford-Perricaudet LD et al., Evaluation of the transfer and expression in mice of an enzyme-encoding gene using a human adenovirus vector, Hum Gene Ther., 1(3):241-56, 1990.
Strohl WR, Optimization of Fc-Mediated Effector Functions of Monoclonal Antibodies, Current Opinion in Biotechnology, 20(6):685-91, Dec. 2009. (Epub Nov. 4, 2009).
Sui J et al., Structural and functional bases for broad-spectrum neutralization of avian and human influenza A viruses, Nature structural & molecular biology, 16(3):265-73. (Epub Feb. 22, 2009).
Tan GS et al., A pan-H1 anti-hemagglutinin monoclonal antibody with potent broad-spectrum efficacy in vivo, 86(11):6179-88, Jun. 2012. (Epub Apr. 4, 2012).
Tang G et al., EMAN2: an extensible image processing suite for electron microscopy, J. Struct. Biol., 157(1):38-46, Jan. 2007. (Epub Jun. 8, 2006).
Thomson JD et al., A comprehensive comparison of multiple sequence alignments, Nucleic Acids Research, 27(13):2682-90, Jul. 1, 1999.
Throsby M et al., Heterosubtypic neutralizing monoclonal antibodies cross-protective against H5N1 and H1N1 recovered from human IgM+ memory B cells, PLoS One, 3(12): e3942, 2008. (Epub Dec. 16, 2008).
Tillib et al., Formatted single-domain antibodies can protect mice against infection with influenza virus (H5N2), Antiviral Research. 97(3):245-54, Mar. 2013. (Epub Dec. 25, 2012).
Tsibane et al., Influenza human monoclonal antibody 1F1 interacts with three major antigenic sites and residues mediating human receptor specificity in H1N1 viruses, PLoS Pathog., 8(12):e1003067, 2012. (Epub Dec. 6, 2012).
Tycko J et al. 701. Intranasal Delivery of Neutralizing Antibodies by AAV9 to Protect Mice Against RSV Infection. Vaccines and Immunotherapy, Molecular Therapy, vol. 22, Supplement 1, p. S271, May 2014.
U.S. Department of Health and Human Services, Food and Drug Administration, Center for Biologics Evaluation, "Research Points to Consider in the Manufacture and Testing of Monoclonal Ab Products for Human Use," published in Feb. 1997.
Urrutia R., KRAB-containing zinc-finger repressor proteins, Genome Biol., 4(10):231, 2003. (Epub Sep. 23, 2003).
Vafa O et al., An engineered Fc variant of an IgG eliminates all immune effector functions via structural perturbations, Methods, 65(1):114-26, Jan. 1, 2014. (Epub Jul. 17, 2013).
Vanlandschoot P et al., Nanobodies: new ammunition to battle viruses, Antiviral Res., 92(3):389-407, Dec. 2011. (Epub Sep. 10, 2011).
Verhoeyen M et al., Reshaping human antibodies: grafting an antilysozyme activity, Science, 239(4847):1534-6, Mar. 1988.
Wang TT et al., Broadly protective monoclonal antibodies against H3 influenza viruses following sequential immunization with different hemagglutinins, PLoS Pathog., 6(2):e1000796, Feb. 26, 2010.
Wang Y et al., A regulatory system for use in gene transfer, Proc. Natl. Acad. Sci. USA., 91(17):8180-4, Aug. 1994.
WHO Manual on Animal Influenza Diagnosis and Surveillance, Geneva: World Health Organisation, 2002, version 2002.5.
Willey R et al., Neutralizing antibody titers conferring protection to macaques from a simian/human immunodeficiency virus challenge using the TZM-bl assay, AIDS research and human retroviruses, 26(1):89-98, Jan. 10, 2010.
Williams DA et al., Introduction of new genetic material into pluripotent haematopoietic stem cells of the mouse, Nature, 310(5977):476-80, Aug. 9, 1984.
Wobus CE et al., Monoclonal antibodies against the adeno-associated virus type 2 (AAV-2) capsid: epitope mapping and identification of capsid domains involved in AAV-2-cell interaction and neutralization of AAV-2 infection, J. Virol. 74(19):9281-93, Oct. 2000.
Wu Y et al., A potent broad-spectrum protective human monoclonal antibody crosslinking two haemagglutinin monomers of influenza A virus, Nat. Commun., 6:7708, Jul. 21, 2015.

(56) References Cited

OTHER PUBLICATIONS

Wu Z et al., Effect of genome size on AAV vector packaging, Mol Ther, 18(1):806, Jan. 2010. (Epub Nov. 10, 2009).
Xia H et al., siRNA-mediated gene silencing in vitro and in vivo, Nat Biotechnol, 20(10):1006-10, Oct. 2002. (Epub Sep. 16, 2002).
Xie H et al., H3N2 Mismatch of 2014-15 Northern Hemisphere Influenza Vaccines and Head-to-head Comparison between Human and Ferret Antisera derived Antigenic Maps, Sci. Rep., 5:15279, Oct. 16, 2015.
Xin K-Q et al., A novel recombinant adeno-associated virus vaccine induces a long-term humoral immune response to human immunodeficiency virus, Human Gene Ther., 12(9):1047-61, Jun. 2001.
Xu R et al., Structural basis of preexisting immunity to the 2009 H1N1 pandemic influenza virus, Science, 328(5976):357-60, Apr. 16, 2010. (Epub Mar. 25, 2010).
Yang Z et al., Iterative stable alignment and clustering of 2D transmission electron microscope images, Structure, 20(2):237-47, Feb. 8, 2012.
Yoshida R et al., Cross-protective potential of a novel monoclonal antibody directed against antigenic site B of the hemagglutinin of influenza A viruses, PLoS Pathog., 5(3):e1000350, Mar. 2009. (Epub Mar. 20, 2009).
Zanta-Boussif MA et al., Validation of a mutated PRE sequence allowing high and sustained transgene expression while abrogating WHV-X protein synthesis: application to the gene therapy of WAS, Gene Therapy, 16(5):605-19, May 2009. (Epub Mar. 5, 2009).
Zhang L et al., Alteration in the IL-2 signal peptide affects secretion of proteins in vitro and in vivo, J Gene Med., 7(3):354-65, Mar. 2005. (Published online Dec. 23, 2004 ).
Zhang H et al., Adenovirus-adeno-associated virus hybrid for large-scale recombinant adeno-associated virus production, Human Gene Therapy, 20(9):922-9, Sep. 2009.
GenBank: AEL31310.1, Web page <https://www.ncbi.nlm.nih.gov/protein/AEL31310.1>, 2 pages, retrieved from Internet on May 11, 2018.
NCBI Reference Sequence: NC_001401.2, Web page <https://www.ncbi.nlm.nih.gov/nuccore/NC_001401>, 5 pages, retrieved from Internet on May 11, 2018.
GenBank: K03104.1, Web page <https://www.ncbi.nlm.nih.gov/nuccore/K03104.1>, 1 page, retrieved from Internet on May 11, 2018.
GenBank: X00182.1, Web page <https://www.ncbi.nlm.nih.gov/nuccore/X00182.1>, 3 pages, retrieved from Internet on May 11, 2018.
NCBI Reference Sequence: NM_002467.5, Web page <https://www.ncbi.nlm.nih.gov/nuccore/NM_002467>, 4 pages, retrieved from Internet on May 11, 2018.
GenBank: AEL31303.1, Web page <https://www.ncbi.nlm.nih.gov/protein/AEL31303.1>, 2 pages, retrieved from Internet on May 11, 2018.
GenBank: BAF64540.1, Web page <https://www.ncbi.nlm.nih.gov/protein/BAF64540.1>, 2 pages, retrieved from Internet on May 11, 2018.
GenBank: ACJ71709.1, Web page <https://www.ncbi.nlm.nih.gov/protein/ACJ71709.1>, 2 pages, retrieved from Internet on May 11, 2018.
GenBank: AGH70219.1, Web page <https://www.ncbi.nlm.nih.gov/protein/AGH70219.1>, 1 page, retrieved from Internet on May 11, 2018.
GenBank: V00882.1, Web page <https://www.ncbi.nlm.nih.gov/protein/AGH70219.1>, 2 pages, retrieved from Internet on May 11, 2018.
GenBank: CAA24362.1, Web page <https://www.ncbi.nlm.nih.gov/protein/AGH70219.1>, 1 page, retrieved from Internet on May 11, 2018.
GenBank: AAS99264.1, Web page <https://www.ncbi.nlm.nih.gov/protein/AAS99264>, 1 page, retrieved from Internet on May 11, 2018.
GenBank: AFP87542.1, Web page <https://www.ncbi.nlm.nih.gov/protein/AFP87542.1>, 2 pages, retrieved from Internet on May 11, 2018.
GenBank: AAB86861.1, Web page <https://www.ncbi.nlm.nih.gov/protein/AAB86861.1>, 1 page, retrieved from Internet on May 11, 2018.
PDB: 2J6E_A, Web page <https://www.ncbi.nlm.nih.gov/protein/2J6E_A>, 2 pages, retrieved from Internet on May 11, 2018.
PDB: 4FQL_H, Web page <https://www.ncbi.nlm.nih.gov/protein/4FQL_H>, 3 pages, retrieved from Internet on May 11, 2018.
U.S. Appl. No. 15/571,708, filed Nov. 3, 2017.
International Search Report and Written Opinion in International Application No. PCT/US2018/019974 dated Apr. 11, 2018.
International Preliminary Report on Patentability dated Oct. 22, 2013 in International Patent Application No. PCT/US2012/034355.
International Search Report and Written Opinion in International Patent Application No. PCT/US2012/034355 dated Sep. 14, 2012.
Response to Communication Pursuant to Article 94(3) EPC dated Aug. 2, 2017, filed on Dec. 12, 2017 in European Patent Application No. 12719540.2.
Communication Pursuant to Article 94(3) EPC issued on European Patent Application No. 12719540.2, dated Aug. 2, 2017.
Response to Communication Pursuant to Article 94(3) EPC dated Jun. 10, 2016, filed on Dec. 19, 2016 in European Patent Application No. 12719540.2.
Communication Pursuant to Article 94(3) EPC issued on European Patent Application No. 12719540.2, dated Jun. 10, 2016.
Response to Communication Pursuant to Rules 161(1) and 162 EPC filed for European Patent Application No. 12719540.2, dated Jun. 9, 2014.
Office Action dated Sep. 9, 2016 in U.S. Appl. No. 14/112,802 and Responses filed Mar. 8, 2017 and Mar. 9, 2017.
Office Action dated Jun. 21, 2017 in U.S. Appl. No. 14/112,802 and Response filed Sep. 20, 2017.
Office Action dated Dec. 29, 2017 in U.S. Appl. No. 14/112,802.
International Preliminary Report on Patentability dated Nov. 14, 2017 in International Patent Application No. PCT/US2016/032063.
International Search Report and Written Opinion dated Dec. 19, 2016 in International Patent Application No. PCT/US2016/032063.
International Preliminary Report on Patentability dated Nov. 15, 2016 in International Patent Application No. PCT/US2015/030533.
International Search Report and Written Opinion dated Aug. 14, 2015 in International Patent Application No. PCT/US2015/030533.
International Search Report and Written Opinion dated Jan. 8, 2018 in International Patent Application No. PCT/US2017/052991.
Foster et al., Codon and mRNA sequence optimization for microdystrophin transgenes improves expression and physiological outcome in dystrophic mdx mice following AAV2/8 gene transfer. Mol. Ther. 2008; 16:1825-32 and Supplementary Material, Figure S1 and S2. Epub Sep. 2, 2008.
Lai et al., Antisense RNA complimentary to 3' coding and noncoding sequences of creatine kinase is a potent inhibitor of translation in vivo, Proc. Natl. Acad. Sci. USA, vol. 86(24):10006-10 (Dec. 1989).
Laube et al., The expanding role of aerosols in systemic drug delivery, gene therapy and vaccination: an update. Transl. Respir. Med. Jan. 13, 2014; 2:3. DOI: 10.1186/2213-0802-2-3. Ecollection 2014. (Jan. 13, 2014).
UniProtKB—P60568 (IL2_Human), Web page http://www.uniprot.org/uniprot/P60568, 9 pages, retrieved from Internet on May 11, 2018.
Ward et al., Codon optimization of human factor VIII cDNA leads to high-level expression, Blood, Jan. 20, 2011; 117(3):798-807. DOI: 10.1182/blood-2010-05-282707 Epub Nov. 1, 2010.
Office Action Issued on GCC Patent Application No. GC 2018-34843, dated Aug. 9, 2019.
Non-final Office Action Issued on U.S. Appl. No. 16/358,875, dated Feb. 6, 2020.
Final Office Action Issued on U.S. Appl. No. 14/112,802, dated Sep. 20, 2018.
Summons to attend oral proceeding pursuant to Rule 115(1) EPC issued on European Patent Application No. 12719540.2, dated Feb. 26, 2019.

(56) References Cited

OTHER PUBLICATIONS

Requirement for Restriction/Election issued in U.S. Appl. No. 15/627,805, dated Jun. 26, 2018.
Response to the Jun. 26, 2018 Requirement for Restriction/Election issued in parent U.S. Appl. No. 15/627,805, filed Aug. 24, 2018.
Non-final Office Action issued in U.S. Appl. No. 15/627,805, dated Nov. 2, 2018.
Response to the Nov. 2, 2018 Office Action issued in U.S. Appl. No. 15/627,805, filed May 1, 2019.
Final Office Action issued in U.S. Appl. No. 15/627,805, dated Aug. 21, 2019.
Response to the Aug. 21, 2019 Final Office Action issued in U.S. Appl. No. 15/627,805, filed Dec. 20, 2019.
Notice of Allowance Issued on U.S. Appl. No. 15/627,805, dated Jan. 3, 2020.
Office Action dated Apr. 16, 2019 in the corresponding Eurasian patent application No. 201792500 with an unofficial translation prepared by the Eurasian agent.
Communication pursuant to Rules 161(1) and 162 EPC issues on European Patent Application 18710971.5, dated Nov. 15, 2019.
Office Action Issued on Pakistani application No. 117/2018 dated Nov. 21, 2019.

\* cited by examiner

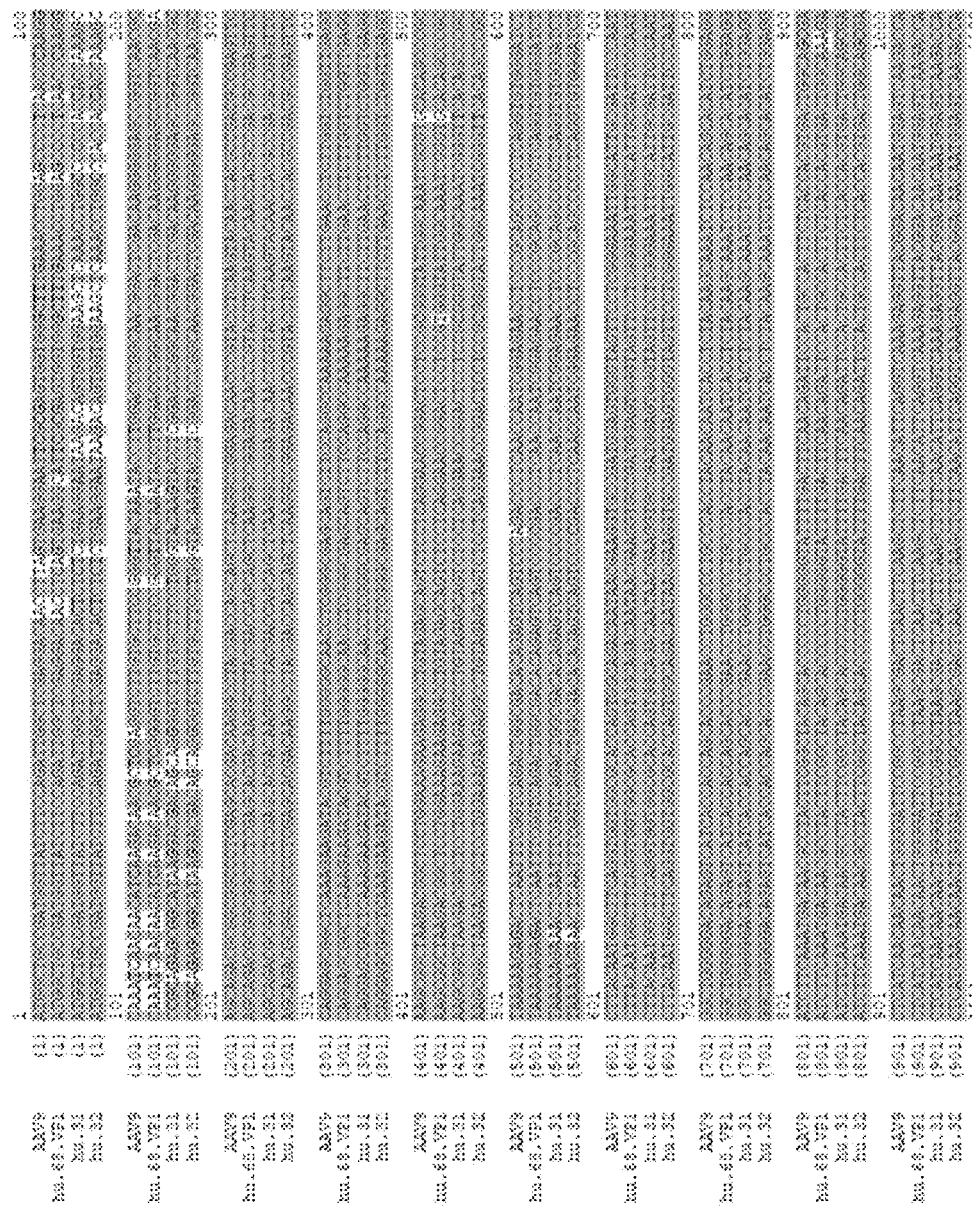

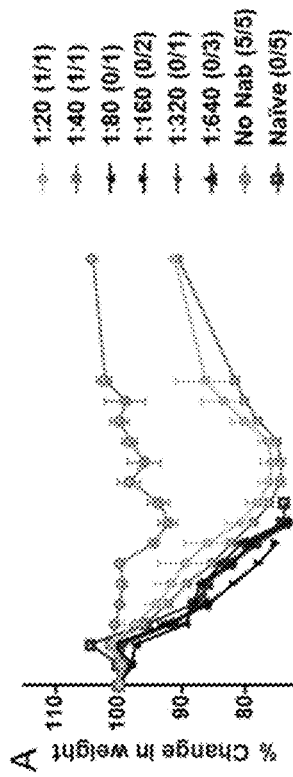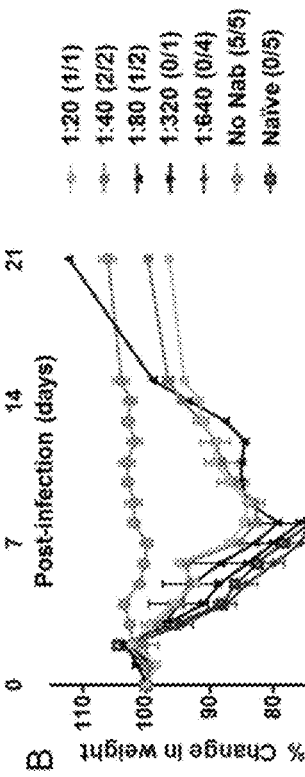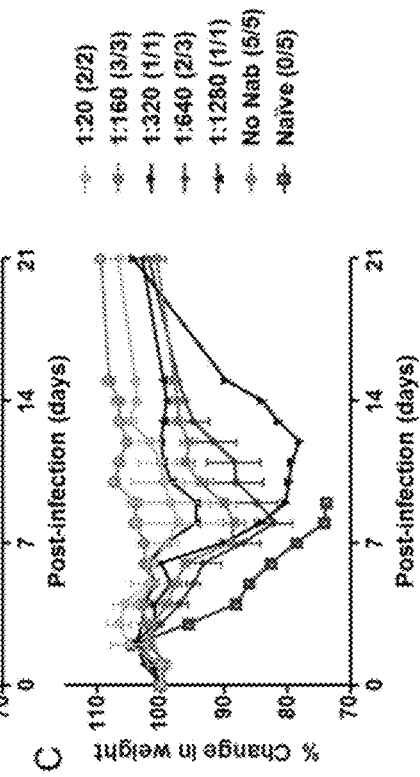
FIG. 10A
FIG. 10B
FIG. 10C

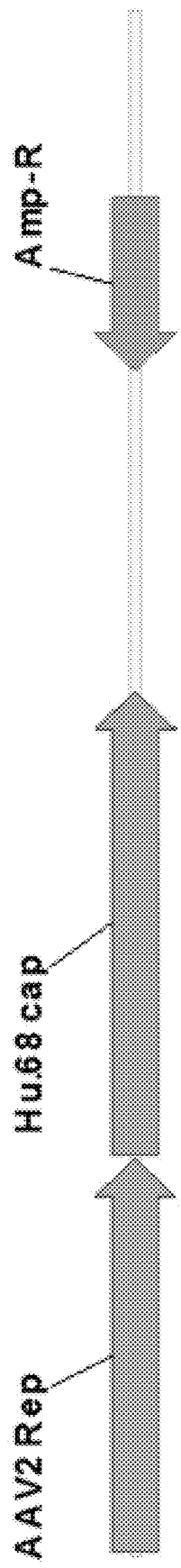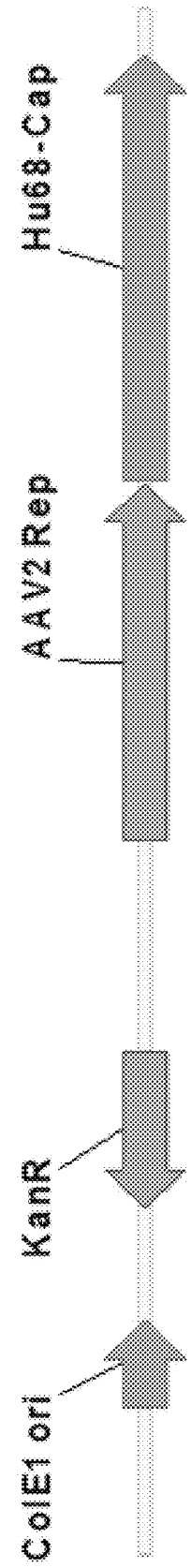

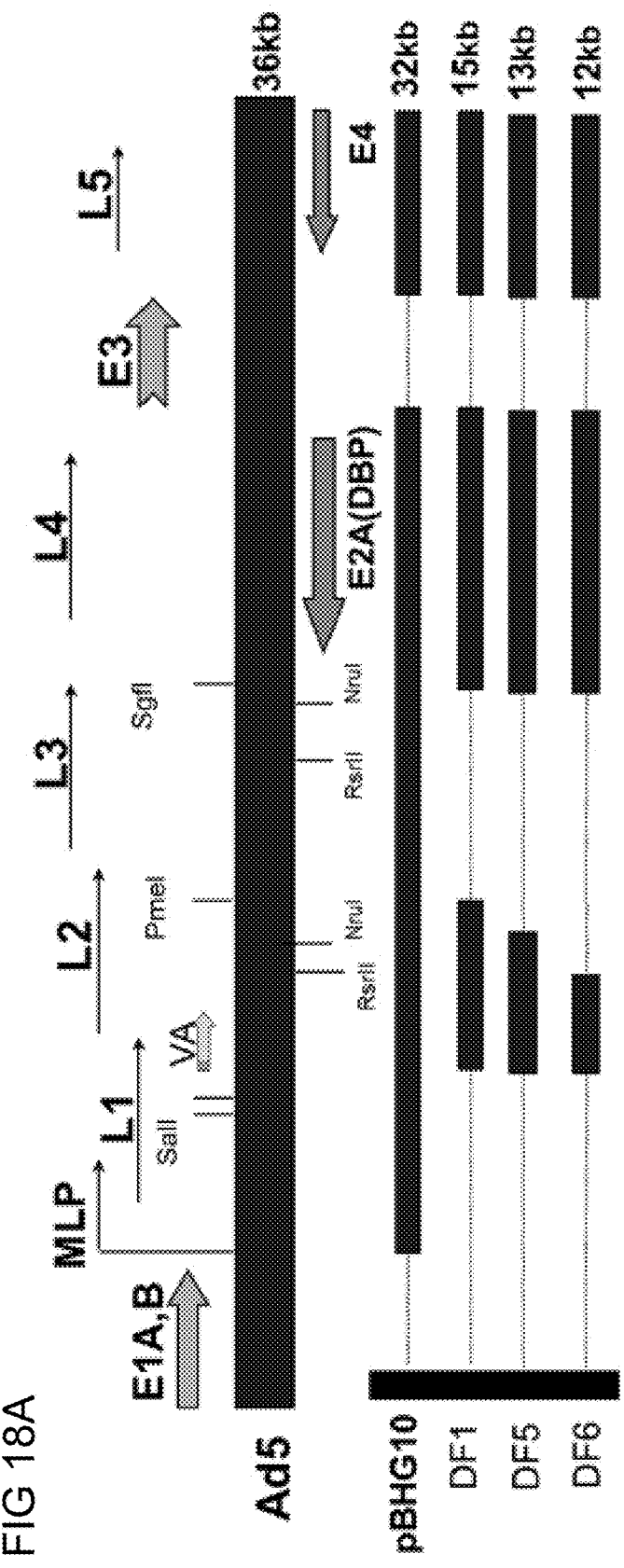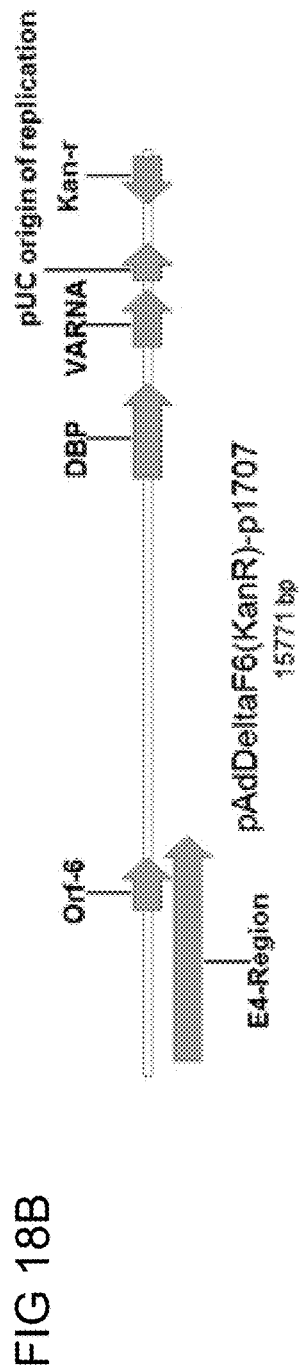
FIG 18A
FIG 18B

AAV MEDIATED INFLUENZA VACCINES

CROSS-REFERENCE TO RELATED APPLICATIONS

This application claims the benefit of the priority of U.S. Provisional Patent Application No. 62/618,443, filed Jan. 17, 2018, U.S. Provisional Patent Application Application No. 62/560,834, filed Sep. 20, 2017, U.S. Provisional Patent Application No. 62/504,293, filed May 10, 2017 and U.S. Provisional Patent Application No. 62/464,753, filed Feb. 28, 2017, which are incorporated herein in their entirety.

STATEMENT REGARDING FEDERALLY SPONSORED RESEARCH OR DEVELOPMENT

This invention was made with government support under W911NF-13-2-0036 awarded by the Defense Advanced Research Projects Agency (DARPA). The government has certain rights in the invention.

BACKGROUND OF THE INVENTION

Influenza infections are the seventh leading cause of death in the U.S.A., equating to approximately 49,000 deaths per year, a significant proportion of the almost 500,000 deaths worldwide. Vaccines are not always effective at protecting humans from influenza. Furthermore, the emergence of a new influenza pandemic remains a threat that could result in substantial loss of life and worldwide economic disruption. The vast reservoir of influenza A viruses in aquatic birds represents a continuous pandemic threat as exemplified by the emergence of the highly pathogenic avian influenza H5N1 in 1997 and H7N9 in 2013 in the human population (J. Liu et al., Highly pathogenic H5N1 influenza virus infection in migratory birds. Science 309, 1206 (2005); H. Chen et al., Avian flu: H5N1 virus outbreak in migratory waterfowl. Nature 436, 191-192 (2005); and R. Gao et al., Human infection with a novel avian-origin influenza A (H7N9) virus. N. Engl. J. Med. 368, 1888-1897 (2013)). The economic burden of annual influenza epidemics is estimated to be in the order of approximately $87 billion. More than half of this cost covers the hospital care required for the almost 1 million patients, of which 70% are elderly patients (>65 years of age).

Adeno-associated virus (AAV) is a nonenveloped, icosahedral, single-stranded DNA virus, 20-26 nm in diameter. Since the first genetic engineering of wild-type AAV as a gene delivery vector in the early 1980s, recombinant AAV has become a promising gene delivery vehicle for effective and safe clinical applications in gene therapy for chronic diseases. AAV serotype 2 (AAV2) was the first AAV that was vectored for gene transfer applications. Several limitations of AAV2 vectors have emerged including low transduction efficiency, high seroprevalence of neutralizing antibodies (NAbs) in humans, and potentially destructive T-cell responses to capsids.

Figure 5A:
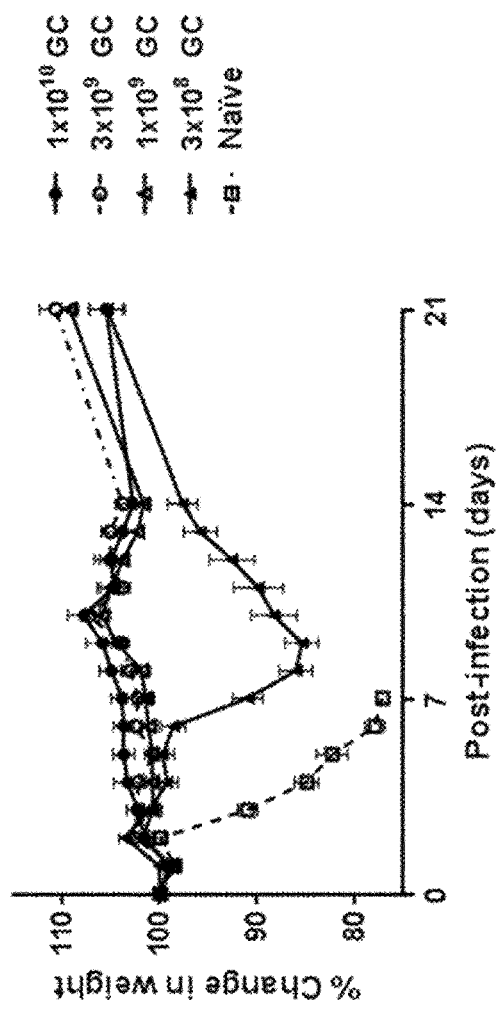
Figure 5B:
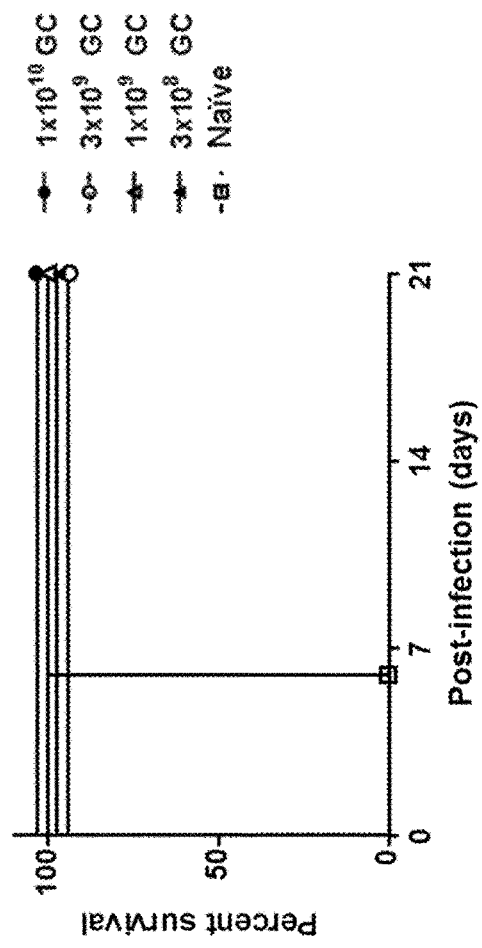

The ideal AAV capsid for delivery of antibody against influenza would have a low seroprevalence in humans, be able to confer high and stable transgene expression, minimally biodistribute to the central nervous system or gonads and have a favorable immunological profile. The selected capsid should be easy to manufacture at high yield and have a history of clinical safety. AAV capsids to consider for selection include those AAV capsids that have been tested in gene therapy clinical trials: AAV1, 2, 6, 8, 9 and rh10. Previous work demonstrated that AAV9 effectively targets the airway and can be effectively readministered in the setting of pre-existing AAV9-specific NAb (Limberis and Wilson, 2006, Proc Natl Acad Sci USA, 103, 35, 12993-12998 (2006)). More recently, we demonstrated that AAV9 vector expressing the FI6 antibody protected both mice and ferrets against lethal airborne challenge with various clinical isolates of H1N1 and H5N1 influenza strains (Limberis, et al, Sci Transl Med. 2013 May 29; 5(187):187ra72).

Suitable alterative influenza vaccines, with enhanced performance profiles, are still needed.

BRIEF DESCRIPTION OF THE DRAWINGS

FIG. 1A provides an alignment showing the amino acid sequence of the vp1 capsid protein of AAVhu68 (SEQ ID NO:16, labelled hu.68.VP1 in alignment), with AAV9 (SEQ ID NO:17), AAVhu31 (SEQ ID NO: 34, labelled hu.31 in alignment) and AAVhu32 (SEQ ID NO: 35, labelled hu.32 in alignment). Compared to AAV9, AAVhu31 and AAVhu32, two mutations (A67E and A157V) were found critical in AAVhu68 and circled in FIG. 1A.

FIGS. 1B-1D provide an alignment of the nucleic acid sequence encoding the vp1 capsid of AAVhu68 (SEQ ID NO: 18 labelled hu.68.VP1 in alignment), with AAV9 (SEQ ID NO: 36), AAVhu31 (SEQ ID NO: 37 labelled hu.31 in alignment) and AAVhu32 (SEQ ID NO: 38 labelled hu.32 in alignment).

FIGS. 2A-2B show results of an assessment of the protective efficacy of AAV1, AAV9 and AAVhu68 vectors expressing hJAb against lethal challenge with mouse adapted influenza A (PR8). In FIG. 2A, 6 week old female BALB/c mice were given intranasally $10^9$ genome copies (GC) of AAV1, AAV9 or AAVhu68 vectors expressing hJAb (AAV1.hJAb, square; AAV9.hJAb, circle; AAVhu68.hJAB, upright triangle; and Naïve, inverted triangle) under the transcriptional control of the CB7 promoter (i.e. AAV.CB7.hJAb, etc). Mice were challenged seven days later (noted here as day 0) with $5LD_{50}$ of PR8 and weighed daily. Percentage weight loss was calculated based on the mouse weight at day of challenge. In FIG. 2B, mice were euthanized when they appeared in distress or their body weight declined >30% as depicted in the Kaplan-Meier plot.

FIGS. 3A-3B show results of an assessment of the protective efficacy of AAV1, AAV9 and AAVhu68 vectors expressing hJAb against lethal challenge with mouse adapted influenza B (B/Lee/40). FIG. 3A shows results of 6 week old female BALB/c mice which were given intranasally $10^9$ GC of AAV vectors expressing hJAb (AAV1.hJAb, square; AAV9.hJAb, circle; AAVhu68.hJAb, upright triangle; and Naïve, inverted triangle) were challenged seven days later (noted here as day 0) with $5LD_{50}$ of B/Lee/40 and weighed daily. Percentage weight loss was calculated based on the mouse weight at day of challenge. FIG. 3B shows results of mice were euthanized when they appeared in distress or their body weight declined >30% as depicted in the Kaplan-Meier plots.

FIG. 4 provides the profile of AAVhu68-mediated expression of hJAb in the bronchoalveolar lavage fluid (BALF). Six week old female BALB/c mice were given intranasally (IN) AAVhu68 vector expressing hJAb at doses ranging from $10^9$ GC to $10^{11}$ GC. Mice were sacrificed seven days later and BALF harvested for determination of hJAb concentration by protein A ELISA.

FIGS. 5A and 5B show the determination of the MED of AAVhu68.CB7.JAb210a for effective prophylaxis against influenza A (PR8). Six-week old female BALB/c mice were given IN AAVhu68.CB7. JAb210a vector at doses ranging from $3 \times 10^8$ GC to $10^{10}$ GC and challenged seven days later (noted here as day 0) with $5LD_{50}$ of PR8 and weighed daily. Percentage weight loss was calculated based on the weight of the mouse at day of challenge and plotted in FIG. 5A. FIG. 5B graphs the percent survival. All mice survived the challenge irrespective of the vector dose.

Figure 6A:
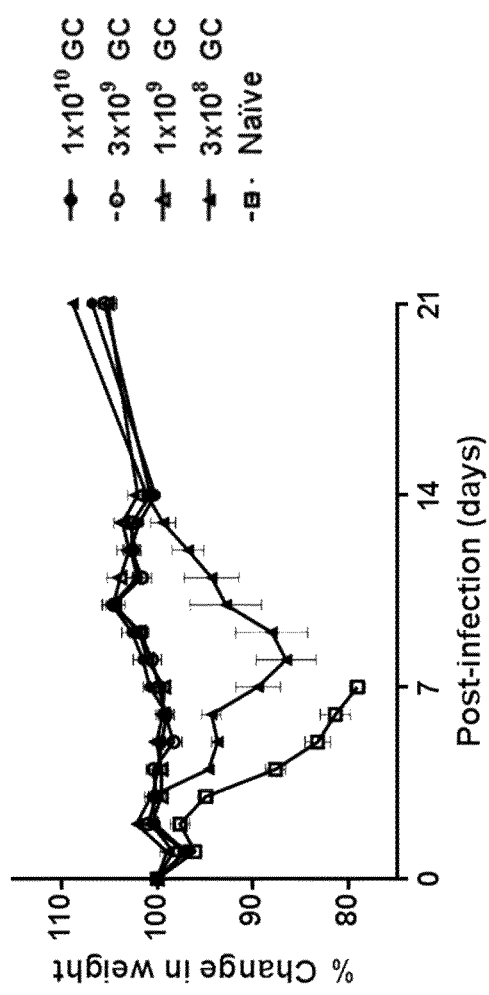
Figure 6B:
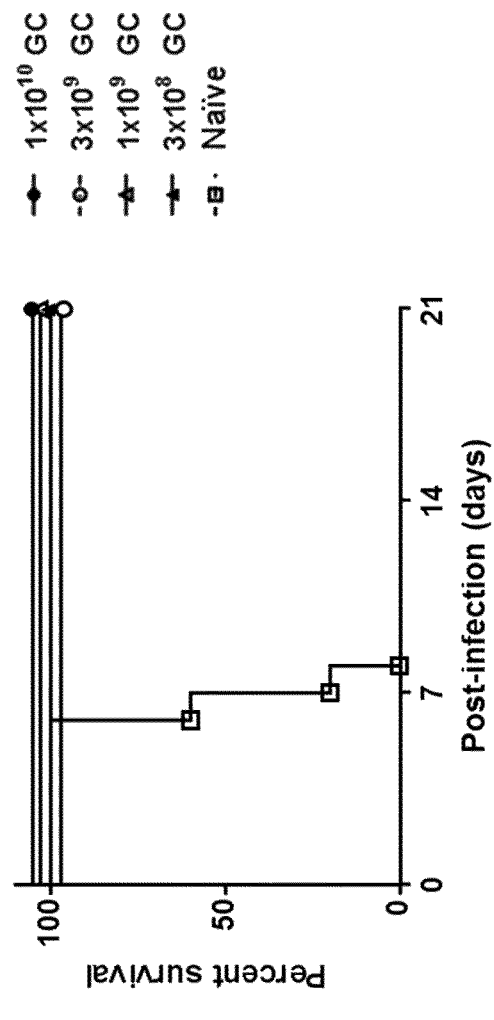

FIGS. 6A and 6B show the determination of the MED of AAVhu68.CB7.JAb210a for effective prophylaxis against influenza B (B/Lee/40). Six-week old female BALB/c mice were given IN AAVhu68.CB7. JAb210a vector at doses ranging from $3 \times 10^8$ GC to $10^{10}$ GC and challenged seven days later (noted here as day 0) with $5LD_{50}$ of B/Lee/40 and weighed daily. Percentage weight loss was calculated based on the weight of the mouse at day of challenge and plotted in FIG. 6A. FIG. 6B graphs the percent survival. All mice survived the challenge irrespective of the vector dose.

Figures 7A, 7B, 7C:
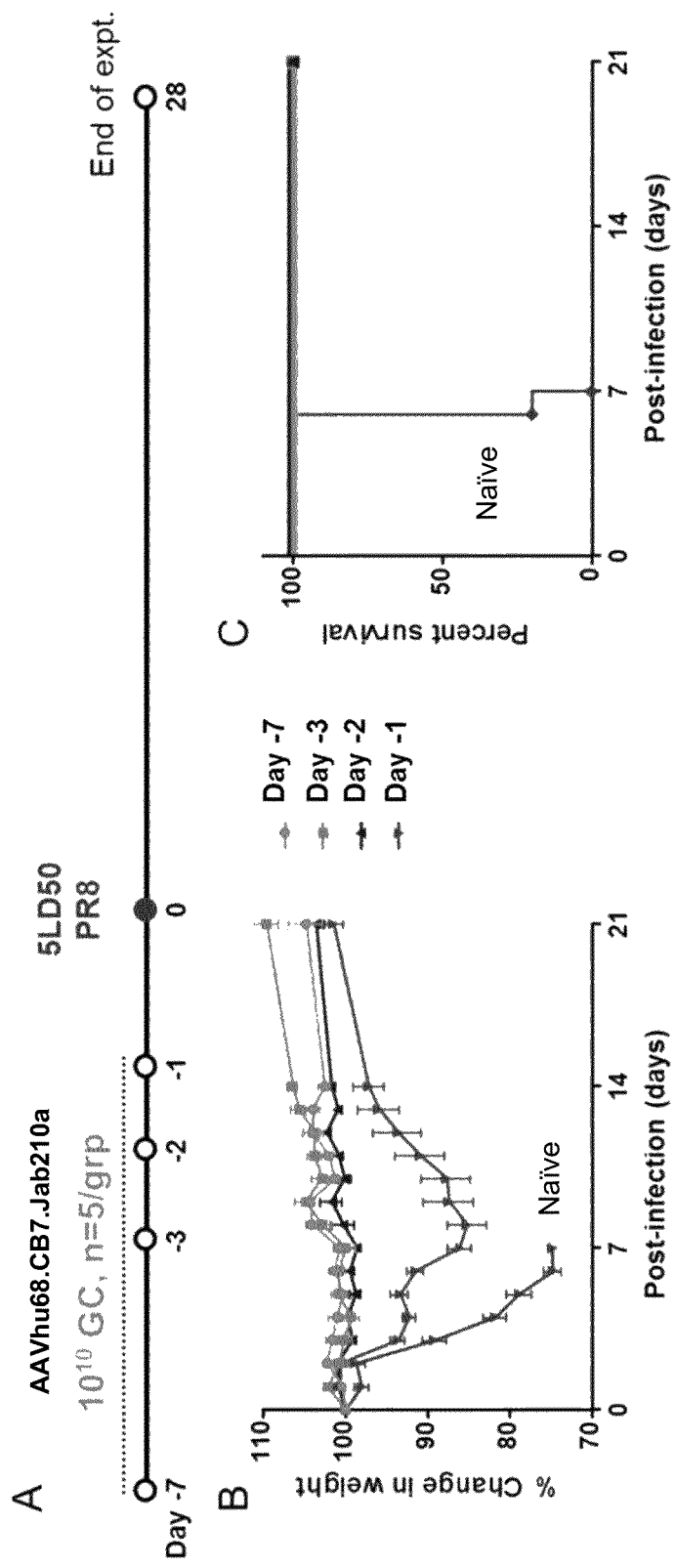

FIGS. 7A-7C show the rapid onset of AAVhu68.CB7.CI.JAb210a-mediated prophylaxis against influenza A (PR8). FIG. 7A provides a timeline showing that 6-week old female BALB/c mice received $10^{10}$ GC of AAVhu68.CB7.CI.JAb210a and groups of vector-treated mice were challenged one day, two days, three days or seven days later, with $5LD_{50}$ of PR8. FIG. 7B is a line graph showing percent (%) change in weight for animals challenged at the various time points post-vector administration. Challenged animals were weighed daily, as represented by the datapoints on the x axis. Percentage weight loss was calculated based on the weight of the mouse at day of challenge. FIG. 7C graphs the percent survival following the PR8 challenge. These data show that all mice receiving AAVhu68.CB7.CI.JAb210a vector survived the challenge irrespective of the time interval between vector dosing and challenge with $5LD_{50}$ of PR8.

Figures 8A, 8B, 8C, 8D:
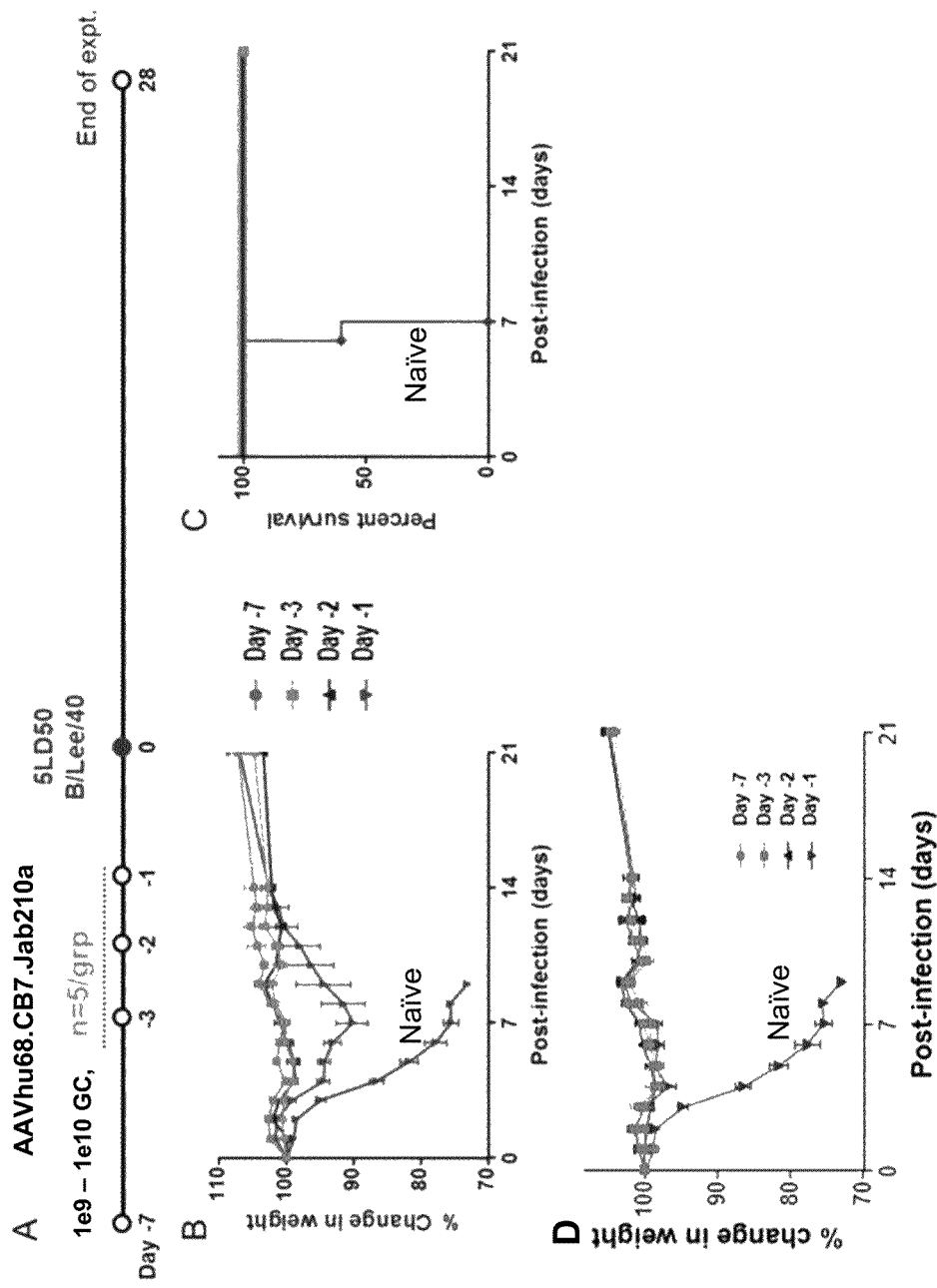

FIGS. 8A-8D illustrate the rapid onset of AAVhu68.CB7.CI.JAb210a-mediated prophylaxis against influenza B (B/Lee/40). FIG. 8A is a timeline, showing that 6-week old female BALB/c mice received $10^9$ or $10^{10}$ GC of AAVhu68.CB7.CI.JAb210a and groups of mice were challenged one day, two days, three days or seven days later, with $5LD_{50}$ of B/Lee/40 and weighed daily. FIG. 8B shows for mice given $10^9$ GC of AAVhu68.CB7.CI.JAb210a the percentage weight loss calculated based on the weight of the mouse at day of challenge. FIG. 8C shows that all mice survived the challenge irrespective of the time interval between vector dosing and challenge with B/Lee/40. FIG. 8D shows for mice given $10^{10}$ GC of AAVhu68.CB7.CI.JAb210a, the percentage weight loss calculated based on the weight of the mouse at day of challenge. All mice survived the challenge irrespective of the time interval between vector dosing and challenge with B/Lee/40.

FIGS. 9A-9F show the impact of serum-circulating AAVhu68 neutralizing antibody (NAb) on the effectiveness of AAVhu68.CB7.CI.JAb210a-mediated prophylaxis against lethal challenge with PR8. Groups of 6-week old female BALB/c mice with varying levels of pre-existing serum-circulating AAVhu68-specific NAb were given IN $10^9$ GC (FIG. 9A), $3 \times 10^9$ GC (FIG. 9B), and $10^{10}$ GC (FIGS. 9C-9F) of AAVhu68.CB7.CI.JAb210a vector approximately 30 days following initial exposure to AAVhu68.CB.LacZ vector (given to induce NAb to AAVhu68). Mice were challenged seven days later (noted here as day 0) with $5LD_{50}$ of PR8 and weighed daily. Percentage weight was calculated based on weight at day of infection.

FIGS. 10A-10C show the impact of serum-circulating AAVhu68 NAb on the effectiveness of AAVhu68.CB7.CI.JAb210a-mediated prophylaxis against lethal challenge with PR8 (day 90). Groups of female BALB/c mice with varying levels of pre-existing serum-circulating AAVhu68-specific NAb were given IN $10^9$ GC (FIG. 10A), $3 \times 10^9$ GC (FIG. 10B), or $10^{10}$ GC (FIG. 10C) of AAVhu68.CB7.CI.JAb210a vector 90 days following initial exposure to AAVhu68.CB.LacZ vector (given to induce NAb to AAVhu68). Mice were challenged seven days later (noted here as day 0) with $5LD_{50}$ of PR8 and weighed daily. Percentage weight loss was calculated based on weight at day of infection.

Figure 11:
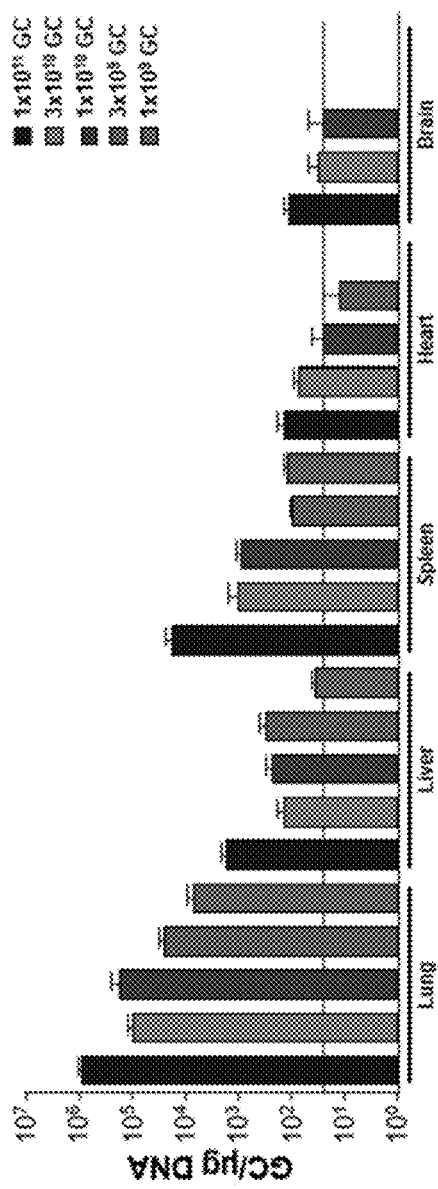

FIG. 11 depicts the biodistribution profile of AAVhu68 vector expressing hJAb in mice. Six week old female BALB/c mice were given IN AAVhu68.CB7.hJAb vector at doses ranging from $10^{11}$ GC (high) to $10^9$ GC (low) and seven days later necropsied. Tissues (lung, liver, spleen, heart and brain) were harvested for biodistribution analysis. The dotted line represents the assay background. For each tissue, five bars from left to right represent data collected from mice treated with $10^{11}$ GC, $3 \times 10^{10}$ GC, $10^{10}$ GC, $3 \times 10^9$ GC, and $10^9$ GC, respectively. When using high doses of AAVhu68 vector (FIGS. 11 and 12), AAVhu68 vector genomes were detected in tissues other than the lung.

Figure 12A:
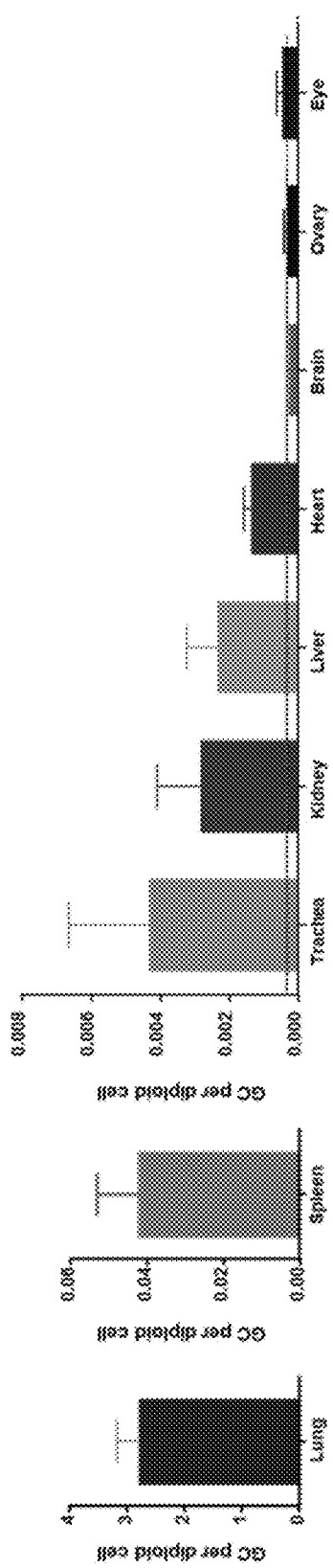
Figure 12B:
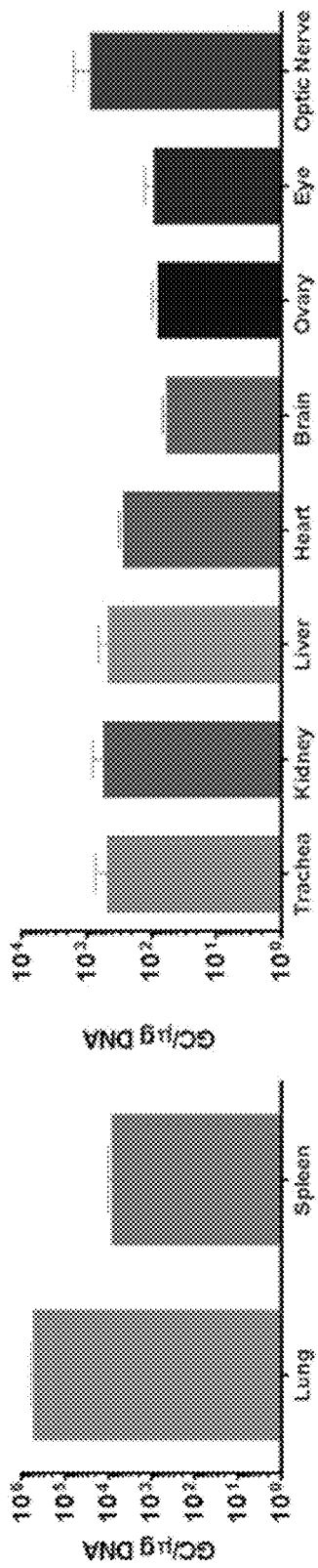

FIGS. 12A and 12B provide a biodistribution profile of AAVhu68 vector expressing JAb210a in mice. Six week old female BALB/c mice were given IN AAVhu68.CB7.CI.JAb210a vector at a high dose, $10^{11}$ GC. Thirty days later the mice were necropsied. Tissues (lung, spleen, trachea, kidney, liver, heart, brain, ovary and eye) were harvested for biodistribution analysis. The dotted line represents the assay background. FIG. 12A shows the data as GC per diploid cell while FIG. 12B shows the data as GC per µg DNA. When using high doses of AAVhu68 vector (FIGS. 11 and 12), AAVhu68 genomes were detected in tissues other than the lung. FIG. 12A shows that the majority of vector genome deposition occurred in the lung, followed by the spleen. Very low levels of AAVhu68 vector genome were present in the kidney, liver and heart (FIG. 12A). Furthermore, the level of AAVhu68 genomes in the brain, ovary or eye was too close to background to allow for accurate interpretation of the data (FIG. 12A). In FIG. 12B, for lung and spleen (left) the scale depicting GC/µg DNA is $10^0$-$10^6$ as opposed to the scale of the bar graph presenting trachea, kidney, liver, heart, brain, ovary, eye and optic nerve which is $10^0$-$10^4$.

Figure 13A:
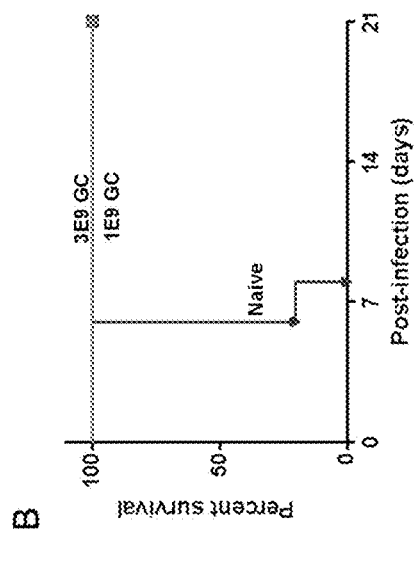
Figure 13B:
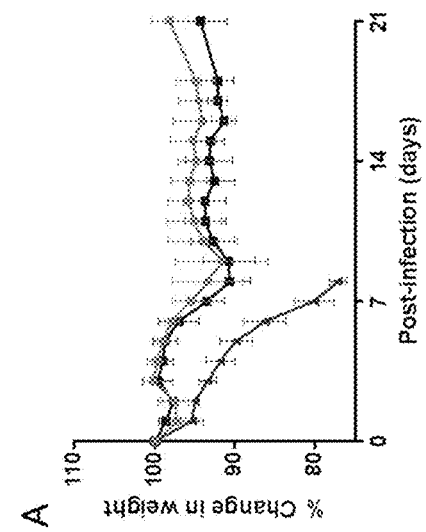

FIGS. 13A and 13B demonstrate the protective profile of AAVhu68.CB7.CI.JAb210a in old mice (9-18 months of age). BALB/c mice received $10^9$ GC or $3 \times 10^9$ GC of AAVhu68.CB7.CI.JAb210a and seven days later challenged with $5LD_{50}$ of PR8. FIG. 13A is a line graph showing percent (%) change in weight for old mice challenged seven days post-vector administration. Mice were weighed daily, as represented by the datapoints on the x axis. Percentage weight loss was calculated based on weight at day of influenza challenge. FIG. 13B graphs the percent survival following the PR8 challenge. These data shows that all mice receiving AAVhu68.CB7.CI.JAb210a survived the challenge with $5LD_{50}$ of PR8. Naïve mice were euthanized by day 8.

Figure 14:
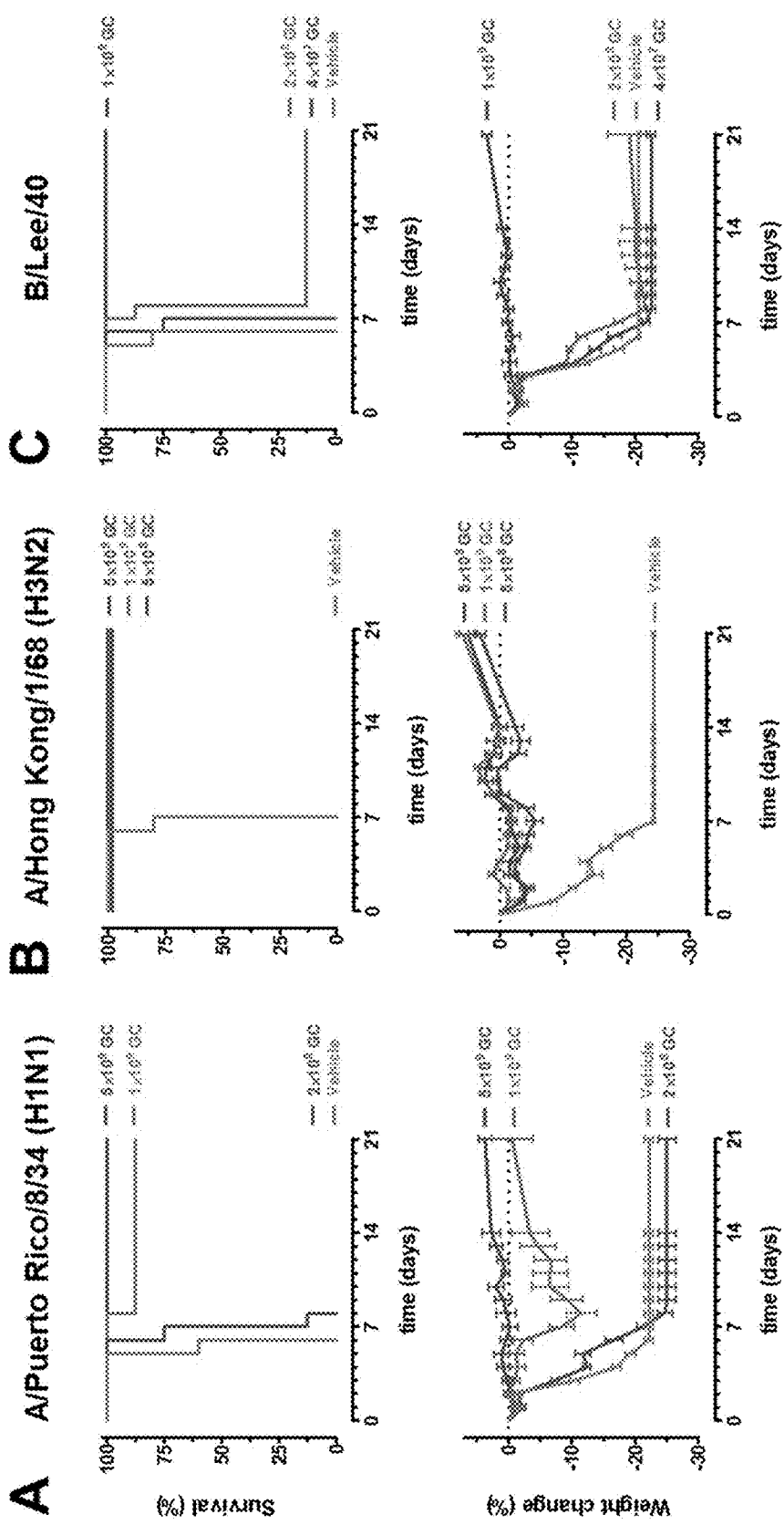

FIGS. 14A to 14C show prophylactic efficacy of AAV-expressed MD3606 in mice challenged with influenza virus. Survival curves (top) and weight loss (bottom) of BALB/c mice treated intranasally with the indicated doses of AAV9.MD3606 vector [expressed as genome copies (GC)] 7 days before challenge with a lethal dose ($5LD_{50}$) of mouse-adapted H1N1 (A/Puerto Rico/8/34-MA) (FIG.

14A), mouse-adapted H3N2 (A/Hong Kong/1/68-MA) (FIG. 14B) or mouse-adapted B (B/Lee/40-MA) virus (FIG. 14C).

Figure 15:
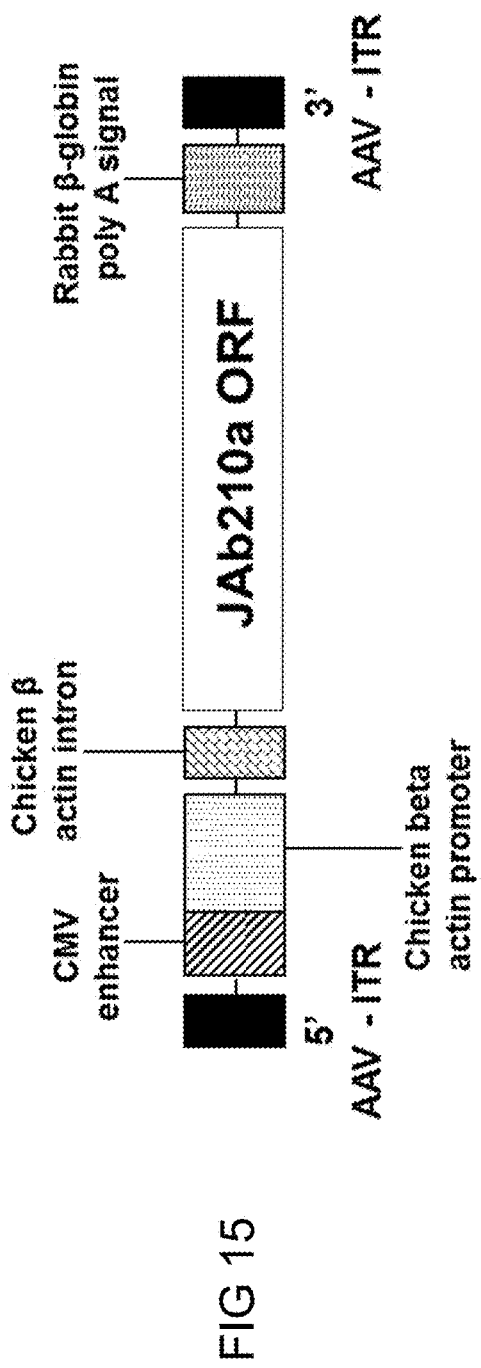

FIG. 15 provides a schematic representation of the AAVhu68.CB7.CI.JAb210a.rBG Vector Genome.

Figure 16:
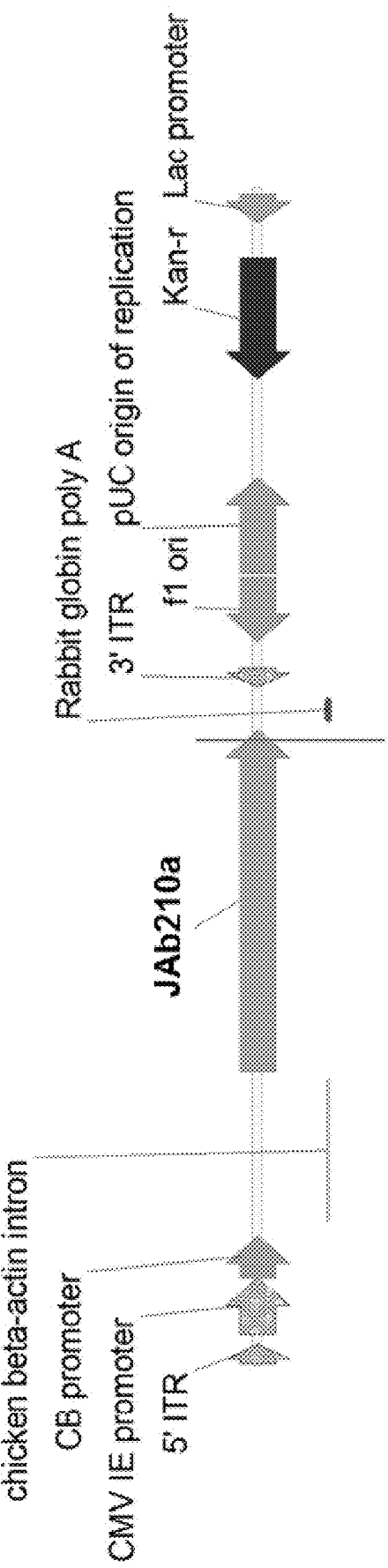

FIG. 16 provides a schematic representation of the vector genome plasmid as described in Example 16.

FIGS. 17A to 17B provide schematic representations of the AAV trans plasmid. FIG. 17A provides a linear representation of the AAV2/hu68 trans packaging plasmid pAAV2/hu68. In FIG. 17B, the ampicillin resistance gene in pAAV2/hu68 (p0065) was replaced by the kanamycin resistance gene to give pAAV2/hu68.KanR (p0068).

FIGS. 18A to 18B provide schematic representations of adenovirus helper plasmid. FIG. 18A provides a derivation of the helper plasmid pAdΔF6 from parental plasmid pBHG10 through intermediates pAdΔF1 and pAdΔF5. In FIG. 18B, the ampicillin resistance gene in pAdΔF6 was replaced by the kanamycin resistance gene to give pAdΔF6 (Kan). The identities of these three adenovirus genes were confirmed by DNA plasmid sequencing performed by Qiagen Genomic Services. DNA Analysis revealed 100% homology with the three Adenovirus type 5 gene regions (GenBank Accession number AF369965).

Figure 19A:
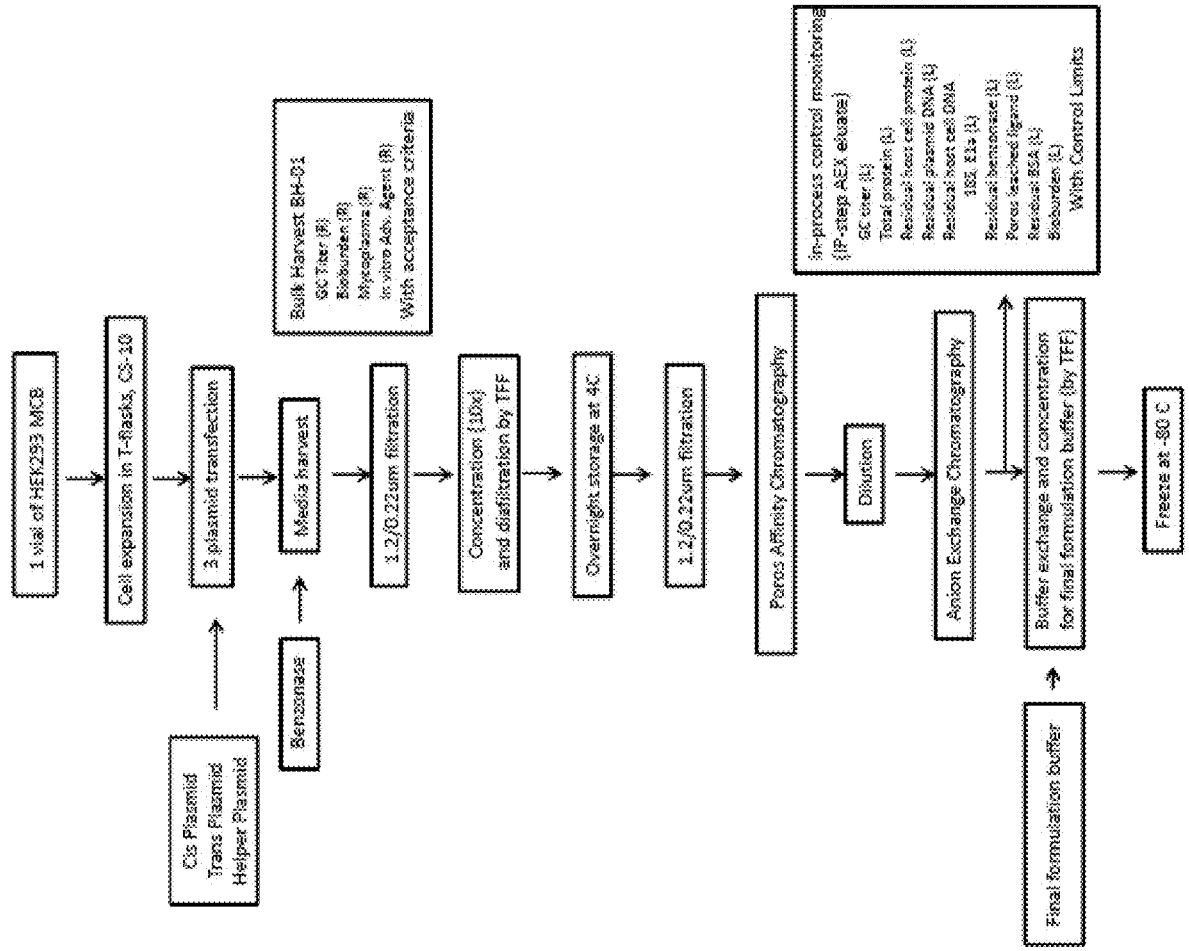
Figure 19B:
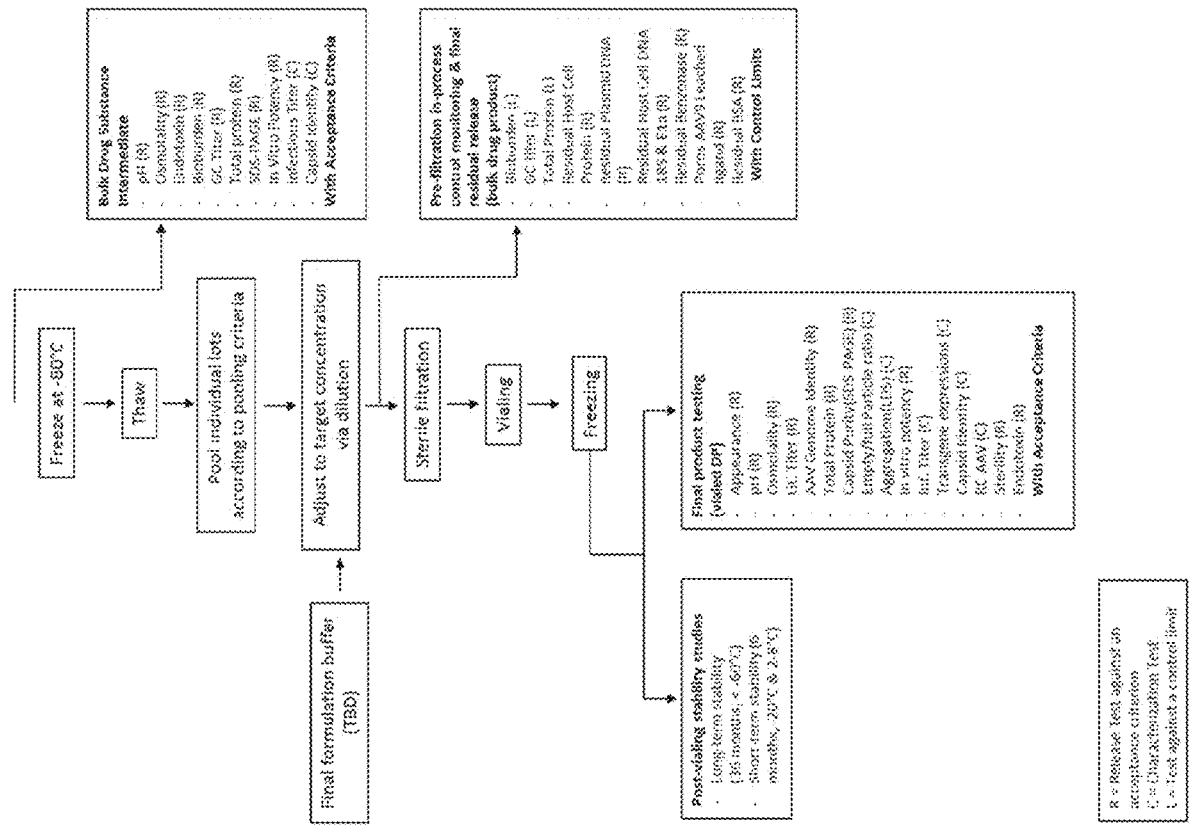

FIGS. 19A to 19B provide a manufacturing process flow diagram as described in Example 16.

Figure 20:
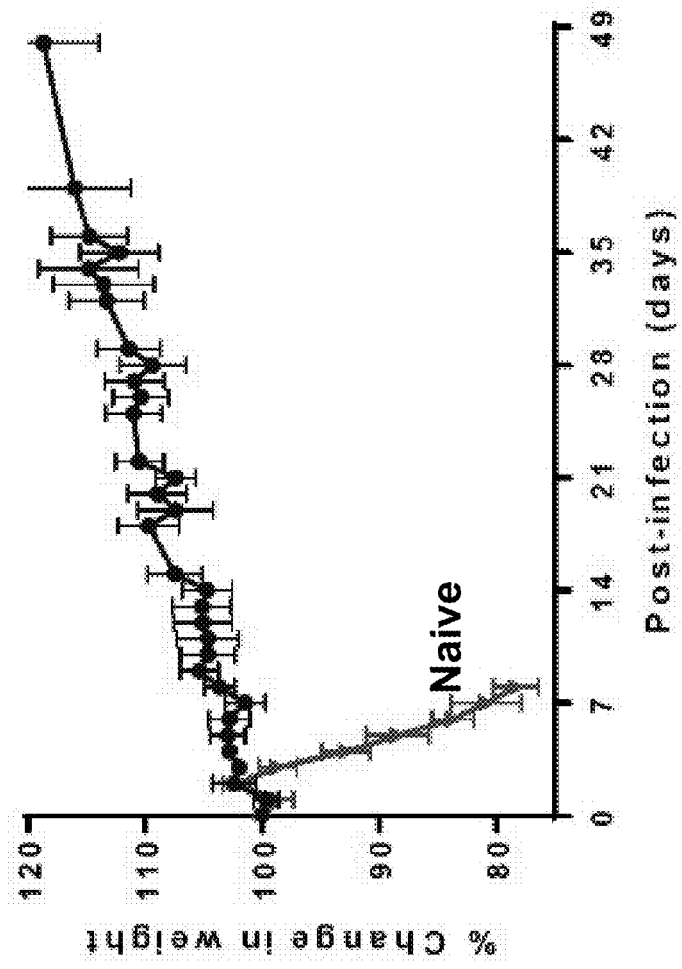

FIG. 20 shows AAVhu68.CB7.CI.JAb210a.rBG-mediated prophylaxis of Rag KO mice against challenge with Influenza A. Rag KO mice received $10^{10}$ GC of AAVhu68.CB7.CI.JAb210a.rBG (noted in circles) and mice were challenged seven days later with $5LD_{50}$ of PR8 and weighed daily. Naïve mice (inverted triangles) were euthanized due to progressive weight loss by day 8.

Figure 21A:
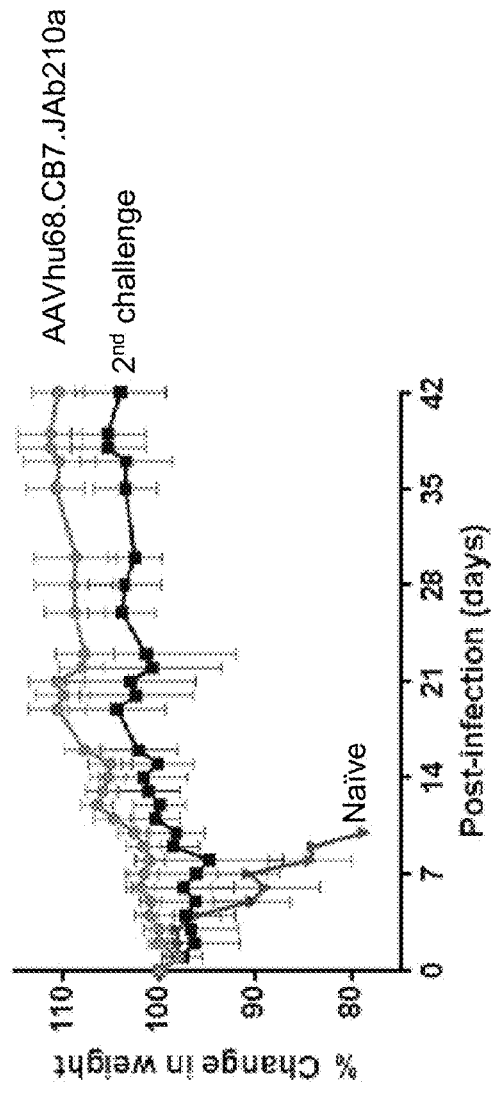
Figure 21B:
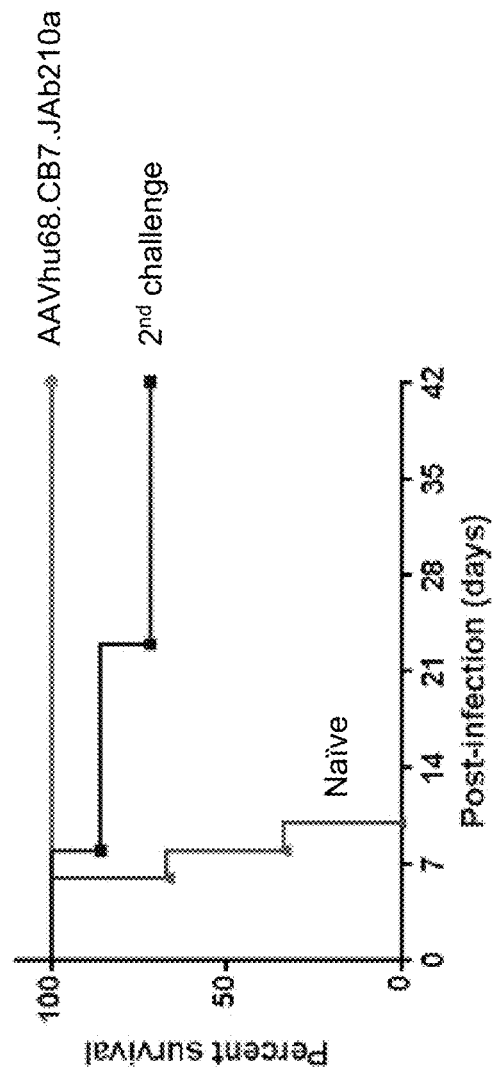

FIGS. 21A to 21B show AAVhu68.CB7.CI.JAb210a.rBG-mediated prophylaxis of Rag KO mice against second challenge with Influenza. Vector treated Rag KO mice that survived a challenge with 5LDL50 PR8 were re-challenged with $5LD_{50}$ of B/Lee/40 and weighed daily. Naïve mice (triangles) were euthanized due to progressive weigh loss by day 8. Positive control mice (circles) were mice given AAVhu68.CB7.CI.JAb210a.rBG vector and challenged seven days later with $5LD_{50}$ of B/Lee/40; all mice survived the challenge. In squares are depicted vector treated mice that were subjected to the B/Lee/40 challenge following prior exposure to influenza A (PR8, FIG. 20).

Figure 22:
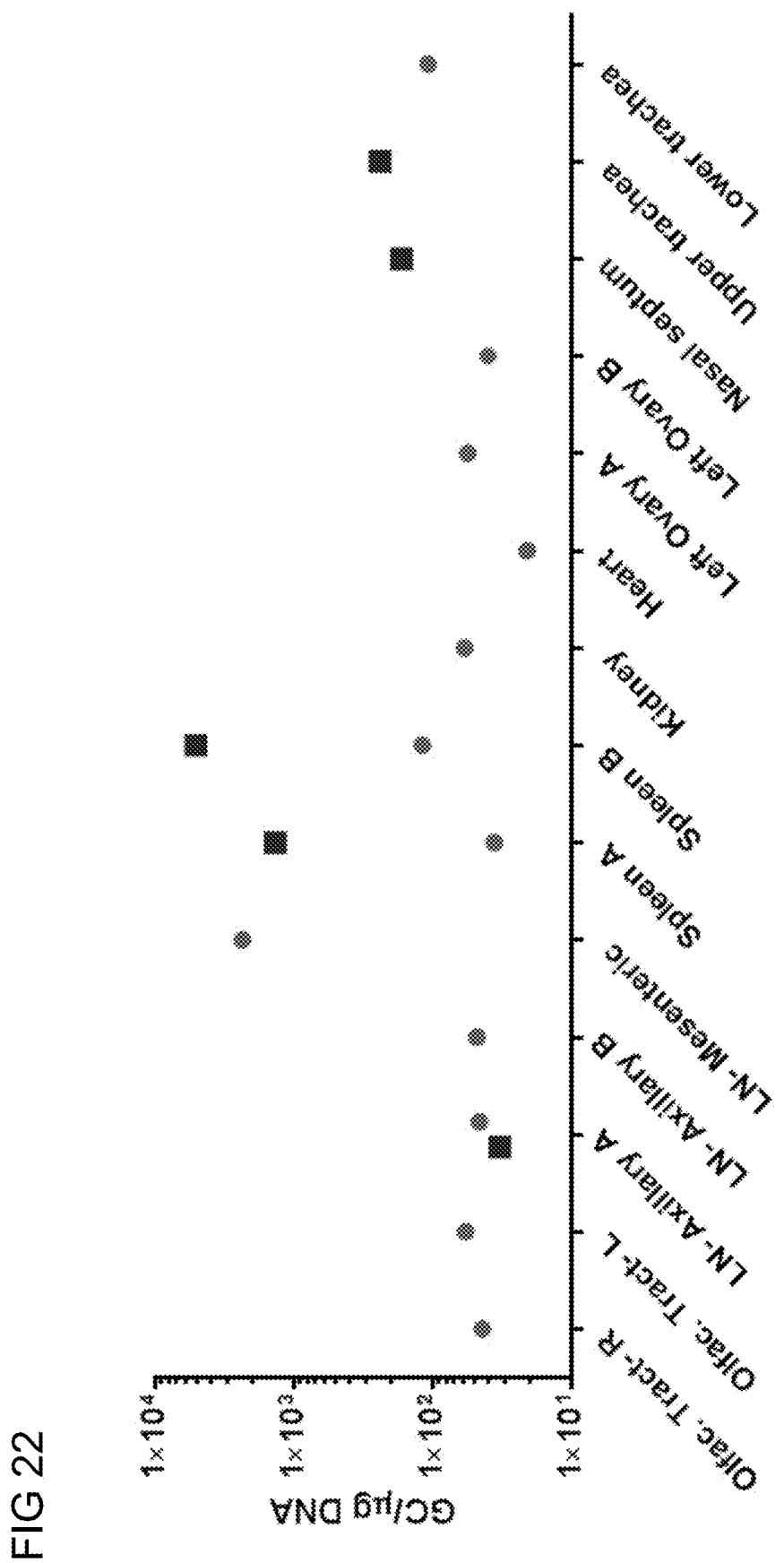

FIG. 22 provides biodistribution profile of AAV9 vector expressing rhesus alpha fetoprotein (rhAFP) in Macaques Animals were given a total dose of $2 \times 10^{13}$ GC of AAV9.CB7.rhAFP either as a direct liquid instillation (circles) or via the MAD Nasal™ (blue squares) and necropsied 99 days later. Tissues were harvested for biodistribution analysis. Assay background was 25 genome copies/500 ng tissue DNA.

SUMMARY OF THE INVENTION

A non-replicating recombinant adeno-associated associated virus (rAAV) encoding an anti-influenza construct is provided. The rAAV has a vector genome packaged in an AAV capsid. Compositions provided herein comprise vector genomes coding sequences for a combination of the following anti-influenza immunoglobulin regions expressed from the rAAV. A first immunoglobulin region has the amino acid sequence of SEQ ID NO:1: (Gln Val Gln Leu Val Glu Ser Gly Gly Gly Val Val Gln Pro Gly Gly Ser Leu Arg Leu Ser Cys Ala Ala Ser Ile Ser Ile Phe Asp Ile Tyr Ala Met Asp Trp Tyr Arg Gln Ala Pro Gly Lys Gln Arg Glu Leu Val Ala Val Ser Phe Arg Asp Gly Ser Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys His Val Ser Leu Tyr Arg Asp Pro Leu Gly Val Ala Gly Gly Ile Gly Val Tyr Trp Gly Gln Gly Thr Leu Val Thr Val Ser Ser). In certain embodiments, in place of SEQ ID NO: 1, an alternate immunoglobulin region with the amino acid sequence of SEQ ID NO: 1 with an I110M mutation, which is reproduced as aa 24 to aa 147 of SEQ ID NO: 30, may be selected for use. A second immunoglobulin region has an amino acid sequence of SEQ ID NO: 2: Glu Val Gln Leu Leu Glu Ser Gly Gly Gly Leu Val Gln Pro Gly Gly Ser Leu Arg Leu Ser Cys Ala Ala Ser Gly Arg Thr Tyr Ala Met Gly Trp Phe Arg Gln Ala Pro Gly Lys Glu Arg Glu Phe Val Ala Ala Ile Asn Ala Leu Gly Thr Arg Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Thr Ala Gln Gly Gln Trp Arg Ala Pro Val Ala Val Ala Ala Glu Tyr Glu Phe Trp Gly Gln Gly Thr Leu Val Thr Val Ser Ser). A third immunoglobulin region has an amino acid sequence of SEQ ID NO: 3: (Glu Val Gln Leu Leu Glu Ser Gly Gly Gly Leu Val Gln Pro Gly Gly Ser Leu Arg Leu Ser Cys Ala Ala Ser Gly Phe Thr Leu Glu Asn Lys Ala Ile Gly Trp Phe Arg Gln Ala Pro Gly Lys Glu Arg Glu Gly Val Leu Cys Ile Ser Lys Ser Gly Ser Trp Thr Tyr Tyr Ala Asp Ser Val Lys Gly Arg Phe Thr Ile Ser Arg Asp Asn Ser Lys Asn Thr Val Tyr Leu Gln Met Asn Ser Leu Arg Pro Glu Asp Thr Ala Val Tyr Tyr Cys Ala Thr Thr Thr Ala Gly Gly Leu Cys Trp Asp Gly Thr Thr Phe Ser Arg Leu Ala Ser Ser Trp Gly Gln Gly Thr Leu Val Thr Val Ser Ser). A fourth immunoglobulin region has an amino acid sequence of SEQ ID NO:4: (Glu Val Gln Leu Val Glu Ser Gly Gly Gly Leu Val Gln Pro Gly Gly Ser Leu Arg Leu Ser Cys Ala Ala Ser Gly Phe Thr Phe Ser Thr Ser Trp Met Tyr Trp Leu Arg Gln Ala Pro Gly Lys Gly Leu Glu Trp Val Ser Val Ile Asn Thr Asp Gly Gly Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Ala Lys Asp Trp Gly Gly Pro Glu Pro Thr Arg Gly Gln Gly Thr Leu Val Thr Val Ser Ser).

In certain embodiments, more than one immunoglobulin regions described herein are in a fusion construct which further comprises an Fc region, wherein there is optionally a linking sequence joining the four immunoglobulin regions and the Fc region.

In certain embodiments, the vector genome comprises a nucleic acid sequence selected from the group consisting of: SEQ ID NO: 26, SEQ ID NO: 21, SEQ ID NO: 20, SEQ ID NO: 19; SEQ ID NO: 15, SEQ ID NO: 14, SEQ ID NO: 13, SEQ ID NO: 5, SEQ ID NO: 31 and SEQ ID NO: 32. In certain embodiments, a composition is provided which comprises a carrier, diluent or excipient and a stock of at least the non-replicating rAAV as described herein. The composition may be formulated for intranasal, or intramuscular or intravenous administration.

In certain embodiments, a method for immunizing human patients against influenza is provided, which involves administering an effective amount of a composition comprising the rAAV.JAb, rAAV.hJAb, or rAAV.JAb210a as described herein. The composition may comprise a dose of about $10^9$ GC to about $7 \times 10^{13}$ GC of the rAAV.JAb, rAAV.h-JAb, or rAAV.JAb210a. In certain embodiments, an AAVhu68 capsid is selected. In other embodiments, a product is provided which comprises a container and a composition comprising the rAAV.JAb, rAAV.hJAb, or rAAV.JAb210a as described herein, optionally with a diluent and instructions for administration.

In currently preferred versions of the above embodiments, the rAAV has an AAVhu68 capsid. In another embodiment, the rAAV has an AAV9 capsid. In yet another embodiment, the rAAV has an AAV1 capsid.

In certain embodiments, rAAV.JAb provided herein and compositions containing same are useful for vaccinating or immunizing human patients against influenza.

In certain embodiments, use of the rAAV.JAb or composition containing same are provided for vaccinating or immunizing human patients against influenza.

These and other advantages of the invention will be apparent from the following detailed description of the invention.

DETAILED DESCRIPTION OF THE INVENTION

Provided by the present invention are recombinant vectors which express anti-influenza antibody constructs in vivo and are useful for providing passive immunity against infection with influenza A and/or influenza B infection. In certain embodiments, the vectors are replication-defective recombinant adeno-associated virus (rAAV) having a novel clade F capsid, termed herein AAVhu68.

In certain embodiments, the rAAV-expressed antibody (Ab) constructs exhibit neutralization activity against influenza A and/or B viruses. In certain embodiment, the Ab constructs of the invention prevent an influenza A or B virus from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by said influenza virus in the absence of the Ab constructs. Antibody mediated neutralizing activity can for instance be measured as described herein. Alternative assays measuring neutralizing activity are described in for instance WHO Manual on Animal Influenza Diagnosis and Surveillance, Geneva: World Health Organisation, 2005, version 2002.5. Typically, the binding molecules according to the invention have a neutralizing activity of 1000 nM or less, preferably 100 nM or less, more preferably a neutralizing activity of 10 nM or less, even more preferably 1 nM or less, as determined in an in vitro virus neutralization assay (VNA).

In certain preferred embodiments, compositions are provided in which replication-defective adeno-associated vectors express each of four anti-influenza immunoglobulin domains which are designed to provide immunity against influenza A and influenza B strains. In certain embodiments, all four of the immunoglobulin domains are expressed from a single rAAV vector stock. In this embodiment, the single rAAV vector stock may contain a monocistronic expression cassette or a bicistronic expression cassette. In other embodiments, the immunoglobulin domains are expressed from more than rAAV vector stock. In this embodiment, the rAAV may have monocistronic or bicistronic expression cassettes.

In one embodiment, an rAAV vector stock contains a vector genome in which one, two, three or four of the immunoglobulin domains as described herein is expressed as a fusion protein. Such a fusion protein may include an immunogbubulin Fc region and/or a hinge region, wherein there is optionally a linking sequence joining two or more of the four immunoglobulin regions. Optionally, a linking sequence may be present between an immunoglobulin domain and the Fc region and/or hinge region. The linking sequence may be immediately adjacent to the C-terminus of a first domain (region) and N-terminus of a second domain (region), being used to separate two, three or four of the domains or regions. Any suitable sequence of about 1 to 20 amino acids in length may be selected, but it is preferably 3 to 18 amino acids, or about 5 to about 12 amino acids in length. Multiple linking sequences may be present in a single encoded protein sequence, and these may be independently selected. In one embodiment, at least one linking sequence is (SEQ ID NO: 7)
GGGGSGGGGS.

In certain embodiments, the expressed immunoglobulins or the immunoglobulin fusion proteins contain a signal peptide which directs the expressed protein within the host cell. Optionally, the signal peptide may be from a source exogenous to the immunoglobulin. The examples below illustrate use of a human interleukin-2 signal peptide. However, another suitable signal peptide, e.g., human or a viral, may be selected. In one embodiment, the amino acid sequence of the signal peptide is reproduced in SEQ ID NO: 6.

In certain embodiments, two of the immunoglobulin regions are linked to a first Fc to form a first chain and the other two immunoglobulin regions are linked to a second Fc to form a second chain Such an expression cassette construct will typically contain an F2A or IRES between the coding sequences for the two chains.

In certain embodiments, four of the immunoglobulin regions are linked to a Fc region in a single open reading frame. In one embodiment, a fusion construct comprises an amino acid sequence of SEQ ID NO: 30.

These and other configurations of the four immunoglobulin domains provided herein will be apparent to one of skill in the art in view of the following description of the domains.

An antibody "Fc region" refers to the crystallizable fragment which is the region of an antibody which interacts with the cell surface receptors (Fc receptors). In one embodiment, the Fc region is a human IgG1 Fc. In one embodiment, the Fc region is a human IgG2 Fc. In one embodiment, the Fc region is a human IgG4 Fc. In one embodiment, the Fc region is an engineered Fc fragment. See, e.g., Lobner, Elisabeth, et al. "Engineered IgG1-Fc-one fragment to bind them all." Immunological reviews 270.1 (2016): 113-131; Saxena, Abhishek, and Donghui Wu. "Advances in therapeutic Fc engineering-modulation of IgG-Associated effector functions and serum half-life." Frontiers in immunology 7 (2016); Irani, Vashti, et al. "Molecular properties of human IgG subclasses and their implications for designing therapeutic monoclonal antibodies against infectious diseases." Molecular immunology 67.2 (2015): 171-182; Rath, Timo, et al. "Fc-fusion proteins and FcRn: structural insights for longer-lasting and more effective therapeutics." Critical reviews in biotechnology 35.2 (2015): 235-254; and Invivogen, IgG-Fc Engineering For Therapeutic Use, www.invivogen.com/docs/Insight200605.pdf, April 2006; each of which is incorporated by reference herein. In a further embodiment, the Fc region has an amino acid sequence reproduced in SEQ ID NO: 11. In certain embodiments, the Fc region is able to induce antibody-dependent cellular cytotoxicity (ADCC) in the target issue. In certain embodiment, the Fc region is able to induce complement dependent cytotoxicity (CDC).

An antibody "hinge region" is a flexible amino acid portion of the heavy chains of IgG and IgA immunoglobulin classes, which links these two chains by disulfide bonds. In one embodiment, the hinge has an amino acid sequence of SEQ ID NO: 8.

An "immunoglobulin molecule" is a protein containing the immunologically-active portions of an immunoglobulin heavy chain and immunoglobulin light chain covalently coupled together and capable of specifically combining with antigen. Immunoglobulin molecules are of any type (e.g., IgG, IgE, IgM, IgD, IgA and IgY), class (e.g., IgG1, IgG2, IgG3, IgG4, IgA1 and IgA2) or subclass. The terms "antibody" and "immunoglobulin" may be used interchangeably herein.

An "immunoglobulin heavy chain" is a polypeptide that contains at least a portion of the antigen binding domain of an immunoglobulin and at least a portion of a variable region of an immunoglobulin heavy chain or at least a portion of a constant region of an immunoglobulin heavy chain. Thus, the immunoglobulin derived heavy chain has significant regions of amino acid sequence homology with a member of the immunoglobulin gene superfamily. For example, the heavy chain in a Fab fragment is an immunoglobulin-derived heavy chain.

An "immunoglobulin light chain" is a polypeptide that contains at least a portion of the antigen binding domain of an immunoglobulin and at least a portion of the variable region or at least a portion of a constant region of an immunoglobulin light chain. Thus, the immunoglobulin-derived light chain has significant regions of amino acid homology with a member of the immunoglobulin gene superfamily.

An "immunoadhesin" is a chimeric, antibody-like molecule that combines the functional domain of a binding protein, usually a receptor, ligand, antibody scFv fragment, or cell-adhesion molecule, with immunoglobulin constant domains, usually including the hinge and Fc regions.

A "fragment antigen-binding" (Fab) fragment" is a region on an antibody that binds to antigens. It is composed of one constant and one variable domain of each of the heavy and the light chain.

As used herein a single-domain antibody (sdAb) is a binding molecule consisting of a single monomeric variable antibody domain that specifically binds an antigen or epitope independently of other V regions or domains. Single domain antibodies (sdAbs) are known in the art and are usually derived from naturally occurring "heavy chain only" antibodies, i.e. heavy chain antibodies devoid of light chains. Such heavy chain only antibodies can be obtained from *Camelidae* species, for example in camel, llama, dromedary, or alpaca (also referred to as camelid antibodies). The variable region derived from said heavy chain only antibody is generally known as a VHH domain or sdAb. A sdAb as used herein also refers to an isolated single variable domain (VL or VH) from a conventional immunoglobulin comprising two heavy chains and two light chains This immunoglobulin may contain humanized sequences, or regions from other non-camelid sources.

As used herein the terms "multi-domain antibody", refer to a binding molecule comprising at least two humanized VHH antibodies, linked to each other either directly or by a linking sequence.

As used herein, the term "NAb titer" a measurement of how much neutralizing antibody (e.g., anti-AAV NAb) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009, 199 (3): p. 381-390, which is incorporated by reference herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

As used herein, the term "operably linked" refers to both expression control sequences that are contiguous with the gene of interest and expression control sequences that act in trans or at a distance to control the gene of interest.

As used herein, "different specificities" indicates that the referenced immunoglobulin constructs (e.g., a full-length antibody, a heavy chain, or other construct capable of binding a specific target) bind to different target sites. These may refer to different targets on the same antigen, different strains of the same pathogen (e.g., different viral strains) or to different antigens.

The "same specificity" refers to the ability of the immunoglobulin to bind to specific target site which may be present on multiple strains of a pathogen (e.g., influenza virus) or for a single, or subset of strains, of the virus or other pathogen. Suitably, these specificities are such that there is no significant or measurable binding to non-target sites.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. The term "heterologous light chain" is a light chain containing a variable domain and/or constant domain from an antibody which has a different target specificity from the specificity of the heavy chain.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

A "recombinant AAV" or "rAAV" is a DNAse-resistant viral particle containing two elements, an AAV capsid and a vector genome containing at least non-AAV coding sequences packaged within the AAV capsid. In certain embodiments, the capsid contains about 60 proteins composed of vp1 proteins, vp2 proteins, and vp3 proteins, which self-assemble to form the capsid. Unless otherwise specified, "recombinant AAV" or "rAAV" may be used interchangeably with the phrase "rAAV vector". The rAAV is a "replication-defective virus" or "viral vector", as it lacks any functional AAV rep gene or functional AAV cap gene and cannot generate progeny. In certain embodiments, the only AAV sequences are the AAV inverted terminal repeat sequences (ITRs), typically located at the extreme 5' and 3' ends of the vector genome in order to allow the gene and regulatory sequences located between the ITRs to be packaged within the AAV capsid.

The term "nuclease-resistant" indicates that the AAV capsid has assembled around the expression cassette which is designed to deliver a transgene to a host cell and protects these packaged genomic sequences from degradation (digestion) during nuclease incubation steps designed to remove contaminating nucleic acids which may be present from the production process.

As used herein, a "vector genome" refers to the nucleic acid sequence packaged inside the rAAV capsid which forms a viral particle. Such a nucleic acid sequence contains AAV inverted terminal repeat sequences (ITRs). In the examples herein, a vector genome contains, at a minimum, from 5' to 3', an AAV 5' ITR, coding sequence(s), and an AAV 3' ITR. ITRs from AAV2, a different source AAV than the capsid, or other than full-length ITRs may be selected. In certain embodiments, the ITRs are from the same AAV source as the AAV which provides the rep function during production or a transcomplementing AAV. Further, other ITRs may be used. Further, the vector genome contains regulatory sequences which direct expression of the gene products. Suitable components of a vector genome are discussed in more detail herein.

In certain embodiments, non-viral genetic elements used in manufacture of a rAAV, will be referred to as vectors (e.g., production vectors). In certain embodiments, these vectors are plasmids, but the use of other suitable genetic elements is contemplated. Such production plasmids may encode sequences expressed during rAAV production, e.g., AAV capsid or rep proteins required for production of a rAAV, which are not packaged into the rAAV. Alternatively, such a production plasmid may carry the vector genome which is packaged into the rAAV.

As used herein, an "expression cassette" refers to a nucleic acid molecule which comprises a coding sequence, promoter, and may include other regulatory sequences therefor. In certain embodiments, a vector genome may contain two or more expression cassettes. In other embodiments, the term "transgene" may be used interchangeably with "expression cassette".

The term "translation" in the context of the present invention relates to a process at the ribosome, wherein an mRNA strand controls the assembly of an amino acid sequence to generate a protein or a peptide.

The term "influenza virus subtype" in relation to influenza A viruses refers to influenza A virus strains that are characterized by various combinations of the hemagglutinin (H) and neuraminidase (N) viral surface proteins. Influenza A virus subtypes may be referred to by their H number, such as for example "influenza virus comprising HA of the H1 or H3 subtype", or "H1 influenza virus" "H3 influenza virus", or by a combination of an H number and an N number, such as for example "influenza virus subtype "H3N2" or "H5N1 ". The term influenza virus "subtype" specifically includes all individual influenza virus "strains" within such subtype, which usually result from mutations and show different pathogenic profiles and include natural isolates as well as man-made mutants or reassortants and the like. Such strains may also be referred to as various "isolates" of a viral subtype. Accordingly, as used herein, the terms "strains" and "isolates" may be used interchangeably.

As used herein, the term "influenza", or "influenza virus disease" refers to the pathological condition resulting from an infection of a cell or a subject by an influenza A or B virus. In specific embodiments, the term refers to a respiratory illness caused by an influenza A or B virus. As used herein, the term "influenza virus infection" means the invasion by, multiplication and/or presence of an influenza virus in a cell or a subject.

The vector described herein expresses a novel anti-influenza antibody construct which provides passive immunity and is therapeutically effective if it protects against infection with one or more strains of influenza A and/or influenza B infection in a human population following administration, and/or reduces the symptoms associated with influenza infection. Such symptoms may include, without limitation, fever (chills), cough, sore throat, runny or stuffy nose, muscle or body aches, headaches, fatigue (tiredness), and the risk of secondary bacterial infections, such as bronchitis and pneumonia.

As used herein, "immunoglobulin construct(s)", "antibody construct(s)" or "aAb construct(s)", which are used interchangeably, refer to a construct which is capable of binding to a target site. In one embodiment, the target site is an epitope of an antigen, or a site of a pathogen. In a further embodiment, the target site is an epitope of an influenza virus. In one embodiment, Ab construct is selected from, without limitation, an immunoglobulin molecule, an immunoadhesin, a single-domain antibody, a multi-domain antibody, a full-length antibody, an immunoglobulin heavy chain, and an immunoglobulin light chain.

The term "expression" is used herein in its broadest meaning and comprises the production of RNA or of RNA and protein. With respect to RNA, the term "expression" or "translation" relates in particular to the production of peptides or proteins. Expression may be transient or may be stable.

As used herein, an "effective amount" refers to the amount of the rAAV composition which delivers and expresses in the target cells an amount of anti-influenza antibodies sufficient to reduce or prevent influenza infection. An effective amount may be determined based on an animal model, rather than a human patient. Examples of a suitable murine model are described herein.

As used herein, the term "target tissue" refers to a tissue, an organ or a cell type, that an embodiment, a regimen or a composition as described herein targets. In one embodiment, the target tissue is a respiratory organ or a respiratory tissue. In an alternative or additional embodiment, the target tissue is lung. In an alternative or additional embodiment, the target tissue is nose. In an alternative or additional embodiment, the target tissue is nasopharynx. In an alternative or additional embodiment, the target tissue is respiratory epithelium. In an alternative or additional embodiment, the target tissue is nasal airway epithelium. In an alternative or additional embodiment, the target tissue is nasal cells. In an alternative or additional embodiment, the target tissue is nasopharynx cells. In an alternative or additional embodiment, the target tissue is nasal epithelial cells, which may be ciliated nasal epithelial cells, columnar epithelial cells, goblet cells (which secrete mucous onto the surface of the nasal cavity which is composed of the ciliated epithelial cells) and stratified squamous nasal epithelial cells which line the surface of the nasopharynx. In an alternative or additional embodiment, the target tissue is lung epithelial cells. In still other embodiments, the target tissue is muscle, e.g., skeletal muscle.

As described above, the term "about" when used to modify a numerical value means a variation of ±10%, unless otherwise specified.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

It is to be noted that the term "a" or "an", refers to one or more, for example, "an enhancer", is understood to represent one or more enhancer(s). As such, the terms "a" (or "an"), "one or more," and "at least one" is used interchangeably herein.

With regard to the description of these inventions, it is intended that each of the compositions herein described, is useful, in another embodiment, in the methods of the invention. In addition, it is also intended that each of the compositions herein described as useful in the methods, is, in another embodiment, itself an embodiment of the invention.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

I. Anti-Influenza Antibody Transgenes

The compositions described herein are designed to express four anti-immunoglobulin regions, which are optionally expressed as one or more fusion proteins. It will be understood that the following references to "first", "second", "third" and "fourth", is used to clarify which region is being referenced. However, this is not limited to the order in which these are expressed from the vector genome(s) or the order in which these appear in a fusion protein. Thus, a fusion protein may contain the "third" region located either upstream or downstream of the first region or the second region, and/or the "first" region may be located downstream of the "second", "third" or "fourth" region.

In certain embodiments, the first immunoglobulin region having the amino acid sequence of SEQ ID NO:1 is selected: Gln Val Gln Leu Val Glu Ser Gly Gly Gly Val Val Gln Pro Gly Gly Ser Leu Arg Leu Ser Cys Ala Ala Ser Ile Ser Ile Phe Asp Ile Tyr Ala Met Asp Trp Tyr Arg Gln Ala Pro Gly Lys Gln Arg Glu Leu Val Ala Val Ser Phe Arg Asp Gly Ser Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys His Val Ser Leu Tyr Arg Asp Pro Leu Gly Val Ala Gly Gly Ile Gly Val Tyr Trp Gly Gln Gly Thr Leu Val Thr Val Ser Ser. In certain embodiments, some variation is permitted in this amino acid sequence, i.e., sequences about 95% to about 99% identical to this sequence are encompassed by the invention. In other words, 1, 2, 3, 4, 5, or 6 amino acids of SEQ ID NO: 1 may be modified. In one embodiment, an alternative first immunoglobulin region refers to an immunoglobulin region with the amino acid sequence of SEQ ID NO: 1 with an I110M mutation, which is reproduced as aa 24 to aa 147 of SEQ ID NO: 30. In certain embodiments, these amino acid sequences are conserved changes. However, non-conserved residues may be selected. As used herein, the term "conserved change" refer to changing an amino acid into another amino acid with similar biochemical properties (e.g., charge, hydrophobicity and size).

In certain embodiments, the second immunoglobulin region has an amino acid sequence of SEQ ID NO: 2: Glu Val Gln Leu Leu Glu Ser Gly Gly Gly Leu Val Gln Pro Gly Gly Ser Leu Arg Leu Ser Cys Ala Ala Ser Gly Arg Thr Tyr Ala Met Gly Trp Phe Arg Gln Ala Pro Gly Lys Glu Arg Glu Phe Val Ala Ala Ile Asn Ala Leu Gly Thr Arg Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Thr Ala Gln Gly Gln Trp Arg Ala Ala Pro Val Ala Val Ala Ala Glu Tyr Glu Phe Trp Gly Gln Gly Thr Leu Val Thr Val Ser Ser. In certain embodiments, some variation is permitted in this amino acid sequence, i.e., sequences about 95% to about 99% identical to this sequence are encompassed by the invention. In other words, 1, 2, 3, 4, 5, or 6 amino acids of SEQ ID NO: 2 may be modified. In certain embodiments, these amino acid sequences are conserved changes.

The third immunoglobulin region has an amino acid sequence of SEQ ID NO: 3: Glu Val Gln Leu Leu Glu Ser Gly Gly Gly Leu Val Gln Pro Gly Gly Ser Leu Arg Leu Ser Cys Ala Ala Ser Gly Phe Thr Leu Glu Asn Lys Ala Ile Gly Trp Phe Arg Gln Ala Pro Gly Lys Glu Arg Glu Gly Val Leu Cys Ile Ser Lys Ser Gly Ser Trp Thr Tyr Tyr Ala Asp Ser Val Lys Gly Arg Phe Thr Ile Ser Arg Asp Asn Ser Lys Asn Thr Val Tyr Leu Gln Met Asn Ser Leu Arg Pro Glu Asp Thr Ala Val Tyr Tyr Cys Ala Thr Thr Thr Ala Gly Gly Gly Leu Cys Trp Asp Gly Thr Thr Phe Ser Arg Leu Ala Ser Ser Trp Gly Gln Gly Thr Leu Val Thr Val Ser Ser. In certain embodiments, some variation is permitted in this amino acid sequence, i.e., sequences about 95% to about 99% identical to this sequence are encompassed by the invention. In other words, 1, 2, 3, 4, 5, or 6 amino acids of SEQ ID NO: 3 may be modified. In certain embodiments, these amino acid sequences are conserved changes.

The fourth immunoglobulin region has an amino acid sequence of SEQ ID NO:4: Glu Val Gln Leu Val Glu Ser Gly Gly Gly Leu Val Gln Pro Gly Gly Ser Leu Arg Leu Ser Cys Ala Ala Ser Gly Phe Thr Phe Ser Thr Ser Trp Met Tyr Trp Leu Arg Gln Ala Pro Gly Lys Gly Leu Glu Trp Val Ser Val Ile Asn Thr Asp Gly Gly Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Ala Lys Asp Trp Gly Gly Pro Glu Pro Thr Arg Gly Gln Gly Thr Leu Val Thr Val Ser Ser. In certain embodiments, some variation is permitted in this amino acid sequence, i.e., sequences about 95% to about 99% identical to this sequence are encompassed by the invention. In other words, 1, 2, 3, 4, 5, or 6 amino acids of SEQ ID NO: 4 may be modified. In certain embodiments, these amino acid sequences are conserved changes.

Further within the scope of invention are nucleic acid sequences encoding the immunoglobulin regions and other proteins, peptides and fragments described herein. Examples of suitable coding sequences for the immunoglobulin region having the amino acid sequence of SEQ ID NO: 1 are provided, e.g., in nt 2052-2423 of SEQ ID NO: 5, nt 1840-2211 of SEQ ID NO: 13, nt 2052-2423 of SEQ ID NO: 14, nt 2052-2423 of SEQ ID NO: 15, nt 1840-2111 of SEQ ID NO: 19, nt 1210-1581 of SEQ ID NO: 20, nt 55-486 of SEQ ID NO: 21, and nt 70-441 of SEQ ID NO: 32.

Examples of suitable coding sequences for the immunoglobulin region having the amino acid sequence of SEQ ID NO: 2 are provided, e.g., in nt 2454-2822 of SEQ ID NO: 5, nt 2242-2160 of SEQ ID NO: 13, nt 2454-2822 of SEQ ID NO: 14, nt 2454-2822 of SEQ ID NO: 15, nt 2242-2610 of SEQ ID NO: 19, nt 1612-1980 of SEQ ID NO: 20, nt 517-885 of SEQ ID NO: 21, and nt 472-840 of SEQ ID NO: 32.

Examples of suitable coding sequences for the immunoglobulin region having the amino acid sequence of SEQ ID NO: 3 are provided, e.g., in nt 2853-3239 of SEQ ID NO: 5, nt 2641-3027 of SEQ ID NO: 13, nt 2853-3239 of SEQ ID NO: 14, nt 2853-3239 of SEQ ID NO: 15, nt 3448-3834 of SEQ ID NO: 19, nt 2803-3189 of SEQ ID NO: 20, nt 916-1302 of SEQ ID NO: 21, and nt 871-1257 of SEQ ID NO: 32.

Examples of suitable coding sequences for the immunoglobulin region having the amino acid sequence of SEQ ID NO: 4 are provided, e.g., in nt 3270-3617 of SEQ ID NO: 5, nt 3058-3405 of SEQ ID NO: 13, nt 3270-3617 of SEQ ID NO: 14, nt 3270-3617 of SEQ ID NO: 15, nt 3865-4212 of SEQ ID NO: 19, nt 3220-3567 of SEQ ID NO: 20, nt 1333-1680 of SEQ ID NO: 21, and nt 1288-1635 of SEQ ID NO: 32.

A nucleic acid refers to a polymeric form of nucleotides and includes RNA, mRNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules. In preferred embodiments, the nucleic acid molecules encoding immunoglobulin domains, fusion proteins, and other constructs are encompassed by the present invention and useful in generating expression cassettes and vector genomes. These sequences may be codon-optimized for expression in yeast cells or mammalian cells, such as human cells. Methods of codon-optimization are known and have been described previously (e.g. WO 96/09378). A sequence is considered codon-optimized if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in www.kazusa.jp/codon. Preferably more than one non-preferred codon, preferably most or all non-preferred codons, are replaced by codons that are more preferred. Preferably the most frequently used codons in an organism are used in a codon-optimized sequence. Replacement by preferred codons generally leads to higher expression. It will also be understood by a skilled person that numerous different nucleic acid molecules can encode the same polypeptide as a result of the degeneracy of the genetic code. It is also understood that skilled persons may, using routine techniques, make nucleotide substitutions that do not affect the amino acid sequence encoded by the nucleic acid molecules to reflect the codon usage of any particular host organism in which the polypeptides are to be expressed. Therefore, unless otherwise specified, a "nucleic acid sequence encoding an amino acid sequence" includes all nucleotide sequences that are degenerate versions of each other and that encode the same amino acid sequence. Nucleic acid sequences can be cloned using routine molecular biology techniques, or generated de novo by DNA synthesis, which can be performed using routine procedures by service companies having business in the field of DNA synthesis and/or molecular cloning (e.g., GeneArt, GenScript, Life Technologies, Eurofins).

In one embodiment, an rAAV vector stock contains a vector genome in which one, two, three or four of the immunoglobulin domains is expressed as a fusion protein.

In certain embodiments, the immunoglobulin domains may be linked by chemical linkage, or may be linked together either directly or by short polypeptide linkers. Such linker sequence may be a naturally occurring sequence or a non-naturally occurring sequence. The linker sequence preferably provides sufficient flexibility to the resulting antibody construct and at the same time is resistant to proteolytic degradation.

Optionally, for the creation of homo- and hetero-dimers, the immunoglobulin coding sequences are either cloned together or the full-length gene can be directly synthesized (Genscript) and ligated into an expression vector. In dimer constructs the C-terminus of the first immunoglobulin region may be linked to the terminus of the second immunoglobulin region. The linker sequences of different length (10, 15, 35, and 57 amino acids) consist of amino acids glycine (G) and serine (S). The linking sequence may be immediately adjacent to the C-terminus of a first domain (region) and N-terminus of a second domain (region), being used to separate two, three or four of the domains or regions. Any suitable sequence of about 1 to 60 amino acids in length may be selected, but it is preferably 3 to 35 amino acids, or about 5 to about 15 amino acids in length. Multiple linking sequences may be present in a single encoded protein sequence, and these may be independently selected.

Examples of suitable linkers include:

```
SEQ ID NO: 7:    GGGGS GGGGS;

SEQ ID NO: 23:   GGGGS GGGGS GGGGS;

SEQ ID NO: 24:   GGGGS GGGGS GGGGS GGGGS GGGGS
                 GGGGS GGGGS

SEQ ID NO: 25:   GGGGS GGGGS GGGGS GGGGS GGGGGS
                 GGGGS GGGGS GGGGS GGGGS GGGGS GGGGS.
```

Examples of suitable linker coding sequences are provided in, e.g., nt 2212-2241, nt 2611-nt 2640, nt 3028-3057, nt 3406-3435 of SEQ ID NO: 13; nt 2212-2241, nt 2611-2640, nt 3835-3864, and nt 4213-4242 of SEQ ID NO: 19; nt 1582-1611, nt 3190-3219 of SEQ ID NO: 20; nt 487-516, nt 886-915, nt 1303-1332 of SEQ ID NO: 21; and nt 442-471, nt 841-870, nt 1258-1287 of SEQ ID NO: 32.

In certain embodiments, the proteins further comprise an Fc tail. Thus, in certain embodiments, the immunoglobulin binding domains, as described above, are linked to an Fc fragment of an antibody, preferably a human antibody, such as the Fc fragment of a human IgG antibody, e.g., an IgG1, IgG2, IgG3, IgG4, or IgG4. The domains may be genetically fused to an Fc fragment, either directly or using a linker. In certain embodiments, the binding molecules are linked to the Fc fragment by a linking sequence comprising from 1 to 100 amino acids, preferably from 1 to 60 amino acids, or from 10 to 60 amino acids. Examples of linkers include, but are not limited to, the linking sequences listed above. In certain embodiments, an immunoglobulin domain is genetically fused to the C-terminus of an Fc fragment. In further embodiments, an immunoglobulin domain or fusion protein is fused to both the N- and the C-terminus of an Fc fragment. See, e.g., WO 2016/124768, which is incorporated by reference herein. In one embodiment, the Fc fragment has an amino acid sequence reproduced in aa 551 to aa 772 of SEQ ID NO: 30. In one embodiment, the nucleic acid sequence encoding the Fc fragment is SEQ ID NO: 10.

In certain embodiments, the vector genome encodes an anti-influenza fusion construct having the amino acid sequences of SEQ ID NO: 1, 2, 3 and 4. One example of such a construct is provided is SEQ ID NO: 12. In another example is SEQ ID NO: 27. In both of these examples, one leader sequence is engineered into the vector genome immediately upstream of the 5' immunoglobulin coding region. However, in certain embodiments, a vector genome may contain more than one leader sequence, each located upstream of an immunoglobulin coding region. In certain embodiments, these fusion proteins further comprise at least one immunoglobulin hinge region and an Fc region [e.g., SEQ ID NO: 12]. Further, each of these fusion proteins contains multiple linker sequences. In other embodiments, an Fc region may be included in the fusion protein without a hinge region. In one embodiment, the vector genome is SEQ ID NO: 31.

In certain embodiments, presented herein is a single, antibody-like protein (referred to as a multi-domain antibody or mdAb or MDAb) with anti-influenza A and B activity, wherein the protein is a fusion protein comprising one or more immunoglobulin domains and one or more linkers as described herein. In certain embodiment, presented herein are compositions for expression of an MDAb as described herein.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., an immunoglobulin region or domain, an AAV cap protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As described herein, the nucleic acid sequences may be engineered into any suitable vector. The term "vector" refers to a nucleic acid molecule into which a second nucleic acid molecule can be inserted for introduction into a host cell where it will be replicated, and in some cases expressed. In other words, a vector is capable of transporting a nucleic acid molecule to which it has been linked. Cloning vectors as well as expression vectors are contemplated by the term "vector", as used herein. Certain vectors are capable of autonomous replication in a host into which they are introduced (e.g., vectors having a bacterial origin of replication can replicate in bacteria). Other vectors can be integrated into the genome of a host upon introduction into the host cell, and thereby are replicated along with the host genome. Vectors according to the invention can easily be made by methods well known to the person skilled in the art.

II. Clade F AAVhu68

As used herein, the term "clade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, *Molecular Evolution and Phylogenetics* (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See, e.g., G Gao, et al, J Virol, 2004 June; 78(12): 6381-6388, which identifies Clades A, B, C, D, E and F, and provides nucleic acid sequences of novel AAV, GenBank Accession Numbers AY530553 to AY530629. See, also, WO 2005/033321.

As used herein, an "AAV9 capsid" is a self-assembled AAV capsid composed of multiple AAV9 vp proteins. The AAV9 vp proteins are typically expressed as alternative splice variants encoded by a nucleic acid sequence of SEQ ID NO: 36 or a sequence at least 70%, at least 75%, at least 80%, at least 85%, at least 90%, at least 95%, at least 97%, at least 99% thereto, which encodes the vp1 amino acid sequence of SEQ ID NO: 17 (GenBank accession: AAS99264). These splice variants result in proteins of different length of SEQ ID NO: 17. In certain embodiments, "AAV9 capsid" includes an AAV having an amino acid sequence which is 99% identical to AAS99264 or 99% identical to SEQ ID NO: 17. See, also U.S. Pat. No. 7,906,111 and WO 2005/033321. As used herein "AAV9 variants" include those described in, e.g., WO2016/049230, U.S. Pat. No. 8,927,514, US 2015/0344911, and U.S. Pat. No. 8,734,809.

A rAAVhu68 is composed of an AAVhu68 capsid and a vector genome. An AAVhu68 capsid is an assembly of a heterogenous population of vp1, a heterogenous population of vp2, and a heterogenous population of vp3 proteins. As used herein when used to refer to vp capsid proteins, the term "heterogenous" or any grammatical variation thereof, refers to a population consisting of elements that are not the same, for example, having vp1, vp2 or vp3 monomers (proteins) with different modified amino acid sequences. SEQ ID NO: 16 provides the encoded amino acid sequence of the AAVhu68 vp1 protein. See, also, U.S. Provisional Patent Applications Nos. 62/614,002, 62/591,002 and 62/464,748, each of which is entitled "Novel Adeno-Associated Virus (AAV) Clade F Vector and Uses Therefor", and which are incorporated herein by reference in its entirety.

The AAVhu68 capsid contains subpopulations within the vp1 proteins, within the vp2 proteins and within the vp3 proteins which have modifications from the predicted amino acid residues in SEQ ID NO:16. These subpopulations include, at a minimum, certain deamidated asparagine (N or Asn) residues. For example, certain subpopulations comprise at least one, two, three or four highly deamidated asparagines (N) positions in asparagine-glycine pairs in SEQ ID NO: 16 and optionally further comprising other deamidated amino acids, wherein the deamidation results in an amino acid change and other optional modifications. SEQ ID NO: 39 provides the amino acid sequence of a modified AAVhu68 capsid, illustrating residue positions which may be deamidated or otherwise modified.

As used herein, a "subpopulation" of vp proteins refers to a group of vp proteins which has at least one defined characteristic in common and which consists of at least one group member to less than all members of the reference group, unless otherwise specified. For example, a "subpopulation" of vp1 proteins is at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine-glycine pairs.

Unless otherwise specified, highly deamidated refers to at least 45% deamidated, at least 50% deamidated, at least 60% deamidated, at least 65% deamidated, at least 70%, at least 75%, at least 80%, at least 85%, at least 90%, at least 95%, 97%, 99%, up to about 100% deamidated at a referenced amino acid position, as compared to the predicted amino acid sequence at the reference amino acid position (e.g., at least 80% of the asparagines at amino acid 57 of SEQ ID NO:16 may be deamidated based on the total vp1 proteins or 10% of the asparagines at amino acid 409 of SEQ ID NO: 16 may be deamidated based on the total vp1, vp2 and vp3 proteins). Such percentages may be determined using 2D-gel, mass spectrometry techniques, or other suitable techniques.

Without wishing to be bound by theory, the deamidation of at least highly deamidated residues in the vp proteins in the AAVhu68 capsid is believed to be primarily non-enzymatic in nature, being caused by functional groups within the capsid protein which deamidate selected asparagines, and to a lesser extent, glutamine residues. Efficient capsid assembly of the majority of deamidation vp1 proteins indicates that either these events occur following capsid assembly or that deamidation in individual monomers (vp1, vp2 or vp3) is well-tolerated structurally and largely does not affect assembly dynamics. Extensive deamidation in the VP1-unique (VP1-u) region (~aa 1-137), generally considered to be located internally prior to cellular entry, suggests that VP deamidation may occur prior to capsid assembly.

Without wishing to be bound by theory, the deamidation of N may occur through its C-terminus residue's backbone nitrogen atom conducts a nucleophilic attack to the Asn's side chain amide group carbon atom. An intermediate ring-closed succinimide residue is believed to form. The succinimide residue then conducts fast hydrolysis to lead to the final product aspartic acid (Asp) or iso aspartic acid (IsoAsp). Therefore, in certain embodiments, the deamidation of asparagine (N or Asn) leads to an Asp or IsoAsp, which may interconvert through the succinimide intermediate e.g., as illustrated below.

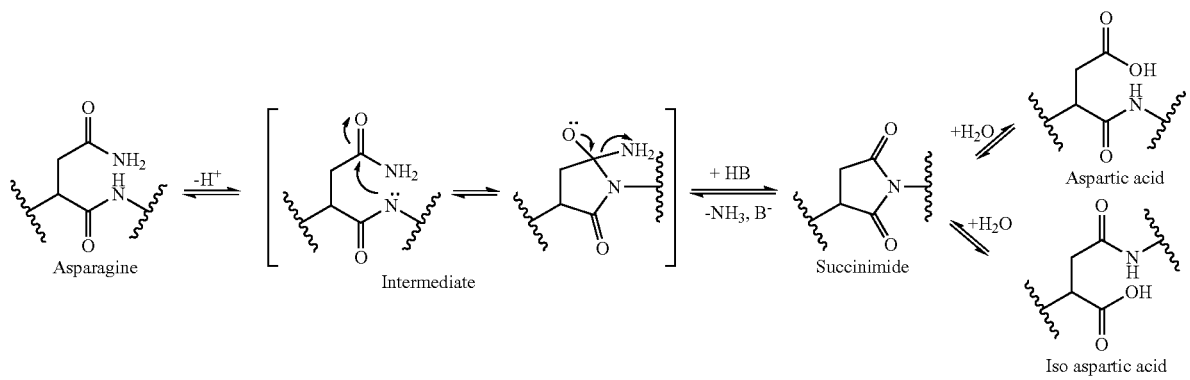

As provided herein, each deamidated N of SEQ ID NO: 16 may independently be aspartic acid (Asp), isoaspartic acid (isoAsp), aspartate, and/or an interconverting blend of Asp and isoAsp, or combinations thereof. Any suitable ratio of α- and isoaspartic acid may be present. For example, in certain embodiments, the ratio may be from 10:1 to 1:10 aspartic to isoaspartic, about 50:50 aspartic: isoaspartic, or about 1:3 aspartic: isoaspartic, or another selected ratio.

In certain embodiments, one or more glutamine (Q) in SEQ ID NO: 16 deamidates to glutamic acid (Glu), i.e., α-glutamic acid, γ-glutamic acid (Glu), or a blend of α- and γ-glutamic acid, which may interconvert through a common glutarinimide intermediate. Any suitable ratio of α- and γ-glutamic acid may be present. For example, in certain embodiments, the ratio may be from 10:1 to 1:10 α to γ, about 50:50 α:γ, or about 1:3 α:γ, or another selected ratio.

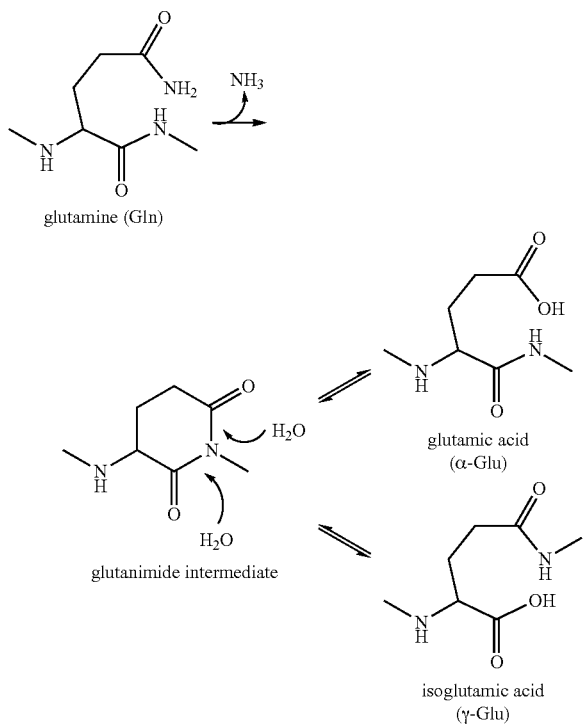

Thus, an rAAVhu68 includes subpopulations within the rAAVhu68 capsid of vp1, vp2 and/or vp3 proteins with deamidated amino acids, including at a minimum, at least one subpopulation comprising at least one highly deamidated asparagine. In addition, other modifications may include isomerization, particularly at selected aspartic acid (D or Asp) residue positions. In still other embodiments, modifications may include an amidation at an Asp position.

In certain embodiments, an AAVhu68 capsid contains subpopulations of vp1, vp2 and vp3 having at least 4 to at least about 25 deamidated amino acid residue positions, of which at least 1 to 10% are deamidated as compared to the encoded amino acid sequence of SEQ ID NO: 16. The majority of these may be N residues. However, Q residues may also be deamidated.

In certain embodiments, an AAV68 capsid is further characterized by one or more of the following. AAV hu68 capsid proteins comprise: AAVhu68 vp1 proteins produced by expression from a nucleic acid sequence which encodes the predicted amino acid sequence of 1 to 736 of SEQ ID NO:16, vp1 proteins produced from SEQ ID NO:18, or vp1 proteins produced from a nucleic acid sequence at least 70% identical to SEQ ID NO:18 which encodes the predicted amino acid sequence of 1 to 736 of SEQ ID NO:16; AAVhu68 vp2 proteins produced by expression from a nucleic acid sequence which encodes the predicted amino acid sequence of at least about amino acids 138 to 736 of SEQ ID NO:16, vp2 proteins produced from a sequence comprising at least nucleotides 412 to 2211 of SEQ ID NO:18, or vp2 proteins produced from a nucleic acid sequence at least 70% identical to at least nucleotides 412 to 2211 of SEQ ID NO:18 which encodes the predicted amino acid sequence of at least about amino acids 138 to 736 of SEQ ID NO:16, and/or AAVhu68 vp3 proteins produced by expression from a nucleic acid sequence which encodes the predicted amino acid sequence of at least about amino acids 203 to 736 of SEQ ID NO:16, vp3 proteins produced from a sequence comprising at least nucleotides 607 to 2211 of SEQ ID NO:18, or vp3 proteins produced from a nucleic acid sequence at least 70% identical to at least nucleotides 607 to 2211 of SEQ ID NO:18 which encodes the predicted amino acid sequence of at least about amino acids 203 to 736 of SEQ ID NO:16.

Additionally or alternatively, an AAV capsid is provided which comprise a heterogenous population of vp1 proteins, a heterogenous population of vp2 proteins optionally comprising a valine at position 157, and a heterogenous population of vp3 proteins, wherein at least a subpopulation of the vp1 and vp2 proteins comprise a valine at position 157 and optionally further comprising a glutamine at position 57 based on the numbering of the vp1 capsid of SEQ ID NO:16. Additionally or alternatively, an AAVhu68 capsid is provided which comprises a heterogenous population of vp1 proteins which are the product of a nucleic acid sequence encoding the amino acid sequence of SEQ ID NO: 16, a heterogenous population of vp2 proteins which are the product of a nucleic acid sequence encoding the amino acid sequence of at least about amino acids 138 to 736 of SEQ ID NO: 16, and a heterogenous population of vp3 proteins which are the product of a nucleic acid sequence encoding at least amino acids 203 to 736 of SEQ ID NO:16, wherein: the vp1, vp2 and vp3 proteins contain subpopulations with amino acid modifications The AAVhu68 vp1, vp2 and vp3 proteins are typically expressed as alternative splice variants encoded by the same nucleic acid sequence which encodes the full-length vp1 amino acid sequence of SEQ ID NO: 16 (amino acid 1 to 736). Optionally the vp1-encoding sequence is used alone to express the vp1, vp2 and vp3 proteins. Alternatively, this sequence may be co-expressed with one or more of a nucleic acid sequence which encodes the AAVhu68 vp3 amino acid sequence of SEQ ID NO: 16 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 18), or a sequence at least 70% to at least 99% (e.g., at least 85%, at least 90%, at least 95%, at least 97%, at least 98% or at least 99%) identical to SEQ ID NO: 18 which encodes aa 203 to 736 of SEQ ID NO: 16. Additionally, or alternatively, the vp1-encoding and/or the vp2-encoding sequence may be co-expressed with the nucleic acid sequence which encodes the AAVhu68 vp2 amino acid sequence of SEQ ID NO: 16 (about aa 138 to 736) without the vp1-unique region (about aa 1 to about 137), or a strand complementary thereto, the corresponding mRNA or tRNA (nt 412 to 2211 of SEQ ID NO: 18), or a sequence at least 70% to at least 99% (e.g., at least 85%, at least 90%, at least 95%, at least 97%, at least 98% or at least 99%) identical to SEQ ID NO: 18 which encodes about aa 138 to 736 of SEQ ID NO: 16.

As described herein, a rAAVhu68 has a rAAVhu68 capsid produced in a production system expressing capsids from an AAVhu68 nucleic acid which encodes the vp1 amino acid sequence of SEQ ID NO: 16, and optionally additional nucleic acid sequences, e.g., encoding a vp 3 protein free of the vp1 and/or vp2-unique regions. The rAAVhu68 resulting from production using a single nucleic acid sequence vp1 produces the heterogenous populations of vp1 proteins, vp2 proteins and vp3 proteins. More particularly, the AAVhu68 capsid contains subpopulations within the vp1 proteins, within the vp2 proteins and within the vp3 proteins which have modifications from the predicted amino acid residues in SEQ ID NO: 16. These subpopulations include, at a minimum, deamidated asparagine (N or Asn) residues. For example, asparagines in asparagine-glycine pairs are highly deamidated.

In one embodiment, the AAVhu68 vp1 nucleic acid sequence has the sequence of SEQ ID NO: 18, or a strand complementary thereto, e.g., the corresponding mRNA or tRNA. In certain embodiments, the vp2 and/or vp3 proteins may be expressed additionally or alternatively from different nucleic acid sequences than the vp1, e.g., to alter the ratio of the vp proteins in a selected expression system. In certain embodiments, also provided is a nucleic acid sequence which encodes the AAVhu68 vp3 amino acid sequence of SEQ ID NO: 16 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 18). In certain embodiments, also provided is a nucleic acid sequence which encodes the AAVhu68 vp2 amino acid sequence of SEQ ID NO: 16 (about aa 138 to 736) without the vp1-unique region (about aa 1 to about 137), or a strand complementary thereto, the corresponding mRNA or tRNA (nt 412 to 2211 of SEQ ID NO: 18).

However, other nucleic acid sequences which encode the amino acid sequence of SEQ ID NO: 16 may be selected for use in producing rAAVhu68 capsids. In certain embodiments, the nucleic acid sequence has the nucleic acid sequence of SEQ ID NO: 18 or a sequence at least 70% to 99.%, identical, at least 75%, at least 80%, at least 85%, at least 90%, at least 95%, at least 97%, at least 99%, identical to SEQ ID NO: 18 which encodes SEQ ID NO: 16. In certain embodiments, the nucleic acid sequence has the nucleic acid sequence of SEQ ID NO: 18 or a sequence at least 70% to 99.%, at least 75%, at least 80%, at least 85%, at least 90%, at least 95%, at least 97%, at least 99%, identical to about nt 412 to about nt 2211 of SEQ ID NO: 18 which encodes the vp2 capsid protein (about aa 138 to 736) of SEQ ID NO: 16. In certain embodiments, the nucleic acid sequence has the nucleic acid sequence of about nt 607 to about nt 2211 of SEQ ID NO:18 or a sequence at least 70% to 99.%, at least 75%, at least 80%, at least 85%, at least 90%, at least 95%, at least 97%, at least 99%, identical to nt SEQ ID NO: 18 which encodes the vp3 capsid protein (about aa 203 to 736) of SEQ ID NO: 16.

Figure 1C:
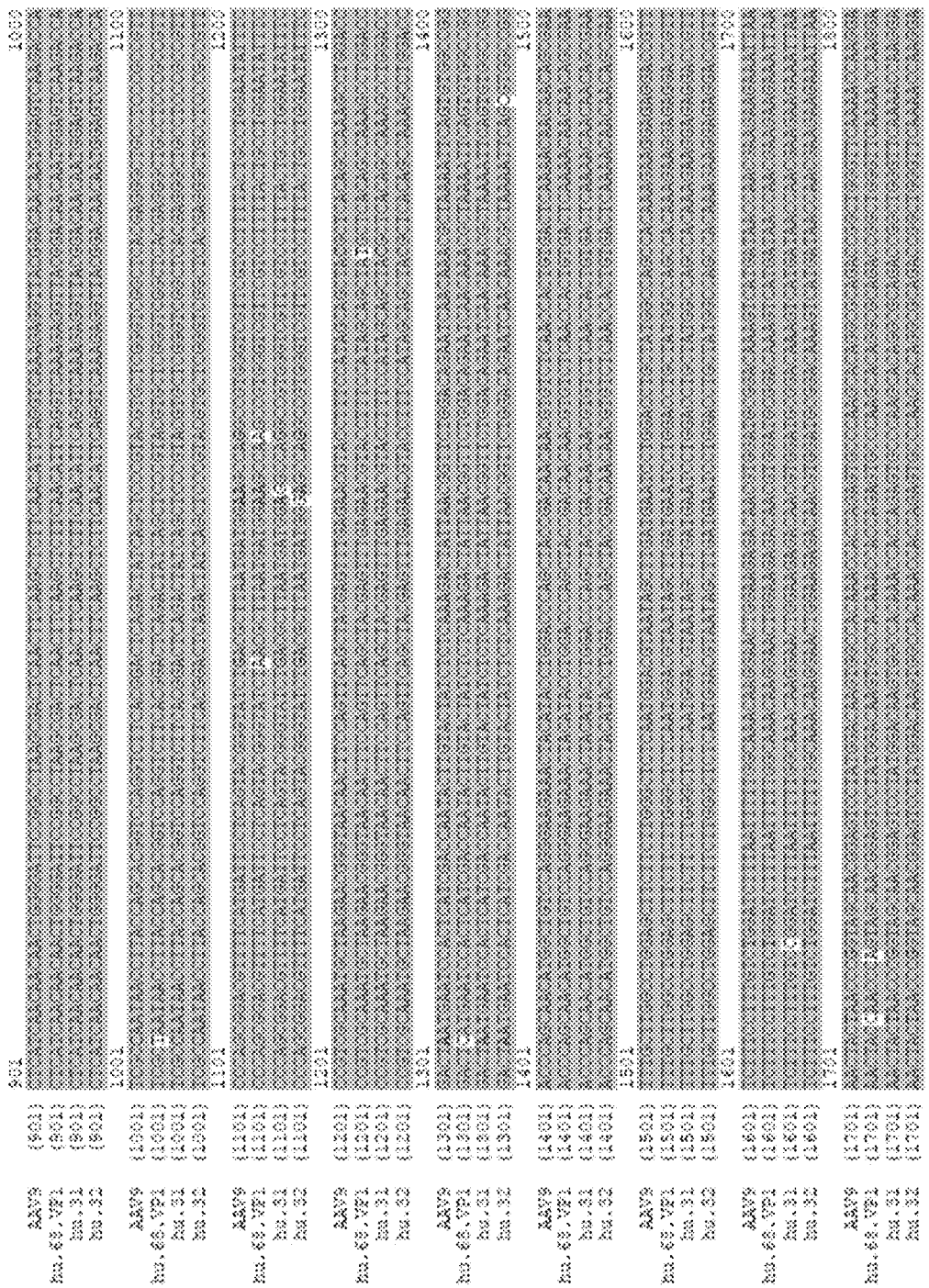
Figure 1D:
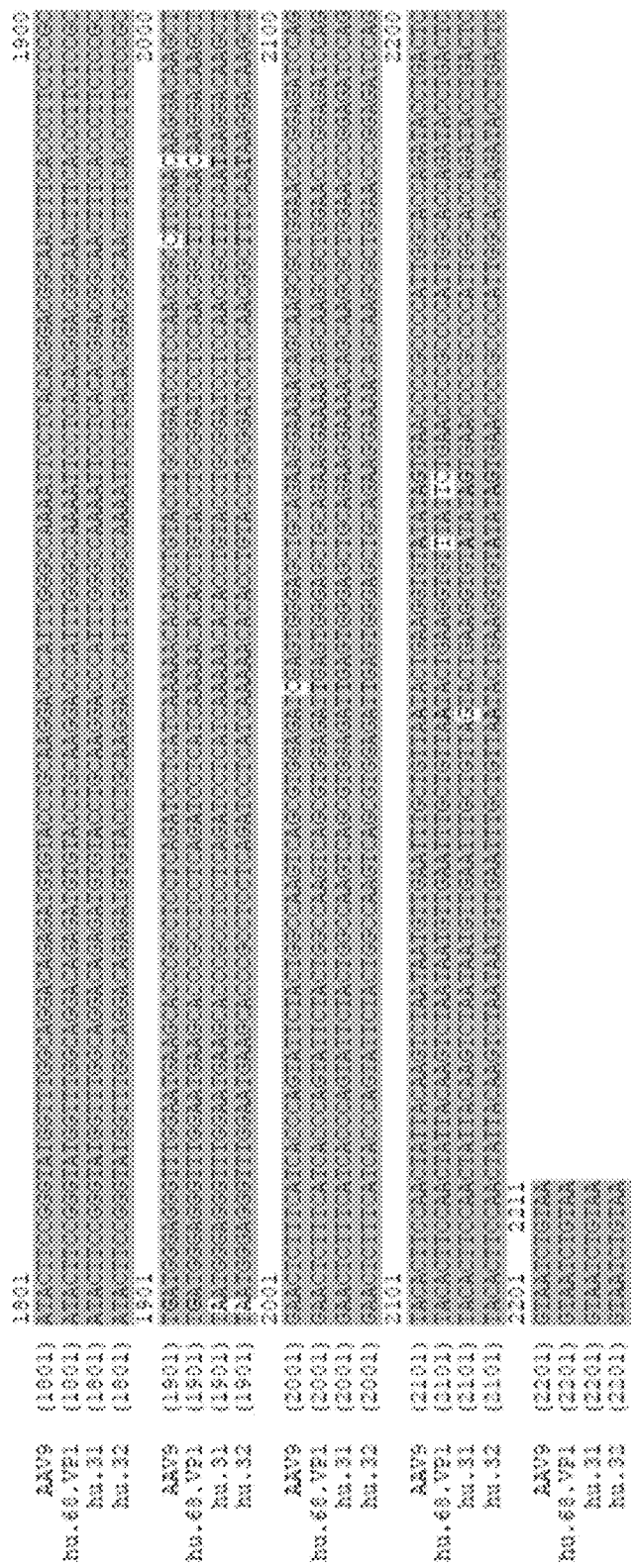

It is within the skill in the art to design nucleic acid sequences encoding this AAVhu68 capsid, including DNA (genomic or cDNA), or RNA (e.g., mRNA). In certain embodiments, the nucleic acid sequence encoding the AAVhu68 vp 1 capsid protein is provided in SEQ ID NO: 18. See, also, FIGS. 1B-1D. In other embodiments, a nucleic acid sequence of 70% to 99.9% identity to SEQ ID NO: 18 may be selected to express the AAVhu68 capsid proteins. In certain other embodiments, the nucleic acid sequence is at least about 75% identical, at least 80% identical, at least 85%, at least 90%, at least 95%, at least 97% identical, or at least 99% to 99.9% identical to SEQ ID NO: 18. Such nucleic acid sequences may be codon-optimized for expression in a selected system (i.e., cell type) can be designed by various methods. This optimization may be performed using methods which are available on-line (e.g., GeneArt), published methods, or a company which provides codon optimizing services, e.g., DNA2.0 (Menlo Park, Calif.). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide. A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, the asparagine (N) in N-G pairs in the AAVhu68 vp1, vp2 and vp3 proteins are highly deamidated. In certain embodiments, an AAVhu68 capsid contains subpopulations of AAV vp 1, vp2 and/or vp3 capsid proteins having at least four asparagine (N) positions in the AAVhu68 capsid proteins which are highly deamidated. In certain embodiments, about 20 to 50% of the N—N pairs (exclusive of N—N—N triplets) show deamidation. In certain embodiments, the first N is deamidated. In certain embodiments, the second N is deamidated. In certain embodiments, the deamidation is between about 15% to about 25% deamidation. Deamidation at the Q at position 259 of SEQ ID NO: 16 is about 8% to about 42% of the AAVhu68 vp 1, vp2 and vp3 capsid proteins of an AAVhu68 protein.

In certain embodiments, the rAAVhu68 capsid is further characterized by an amidation in D297 the vp1, vp2 and vp3 proteins. In certain embodiments, about 70% to about 75% of the D at position 297 of the vp1, vp2 and/or vp3 proteins in a AAVhu68 capsid are amidated, based on the numbering of SEQ ID NO: 16.

In certain embodiments, at least one Asp in the vp1, vp2 and/or vp3 of the capsid is isomerized to D-Asp. Such isomers are generally present in an amount of less than about 1% of the Asp at one or more of residue positions 97, 107, 384, based on the numbering of SEQ ID NO: 16.

In certain embodiments, a rAAVhu68 has an AAVhu68 capsid having vp1, vp2 and vp3 proteins having subpopulations comprising combinations of two, three, four or more deamidated residues at the positions set forth in the table below. Deamidation in the rAAV may be determined using 2D gel electrophoresis, and/or mass spectrometry, and/or protein modelling techniques. Online chromatography may be performed with an Acclaim PepMap column and a Thermo UltiMate 3000 RSLC system (Thermo Fisher Scientific) coupled to a Q Exactive HF with a NanoFlex source (Thermo Fisher Scientific). MS data is acquired using a data-dependent top-20 method for the Q Exactive HF, dynamically choosing the most abundant not-yet-sequenced precursor ions from the survey scans (200-2000 m/z). Sequencing is performed via higher energy collisional dissociation fragmentation with a target value 1e5 ions determined with predictive automatic gain control and an isolation of precursors was performed with a window of 4 m/z. Survey scans were acquired at a resolution of 120,000 at m/z 200. Resolution for HCD spectra may be set to 30,000 at m/z200 with a maximum ion injection time of 50 ms and a normalized collision energy of 30. The S-lens RF level may be set at 50, to give optimal transmission of the m/z region occupied by the peptides from the digest. Precursor ions may be excluded with single, unassigned, or six and higher charge states from fragmentation selection. BioPharma Finder 1.0 software (Thermo Fischer Scientific) may be used for analysis of the data acquired. For peptide mapping, searches are performed using a single-entry protein FASTA database with carbamidomethylation set as a fixed modification; and oxidation, deamidation, and phosphorylation set as variable modifications, a 10-ppm mass accuracy, a high protease specificity, and a confidence level of 0.8 for MS/MS spectra. Examples of suitable proteases may include, e.g., trypsin or chymotrypsin. Mass spectrometric identification of deamidated peptides is relatively straightforward, as deamidation adds to the mass of intact molecule +0.984 Da (the mass difference between —OH and —NH$_2$ groups). The percent deamidation of a particular peptide is determined mass area of the deamidated peptide divided by the sum of the area of the deamidated and native peptides. Considering the number of possible deamidation sites, isobaric species which are deamidated at different sites may co-migrate in a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent on the site of deamidation. It will be understood by one of skill in the art that a number of variations on these illustrative methods can be used. For example, suitable mass spectrometers may include, e.g, a quadrupole time of flight mass spectrometer (QTOF), such as a Waters Xevo or Agilent 6530 or an orbitrap instrument, such as the Orbitrap Fusion or Orbitrap Velos (Thermo Fisher). Suitably liquid chromatography systems include, e.g., Acquity UPLC system from Waters or Agilent systems (1100 or 1200 series). Suitable data analysis software may include, e.g., MassLynx (Waters), Pinpoint and Pepfinder (Thermo Fischer Scientific), Mascot (Matrix Science), Peaks DB (Bioinformatics Solutions). Still other techniques may be described, e.g., in X. Jin et al, Hu Gene Therapy Methods, Vol. 28, No. 5, pp. 255-267, published online Jun. 16, 2017.

| Deamidation Based on Predicted AAVHu68 [SEQ ID NO: 16] | Average % Based on VP1/VP2/VP3 Proteins in AAVhu68 Capsid | |
|---|---|---|
| Deamidated Residue + 1 (Neighboring AA) | Broad Range of Percentages (%) | Narrow Ranges (%) |
| N57 (N-G) | 78 to 100% | 80 to 100, 85 to 97 |
| N66 (N-E) | 0 to 5 | 0, 1 to 5 |
| N94 (N-H) | 0 to 15, | 0, 1 to 15, 5 to 12, 8 |
| N113 (N-L) | 0 to 2 | 0, 1 to 2 |

-continued

| Deamidation Based on Predicted AAVHu68 [SEQ ID NO: 16] | Average % Based on VP1/VP2/VP3 Proteins in AAVhu68 Capsid | |
|---|---|---|
| Deamidated Residue + 1 (Neighboring AA) | Broad Range of Percentages (%) | Narrow Ranges (%) |
| ~N253 (N-N) | 10 to 25 | 15 to 22 |
| Q259 (Q-I) | 8 to 42 | 10 to 40, 20 to 35 |
| ~N270 (N-D) | 12 to 30 | 15 to 28 |
| ~N304 (N-N) (position 303 also N) | 0 to 5 | 1 to 4 |
| N319 (N-I) | 0 to 5 | 0, 1 to 5, 1 to 3 |
| N329* (N-G)* (position 328 also N) | 65 to 100 | 70 to 95, 85 to 95, 80 to 100, 85 to 100, |
| N336 (N-N) | 0 to 100 | 0, 1 to 10, 25 to 100, 30 to 100, 30 to 95 |
| ~N409 (N-N) | 15 to 30 | 20 to 25 |
| N452 (N-G) | 75 to 100 | 80 to 100, 90 to 100, 95 to 100, |
| N477 (N-Y) | 0 to 8 | 0, 1 to 5 |
| N512 (N-G) | 65 to 100 | 70 to 95, 85 to 95, 80 to 100, 85 to 100, |
| ~N515 (N-S) | 0 to 25 | 0, 1 to 10, 5 to 25, 15 to 25 |
| ~Q599 (Asn-Q-Gly) | 1 to 20 | 2 to 20, 5 to 15 |
| N628 (N-F) | 0 to 10 | 0, 1 to 10, 2 to 8 |
| N651 (N-T) | 0 to 3 | 0, 1 to 3 |
| N663 (N-K) | 0 to 5 | 0, 1 to 5, 2 to 4 |
| N709 (N-N) | 0 to 25 | 0, 1 to 22, 15 to 25 |
| N735 | 0 to 40 | 0. 1 to 35, 5 to 50, 20 to 35 |

In certain embodiments, the AAVhu68 capsid is characterized, by having, capsid proteins in which at least 45% of N residues are deamidated at least one of positions N57, N329, N452, and/or N512 based on the numbering of amino acid sequence of SEQ ID NO: 16. In certain embodiments, at least about 60%, at least about 70%, at least about 80%, or at least 90% of the N residues at one or more of these N-G positions (i.e., N57, N329, N452, and/or N512, based on the numbering of amino acid sequence of SEQ ID NO: 16) are deamidated. In these and other embodiments, an AAVhu68 capsid is further characterized by having a population of proteins in which about 1% to about 20% of the N residues have deamidations at one or more of positions: N94, N253, N270, N304, N409, N477, and/or Q599, based on the numbering of amino acid sequence of SEQ ID NO: 16. In certain embodiments, the AAVhu68 comprises at least a subpopulation of vp1, vp2 and/or vp3 proteins which are deamidated at one or more of positions N35, N57, N66, N94, N113, N252, N253, Q259, N270, N303, N304, N305, N319, N328, N329, N336, N409, N410, N452, N477, N515, N598, Q599, N628, N651, N663, N709, N735, based on the numbering of amino acid sequence of SEQ ID NO: 16, or combinations thereof. In certain embodiments, the capsid proteins may have one or more amidated amino acids.

Still other modifications are observed, most of which do not result in conversion of one amino acid to a different amino acid residue. Optionally, at least one Lys in the vp1, vp2 and vp3 of the capsid are acetylated. Optionally, at least one Asp in the vp1, vp2 and/or vp3 of the capsid is isomerized to D-Asp. Optionally, at least one S (Ser, Serine) in the vp1, vp2 and/or vp3 of the capsid is phosphorylated. Optionally, at least one T (Thr, threonine) in the vp1, vp2 and/or vp3 of the capsid is phosphorylated. Optionally, at least one W (trp, tryptophan) in the vp1, vp2 and/or vp3 of the capsid is oxidized. Optionally, at least one M (Met, Methionine) in the vp1, vp2 and/or vp3 of the capsid is oxidized. In certain embodiments, the capsid proteins have one or more phosphorylations. For example, certain vp1 capsid proteins may be phosphorylated at position 149.

In certain embodiments, an AAVhu68 capsid comprises a heterogenous population of vp1 proteins which are the product of a nucleic acid sequence encoding the amino acid sequence of SEQ ID NO: 16, wherein the vp1 proteins comprise a Glutamic acid (Glu) at position 67 and/or a valine (Val) at position 157; a heterogenous population of vp2 proteins optionally comprising a valine (Val) at position 157; and a heterogenous population of vp3 proteins. The AAVhu68 capsid contains at least one subpopulation in which at least 65% of asparagines (N) in asparagine-glycine pairs located at position 57 of the vp1 proteins and at least 70% of asparagines (N) in asparagine-glycine pairs at positions 329, 452 and/or 512 of the vp1, v2 and vp3 proteins are deamidated, based on the residue numbering of the amino acid sequence of SEQ ID NO: 16, wherein the deamidation results in an amino acid change. As discussed in more detail herein, the deamidated asparagines may be deamidated to aspartic acid, isoaspartic acid, an interconverting aspartic acid/isoaspartic acid pair, or combinations thereof In certain embodiments, the rAAVhu68 are further characterized by one or more of: (a) each of the vp2 proteins is independently the product of a nucleic acid sequence encoding at least the vp2 protein of SEQ ID NO: 16; (b) each of the vp3 proteins is independently the product of a nucleic acid sequence encoding at least the vp3 protein of SEQ ID NO: 16; (c) the nucleic acid sequence encoding the vp1 proteins is SEQ ID NO: 18, or a sequence at least 70% to at least 99% (e.g., at least 85%, at least 90%, at least 95%, at least 97%, at least 98% or at least 99%) identical to SEQ ID NO: 18 which encodes the amino acid sequence of SEQ ID NO:16. Optionally that sequence is used alone to express the vp1, vp2 and vp3 proteins. Alternatively, this sequence may be co-expressed with one or more of a nucleic acid sequence which encodes the AAVhu68 vp3 amino acid sequence of SEQ ID NO: 16 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 18), or a sequence at least 70% to at least 99% (e.g., at least 85%, at least 90%, at least 95%, at least 97%, at least 98% or at least 99%) identical to SEQ ID NO: 18 which encodes aa 203 to 736 of SEQ ID NO: 16. Additionally, or alternatively, the vp1-encoding and/or the vp2-encoding sequence may be co-expressed with the nucleic acid sequence which encodes the AAVhu68 vp2 amino acid sequence of SEQ ID NO: 16 (about aa 138 to 736) without the vp1-unique region (about aa 1 to about 137), or a strand complementary thereto, the corresponding mRNA or tRNA (nt 412 to 2211 of SEQ ID NO: 18), or a sequence at least 70% to at least 99% (e.g., at least 85%, at least 90%, at least 95%, at least 97%, at least 98% or at least 99%) identical to SEQ ID NO: 18 which encodes about aa 138 to 736 of SEQ ID NO: 16.

Additionally or alternatively, the rAAVhu68 capsid comprises at least a subpopulation of vp1, vp2 and/or vp3 proteins which are deamidated at one or more of positions N57, N66, N94, N113, N252, N253, Q259, N270, N303, N304, N305, N319, N328, N329, N336, N409, N410, N452, N477, N512, N515, N598, Q599, N628, N651, N663, N709, based on the numbering of SEQ ID NO:16, or combinations thereof; (e) rAAVhu68 capsid comprises a subpopulation of vp1, vp2 and/or vp3 proteins which comprise 1% to 20% deamidation at one or more of positions N66, N94, N113, N252, N253, Q259, N270, N303, N304, N305, N319, N328, N336, N409, N410, N477, N515, N598, Q599, N628, N651, N663, N709, based on the numbering of SEQ ID NO:16, or combinations thereof; (f) the rAAVhu68 capsid comprises a subpopulation of vp1 in which 65% to 100% of the N at position 57 of the vp1 proteins, based on the numbering of SEQ ID NO:16, are deamidated; (g) the rAAVhu68 capsid comprises subpopulation of vp1 proteins in which 75% to 100% of the N at position 57 of the vp1 proteins are deamidated; (h) the rAAVhu68 capsid comprises subpopulation of vp1 proteins, vp2 proteins, and/or vp3 proteins in which 80% to 100% of the N at position 329, based on the numbering of SEQ ID NO:16, are deamidated; (i) the rAAVhu68 capsid comprises subpopulation of vp1 proteins, vp2 proteins, and/or vp3 proteins in which 80% to 100% of the N at position 452, based on the numbering of SEQ ID NO:16, are deamidated; (j) the rAAVhu68 capsid comprises subpopulation of vp1 proteins, vp2 proteins, and/or vp3 proteins in which 80% to 100% of the N at position 512, based on the numbering of SEQ ID NO:16, are deamidated; (k) the rAAV comprises about 60 total capsid proteins in a ratio of about 1 vp1 to about 1 to 1.5 vp2 to 3 to 10 vp3 proteins; (1) the rAAV comprises about 60 total capsid proteins in a ratio of about 1 vp1 to about 1 vp2 to 3 to 9 vp3 proteins.

In certain embodiments, the AAVhu68 is modified to change the glycine in an asparagine-glycine pair, to reduce deamidation. In other embodiments, the asparagine is altered to a different amino acid, e.g., a glutamine which deamidates at a slower rate; or to an amino acid which lacks amide groups (e.g., glutamine and asparagine contain amide groups); and/or to an amino acid which lacks amine groups (e.g., lysine, arginine and histidine contain amide groups). As used herein, amino acids lacking amide or amine side groups refer to, e.g., glycine, alanine, valine, leucine, isoleucine, serine, threonine, cystine, phenylalanine, tyrosine, or tryptophan, and/or proline. Modifications such as described may be in one, two, or three of the asparagine-glycine pairs found in the encoded AAVhu68 amino acid sequence. In certain embodiments, such modifications are not made in all four of the asparagine-glycine pairs. Thus, a method for reducing deamidation of AAVhu68 and/or engineered AAVhu68 variants having lower deamidation rates. Additionally, or alternative one or more other amide amino acids may be changed to a non-amide amino acid to reduce deamidation of the AAVhu68.

These amino acid modifications may be made by conventional genetic engineering techniques. For example, a nucleic acid sequence containing modified AAVhu68 vp codons may be generated in which one to three of the codons encoding glycine at position 58, 330, 453 and/or 513 in SEQ ID NO: 16 (arginine-glycine pairs) are modified to encode an amino acid other than glycine. In certain embodiments, a nucleic acid sequence containing modified arginine codons may be engineered at one to three of the arginine-glycine pairs located at position 57, 329, 452 and/or 512 in SEQ ID NO: 16, such that the modified codon encodes an amino acid other than arginine. Each modified codon may encode a different amino acid. Alternatively, one or more of the altered codons may encode the same amino acid. In certain embodiments, these modified AAVhu68 nucleic acid sequences may be used to generate a mutant rAAVhu68 having a capsid with lower deamidation than the native hu68 capsid. Such mutant rAAVhu68 may have reduced immunogenicity and/or increase stability on storage, particularly storage in suspension form.

In one embodiment, a recombinant adeno-associated virus (rAAV) is provided which comprises: (A) an AAV68 capsid comprising one or more of: (1) AAV hu68 capsid proteins comprising: AAVhu68 vp1 proteins produced by expression from a nucleic acid sequence which encodes the predicted amino acid sequence of 1 to 736 of SEQ ID NO:16, vp1 proteins produced from SEQ ID NO:18, or vp1 proteins produced from a nucleic acid sequence at least 70% identical to SEQ ID NO:18 which encodes the predicted amino acid sequence of 1 to 736 of SEQ ID NO:16, AAVhu68 vp2 proteins produced by expression from a nucleic acid sequence which encodes the predicted amino acid sequence of at least about amino acids 138 to 736 of SEQ ID NO:16, vp2 proteins produced from a sequence comprising at least nucleotides 412 to 2211 of SEQ ID NO:18, or vp2 proteins produced from a nucleic acid sequence at least 70% identical to at least nucleotides 412 to 2211 of SEQ ID NO:18 which encodes the predicted amino acid sequence of at least about amino acids 138 to 736 of SEQ ID NO:16, AAVhu68 vp3 proteins produced by expression from a nucleic acid sequence which encodes the predicted amino acid sequence of at least about amino acids 203 to 736 of SEQ ID NO:16, vp3 proteins produced from a sequence comprising at least nucleotides 607 to 2211 of SEQ ID NO:18, or vp3 proteins produced from a nucleic acid sequence at least 70% identical to at least nucleotides 607 to 2211 of SEQ ID NO:18 which encodes the predicted amino acid sequence of at least about amino acids 203 to 736 of SEQ ID NO:16; and/or (2) AAV capsid proteins comprising a heterogenous population of vp1 proteins, a heterogenous population of vp2 proteins optionally comprising a valine at position 157, and a heterogenous population of vp3 proteins, wherein at least a subpopulation of the vp1 and vp2 proteins comprise a valine at position 157 and optionally further comprising a glutamine at position 57 based on the numbering of the vp1 capsid of SEQ ID NO:16; and/or (3) a heterogenous population of vp1 proteins which are the product of a nucleic acid sequence encoding the amino acid sequence of SEQ ID NO: 16, a heterogenous population of vp2 proteins which are the product of a nucleic acid sequence encoding the amino acid sequence of at least about amino acids 138 to 736 of SEQ ID NO: 16, and a heterogenous population of vp3 proteins which are the product of a nucleic acid sequence encoding at least amino acids 203 to 736 of SEQ ID NO:16, wherein: the vp1, vp2 and vp3 proteins contain subpopulations with amino acid modifications comprising at least two highly deamidated asparagines (N) in asparagine-glycine pairs in SEQ ID NO: 16 and optionally further comprising subpopulations comprising other deamidated amino acids, wherein the deamidation results in an amino acid change; and (B) a vector genome in the AAVhu68 capsid, the vector genome comprising a nucleic acid molecule comprising AAV inverted terminal repeat sequences and a non-AAV nucleic acid sequence encoding a product operably linked to sequences which direct expression of the product in a host cell. For example, four residues (N57, N329, N452, N512) routinely display high levels of deamidation. Additional residues (N94, N253, N270, N304, N409, N477 and Q599) also display deamidation levels up to ~20% across various lots.

In certain embodiments, the deamidated asparagines are deamidated to aspartic acid, isoaspartic acid, an interconverting aspartic acid/isoaspartic acid pair, or combinations thereof. In certain embodiments, the deamidated glutamine(s) are deamidated to ($\alpha$)-glutamic acid, $\gamma$-glutamic acid, an interconverting ($\alpha$)-glutamic acid/$\gamma$-glutamic acid pair, or combinations thereof.

In certain embodiments, the AAVhu68 capsid comprises subpopulations having one or more of: (a) at least 65% of asparagines (N) in asparagine-glycine pairs located at positions 57 of the vp1 proteins are deamidated, based on the numbering of SEQ ID NO:16; (b) at least 75% of N in asparagine-glycine pairs in position 329 of the vp1, v2 and vp3 proteins are deamidated, based on the residue numbering of the amino acid sequence of SEQ ID NO: 16; (c) at least 50% of N in asparagine-glycine pairs in position 452 of the vp1, v2 and vp3 proteins are deamidated, based on the residue numbering of the amino acid sequence of SEQ ID NO: 16; and/or (d) at least 75% of N in asparagine-glycine pairs in position 512 of the vp1, v2 and vp3 proteins are deamidated, based on the residue numbering of the amino acid sequence of SEQ ID NO: 16. In certain embodiments, the hu68 capsid comprises a subpopulation of vp1 in which 75% to 100% of the N at position 57 of the vp1 proteins are deamidated, as determined using mass spectrometry. In certain embodiments, the hu68 capsid comprises subpopulation of vp1 proteins, vp2 proteins, and/or vp3 proteins in which 75% to 100% of the N at position 329, based on the numbering of SEQ ID NO:16, are deamidated as determined using mass spectrometry. In certain embodiments, the hu68 capsid comprises subpopulation of vp1 proteins, vp2 proteins, and/or vp3 proteins in which 75% to 100% of the N at position 452, based on the numbering of SEQ ID NO:16, are deamidated as determined using mass spectrometry. In certain embodiments, the hu68 capsid comprises subpopulation of vp1 proteins, vp2 proteins, and/or vp3 proteins in which 75% to 100% of the N at position 512, based on the numbering of SEQ ID NO:16, are deamidated. In certain embodiments, the nucleic acid sequence encoding the proteins is SEQ ID NO: 18, or a sequence at least 80% to at least 99% identical to SEQ ID NO: 18 which encodes the amino acid sequence of SEQ ID NO:16. In certain embodiments, the sequence is at least 80% to 97% identical to SEQ ID NO: 18. In certain embodiments, the rAAVhu68 capsid further comprises at least subpopulation of vp1, vp2 and/or vp3 proteins having amino acid modifications from SEQ ID NO: 16 comprising at least about 50 to 100% deamidation at least four positions selected from one or more of N57, 329, 452, 512, or combinations thereof. In certain embodiments, the hu68 capsid comprises subpopulations of vp1, vp2 and/or vp3 proteins which further comprise 1% to about 40% deamidation in at least one or more of positions N94, N113, N252, N253, Q259, N270, N303, N304, N305, N319, N328, N336, N409, N410, N477, N515, N598, Q599, N628, N651, N663, N709, or combinations thereof. In certain embodiments, the hu68 capsid comprises subpopulations of vp1, vp2 and/or vp3 proteins which further comprise one or more modifications selected from one or more modification in one or more of the following: acetylated lysine, phosphorylated serine and/or threonine, isomerized aspartic acid, oxidized tryptophan and/or methionine, or an amidated amino acid. In certain embodiments, the rAAVhu68 comprises about 60 total capsid proteins in a ratio of about 1 vp1 to about 1 to 1.5 vp2 to 3 to 10 vp3 proteins. In certain embodiments, the AAVhu68 capsid about 60 total capsid proteins in a ratio of about 1 vp1 to about 1 vp2 to 3 to 9 vp3 proteins. In certain embodiments, the vector genome comprises AAV ITR sequences from an AAV source other than AAVhu68.

In certain embodiments, a composition is provided which comprises a mixed population of recombinant adeno-associated virus hu68 (rAAVhu68), wherein each of the rAAVhu68 is independently selected from an rAAVhu68 as described herein. In certain embodiments, the average AAVhu68 capsid comprises about 60 total capsid proteins in a ratio of about 1 vp1 to about 1 to 1.5 vp2 to 3 to 10 vp3 proteins. In certain embodiments, the average AAVhu68 capsid comprises about 60 total capsid proteins in a ratio of about 1 vp1 to about 1 vp2 to 3 to 6 vp3 proteins. In certain embodiments, the composition is formulated for intravenous delivery. In certain embodiments, the composition is formulated for intranasal or intramuscular delivery. In certain embodiments, a composition comprises at least an rAAVhu68 vector stock and an optional carrier, excipient and/or preservative.

Any suitable rAAV production system useful for producing a recombinant AAVhu68 may be used. For example, such a production system may comprise: (a) an AAVhu68 capsid nucleic acid sequence encoding the amino acid sequence of SEQ ID NO:16; (b) a nucleic acid molecule suitable for packaging into the AAVhu68 capsid, said nucleic acid molecule comprising at least one AAV inverted terminal repeat (ITR) and a non-AAV nucleic acid sequence encoding a gene product operably linked to sequences which direct expression of the product in a host cell; and (c) sufficient AAV rep functions and helper functions to permit packaging of the nucleic acid molecule into the recombinant AAVhu68 capsid. In certain embodiments, the nucleic acid sequence of (a) comprises at least SEQ ID NO: 18, or a sequence at least 70% to at least 99% identical to SEQ ID NO: 18 which encodes the amino acid sequence of SEQ ID NO:16. In certain embodiments, the system optionally further comprises a nucleic acid sequence of about nt 607 to about nt 2211 of SEQ ID NO:18 encoding the AAVhu68 vp3 of about aa 203 to about amino acid 736 of SEQ ID NO: 16. In certain embodiments, the system comprises human embryonic kidney 293 cells or a baculovirus system.

In certain embodiments, a method for reducing deamidation of an AAVhu68 capsid is provided. The method comprises producing an AAVhu68 capsid from a nucleic acid sequence containing modified AAVhu68 vp codons, the nucleic acid sequence comprising independently modified glycine codons at one to three of the arginine-glycine pairs located at position 58, 330, 453 and/or 513 in SEQ ID NO: 16, such that the modified codon encodes an amino acid other than glycine. In certain embodiments, the method comprises producing an AAVhu68 capsid from a nucleic acid sequence containing modified AAVhu68 vp codons, the nucleic acid sequence comprising independently modified arginine codons at one to three of the arginine-glycine pairs located at position 57, 329, 452 and/or 512 in SEQ ID NO: 16, such that the modified codon encodes an amino acid other than arginine. In certain embodiments, each modified codon encodes a different amino acid. In certain embodiments, two or more modified codons encode the same amino acid. In certain embodiments, a mutant AAVhu68 capsid as described herein contains a mutation in an arginine-glycine pair, such that the glycine is changed to an alanine or a serine. A mutant AAVhu68 capsid may contain one, two or three mutants where the reference AAVhu68 natively contains four NG pairs. In certain embodiments, a mutant AAVhu68 capsid contains only a single mutation in an NG pair. In certain embodiments, a mutant AAVhu68 capsid contains mutations in two different NG pairs. In certain embodiments, a mutant AAVhu68 capsid contains mutation is two different NG pairs which are located in structurally separate location in the AAVhu68 capsid. In certain embodiments, the mutation is not in the VP1-unique region. In certain embodiments, one of the mutations is in the VP1-unique region. Optionally, a mutant AAVhu68 capsid contains no modifications in the NG pairs, but contains mutations to minimize or eliminate deamidation in one or more asparagines, or a glutamine, located outside of an NG pair.

As used herein, "encoded amino acid sequence" refers to the amino acid which is predicted based on the translation of a known DNA codon of a referenced nucleic acid sequence being translated to an amino acid. The following table illustrates DNA codons and twenty common amino acids, showing both the single letter code (SLC) and three letter code (3LC).

| Amino Acid | SLC | 3 LC | DNA codons |
|---|---|---|---|
| Isoleucine | I | Ile | ATT, ATC, ATA |
| Leucine | L | Leu | CTT, CTC, CTA, CTG, TTA, TTG |
| Valine | V | Val | GTT, GTC, GTA, GTG |
| Phenylalanine | F | Phe | TTT, TTC |
| Methionine | M | Met | ATG |
| Cysteine | C | Cys | TGT, TGC |
| Alanine | A | Ala | GCT, GCC, GCA, GCG |
| Glycine | G | Gly | GGT, GGC, GGA, GGG |
| Proline | P | Pro | CCT, CCC, CCA, CCG |
| Threonine | T | Thr | ACT, ACC, ACA, ACG |
| Serine | S | Ser | TCT, TCC, TCA, TCG, AGT, AGC |
| Tyrosine | Y | Tyr | TAT, TAC |
| Tryptophan | W | Trp | TGG |
| Glutamine | Q | Gln | CAA, CAG |
| Asparagine | N | Asn | AAT, AAC |
| Histidine | H | His | CAT, CAC |
| Glutamic acid | E | Glu | GAA, GAG |
| Aspartic acid | D | Asp | GAT, GAC |
| Lysine | K | Lys | AAA, AAG |
| Arginine | R | Arg | CGT, CGC, CGA, CGG, AGA, AGG |
| Stop codons | Stop | | TAA, TAG, TGA |

Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

As indicated above, the AAVhu68 sequences and proteins are useful in production of rAAV. The examples below describe production of rAAV vectors having AAVhu68 or AAV9 vectors. However, in other embodiments, another AAV capsid is selected. Tissue specificity is determined by the capsid type. For example, a viral vector having an AAVhu68 is illustrated in the examples below as being useful for transducing nasal epithelial cells. The sequences of AAVhu68 are described herein. Further, methods of generating vectors having the AAV9 capsid and chimeric capsids derived from AAV9 have been described. See, e.g., U.S. Pat. No. 7,906,111, which is incorporated by reference herein. Other AAV serotypes which transduce nasal cells or another suitable target (e.g., muscle or lung) may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8 (See, e.g., US Published Patent Application No. 2007-0036760-A1; US Published Patent Application No. 2009-0197338-A1; and EP 1310571). See also, WO 2003/042397 (AAV7 and other simian AAV), U.S. Pat. Nos. 7,790,449 and 7,282,199 (AAV8), WO 2005/033321 (AAV9), and WO 2006/110689, or yet to be discovered, or a recombinant AAV based thereon, may be used as a source for the AAV capsid. These documents also describe other AAV which may be selected for generating AAV and are incorporated by reference. In some embodiments, an AAV capsid (cap) for use in the viral vector can be generated by mutagenesis (i.e., by insertions, deletions, or substitutions) of one of the aforementioned AAV caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned caps.

III. Expression Cassette and Vectors

Genomic sequences which are packaged into an AAV capsid and delivered to a host cell are typically composed of, at a minimum, a transgene and its regulatory sequences, and AAV inverted terminal repeats (ITRs). Both single-stranded AAV and self-complementary (sc) AAV are encompassed with the rAAV. The transgene is a nucleic acid coding sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences from AAV2. A shortened version of the 5' ITR, termed ΔITR, has been described in which the D-sequence and terminal resolution site (trs) are deleted. In other embodiments, the full-length AAV 5' and 3' ITRs are used. However, ITRs from other AAV sources may be selected. Where the source of the ITRs is from AAV2 and the AAV capsid is from another AAV source, the resulting vector may be termed pseudotyped. However, other configurations of these elements may be suitable.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

The regulatory control elements typically contain a promoter sequence as part of the expression control sequences, e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be used may be utilized in the vectors described herein.

Examples of constitutive promoters suitable for controlling expression of the therapeutic products include, but are not limited to chicken β-actin (CB) promoter, CB7 promoter, human cytomegalovirus (CMV) promoter, ubiquitin C promoter (UbC), the early and late promoters of simian virus 40 (SV40), U6 promoter, metallothionein promoters, EF1α promoter, ubiquitin promoter, hypoxanthine phosphoribosyl transferase (HPRT) promoter, dihydrofolate reductase (DHFR) promoter (Scharfmann et al., Proc. Natl. Acad. Sci. USA 88:4626-4630 (1991), adenosine deaminase promoter, phosphoglycerol kinase (PGK) promoter, pyruvate kinase promoter phosphoglycerol mutase promoter, the β-actin promoter (Lai et al., Proc. Natl. Acad. Sci. USA 86: 10006-10010 (1989)), the long terminal repeats (LTR) of Moloney Leukemia Virus and other retroviruses, the thymidine kinase promoter of Herpes Simplex Virus and other constitutive promoters known to those of skill in the art. Examples of tissue- or cell-specific promoters suitable for use in the present invention include, but are not limited to, endothelin-I (ET-I) and Flt-I, which are specific for endothelial cells, FoxJ1 (that targets ciliated cells).

Inducible promoters suitable for controlling expression of the therapeutic product include promoters responsive to exogenous agents (e.g., pharmacological agents) or to physiological cues. These response elements include, but are not limited to a hypoxia response element (HRE) that binds HIF-1α and β, a metal-ion response element such as described by Mayo et al. (1982, Cell 29:99-108); Brinster et al. (1982, Nature 296:39-42) and Searle et al. (1985, Mol. Cell. Biol. 5:1480-1489); or a heat shock response element such as described by Nouer et al. (in: Heat Shock Response, ed. Nouer, L., CRC, Boca Raton, Fla., ppl67-220, 1991).

In one embodiment, expression of the neutralizing antibody construct is controlled by a regulatable promoter that provides tight control over the transcription of the gene encoding the neutralizing antibody construct, e.g., a pharmacological agent, or transcription factors activated by a pharmacological agent or in alternative embodiments, physiological cues. Promoter systems that are non-leaky and that can be tightly controlled are preferred.

Examples of regulatable promoters which are ligand-dependent transcription factor complexes that may be used in the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.).

Still other promoter systems may include response elements including but not limited to a tetracycline (tet) response element (such as described by Gossen & Bujard (1992, Proc. Natl. Acad. Sci. USA 89:5547-551); or a hormone response element such as described by Lee et al. (1981, Nature 294:228-232); Hynes et al. (1981, Proc. Natl. Acad. Sci. USA 78:2038-2042); Klock et al. (1987, Nature 329:734-736); and Israel & Kaufman (1989, Nucl. Acids Res. 17:2589-2604) and other inducible promoters known in the art. Using such promoters, expression of the neutralizing antibody construct can be controlled, for example, by the Tet-on/off system (Gossen et al., 1995, Science 268:1766-9; Gossen et al., 1992, Proc. Natl. Acad. Sci. USA., 89(12): 5547-51); the TetR-KRAB system (Urrutia R., 2003, Genome Biol., 4(10):231; Deuschle U et al., 1995, Mol Cell Biol. (4):1907-14); the mifepristone (RU486) regulatable system (Geneswitch; Wang Y et al., 1994, Proc. Natl. Acad. Sci. USA., 91(17):8180-4; Schillinger et al., 2005, Proc. Natl. Acad. Sci. USA. 102(39):13789-94); and the humanized tamoxifen-dep regulatable system (Roscilli et al., 2002, Mol. Ther. 6(5):653-63).

In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,680, 6,479,653, 6,187,757, and 6,649,595, U.S. Publication No. 2002/0173474, U.S. Publication No. 200910100535, U.S. Pat. Nos. 5,834,266, 7,109,317, 7,485,441, 5,830,462, 5,869,337, 5,871,753, 6,011,018, 6,043,082, 6,046,047, 6,063,625, 6,140,120, 6,165,787, 6,972,193, 6,326,166, 7,008,780, 6,133,456, 6,150,527, 6,506,379, 6,258,823, 6,693,189, 6,127,521, 6,150,137, 6,464,974, 6,509,152, 6,015,709, 6,117,680, 6,479,653, 6,187,757, 6,649,595, 6,984,635, 7,067,526, 7,196,192, 6,476,200, 6,492,106, WO 94/18347, WO 96/20951, WO 96/06097, WO 97/31898, WO 96/41865, WO 98/02441, WO 95/33052, WO 99110508, WO 99110510, WO 99/36553, WO 99/41258, WO 01114387, ARGENT™ Regulated Transcription Retrovirus Kit, Version 2.0 (9109102), and ARGENT™ Regulated Transcription Plasmid Kit, Version 2.0 (9109/02), each of which is incorporated herein by reference in its entirety. The Ariad system is designed to be induced by rapamycin and analogs thereof referred to as "rapalogs". Examples of suitable rapamycins are provided in the documents listed above in connection with the description of the ARGENT™ system. In one embodiment, the molecule is rapamycin [e.g., marketed as Rapamune™ by Pfizer]. In another embodiment, a rapalog known as AP21967 [ARIAD] is used. Examples of these dimerizer molecules that can be used in the present invention include, but are not limited to rapamycin, FK506, FK1012 (a homodimer of FK506), rapamycin analogs ("rapalogs") which are readily prepared by chemical modifications of the natural product to add a "bump" that reduces or eliminates affinity for endogenous FKBP and/or FRAP. Examples of rapalogs include, but are not limited to such as AP26113 (Ariad), AP1510 (Amara, J. F., et al., 1997, Proc Natl Acad Sci USA, 94(20): 10618-23) AP22660, AP22594, AP21370, AP22594, AP23054, AP1855, AP1856, AP1701, AP1861, AP1692 and AP1889, with designed 'bumps' that minimize interactions with endogenous FKBP. Still other rapalogs may be selected, e.g., AP23573 [Merck].

Other suitable enhancers include those that are appropriate for a desired target tissue indication. In one embodiment, the expression cassette comprises one or more expression enhancers. In one embodiment, the expression cassette contains two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g., the chicken beta-actin intron. Other suitable introns include those known in the art, e.g., such as are described in WO 2011/126808. Examples of suitable polyA sequences include, e.g., rabbit binding globulin (rBG), SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence (see, e.g., M A Zanta-Boussif, et al, Gene Therapy (2009) 16: 605-619).

An AAV viral vector may include multiple transgenes. In certain situations, a different transgene may be used to encode each subunit of a protein (e.g., an immunoglobulin domain, an immunoglobulin heavy chain, an immunoglobulin light chain). In one embodiment, a cell produces the multi-subunit protein following infected/transfection with the virus containing each of the different subunits. In another embodiment, different subunits of a protein may be encoded by the same transgene. In this case, a single transgene includes the DNA encoding each of the subunits, with the DNA for each subunit separated by an internal ribozyme entry site (IRES) or a self-cleaving peptide (e.g., 2A). An IRES is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M L Donnelly, et al, (January 1997) J. Gen. Vivol., 78(Pt 1):13-21; S. Furler, S et al, (June 2001) Gene Ther., 8(11):864-873; H. Klump, et al., (May 2001) Gene Ther., 8(10):811-817. This 2A peptide is significantly smaller than IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

In addition to the elements identified above for the expression cassette, the vector also includes conventional control elements which are operably linked to the coding sequence in a manner which permits transcription, translation and/or expression of the encoded product (e.g., a neutralizing antibody or a portion thereof) in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate enhancer; transcription factor; transcription terminator; promoter; efficient RNA processing signals such as splicing and polyadenylation (polyA) signals; sequences that stabilize cytoplasmic mRNA, for example Woodchuck Hepatitis Virus (WHP) Posttranscriptional Regulatory Element (WPRE); sequences that enhance translation efficiency (i.e., Kozak consensus sequence); sequences that enhance protein stability; and when desired, sequences that enhance secretion of the encoded product.

In one embodiment, the regulatory sequences are selected such that the total rAAV vector genome is about 2.0 to about 5.5 kilobases in size. In one embodiment, it is desirable that the rAAV vector genome approximate the size of the native AAV genome. Thus, in one embodiment, the regulatory sequences are selected such that the total rAAV vector genome is about 4.7 kb in size. In another embodiment, the total rAAV vector genome is less about 5.2 kb in size. The size of the vector genome may be manipulated based on the size of the regulatory sequences including the promoter, enhancer, intron, poly A, etc. See, Wu et al, Mol Ther, January 2010 18(1):80-6, which is incorporated herein by reference.

Thus, in one embodiment, an intron is included in the vector. Suitable introns include chicken beta-actin intron, the human beta globin IVS2 (Kelly et al, Nucleic Acids Research, 43(9):4721-32 (2015)); the Promega chimeric intron (Almond, B. and Schenborn, E. T. A Comparison of pCI-neo Vector and pcDNA4/HisMax Vector); and the hFIX intron. Various introns suitable herein are known in the art and include, without limitation, those found at bpg.utoledo.edu/~afedorov/lab/eid.html, which is incorporated herein by reference. See also, Shepelev V., Fedorov A. Advances in the Exon-Intron Database. Briefings in Bioinformatics 2006, 7: 178-185, which is incorporated herein by reference.

Several different viral genomes were generated in the studies described herein. However, it will be understood by the skilled artisan that other genomic configurations, including other regulatory sequences may be substituted for the promoter, enhancer and other coding sequences may be selected. Examples of vector genomes and expression cassettes encoding the immunoglobulin domains and/or fusion proteins described herein are provided, e.g., in SEQ ID NO: 5; SEQ ID NO: 14, SEQ ID NO: 15, SEQ ID NO: 19, SEQ ID NO: 20, SEQ ID NO: 21, and SEQ ID NO: 31. Suitably, these illustrative vector genomes include vector elements, including a promoter (e.g., chicken beta-actin, UBC, or TBG), an intron (e.g., SV40 intron or a chimeric intron), a 5' UTR sequence (e.g., c-myc), a Kozak sequence, a poly A (e.g., SV40, bovine growth hormone, or rabbit globin). In certain embodiments, an IRES or a furin, furin/F2A, or both, are included in an expression cassette. It will be understood that other vector elements may be selected.

IV. rAAV Vector Production

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art.

Methods of preparing AAV-based vectors (e.g., having an AAV9 or another AAV capsid) are known. See, e.g., US Published Patent Application No. 2007/0036760 (Feb. 15, 2007), which is incorporated by reference herein. The invention is not limited to the use of AAV9 or other clade F AAV amino acid sequences, but encompasses peptides and/or proteins containing the terminal β-galactose binding generated by other methods known in the art, including, e.g., by chemical synthesis, by other synthetic techniques, or by other methods. The sequences of any of the AAV capsids provided herein can be readily generated using a variety of techniques. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well-known solid phase peptide synthesis methods (Merrifield, (1962) *J. Am. Chem. Soc.*, 85:2149; Stewart and Young, Solid Phase Peptide Synthesis (Freeman, San Francisco, 1969) pp. 27-62). These methods may involve, e.g., culturing a host cell which contains a nucleic acid sequence encoding an AAV capsid; a functional rep gene; a minigene composed of, at a minimum, AAV inverted terminal repeats (ITRs) and a transgene; and sufficient helper functions to permit packaging of the minigene into the AAV capsid protein. These and other suitable production methods are within the knowledge of those of skill in the art and are not a limitation of the present invention.

The components required to be cultured in the host cell to package an AAV minigene in an AAV capsid may be provided to the host cell in trans. Alternatively, any one or more of the required components (e g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

These rAAVs are particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art. Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J. Gene Med.* 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

In one embodiment, the expression cassettes described herein are engineered into a genetic element (e.g., a shuttle plasmid) which transfers the immunoglobulin construct sequences carried thereon into a packaging host cell for production a viral vector. In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, N.Y. (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant AAV described herein may be generated using techniques which are known. See, e.g., WO 2003/

042397; WO 2005/033321, WO 2006/110689; U.S. Pat. No. 7,588,772 B2. Such a method involves culturing a host cell which contains a nucleic acid sequence encoding an AAV capsid; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture useful for producing a recombinant AAVhu68 is provided. Such a cell culture contains a nucleic acid which expresses the AAVhu68 capsid in the host cell; a nucleic acid molecule suitable for packaging into the AAVhu68 capsid, e.g., a vector genome which contains AAV ITRs and a non-AAV nucleic acid sequence encoding a gene product operably linked to sequences which direct expression of the product in a host cell; and sufficient AAV rep functions and adenovirus helper functions to permit packaging of the nucleic acid molecule into the recombinant AAVhu68 capsid. In one embodiment, the cell culture is composed of mammalian cells (e.g., human embryonic kidney 293 cells, among others) or insect cells (e.g., baculovirus). Optionally the rep functions are provided by an AAV other than hu68. In certain embodiments, at least part of the rep functions are from AAVhu68. Optionally, the rep and cap sequences are on the same genetic element in the cell culture. There may be a spacer between the rep sequence and cap gene. Optionally, the spacer is atgacttaaaccaggt (SEQ ID NO: 33). Any of these AAVhu68 or mutant AAV capsid sequences may be under the control of exogenous regulatory control sequences which direct expression thereof in a host cell.

In one embodiment, cells are manufactured in a suitable cell culture (e.g., HEK 293 cells). Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in International Patent Application No. PCT/US2016/065970, filed Dec. 9, 2016 and its priority documents, U.S. Patent Application Nos. 62/322,071, filed Apr. 13, 2016 and 62/226,357, filed Dec. 11, 2015 and entitled "Scalable Purification Method for AAV9", each of which is incorporated by reference herein. Purification methods for AAV8, International Patent Application No. PCT/US2016/065976, filed Dec. 9, 2016 and is priority documents U.S. Patent Application Nos. 62/322,098, filed Apr. 13, 2016 and 62/266,341, filed Dec. 11, 2015, and rh10, International Patent Application No. PCT/US16/66013, filed Dec. 9, 2016 and its priority documents, U.S. Patent Application No. 62/322,055, filed Apr. 13, 2016 and 62/266,347, entitled "Scalable Purification Method for AAVrh10", also filed Dec. 11, 2015, and for AAV1, International Patent Application No. PCT/US2016/065974, filed Dec. 9, 2016 and its priority documents U.S. Patent Application Nos. 62/322,083, filed Apr. 13, 2016 and 62/26,351, for "Scalable Purification Method for AAV1", filed Dec. 11, 2015, are all incorporated by reference herein.

To calculate empty and full particle content, vp3 band volumes for a selected sample (e.g., in examples herein an iodixanol gradient-purified preparation where number of GC=number of particles) are plotted against GC particles loaded. The resulting linear equation (y=mx+c) is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL–GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy* (1999) 6:1322-1330; and Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Vivol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, Calif.) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

Additionally, another example of measuring empty to full particle ratio is also known in the art. Sedimentation velocity, as measured in an analytical ultracentrifuge (AUC) can detect aggregates, other minor components as well as providing good quantitation of relative amounts of different particle species based upon their different sedimentation coefficients. This is an absolute method based on fundamental units of length and time, requiring no standard molecules as references. Vector samples are loaded into cells with 2-channel charcoal-epon centerpieces with 12 mm optical path length. The supplied dilution buffer is loaded into the reference channel of each cell. The loaded cells are then placed into an AN-60Ti analytical rotor and loaded into a Beckman-Coulter ProteomeLab XL-I analytical ultracentrifuge equipped with both absorbance and RI detectors. After full temperature equilibration at 20° C. the rotor is brought to the final run speed of 12,000 rpm. $A_{280}$ scans are recorded approximately every 3 minutes for ~5.5 hours (110 total scans for each sample). The raw data is analyzed using the c(s) method and implemented in the analysis program SEDFIT. The resultant size distributions are graphed and the peaks integrated. The percentage values associated with each peak represent the peak area fraction of the total area under all peaks and are based upon the raw data generated at 280 nm; many labs use these values to calculate empty:full particle ratios. However, because empty and full particles have different extinction coefficients at this wavelength, the raw data can be adjusted accordingly. The ratio of the empty particle and full monomer peak values both before and after extinction coefficient-adjustment is used to determine the empty-full particle ratio.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay. Quantification also can be done using ViroCyt or flow cytometry.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAVhu68 particles having packaged genomic sequences from genome-deficient AAVhu68 intermediates involves subjecting a suspension comprising recombinant AAVhu68 viral particles and AAVhu68 capsid intermediates to fast performance liquid chromatography, wherein the AAVhu68 viral particles and AAVhu68 intermediates are bound to a strong anion exchange resin equilibrated at a pH of 10.2, and subjected to a salt gradient while monitoring eluate for ultraviolet absorbance at about 260 and about 280. Although less optimal for rAAVhu68, the pH may be in the range of about 10.0 to 10.4. In this method, the AAVhu68 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/hu68 serotype. Under these ionic conditions, a significant percentage of residual cellular DNA and proteins flow through the column, while AAV particles are efficiently captured.

V. Compositions and Uses

Provided herein are compositions containing at least one rAAV stock (e.g., an rAAVhu68 stock) and an optional carrier, excipient and/or preservative. An rAAV stock refers to a plurality of rAAV vectors which are the same, e.g., such as in the amounts described below in the discussion of concentrations and dosage units.

As used herein, the term "AAVhu68.JAb" refers to a rAAV having an AAVhu68 capsid as defined herein which has packaged therein a vector genome encoding the anti-influenza antibody (Ab) domains. As used herein, the term "AAV9.JAb" refers to a rAAV having an AAV9 capsid as defined herein which has packaged therein a vector genome encoding the anti-influenza antibody (Ab) domains. In certain embodiments, a single rAAV stock encodes all four of the immunoglobulin regions of SEQ ID NO: 1, SEQ ID NO: 2, SEQ ID NO: 3 and SEQ ID NO:4, optionally in one or more fusion protein(s). The vector genomes may include any of those illustrated herein, e.g., in SEQ ID NO: 19; SEQ ID NO: 15, SEQ ID NO: 14, SEQ ID NO: 5 and SEQ ID NO: 31, or another vector genome engineered as described herein.

In certain embodiments, a composition may contain at least a second, different rAAV stock. This second vector stock may vary from the first by having a different AAV capsid and/or a different vector genome. In certain embodiments, a composition as described herein may contain a different vector expressing an expression cassette as described herein, or another anti-influenza component (e.g., an antibody construct, another biologic, and/or a small molecule drug).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery), lung, heart, eye, kidney), oral, inhalation, intranasal, intrathecal, intratracheal, intraarterial, intraocular, intravenous, intramuscular, subcutaneous, intradermal, and other parenteral routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 25 to about 1000 microliters to about 5 mL of aqueous suspending liquid containing doses of from about $10^9$ to $4 \times 10^{14}$ GC of AAV vector. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

The replication-defective virus compositions can be formulated in dosage units to contain an amount of replication-defective virus that is in the range of about $10^9$ GC to about $10^{16}$ GC (to treat an average subject of 70 kg in body weight) including all integers or fractional amounts within the range, and preferably $10^{12}$ GC to $10^{14}$ GC for a human patient. In one embodiment, the compositions are formulated to contain at least $10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $10^{10}$ to about $10^{12}$ GC per dose including all integers or fractional amounts within the range. In one embodiment, for human application the dose can range from $10^9$ to about $7 \times 10^{13}$ GC per dose including all integers or fractional amounts within the range. In one embodiment, for human application the dose ranges from $6.25 \times 10^{12}$ GC to $5.00 \times 10^{13}$ GC. In a further embodiment, the dose is about $6.25 \times 10^{12}$ GC, about $1.25 \times 10^{13}$ GC, about $2.50 \times 10^{13}$ GC, or about $5.00 \times 10^{13}$ GC. In certain embodiment, the dose is divided into one half thereof equally and administered to each nostril. In certain embodiments, for human application the dose ranges from $6.25 \times 10^{12}$ GC to $5.00 \times 10^{13}$ GC administered as two aliquots of 0.2 ml per nostril for a total volume delivered in each subject of 0.8 ml.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is between about 700 and 1000 µL.

In certain embodiments, the recombinant vectors may be dosed intranasally by using two sprays to each nostril. In one embodiment, the two sprays are administered by alternating to each nostril, e.g., left nostril spray, right nostril spray, then left nostril spray, right nostril spray. In certain embodiments, there may be a delay between alternating sprays. For example, each nostril may receive multiple sprays which are separated by an interval of about 10 to 60 seconds, or 20 to 40 seconds, or about 30 seconds, to a few minutes, or longer. Such sprays may deliver, e.g., about 150 µL to 300 µL, or about 250 µL in each spray, to achieve a total volume dosed of about 200 µL to about 600 µL, 400 µL to 700 µL, or 450 µL to 1000 µL.

In certain embodiment, the recombinant AAV vector may be dosed intranasally to achieve a concentration of 5-20 ng/ml of the expression product of the transgene (e.g., the neutralizing antibody construct, the JAb210a MDAb) as measured in a nasal wash solution post-dosing, e.g., one week to four weeks, or about two weeks after administration of the vector. Methods of acquiring the nasal wash solution in the subjected as well as methods of quantification of the expression product of the transgene are conventional. See, e.g., Examples 18 and 19.

For other routes of administration, e.g., intravenous or intramuscular, dose levels would be higher than for intranasal delivery. For example, such suspensions may be volumes doses of about 1 mL to about 25 mL, with doses of up to about $2.5 \times 10^{15}$ GC.

The above-described recombinant vectors may be delivered to host cells according to published methods. The rAAV, preferably suspended in a physiologically compatible carrier, may be administered to a human or non-human mammalian patient. In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intranasal administration. In another example, the composition is formulated for intramuscular administration. In still another example, the composition is formulated for intravenous administration. In yet another example, the composition is formulated for intraperitoneal administration.

In one embodiment, a composition containing the viral vectors encoding the anti-pathogen construct (e.g., a neutralizing antibody construct) is delivered intranasally as liquid (e.g., atomized, aerosol, spray, etc), to the subject at a relatively low instillation volume in order to minimize lung transduction. In one embodiment, the delivery of low volume AAV restricts more than about 70%, more than 80%, more than 90%, more than about 95%, or more than about 99% of transduction (as measured by expression) to the nasal epithelium. In another embodiment, the viral vectors may be delivered locally through a means other than an intranasal spray, e.g., intranasal injection.

In certain embodiments, the intranasal delivery device provides a spay atomizer which delivers a mist of particles having an average size range of about 30 microns to about 100 microns in size. In certain embodiments, the average size range is about 10 microns to about 50 microns. Suitable devices have been described in the literature and some are commercially available, e.g., the LMA MAD NASAL™ (Teleflex Medical; Ireland); Teleflex VaxINator™ (Teleflex Medical; Ireland); Controlled Particle Dispersion® (CPD) from Kurve Technologies. See, also, PG Djupesland, Drug Deliv and Transl. Res (2013) 3: 42-62. In certain embodiments, the particle size and volume of delivery is controlled in order to preferentially target nasal epithelial cells and minimize targeting to the lung. In other embodiments, the mist of particles is about 0.1 micron to about 20 microns, or less, in order to deliver to lung cells. Such smaller particle sizes may minimize retention in the nasal epithelium.

Any suitable method or route can be used to administer an AAV-containing composition as described herein, and optionally, to co-administer other active drugs or therapies in conjunction with the AAV-mediated antibodies described herein. Routes of administration include, for example, systemic, oral, intravenous, intraperitoneal, subcutaneous, or intramuscular administration.

In one embodiment, a frozen composition is provided which contains an rAAV in a buffer solution as described herein, in frozen form. Optionally, one or more surfactants (e.g., Pluronic F68), stabilizers or preservatives is present in this composition. Suitably, for use, a composition is thawed and titrated to the desired dose with a suitable diluent, e.g., sterile saline or a buffered saline.

Optionally, a composition described herein may be used in combination with other anti-viral medications and/or vaccines against other viral targets, including other influenza vaccines, including: Influenza A, Influenza B, and Influenza C. The type A influenza viruses are the most virulent human pathogens. The serotypes of influenza A which have been associated with pandemics include, H1N1, which caused Spanish Flu in 1918, and Swine Flu in 2009; H2N2, which caused Asian Flu in 1957; H3N2, which caused Hong Kong Flu in 1968; H5N1, which caused Bird Flu in 2004; H7N7; H1N2; H9N2; H7N2; H7N3; and H10N7. Broadly neutralizing antibodies against influenza A have been described. As used herein, a "broadly neutralizing antibody" refers to a neutralizing antibody which can neutralize multiple strains from multiple subtypes. For example, CR6261 [The Scripps Institute/Crucell] has been described as a monoclonal antibody that binds to a broad range of the influenza virus including the 1918 "Spanish flu" (SC1918/H1) and to a virus of the H5N1 class of avian influenza that jumped from chickens to a human in Vietnam in 2004 (Viet04/H5). CR6261 recognizes a highly conserved helical region in the membrane-proximal stem of hemagglutinin, the predominant protein on the surface of the influenza virus. This antibody is described in WO 2010/130636, incorporated by reference herein. Another neutralizing antibody, F10 [XOMA Ltd] has been described as being useful against H1N1 and H5N1 (Sui, Jianhua, et al. "Structural and functional bases for broad-spectrum neutralization of avian and human influenza A viruses." Nature structural & molecular biology 16.3 (2009): 265-273). Other antibodies against influenza, e.g., Fab28 and Fab49, may be selected. See, e.g., WO 2010/140114 and WO 2009/115972, which are incorporated by reference. Still other antibodies, such as those described in WO 2010/010466, US Published Patent Publication US/2011/076265, and WO 2008/156763, may be readily selected.

Methods for using these rAAV, e.g., for passive immunization are described, e.g., in WO 2012/145572. Other methods of delivery and uses will be apparent to one of skill in the art. For example, a regimen as described herein may comprise, in addition to one or more of the combinations described herein, further combination with one or more of a biological drug, a small molecule drug, a chemotherapeutic agent, immune enhancers, radiation, surgery, and the like. A biological drug as described herein, is based on a peptide, polypeptide, protein, enzyme, nucleic acid molecule, vector (including viral vectors), or the like.

In a combination therapy, the AAV-delivered immunoglobulin construct described herein is administered before, during, or after commencing therapy with another agent, e.g., anti-viral therapy, antibiotics, as well as any combination thereof, i.e., before and during, before and after, during and after, or before, during, and after commencing the therapy. For example, the AAV can be administered between 8 hours to 30 days, in certain embodiments, it may be about 12 hours, 1 day, about 3 days, about 3 to 30 days, or 5 to 12 days before commencing therapy.

EXAMPLES

The following examples are illustrative only and are not a limitation on the invention described herein.

Some abbreviations used herein are illustrated below: AAV, Adeno-associated virus; BALF, Bronchoalveolar lavage fluid; CB7, chicken β-actin promoter with cytomegalovirus enhancer elements; cDNA, complementary DNA; GC, Genome copy; HRP, Horseradish peroxidase; IN, Intranasal; IP, Intraperitoneal; ITRs, Inverted terminal repeats; kg, kilogram; ORF, Open reading frame; polyA, Polyadenylation; and rBG, rabbit β-globin.

To develop an adeno-associated virus (AAV) vector-based prophylaxis regimen against influenza A and B as an alternative to the traditional influenza vaccine in the setting of seasonal and/or pandemic influenza infections, novel AAV vectors were discovered with an enhanced performance profile in the airway epithelium. Using highly specialized molecular techniques designed to detect and isolate endogenous AAVs from a variety of human and non-human primate tissues, a novel AAV, AAVhu68, was isolated from human tissue. This vector exhibits a favorable phenotype that includes improved manufacturability and enhanced transduction across many different tissue types. Using AAVhu68 as an exemplified candidate AAV vector serotype, the influenza antibody expression cassette was optimized Only one AAV vector that encodes a single open reading frame for the expression of a multi-domain Ab (MDAb) was tested.

Example 1

Novel Clade F AAV AAVhu68

Tissue DNA was extracted from human tissue samples as PCR template with QIAamp columns (Qiagen) following the manufacturer's recommendations with the following modifications. Q5 DNA polymerase (Q5® Hot Start High-Fidelity 2× Master Mix, NEB) was chosen for its extraordinary high fidelity and robust efficiency to recover full length VP1 gene of potential AAVs in the samples with as described by Gao, et al [Proc Natl Acad Sci USA, 2002 Sep. 3, 99(18): 11854-11859 (Epub 2002 Aug. 21)] with the primer set modified as follows: in the place of the AV1NS, primer, prm504, [GCTGCGTCAACTGGACCAATGAGAAC, SEQ ID NO: 28] was used and in the place of reverse primer AV2CAS, prm505 [CGCAGAGACCAAAGTTCAACTGAAACGA, SEQ ID NO: 29], was used.

The PCR conditions were modified as follows:

| | μL |
|---|---|
| Water | 9 |
| prm504 | 1.25 |
| prm505 | 1.25 |
| template | 1 |
| 2X Q5 | 12.5 |

PCR program

| | Time (seconds) | Cycle(s) |
|---|---|---|
| 98° | 30 | 1 |
| 98° | 10 | 50 |
| 59° | 10 | |

-continued

| | Time (seconds) | Cycle(s) |
|---|---|---|
| 72° | 93 | |
| 72° | 120 | 1 |

The bands of 3 kb from the PCR were cut out from the gel; DNA was extracted with QIAquick Gel Extraction Kit (Qiagen) and cloned into Zero Blunt® TOPO® PCR Cloning Kit (Thermo Fisher Scientific). Plasmids were sequenced to get the full length of AAV VP1 gene. For most of the samples, at least three plasmids were fully sequenced and consensus sequences were drawn as the final AAV sequence for that sample.

The acquired nucleic acid sequence encoding the vp1 capsid protein of AAVhu68 is provided in SEQ ID NO: 18. See, also, FIGS. 1B-1D. The vp1 amino acid sequence of AAVhu68 is provided in FIG. 1A and SEQ ID NO: 16. Compared to AAV9 (SEQ ID NO:17), AAVhu31 (SEQ ID NO: 34) and AAVhu32 (SEQ ID NO: 35), two mutations (A67E and A157V) were identified critical in AAVhu68 (circled in FIG. 1A).

pAAV2/hu68 trans plasmid was then made by loading the VP1 gene of AAVhu68 into a pAAV2/9 backbone in the place of the AAV9 VP1 gene in order to assess packaging efficiency, yield, and transduction properties. The pAAV2/9 plasmid contains AAV2 5' and 3' ITRs flanking the capsid gene and is available from the Penn Vector Core [University of Pennsylvania, Phila, Pa. US, pennvectorcore.med.upenn.edu].

Example 2

Yield of AAVhu68 Vectors

AAVhu68 and AAV9 vectors carrying various transgene cassettes, such as GFP and LacZ were generated and evaluated. Each of the vectors was generated using the triple transfection technique in 293 cells, as described by Gao et al [Gao, Guang-Ping, et al. "Novel adeno-associated viruses from rhesus monkeys as vectors for human gene therapy." Proceedings of the National Academy of Sciences 99.18 (2002): 11854-11859.].

a. Production of pAAVhu68 Trans Plasmid

The nucleic acid sequence encoding the vp1 capsid protein is provided in SEQ ID NO: 18.

pAAV2/hu68 trans plasmid was made by loading the VP1 gene of AAVhu68 into a pAAV2/9 backbone in the place of the AAV9 VP1 gene in order to assess packaging efficiency, yield, and transduction properties. The pAAV2/9 plasmid contains AAV2 5' and 3' ITRs flanking the capsid gene and is available from the Penn Vector Core [University of Pennsylvania, Phila, Pa. US, pennvectorcore.med.upenn.edu].

b. Yield of AAVhu68 Vectors 293 cells were cultured and maintained in Eagle's Minimum Essential Medium with 10% of fetal bovine serum under the atmosphere with 5% $CO_2$ at 37° C. Transfections were performed as described by Gao et al [Gao, Guang-Ping, et al. "Novel adeno-associated viruses from rhesus monkeys as vectors for human gene therapy." Proceedings of the National Academy of Sciences 99.18 (2002): 11854-11859.] with the vector plasmid replaced by pAAV2/hu68 or pAAV2/9. The transfected cells were further cultured in 6-well plates. Total lysate of the cells as well as the supernatant was collected for virus quantification via TaqMan (Applied Biosystems) analysis by using probes and primers targeting polyA regions as described in Gao et al [Gao, Guangping, et al. "Purification of recombinant adeno-associated virus vectors by column chromatography and its performance in vivo." Human gene therapy 11.15 (2000): 2079-2091.]. The yields of six pAAV2/9 plasmids and six pAAV2/hu68 plasmids were compared in 6-well plate, head to head, in terms of both supernatant titer and the total lysate titer. Each plasmid was from an individual bacteria colony.

The yield of AAVhu68 was found to be similar to that of AAV9 in terms of total lysate. However, in the supernatant, the yield of AAVhu68 was significantly higher than that of AAV9. Thus, AAVhu68 was demonstrated as a better vector compared to AAV9 in terms of scalable production since supernatant is preferred for the manufacturing scale up.

c. Comparison of Different AAV Capsids with Antibody Constructs

In one study, there was there was an increased yield for the AAVhu68 vector (Table 1).

TABLE 1

Yield of AAV1, AAV9 and AAVhu68 vectors.

| Vector | Total Yield (GC) |
|---|---|
| AAV1.CB7.CI.hJAb | $1.03 \times 10^{13}$ |
| AAV9.CB7.CI.hJAb | $2.89 \pm 0.08 \times 10^{13}$ |
| AAVhu68.CB7.CI.hJAb | $3.40 \times 10^{13}$ |

Example 3

AAVhu68-Mediated Intranasal Administration to BALB/c Mice to Protect Against Nasal Challenge with A/Puerto Rico/8/34 (PR8-MTS)

The purpose of this study was to evaluate and compare the protective efficacy of AAV1.CB7.hJAb, AAV9.CB7.hJAb and AAVhu68.CB7.hJAb vectors, all of which were designed to confer prophylaxis against influenza A (A/Puerto Rico/8/34) when administered intranasally (IN) in mice. For all studies, female BALB/c mice (6 weeks old) were purchased from the Jackson Laboratory (Bar Harbor, Me.) and housed at the Animal Facility of the Translational Research Laboratories at the University of Pennsylvania. All animal procedures described here were approved by the Institutional Animal Care and Use Committee of the University of Pennsylvania.

Figure 2B:
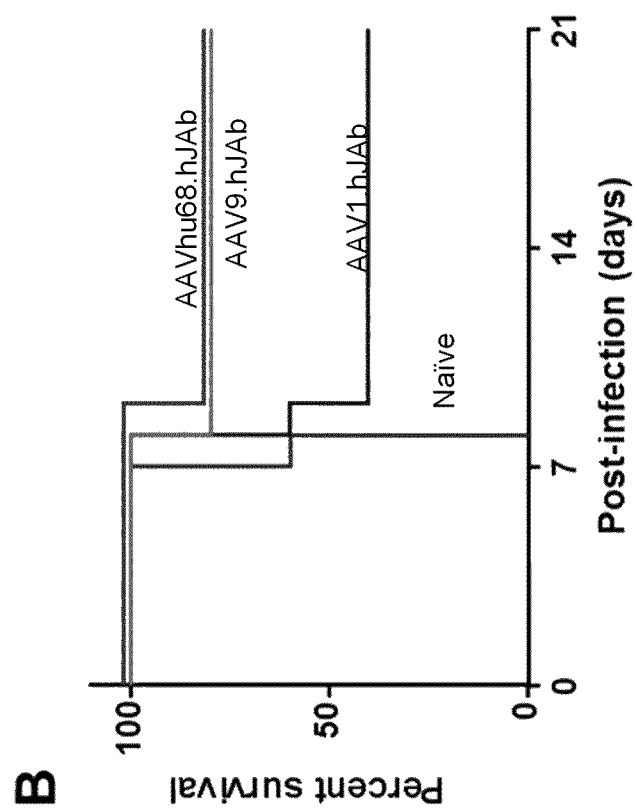
Figure 2A:
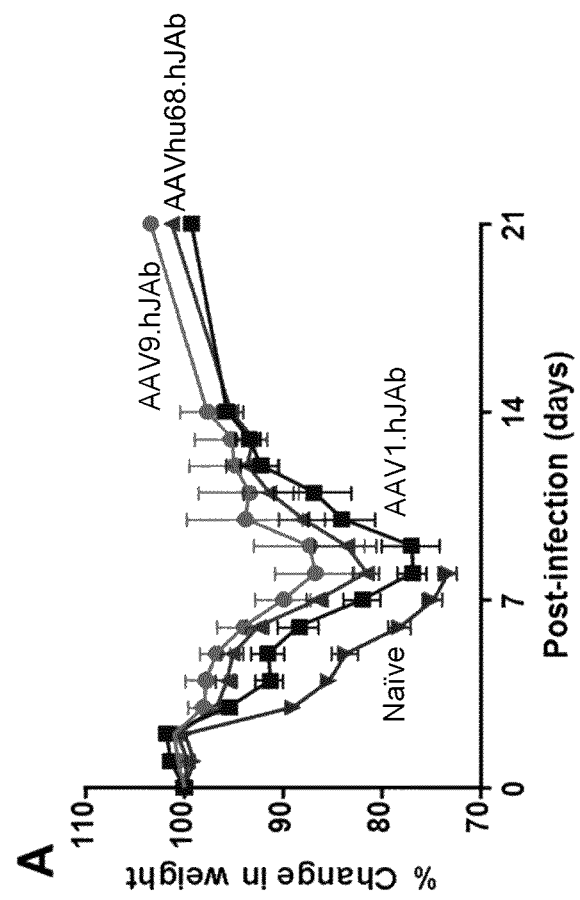

Anaesthetized mice were suspended by their dorsal incisors and they received intranasally (IN) $10^9$ genome copies (GC) of each AAV vector diluted in PBS to a total volume of 51 μl delivered as three aliquots of 17 μl. The challenge studies occurred seven days after vector administration. Anaesthetized mice were suspended by their dorsal incisors and administered IN 51 μl of influenza A/Puerto Rico/8/34 (i.e., PR8) ($5LD_{50}$) delivered as three aliquots of 17 μl. Mice were weighed once daily for the first 14 days. Any mice showing signs of distress or ≥30% weight loss were euthanized. Surviving mice were sacrificed 21 days post-challenge. The results are shown in FIGS. 2A-2B.

In summary, IN delivery of $10^9$ GC of AAV1.CB7.hJAb conferred partial protection (40%) against PR8 challenge coupled with significant weight loss (>20%). In contrast, IN delivery of AAV9.CB7.hJAb and AAVhu68.CB7.hJAb at a dose of $10^9$ GC conferred 80% protection against PR8 challenge which was accompanied by a weight loss of 10-20%.

Example 4

AAVhu68 Vector Administration to BALB/c Mice to Protect Against Nasal Challenge with B/Lee/40

The purpose of this study was to evaluate and compare the protective efficacy of AAV1.CB7.hJAb, AAV9.CB7.hJAb and AAVhu68.CB7.hJAb vectors, all of which were designed to confer prophylaxis against influenza B (B/Lee/40) when administered IN in mice.

Anaesthetized mice were suspended by their dorsal incisors and they received IN $10^9$ GC of each AAV vector diluted in PBS to a total volume of 51 µl delivered as three aliquots of 17 µl.

Figure 3A:
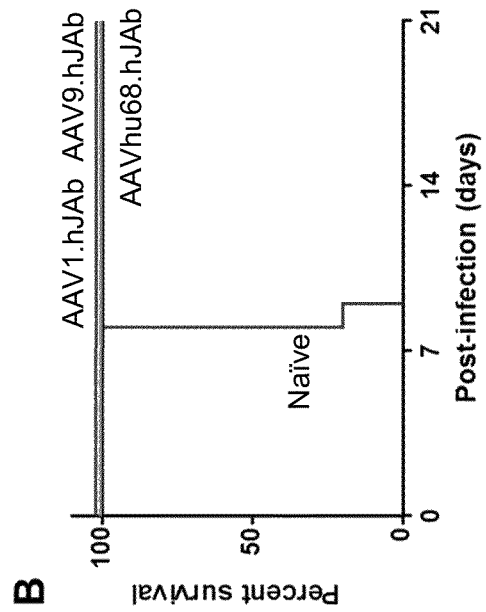
Figure 3B:
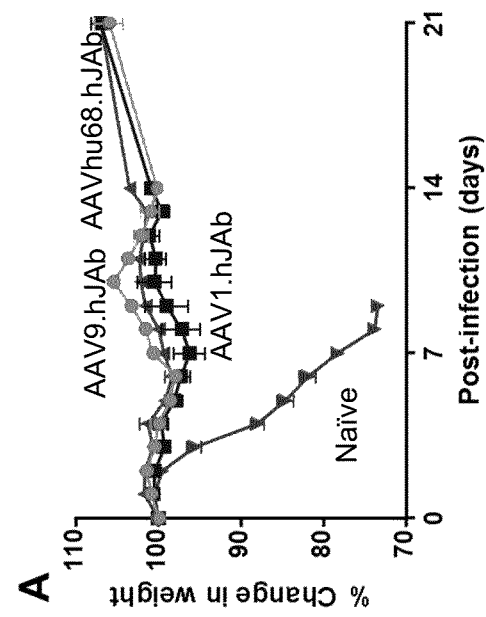
Figure 4:
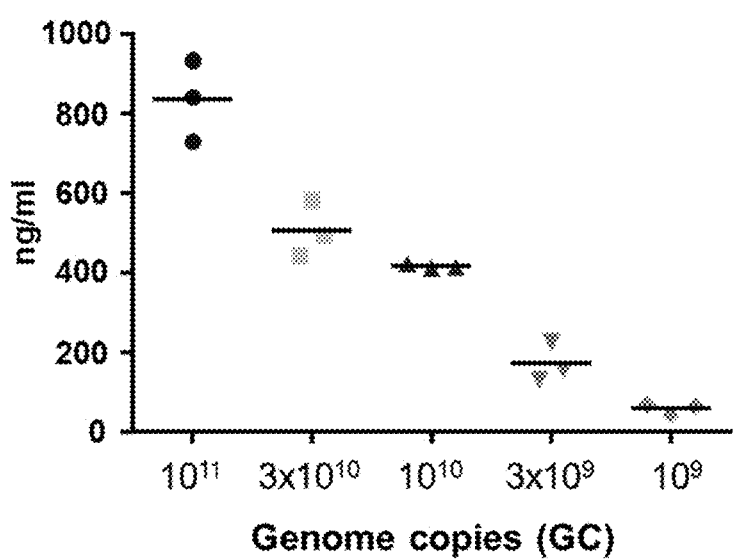

The challenge studies occurred seven days after vector administration. Anaesthetized mice were suspended by their dorsal incisors and administered IN 51 µl of influenza B/Lee/40 ($5LD_{50}$) delivered as three aliquots of 17 µl. Mice were weighed once daily for the first 14 days. Any mice showing signs of distress or ≥30% weight loss were euthanized. Surviving mice were sacrificed 21 days post-challenge. The results are shown in FIGS. 3A-3B.

In brief, IN delivery of $10^9$ GC of AAV1.CB7.hJAb, AAV9.CB7.hJAb or AAVhu68.CB7.hJAb conferred full protection against IN challenge with B/Lee/40 coupled with no significant weight loss throughout the course of the challenge.

Example 5

Expression Profile of AAVhu68-Mediated Expression of hJAb in the BronchoAlveolar Lavage Fluid (BALF) of BALB/c Mice The purpose of this study was to evaluate the level of hJAb expression in the BALF when varying doses of AAVhu68.CB7.hJAb were delivered IN to BALB/c mice.

Mice were delivered IN AAVhu68.CB7.hJAb vector at doses ranging from $10^9$ GC to $10^{11}$ GC. The mice were necropsied seven days later and the BALF collected in 500 µl of PBS. A protein A ELISA was used to quantify the amount of Ab as follows. ELISA plates were coated with protein A. Following an overnight incubation, the plates were washed with 0.05% Tween-20/PBS and blocked. BALF samples were diluted in PBS and added to the plate for 1 hour at 37° C. Binding was detected using a biotin-SP-AffiniPure goat anti-human IgG Fcg-specific Ab (Jackson ImmunoResearch Laboratories, West Grove, Pa.) and a streptavidin-HRP conjugate (Abcam, Cambridge, Mass.). Plates were developed with TMB substrate (Sigma-Aldrich, St. Louis, Mo.). The results are shown in FIG. 4.

Significant expression of hJAb was detected in the BALF of mice seven days after IN delivery of AAVhu68.CB7.hJAb. As expected, expression of hJAb in the BALF of vector-treated mice increased as vector doses increased from $10^9$ GC to $10^{11}$ GC.

Example 6

Determination of the Minimum Effective Dose (MED) of AAVhu68.CB7.JAb210a for Protection Against Influenza A or Influenza B The purpose of this study was to determine the MED of the AAVhu68.CB7.JAb210a vector required for prophylaxis against influenza A or B.

BALB/c mice were given IN AAVhu68.JAb210a vector at doses ranging from $3\times10^8$ GC to $10^{10}$ GC diluted in PBS to a total volume of 51 μl and challenged seven days later (noted here as day 0) with 5 $LD_{50}$ of PR8 or B/LEE/40 and weighed daily for the duration of the study (21 days). Percentage weight was calculated based on weight at day of infection.

Mice were given IN AAVhu68.CB7. JAb210a vector at doses ranging from $10^7$ GC to $10^{11}$ GC in 51 μl, as described previously. The challenge studies occurred seven days after vector administration. Mice were challenged IN with $5LD_{50}$ of either influenza A (PR8) (FIGS. 5A and 5B) or influenza B (B/Lee/40) (FIGS. 6A and 6B) and weighed daily.

Effective protection against PR8 challenge, which was accompanied by no loss of animals or no weight loss was achieved with the $10^9$ GC dose of AAVhu68.CB7.CI.JAb210a.rBG vector as shown in FIGS. 5A and 5B. Survival that was accompanied by significant weight loss was achieved with the $3\times10^8$ GC dose of AAVhu68.CB7.CI.JAb210a.rBG vector as shown in FIGS. 5A and 5B.

Effective protection against B/Lee/40 challenge, which was accompanied by no loss of animals and no weight loss was achieved with the $10^9$ GC dose of AAVhu68.CB7.CI.JAb210a.rBG vector as shown in FIGS. 6A and 6B. Survival that was accompanied by significant weight loss was achieved with the $3\times10^8$ GC dose of AAVhu68.CB7.CI.JAb210a.rBG vector as shown in FIGS. 6A and 6B.

In conclusion, the MED of the AAVhu68.CB7. JAb210a for protection against PR8 is $10^9$ GC. Furthermore, the dose of AAVhu68.CB7. JAb210a that confers full protection against PR8 with no accompanied weight loss is $3\times10^9$ GC.

For protection against B/Lee/40, the MED of the AAVhu68.CB7. JAb210a is $3\times10^8$ GC, which is a significant improvement over a combination therapy which is a mixture of AAV9.FI6 and AAV9.CR8033 as described in WO 2016/200543, published 15 Dec. 2016, which had an MED against B/Lee/40 of $10^9$ GC. The dose of AAVhu68.CB7. JAb210a that confers full protection against B/Lee/40 with no accompanied weight loss is $10^9$ GC.

Example 7

Codon Optimization of hJAb for Improved Expression In Vivo

The purpose of this study was to further improve the proven efficacy of AAV-mediated hJAb expression by achieving preferential expression of hJAb from the cells of the airway epithelium using codon optimization schemas predicted to improve expression of hJAb from the cells that line the airway. Several different codon optimization schemas were used to improve expression of hJAb in airway in vivo. In addition to assessment of its potency in influenza challenge studies, the yield of vector production was also evaluated. Codon optimization resulted in ~20% higher yield of AAVhu68.CB7.CI.JAb210a compared to the parental AAVhu68.CB7.hJAb. Additionally, AAVhu68.CB7.CI.JAb210a was evaluated for protection against influenza A and B in a series of challenge studies designed to (a) establish the MED for protection against IN challenge with either influenza A or B (b) assess the onset of protection conferred by the AAVhu68.CB7.CI.JAb210a vector and to (c) evaluate the ability of the AAVhu68.CB7.CI.JAb210a vector to be effectively readministered in the presence of serum-circulating AAVhu68-specific NAb.

Example 8

Rapid Onset of AAVhu68.CB7.CI.JAb210a-Mediated Protection Against Influenza A or B Infection The purpose of this study was to determine the onset of effective protection against influenza A (PR8) or B (B/Lee/40) by the AAVhu68.CB7.CI.JAb210a vector following IN delivery in mice.

BALB/c mice were given IN AAVhu68.CB7.CI.JAb210a vector at $10^9$ GC or $10^{10}$ GC diluted in PBS to a total volume of 51 μl, as described earlier, and challenged with 5 $LD_{50}$ of PR8 or B/LEE/40 virus one, two, here or seven days later (presented in FIG. 7A (PR8) and 8A (B/Lee/40) as −1, −2, −3 and −7 days prior to challenge, respectively) and weighed daily for the duration of the study. Percentage weight was calculated based on weight at day of infection.

Rapid onset of effective protection against PR8 challenge, which was accompanied by no loss of animals, was achieved with the $10^{10}$ GC dose of AAVhu68.CB7.CI.JAb210a vector as shown in FIGS. 7B and 7C. For protection against B/Lee/40, rapid onset of effective protection was achieved with a $\log_{10}$ lower dose at $10^9$ GC of AAVhu68.CB7.CI.JAb210a vector as shown in FIGS. 8B and 8C.

Example 9

Figures 9A, 9B, 9C:
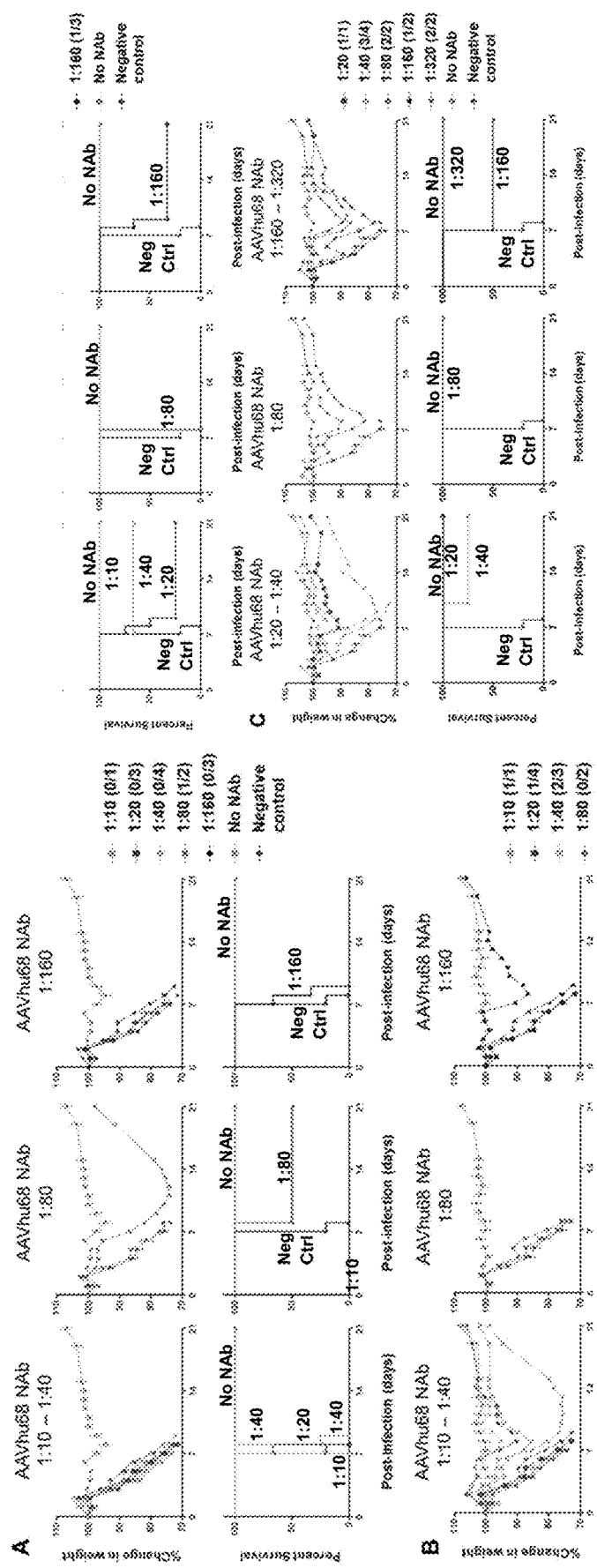
Figures 9D, 9E, 9F:
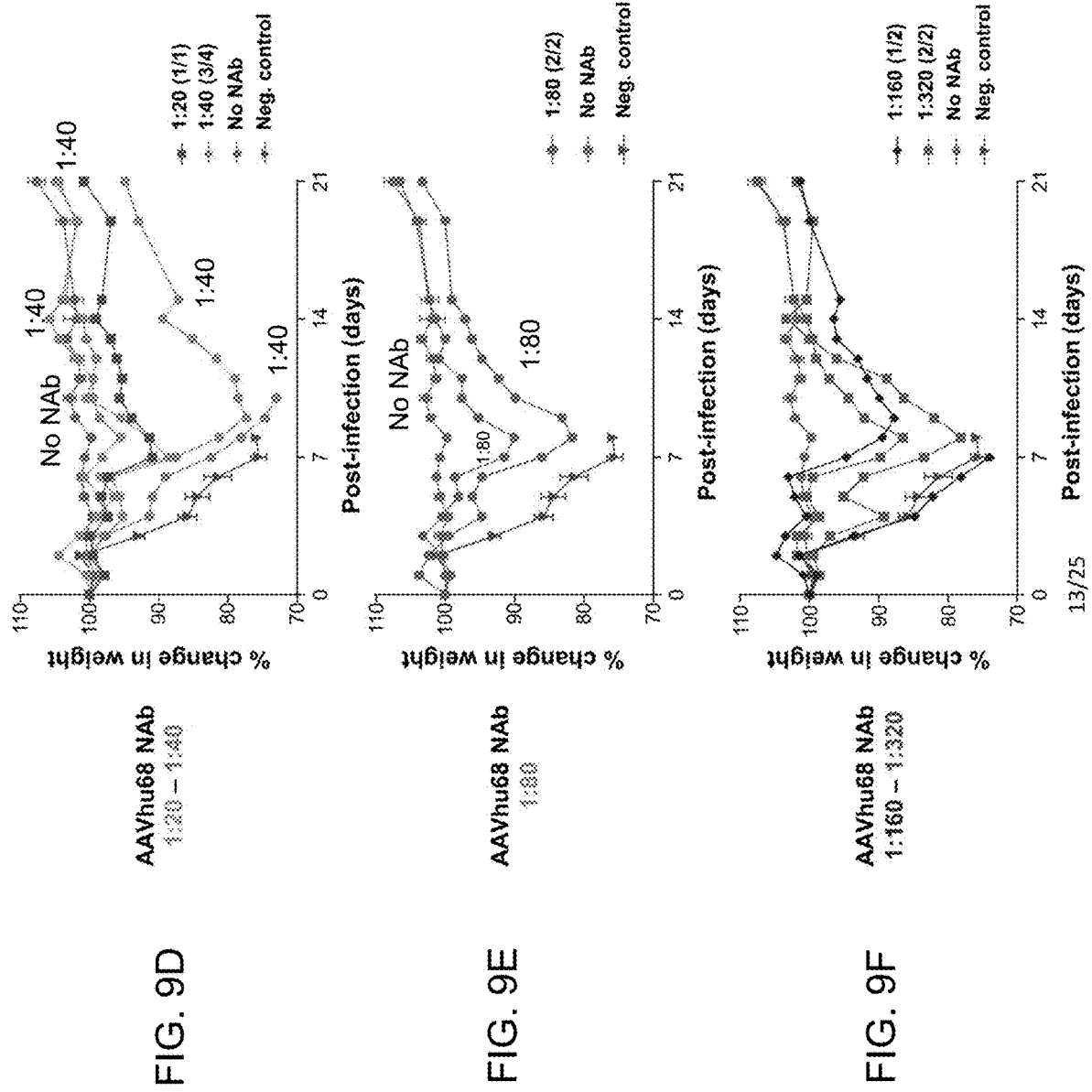

Nasal Administration of AAVhu68.CB7.JAb210a Vector in the Presence of AAVhu68-specific Serum-Circulating Abs The purpose of this study was to determine the ability of the AAVhu68.CB7.JAb210a vector to effectively transduce the cells of the airway epithelium despite the presence of serum-circulating NAb against AAVhu68. Mice were given IN AAVhu68. CB7.nLacZ vector (expressing an irrelevant to influenza transgene) at doses ranging from $10^9$ GC to $3 \times 10^{10}$ GC in 51 μl, as described previously. Twenty-eight days later (at the peak of antibody responses) or day 90 (at which time Nab should be stabilized) serum was isolated from each of the vector-treated (and non-vector treated) mice and the titer of AAVhu68-specific NAb in serum was assayed. The mice in the day 28 and day 90 groups were stratified according to their NAb status and distributed to each of the three groups for administration of the AAVhu68.CB7.CI.JAb210a vector (FIGS. 9A-9F and FIGS. 10A-10C). Group 1 was administered with $10^9$ GC of AAVhu68.CB7.CI.JAb210a (FIG. 9A, day 28 or FIG. 10A, day 90). Group 2 was administered with $3 \times 10^9$ GC of AAVhu68.CB7.CI.JAb210a (FIG. 9B, day 28 or FIG. 10B, day 90). Group 3 was administered with $10^{10}$ GC of AAVhu68.CB7.CI.JAb210a (FIG. 9C, day 28 or FIG. 10C, day 90).

As predicted, IN delivery of AAVhu68.CB.nLacZ vector resulted in the generation of serum circulating AAVhu68-specific NAbs, shown to the right of each graph in FIGS. 9 and 10.

AAVhu68.CB7.CI.JAb210a vector can effectively be readministered in the presence of serum-circulating AAVhu68-specific NAb. Preexisting serum-circulating AAVhu68-specific NAb impacts effective readministration of $10^9$ GC of vector. However, by increasing the dose of the vector by half log 10 to $3 \times 10^9$ GC, or a full log 10 to $10^{10}$ GC we improved significantly the survival of influenza A challenged mice. A dose of $10^{10}$ GC of AAVhu68.CB7.CI.JAb210a delivered IN in mice with a serum-circulating AAVhu68 NAb of 1:20 to 1:1,280 results in effective protection of mice against PR8 challenge. Increasing the time interval between initial exposure to the AAVhu68 capsid and administration with AAVhu68.CB7.CI.JAb210a resulted in a trend toward improved protection against PR8.

Example 10

Biodistribution Profile of AAVhu68.CB7.hJAb Following IN Delivery in Mice

BALB/c mice were given IN AAVhu68.hJAb vector at doses ranging from $10^{11}$ GC (high) to $10^9$ GC (low) and necropsied seven days later. Tissues (lung, liver, spleen, heart, and brain) were harvested for biodistribution analysis. Dotted line represents the level of background in the assay.

The purpose of this study was to determine the biodistribution profile of a) the AAVhu68.CB7.CI.hJAb vector following IN delivery of a vector doses ranging from $10^9$ GC to $10^{11}$ GC and necropsied seven days later; and b) the AAVhu68.CB7.CI.JAb210a vector following IN delivery of a vector dose that is 100-fold higher ($10^{11}$ GC) than the proposed MED. The study was performed in two parts. Part A evaluated the biodistribution profile of AAVhu68.hJAb given IN to mice in doses ranging from $10^9$ to $10^{11}$ GC and necropsied at day 7 post vector delivery. Part B evaluated the biodistribution profile of AAVhu68.CB7.CI.JAb210a given to mice at the highest dose ($10^{11}$ GC), which was 100-fold higher than the MED. Mice were necropsied 30 days after vector administration.

In Part A study, mice received IN $10^9$ GC to $10^{11}$ GC of AAVhu68.CB7.hJAb diluted in PBS to a total volume of 51 μl, as described earlier. Mice were necropsied seven days later and several tissues collected for analysis of AAVhu68 biodistribution.

In Part B study, mice received IN $10^{11}$ GC of AAVhu68.CB7.CI.JAb210a diluted in PBS to a total volume of 51 μl, as described earlier. Mice were necropsied thirty days later and several tissues collected for analysis of AAVhu68 biodistribution.

As predicted when vector is delivered IN, the majority of vector genomes deposit in the lung. At the proposed MED of AAVhu68.CB7.hJAb ($10^9$ GC) there were no AAVhu68 genomes detected in the brain and heart (FIG. 11), while the level of AAVhu68 vector genomes detected in the spleen and liver were close to background (FIG. 11).

As the vector dose increased, the amount of vector genomes deposited in the liver, spleen, heart and brain increased in a dose-dependent manner (FIG. 11).

When using high doses of AAVhu68 vector (FIGS. 11, 12A and 12B), AAVhu68 genomes were detected in tissues other than the lung. As shown in FIGS. 12A and 12B, the majority of vector genome deposition occurred in the lung, followed by the spleen. Very low levels of AAVhu68 vector genome were present in the kidney, liver and heart (FIGS. 12A and 12B). Furthermore, the level of AAVhu68 genomes in the brain, ovary or eye was too close to background to allow for accurate interpretation of the data (FIG. 12A).

At the proposed MED of AAVhu68.CB7.hJAb ($10^9$ GC) there were no AAVhu68 genomes detected in the brain and heart, while the level of AAVhu68 genomes detected in the spleen and liver were close to background. When using high doses of AAVhu68 vector (FIGS. 11, 12A and 12B), AAVhu68 vector genomes were detected in tissues other than the lung. As shown in FIG. 12A, the level of AAVhu68 genomes in the brain, ovary or eye was too close to background to allow for accurate interpretation of the data.

Example 11

The AAVhu68.hJAb and AAVhu68.JAb210a vector exhibited in vivo an impressive prophylaxis profile against lethal challenge with various influenza A and B strains. When applied to the mouse nose, it conferred full protection against influenza A or B strains even when administered at low doses.

Interestingly, the protective low AAV vector dose resulted in the production of low level serum-circulating AAV-specific neutralizing antibodies. We show that these antibodies did not compromise effective vector re-administration, which is beneficial should it be necessary to protect against a pandemic influenza strain that may arise during the window of effective universal AAV prophylaxis.

The safety profile of the vector is currently being evaluated in IND—enabling studies in support of the progression of this prophylaxis product into a phase I clinical trial.

Example 12

Assessment of the Expression and Vector Distribution Profile of AAV9.CB7.hJAb Delivered in Macaque Nose Using the LMA® MAD Nasal™ Intranasal Mucosal Atomization (MAD Nasal) Device This study was designed to evaluate the clinical delivery device, LMA® MAD Nasal™ intranasal Mucosal Atomization (MAD nasal), for delivery of surrogate vector (AAV9) expressing rhesus alpha fetoprotein (rhAFP; a surrogate for JAb210a) to the rhesus nose. The onset and peak expression level of the transgene product, rhAFP, was evaluated in the nasal lavage fluid, and vector biodistribution was evaluated at the time of necropsy.

On the day of vector administration, the animals were sedated, weighed and vital signs were recorded. For nasal lavage fluid (NLF) collection: a pediatric Foley catheter was placed in one of the nares and, once in place, the balloon was inflated with air and the catheter pulled back until resistance was achieved. Up to 5 ml of phosphate-buffered saline were infused into the isolated nasal cavity and the head titled to its side to allow flow of the lavage into a 50 ml Falcon tube positioned right under the nare. At the end of the process the distally placed catheter was released and removed, cleaned externally with sterile PBS and positioned in the adjacent nare where the procedure was repeated. The macaques were intubated with an endotracheal tube to maintain a patent airway and remained in a supine position. For liquid delivery of AAV vector (animal RA0065): a pediatric Foley catheter was placed in one of the nares, the balloon was inflated with air and the catheter pulled back until resistance was achieved. AAV vector (in a volume of 1 mL) at a dose of $10^{13}$ GC was added to each nare and allowed to remain there for ~5 min (total dose $2\times10^{13}$ GC).

For delivery of AAV vector via the MAD nasal (animal RQ9476): AAV vector was delivered through the MAD nasal as $10^{13}$ GC in a total of 0.5 ml per nare, both nares dosed once (total dose $2\times10^{13}$ GC).

On select days (days 7, 21, 35, 50, 81 and 99) the macaques were monitored for vital signs, clinical pathology and for expression of the surrogate transgene product in the nasal lavage fluid collected from both the right and left nares. At necropsy, tissues were collected for analysis of AAV9 vector genome. Adding to the safety profile of the combination of the MAD nasal with the AAV9 vector was the absence of vector genome in the brain and olfactory bulb.

Secreted AFP from AAV9 transduced airway cells was detected using the human alphafetoprotein quantikine ELISA Kit (R&D Systems, Inc, Minneapolis Minn., USA) by assaying NLF samples.

When AAV9 vector expressing rhAFP at a dose of $2\times10^{13}$ GC in a total volume of 0.5 ml was delivered via the MAD nasal to the nares of a rhesus macaque, we were able to assay gene expression in the NLF over time. Interestingly, upon analysis of AAV9 vector biodistribution we observed minimal systemic dissemination of the AAV9 vector delivered via the MAD nasal with the majority of vector genomes detected in the nose and trachea.

A male rhesus macaque was given IN AAV9.CB7.CI.rhAFP.rBG. Specifically, one macaque was given IN $5.45\times10^{12}$ GC of AAV9.CB7.CI.rhAFP.rBG in a total volume of 0.34 ml (given as one aliquot of 0.170 ml per nostril) using the MAD Nasal™ (in squares, FIG. 22). The MAD Nasal™ atomizes approved medications into a fine mist that can be administered IN. For the control macaque (in circles, FIG. 22), vector was delivered as liquid (0.5 ml per nostril). This short-term study was designed to assess the biodistribution profile of AAV9.CB7.CI.rhAFP.rBG, when delivered to the rhesus macaque nose using the MAD Nasal™. Animals were necropsied 99 days later. AAV9 vector was note detected in the brain (data not shown) and olfactory bulb (FIG. 22).

Example 13

Evaluation of the Expression Profile of AAVhu68.CB7.CI.JAb210a in the Nose of a Rhesus Macaque This study was designed to assess the expression profile of AAVhu68.CB7.CI.JAb210a.rBG, when delivered to the rhesus macaque nose using the MAD Nasal™. A male rhesus macaque was administered with $2\times10^{13}$ GC of AAVhu68.CB7.CI.JAb210a in a volume of 0.34 mL divided equally between nares via the MAD Nasal™ device. The MAD nasal atomizes approved medications into a fine mist that can be administered IN. Daily viability checks are performed on all animals, in accordance with SOP 7404. Body weight, temperature, respiratory rate, and heart rate are monitored and recorded at all time points, in accordance with SOPs. Nasal brushings are collected at days 7, 14, 21, 28 and 35 for analysis of JAb210a expression by RT-PCR. Following assessment of the day 35 data, a decision is made on whether the animal is followed long-term or necropsied for vector biodistribution. NLF and blood samples were collected at days 7, 14, 21, 28, 35, 56 and 77 for analysis of JAb210a expression. Expression of JAb210a was confirmed in samples (scrapped nasal cells, collected from the nose using a fine brush) collected at day 77, by a RT-PCR-based assay specifically designed to detect JAb 210a.

Tissue Cross-Reactivity Study

The use of monoclonal Abs as therapeutic agents requires an assessment of the crossreactivity of the Ab to normal human and rhesus macaque tissues. Tissue cross-reactivity studies involve immunohistochemical or cytochemical testing of the monoclonal Ab against a range of normal human and rhesus tissues compliant with the "Points to Consider in the Manufacture and Testing of Monoclonal Ab Products for Human Use" published in February 1997 by the FDA and the "Guideline on Development, Production, Characterisation and Specifications for Monoclonal Antibodies and Related Products" (EMEA/CHMP/BWP/157653/2007) published in December 2008 by the EMA. The objective of this study is to assess, using immunohistochemistry, the potential cross reactivity of the transgene product of AAVhu68.CB7.CI.JAb210a, with a selected panel of human and rhesus tissues.

Example 14

Evaluation of the Protective Efficacy of AAVhu68.CB7.CI.JAb210a Against Influenza A in Old Mice The purpose of this study was to assess the potential for effective prophylaxis of old mice and to evaluate the protective efficacy of AAVhu68.CB7.JAb210a vectors against influenza A (A/Puerto Rico/8/34) when administered IN in old (9-18 months of age) BALB/c female mice. Anaesthetized mice were suspended by their dorsal incisors and they received IN $10^9$ GC or $3 \times 10^9$ GC of AAV vector diluted in PBS to a total volume of 51 µl delivered as three aliquots of 17 µl. The challenge studies occurred seven days after vector administration. Anaesthetized mice were suspended by their dorsal incisors and administered IN 51 µl of PR8 ($5LD_{50}$) delivered as three aliquots of 17 µl. Mice were weighed daily after the challenge as shown in FIG. 13A. Percentage weight loss was calculated based on weight at day of influenza challenge. Any mice showing signs of distress or ≥30% weight loss were euthanized Surviving mice were sacrificed 21 days post-challenge. FIG. 13B graphs the percent survival following the PR8 challenge.

In summary, IN delivery of either $10^9$ GC or $3 \times 10^9$ GC of AAVhu68.CB7.JAb210a conferred full protection against PR8 challenge and resulted in the protection of old mice against a lethal challenge with influenza A ($5LD_{50}$ of PR8).

Example 15

Universal Protection Against Influenza Infection by a Multi-Domain Antibody to Influenza Hemagglutinin Reported herein were multi-domain antibodies which were generated from a panel of diverse llama single-domain antibodies to influenza hemagglutinin and were linked with unprecedented breadth and potency against influenza A and B viruses. Multi-domain antibody protects against influenza A and B infection in mice when administered intravenously or expressed locally from a recombinant adeno-associated virus vector. The results demonstrate that multi-domain antibodies targeting multiple epitopes exhibit enhanced virus cross-reactivity and potency and, when used in combination with adeno-associated virus delivery, provide a prevention of infection with influenza and other highly variable pathogens.

Vaccines remain essential for influenza control and prevention, but most antibodies induced by influenza vaccination recognize the highly variable head region of the hemagglutinin (HA) surface glycoprotein. Such antibodies are mainly strain-specific and confer protection against only a small subset of similar variants. Annual selection of appropriate vaccine strains also presents many challenges and a poor match with circulating viruses can result in suboptimal vaccine effectiveness (H. Xie et al., H3N2 Mismatch of 2014-15 Northern Hemisphere Influenza Vaccines and Head-to-head Comparison between Human and Ferret Antisera derived Antigenic Maps. Sci. Rep. 5, 15279 (2015)). Furthermore, several studies indicate that the efficacy of influenza vaccines is significantly reduced in the elderly, who are at increased risk of developing influenza-related complications. See, e.g., H. Chen et al., Avian flu: H5N1 virus outbreak in migratory waterfowl. Nature 436, 191-192 (2005); M. T. Osterholm, N. S. Kelley, A. Sommer, E. A. Belongia, Efficacy and effectiveness of influenza vaccines: a systematic review and meta-analysis. Lancet Infect Dis. 12, 36-44 (2012); and W. E. Beyer et al., Cochrane re-arranged: support for policies to vaccinate elderly people against influenza. Vaccine 31, 6030-6033 (2013). Broadly neutralizing antibodies (bnAbs) against a wide range of HAs from influenza A and B viruses have been extensively characterized. See, e.g., A. K. Kashyap et al., Combinatorial antibody libraries from survivors of the Turkish H5N1 avian influenza outbreak reveal virus neutralization strategies. Proc. Natl. Acad. Sci. U.S.A. 105, 5986-5991 (2008); M. Throsby et al., Heterosubtypic neutralizing monoclonal antibodies cross-protective against H5N1 and H1N1 recovered from human IgM+ memory B cells. PLoS One 3, e3942 (2008); D. Corti et al., A neutralizing antibody selected from plasma cells that binds to group 1 and group 2 influenza A hemagglutinins. Science 333, 850-856 (2011); C. Dreyfus et al., Highly conserved protective epitopes on influenza B viruses. Science 337, 1343-1348 (2012); D. C. Ekiert et al., Antibody recognition of a highly conserved influenza virus epitope. Science 324, 246-251 (2009); J. Sui et al., Structural and functional bases for broad-spectrum neutralization of avian and human influenza A viruses. Nat. Struct. Mol. Biol. 16, 265-273 (2009); D. C. Ekiert et al., A highly conserved neutralizing epitope on group 2 influenza A viruses. Science 333, 843-850 (2011); R. H. Friesen et al., A common solution to group 2 influenza virus neutralization. Proc. Natl. Acad. Sci. U.S.A. 111, 445-450 (2014); P. S. Lee et al., Heterosubtypic antibody recognition of the influenza virus hemagglutinin receptor binding site enhanced by avidity. Proc. Natl. Acad. Sci. U.S.A. 109, 17040-17045 (2012); and A. Forsman et al., Llama antibody fragments with cross-subtype human immunodeficiency virus type 1 (HIV-1)-neutralizing properties and high affinity for HIV-1 gp120. J. Virol. 82, 12069-12081 (2008). Previously, these bnAbs have been proposed as prophylactic agents in the elderly and other high-risk groups, but such use is seriously hampered by (i) the lack of adequate cross-reactivity and protection against both influenza A and B viruses, which necessitates administration of at least two bnAbs and (ii) the need for multiple, high-dose injections for protection throughout the entire flu season.

Presented herein is a strategy to influenza prevention that is based on mucosal expression of a single, antibody-like protein (referred to as a multi-domain antibody or MDAb or JAb) with anti-influenza A and B activity. The MDAb transgene is expressed at the surface of the respiratory epithelium following intranasal administration of a recombinant adeno-associated virus (AAV) vector encoding MDAb transgene. Previous studies have shown that AAV-mediated bnAb expression at the nasopharyngeal mucosa can provide long-lasting protection against influenza A virus infection. See, e.g., M. P. Limberis et al., Intranasal antibody gene transfer in mice and ferrets elicits broad protection against pandemic influenza. Sci. Transl. Med. 5, 187ra72 (2013); and V. S. Adam et al., Adeno-associated virus 9-mediated airway expression of antibody protects old and immunodeficient mice against influenza virus. Clin. Vaccine Immunol. 21, 1528-1533 (2014).

A. Prophylactic Efficacy of AAV9-Expressed MD3606.

To assess in vivo protection by AAV-expressed MD3606 (AAV9.MD3606), we evaluated the prophylactic efficacy of a recombinant AAV9 vector encoding humanized sequences encoding an anti-influenza antibody (Ab) domains in BALB/c mice challenged with mouse-adapted influenza H1N1, H3N2 and B viruses (FIGS. 14A to 14B). AAV9.MD3606h was administered intranasally 7 days prior to influenza challenge at vector doses ranging from $4 \times 10^7$ to $5 \times 10^9$ genome copies (GC). Administration of $5 \times 10^9$ GC completely protected mice against lethal challenge with an H1N1 virus (A/Puerto Rico/8/34-MA), while 7 of 8 mice survived with a 5-fold lower dose. Mice challenged with an H3N2 virus (A/Hong Kong/1/68-MA) were fully protected by intranasal administration of $5 \times 10^8$ GC of AAV9.MD3606h (lowest dose tested). Finally, mice challenged with an influenza B virus (B/Lee/40-MA) were completely protected by intranasal administration of $1 \times 10^9$ GC of AAV9.MD3606h.

Intranasal delivery of AAV9. MD3606h provided full protection against influenza A and B viruses at vector doses as low as $5 \times 10^8$ GC/mouse. While MD3606 itself may be developed for indications that do not require long-term antibody exposure like post-exposure prophylaxis or treatment of influenza, AAV-expressed MD3606 can be used to provide long-lasting protection against influenza infection. A once yearly intranasal administration of a single AAV vector expressing humanized MD3606 could be sufficient to provide passive protection throughout the entire flu season. Such a prophylactic approach would be of particular benefit to the elderly and other high-risk groups where vaccination is less effective. The safety and efficacy of this prophylactic strategy is assessed. The rapid onset of protection together with the unprecedented cross-reactivity of MD3606 to avian influenza strains also offers a prophylactic treatment immediately upon onset of an influenza pandemic, providing significant advantages over standard egg-based vaccine production.

B. Materials and Methods—Prophylactic efficacy of AAV9.hJAb in Mice

AAV9 vector expressing humanized JAb, hJAb under the control of a hybrid cytomegalovirus (CMV) enhancer chicken β-actin promoter (CB7) was constructed and produced as previously described (M. P. Limberis et al., Intranasal antibody gene transfer in mice and ferrets elicits broad protection against pandemic influenza. Sci. Transl. Med. 5, 187ra72 (2013)). Six-week-old female BALB/c mice, purchased from the Jackson Laboratory, Bar Harbor, Me., USA, were housed at the animal facility of the Translational Research Laboratories at the University of Pennsylvania. Mice were anesthetized by an intraperitoneal injection of a 100 mg/kg ketamine/10 mg/kg xylazine mixture in PBS, suspended by their dorsal incisors with their hind limbs supported on a platform, and administered intranasally AAV9.hJAb vector in a total volume of 51 μl of PBS administered as three 17 μl aliquots in alternate nares. One week after vector administration, treated and naïve mice were weighed, anesthetized as described above, and intranasally administered challenge virus ($5LD_{50}$ A/Puerto Rico/ 8/34-MA H1N1, 5 $LD_{50}$ A/Hong Kong/1/68-MA H3N2 or 5 $LD_{50}$ B/Lee/40-MA) in a total volume of 51 μl of PBS as described above. Mice were weighed daily and monitored for signs of disease or distress. Animals that exhibited behavioral signs of distress or lost 25% of their initial body weight were euthanized. Experiments were approved and performed in accordance with the guidelines of the Institutional Animal Care and Use Committee of the University of Pennsylvania.

Example 16

Production and Manufacture of AAVhu68.CB7.CI.JAb210a.rBG

The AAVhu68.CB7.CI.JAb210a.rBG consists of an external vector component and internal DNA genome. The external vector component is a serotype hu68, T=1 icosahedral capsid consisting of 60 copies of three AAV viral proteins, VP1, VP2, and VP3, at a ratio of 1:1:18. The capsid contains a single-stranded DNA genome consisting of the JAb210a transgene flanked by the two AAV inverted terminal repeats (ITRs). An enhancer, promoter, intron, JAb210a coding sequence and polyadenylation (polyA) signal comprise the JAb210a transgene. The ITRs are the genetic elements responsible for the replication and packaging of the genome during vector production and are the only viral cis elements required to generate rAAV. Expression of the JAb210a coding sequence is driven by a CB7 promoter, a hybrid between a cytomegalovirus (CMV) immediate early enhancer (C4) and the chicken beta actin promoter. Transcription from this promoter is enhanced by the presence of the chicken beta actin intron (CI). A rabbit beta globin polyA signal is included to mediate termination of human JAb210a mRNA transcripts. A schematic of the AAVhu68.CB7.CI.JAb210a.rBG vector genome is shown in FIG. 15.

The manufacturing process for AAVhu68.CB7.CI.JAb210a.rBG involves transient transfection of human embryonic kidney (HEK293) cells with plasmid DNA. The HEK293 master cell bank (MCB) used in the production of the AAVhu68.CB7.CI.JAb210a.rBG is tested and qualified as detailed in FDA and ICH guidelines. Batches of the Bulk Drug Substance (BDS) are produced by polyethylenimine (PEI)-mediated triple transfection of HEK293 cells in Corning 36-layer HYPERStacks® (HS-36). Downstream processes involves disposable, closed bioprocessing systems as far as possible (filtration, tangential flow filtration and column chromatography). Vector purification involves several orthogonal steps and AAVhu68.CB7.CI.JAb210a.rBG is formulated in final formulation buffer (FFB; PBS with total a salt concentration of 200 mM, 0.001% (w/v) pluronic F68 and 5% glycerol). The BDS batches are frozen, subsequently thawed, pooled, adjusted to the target concentration, sterile filtered through a 0.22 μm filter and Daikyo Crystal Zenith® 2 ml vials (West Pharmaceutical Services, Inc.®) filled. Fill data and media qualification are provided as part of the lot documentation package. A GMP production batch size of up to 50×HS-36 cell culture vessels is used with multiple batches planned and used as necessary to satisfy the needed vector amount.

AAVhu68.CB7.CI.JAb210a.rBG is produced by triple plasmid transfection of human HEK 293 MCB cells with: (i) the vector genome plasmid, (ii) an AAV helper plasmid termed pAAVhu68.KanR containing the AAV rep2 and cap hu68 wild-type genes and (iii) a helper adenovirus plasmid termed pAdΔF6(Kan). The size of the pAAVhu68.CB7.JAb210a (p3618) packaged vector genome is 4718 bp.

A. AAV Vector Genome Plasmid: pAAV.CB7.JAb210a.rBG (p3618)

The AAV vector genome plasmid pAAV.CB7.CI.JAb210a.rBG (p3618, FIG. 16) was constructed and is 7976 bp in size. The vector genome derived from this plasmid is a single-stranded DNA genome with AAV2 derived ITRs flanking the JAb210a expression cassette. Expression from the transgene cassette is driven by a CB7 promoter, a hybrid between a cytomegalovirus (CMV) immediate early enhancer (C4) and the chicken beta actin promoter, while transcription from this promoter is enhanced by the presence of the chicken beta actin intron (CI). The polyA signal for the expression cassette is the rabbit beta-globin (rBG) polyA. The plasmid was constructed by codon-optimizing and synthesizing the sequence (GeneArt) encoding human IgG1 FC region fused to MDAb-like polypeptide that recognizes multiple flu antigens and the resulting construct was cloned into the plasmid pN469, an AAV2 ITR-flanked expression cassette containing CB7, CI, and rBG expression elements to give pAAV.CB7.CI.JAb210a.rBG (p3618). All component parts of the plasmid is verified by direct sequencing by Qiagen Genomic Services and is confirmed as part of the manufacturing process at Puresyn.

B. Description of the Sequence Elements

Inverted terminal repeats (ITR): AAV ITRs (GenBank # NC001401) are sequences that are identical on both ends, but in opposite orientation. The AAV2 ITR sequences function as both the origin of vector DNA replication and the packaging signal of the vector genome, when AAV and adenovirus helper functions are provided in trans. As such, the ITR sequences represent the only cis sequences required for vector genome replication and packaging.

CMV immediate-early enhancer (382 bp, GenBank # K03104.1).

Chicken β-actin promoter (282 bp; GenBank # X00182.1) promoter and is used to drive high-level Jab210a expression.

The CB7 promoter was selected to drive the expression of the hJAb as it produces high level, airway-specific expression. A strong and airway-specific expression of different transgenes driven by the CB7 promoter and good translatability between various species, including mice, ferrets and MHPs, have been observed.

Chicken β-actin intron: The 973 bp intron from the chicken β-actin gene (GenBank # X00182.1) is present in the vector expression cassette. The intron is transcribed, but removed from the mature mRNA by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased level of gene expression.

Coding sequence: Human IgG1 FC region fused to MDAb-like polypeptide that recognizes multiple flu antigens was codon-optimized and synthesized. Original variable domains were identified from llama VHH libraries by panning against various flu antigens. Flu-specific llama VHH chains were fully humanized The specificity and the breadth of the humanized multidomain polypeptides was maintained after humanization process. Multi-domain polypeptide contains 4 variable heavy IgG domain linked by flexible Gly-Ser linkers.

Polyadenylation Signal: The 127 bp rabbit β-globin polyadenylation signal (GenBank # V00882.1) provides cis sequences for efficient polyadenylation of the antibody mRNA. This element functions as a signal for transcriptional termination, a specific cleavage event at the 3' end of the nascent transcript and addition of a long polyadenylation tail.

C. AAVhu68 Helper Plasmid: pAAV2/hu68.KanR (p0068)

The AAV2/hu68 helper plasmid pAAV2/hu68 (Lot #: p0065; 7329 bp) was constructed. It is an AAV helper plasmid that encodes the four wild-type AAV2 rep proteins and the three wild-type AAV VP capsid proteins from AAV serotype hu68. A novel AAV sequence was obtained from human heart tissue DNA and designated AAV serotype hu68. To create the chimeric packaging construct, the AAV2 cap gene from plasmid pAAV2/9 (p0061-2), containing the wild type AAV2 rep and AAV9 cap genes, was removed and replaced with the fragment of the AAVhu68 cap gene plasmid pAAV2/hu68 (p0065) (FIG. 17A). The AAV p5 promoter which normally drives rep expression is moved in this construct from the 5' end of rep to the 3' end of cap. This arrangement serves to introduce a spacer between the promoter and the rep gene (i.e. the plasmid backbone), down-regulate expression of rep and increase the ability to support vector production. The plasmid backbone in pAAV2/9 is from pBluescript KS. All component parts of the plasmid were verified by direct sequencing. The ampicillin resistance gene was then replaced by the kanamycin resistance gene to give pAAV2/hu68n.KanR (p0068) (FIG. 17B). The identity of the AAVhu68 capsid gene was confirmed by DNA plasmid sequencing performed by Qiagen Genomic Services.

D. pAdDeltaF6 (Kan) Adenovirus Helper Plasmid

Plasmid pAdDeltaF6(Kan) was constructed and is 15,774 bp in size. The plasmid contains the regions of adenovirus genome that are important for AAV replication, namely E2A, E4, and VA RNA (the adenovirus E1 functions are provided by the 293 cells), but does not contain other adenovirus replication or structural genes. The plasmid does not contain the cis elements critical for replication such as the adenoviral inverted terminal repeats and therefore, no infectious adenovirus is expected to be generated. It was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 Kb to 12 kb (FIG. 18A). Finally, the ampicillin resistance gene was replaced by the kanamycin resistance gene to give pAdeltaF6(Kan) (FIG. 18B). The E2, E4 and VAI adenoviral genes which remain in this plasmid, along with E1, which is present in HEK293 cells, are necessary for AAV vector production.

E. Bacterial Master Cell Banks

Bacterial master cell bank (BMCB) glycerol stocks are made by mixing 1 mL from a 1 L overnight bacterial culture used for plasmid DNA amplification, with an equal volume of sterile, 50% glycerol. Two 0.5-mL aliquots of the BMCB glycerol stocks per construct are prepared from the mixture and stored in Nalgene cryogenic vials in −80° C. To verify BMCB glycerol stocks, amplified plasmid DNA is subjected to structure analysis involving restriction enzyme digestion followed by gel electrophoresis, and full-plasmid sequence analysis by Sanger sequencing at Qiagen. To prepare bacterial working cell bank (BWCB) glycerol stock aliquots for shipping to the plasmid DNA manufacturer (Puresyn), a 3 mL culture is inoculated from a BMCB glycerol stock and grown overnight. One mL of the overnight culture is used to prepare BWCB glycerol stock aliquots as described above. New BWCB glycerol stock aliquots are verified by the aforementioned structure analysis on DNA extracted from the remaining 2 ml of overnight bacterial culture. Once received at the plasmid DNA manufacturer, the BWCB glycerol stock is stored in a project-specific location at −80° C. Production cultures are inoculated by scraping from the frozen BWCB glycerol stock.

F. Plasmid DNA Manufacturing

All plasmids for use in production of the AAV vectors for toxicology/biodistribution studies and phase 1/2 trials were made by Puresyn through their Special Clinical and IND-Ready Program. Puresyn produces supercoiled plasmids to be used in the cGMP manufacture of recombinant viral vectors and other products when the supercoiled plasmid is an intermediate in the production of the final product. All growth media used in the process is "animal-free" (based on the Certificate of Analysis from each vendor for component products). All components used in the process, from fermentation flasks, containers, membranes, resin, columns, tubing, and any component that come into contact with the plasmid are dedicated to a single plasmid and are certified BSE-free. There are no shared components and disposables are used when appropriate. The PolyFlo® resin, columns and components utilized are used exclusively by Puresyn for manufacture of a single plasmid. In addition to the use of components dedicated to a specific plasmid, the plasmid is processed on a campaign basis. The fermentation, lysis, and purification of the plasmid occur in rooms dedicated for the production of the specific plasmid. All rooms are marked with the designated plasmid name and no other plasmids are processed in those rooms at the same time. The rooms and equipment are cleaned between each plasmid production campaign. The specifications for each plasmid are given in Table 2. In addition, each plasmid produced is fully sequenced prior to use in production of the recombinant AAVhu68.CB7.CI.JAb210a.rBG vector.

TABLE 2

Release Specifications for plasmid production

| PARAMETER | SPECIFICATION |
|---|---|
| Appearance | Clear, Colorless, No Visible Particulates |
| A260:280 | 1.7-2.0 |
| Concentration | 1.0-1.1 mg/mL |
| DNA Homogeneity | ≥90% All supercoiled |
| Residual RNA | None Detected @ 1.0 mg load |
| ssDNA, Linear DNA, Chromosomal DNA | None Detected @ 1.0 mg load |
| Endotoxin | <30 EU/mg |
| Identity | Consistent with Provided Information |
| Protein | For information only |
| Five day bioburden | No growth |
| pH | 7.5-8.5 |
| Formulation | TE buffer (10 mM Tris, 1.0 mM EDTA, pH 8.0-8.1) |

G. Human Embryonic Kidney 293 Master Cell Bank

Human Embryonic Kidney (HEK) 293 cells were originally generated by transforming HEK cells with sheared adenovirus type 5 DNA by Frank Graham and colleagues (Graham Fla., et al. Characteristics of a human cell line transformed by DNA from human adenovirus type 5. J Gen Virol 1977; 36:59-74.). The cells express the E1A and E1B gene products required for high-titer rAAV production. HEK293 cells are adherent and highly transfectable yielding high-titers of rAAV upon DNA plasmid transfection.

H. Manufacturing Process

A manufacturing process flow diagram is shown in FIGS. 19A to 19B and represents the AAVhu68.CB7.CI.JAb210a.rBG vector production process.

The major reagents entering into the preparation of the product are indicated on the left side of the diagram and in-process quality assessments are depicted on the right side of the diagram. A description of each production and purification step is also provided. Product manufacturing follows a linear flow of unit operations and utilizes disposable, closed bioprocessing systems unless otherwise specified. AAVhu68.CB7.CI.JAb210a.rBG is the sole product manufactured within a specified production suite. All steps of the production process involving cell culture, from cell seeding to supernatant collection, are performed aseptically using sterile, single-use disposable tubing and bag assemblies. Cells are cultivated in Corning 10-layer CellSTACKs® (CS-10) and HYPERstack®36-layer (S-36) and all open manipulations are performed in class II biosafety cabinets in an ISO Class 5 environment. The purification process is performed in a closed system where possible however, column chromatography manipulations are not viewed as a completely closed system. To minimize this risk, single-use disposable flow paths are utilized as part of the column chromatography production skid platform. After column chromatography purification, the product is diafiltered with FFB. The BDS is then be frozen at ≤−60° C. After BDS batches are individually tested and verified against approved specifications, they are thawed, pooled as necessary, adjusted to target concentration, with final formulation buffer, sterile filtered and filled in sterile Daikyo Crystal Zenith® 2 ml vials (West Pharmaceutical Services, Inc.®) containers in their Fill Suite. Filters used in sterile filtration are filter integrity tested post-use. Following Fill, the AAVhu68.CB7.CI.JAb210a.rBG undergoes release testing and Quality Assurance (QA) review. The entire production process from cell expansion to Final Fill is documented in executed Batch Record Documents (BRDs) that undergoes staff and QA technical review prior to release to clinical sites.

a. Cell Seeding

A qualified HEK293 cell line is used for the production process. A Working Cell Bank (WCB) was produced from a fully characterized MCB. Cell culture used for vector production is initiated from a single thawed WCB vial, and expanded as per a Master Batch Record Document (MBR). Cells are expanded to $5 \times 10^9$-$5 \times 10^{10}$ cells using Corning T-flasks and CS-10, which allows sufficient cell mass to be generated for seeding up to 45 Hyperstack-36 (HS-36) for vector production per BDS lot. Cells are cultivated in medium composed of Dulbecco's Modified Eagle Medium (DMEM), supplemented with 10% gamma irradiated, US-sourced, Fetal Bovine Serum (FBS). The cells are anchorage dependent and cell disassociation is accomplished using TrypLE™ Select, an animal product-free cell dissociation reagent. Cell seeding is accomplished using sterile, single use disposable bioprocess bags and tubing sets. The cells are maintained at 37° C.(±2° C.), in 5%(±0.5%) $CO_2$ atmosphere.

b. Transient Transfection

Following approximately 3 days of growth (DMEM media+10% FBS), HS-36 cell culture media is replaced with fresh, serum free DMEM media and transfected with the 3 production plasmids using an optimized polyethyleneimine (PEI)-based transfection method. All plasmids used in the production process are produced in the context of a CMO quality system and infrastructure utilizing controls to ensure traceability, document control, and materials segregation. Sufficient plasmid DNA transfection complex is prepared in the BSC to transfect 50 HS-36 (per BDS batch). Initially a DNA/PEI mixture is prepared containing cis (vector genome) plasmid, trans (capsid gene) plasmid, and helper (Ad) plasmid in a 0.1:1:2 ratio and GMP grade PEI (PEIPro, PolyPlus Transfection SA). This plasmid ratio was determined to be optimal for AAV production in small scale optimization studies. After mixing well, the solution is allowed to sit at room temperature for 25 min, then added to serum-free media to quench the reaction, and finally added to the HS-36's. The transfection mixture is equalized between all 36 layers of the HS-36 and the cells are incubated at 37° C.(±2° C.) in a 5%(±0.5%) $CO_2$ atmosphere for 5 days.

c. Cell Media Harvesting

Transfected cells and media are harvested from each HS-36 using disposable bioprocess bags by aseptically draining the medium out of the units. Following the harvest of media, the ~200 liter volume is supplemented with $MgCl_2$ to a final concentration of 2 mM (co-factor for Benzonase) and Benzonase nuclease (Cat #: 1.016797.0001, Merck Group) is added to a final concentration of 25 units/mL. The product (in a disposable bioprocess bag) is incubated at 37° C. for 2 hr in an incubator to provide sufficient time for enzymatic digestion of residual cellular and plasmid DNA present in the harvest as a result of the transfection procedure. This step is performed to minimize the amount of residual DNA in the final vector. Following incubation, NaCl is added to a final concentration of 500 mM to aid in the recovery of the product during filtration and downstream tangential flow filtration.

d. Clarification

Cells and cellular debris are removed from the product using a depth filter capsule (1.2/0.22 µm) connected in series as a sterile, closed tubing and bag set that is driven by a peristaltic pump. Clarification assures that downstream filters and chromatography columns is protected from fouling and bioburden reduction filtration ensures that, at the end of the filter train, any bioburden potentially introduced during the upstream production process is removed before downstream purification. The harvest material is passed through a Sartorius Sartoguard PES capsule filter (1.2/0.22 µm) (Sartorius Stedim Biotech Inc.).

e. Large Scale Tangential Flow Filtration

Volume reduction (10-fold) of the clarified product is achieved by Tangential Flow Filtration (TFF) using a custom sterile, closed bioprocessing tubing, bag and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface, preventing membrane pore fouling. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This results in a modest purification of the clarified product, but also achieves buffer exchange compatible with the subsequent affinity column chromatography step. Accordingly, a 100 kDa, PES membrane is utilized for concentration that is then diafiltered with a minimum of 4 diavolumes of a buffer composed of: 20 mM Tris pH 7.5 and 400 mM NaCl. The diafiltered product is stored overnight at 4° C. and then further clarified with a 1.2/0.22 µm depth filter capsule to remove any precipitated material.

f. Affinity Chromatography

The diafiltered product is applied to a Poros™ Capture Select™ AAV9 affinity resin (Life Technologies) that efficiently captures the AAVhu68 serotype. Under these ionic conditions, a significant percentage of residual cellular DNA and proteins flow through the column, while AAV particles are efficiently captured. Following application, the column is treated with 5 volumes of a low salt Benzonase solution (2500 units/mL Benzonase, 20 mM Tris pH 7.5 and 40 mM NaCl, 1.5 mM $MgCl_2$) to remove any remaining host cell and plasmid nucleic acid. The column is washed to remove additional feed impurities followed by a low pH step elution (400 mM NaCl, 20 mM Sodium Citrate; pH 2.5) that is immediately neutralized by collection into a $\frac{1}{10}^{th}$ volume of a neutralization buffer (Bis Tris Propane, 200 mM, pH 10.2).

g. Anion Exchange Chromatography

To achieve further reduction of in-process impurities including empty AAV particles, the Poros-AAVhu68 elution pool is diluted 50-fold (20 mM Bis Tris Propane, 0.001% Pluronic F68; pH 10.2) to reduce ionic strength to enable binding to a CIMultus™ QA monolith matrix (BIA Separations). Following a low-salt wash, vector product is eluted using a 60 column volume (CV) NaCl linear salt gradient (10-180 mM NaCl). This shallow salt gradient effectively separates capsid particles without a vector genome (empty particles) from particles containing vector genome (full particles) and results in a preparation enriched for full capsids. Fractions are collected into sterile polypropylene tubes containing $\frac{1}{100}$th volume of 0.1% pluronic F68 and $\frac{1}{27}$th volume of Bis-Tris pH 6.3 to minimize non-specific binding to tubes and the length of exposure to high pH, respectively. The pooled full particle peak factions are diluted 20-fold in 20 mM Bis-Tris Propane, 0.001% Pluronic F68; pH 10.2 and reapplied to the same column which has been cleaned in place. The 10-180 mM NaCl salt gradient is reapplied and the appropriate full particle peak fractions are collected. The peak area is assessed and compared to previous data for determination of the approximate vector yield.

h. Final Formulation Buffer (FFB) and Bioburden Reduction Filtration to Yield the BDS PBS with total a salt concentration of 200 mM, 0.001% (w/v) pluronic F68 and 5% glycerol) and concentrated to yield the BDS Intermediate at a desired target (i.e. 4.5-5.5× 1013 GC/ml). Samples are removed for BDS Intermediate testing. The BDS Intermediate is sterile filtered (0.22 µm), stored in sterile polypropylene tubes and frozen at <−60° C. in a quarantine location until release for Final Fill.

i. Final Fill

PBS with total a salt concentration of 200 mM, 0.001% (w/v) pluronic F68 and 5% glycerol. The product is then be terminally filtered through a 0.22 µm filter and filled into sterilized Daikyo Crystal Zenith® 2 ml vials (West Pharmaceutical Services, Inc.®) and stoppers with crimp seals at a fill volume ≥0.5 mL to ≤1.0 mL per vial. Vials are individually labeled. Labeled vials are stored at ≤−60° C. Some doses will require dilution in FFB prior to administration. At the time of dosing, the dilution is conducted by the pharmacy at the clinical site.

j. Biocompatibility

An issue which can produce variability in dosing levels is loss of the AAV vector through binding to plastics and other solid surfaces during vector storage and patient administration. In this regard, the clinically suitable surfactant Pluronic F68 is added to the final formulation buffer of the AAV vector and is anticipated to minimize this type of loss.

Example 17

AAVhu68.JAb210a-mediated Prophylaxis of Immunodeficient Mice Against Influenza A The potential for effective prophylaxis of mice that lack a functional immune system was assessed. Rag KO mice (Rag1$^{tm1Mom}$, Jax 002216) which lack mature T cells or B cells were used. Rag KO female mice (6-8 weeks of age) received IN 10$^{10}$ GC of AAVhu68.CB7.CI.JAb210a.rBG diluted in PBS to a total volume of 51 µl delivered as three aliquots of 17 µl. Seven days later, mice were challenged with 5LD$_{50}$ of PR8. FIG. 20 is a line graph showing percent (%) change in weight for Rag KO mice challenged seven days post vector administration. Mice were weighed daily, as represented by the x axis. Percentage weight loss was calculated based on weight at day of infection influenza challenge. Any mice showing signs of distress or >30% weight loss were euthanized. All Rag KO mice receiving AAVhu68.CB7.CI.JAb210a.rBG survived the PR8 challenge.

The Rag KO mice that survived the challenge were then subjected to a second challenge with influenza B. Since Rag KO mice lack a functional immune system, this experiment served to address the impact of a prior infection on the efficacy of prophylaxis against a subsequent influenza challenge. Control Rag KO mice received 10$^{10}$ GC of AAVhu68.CB7.CI.JAb210a.rBG diluted in PBS to a total volume of 51 µl delivered as three aliquots of 17 µl to confirm the efficiency of prophylaxis against influenza B in the absence of a prior infection. Seven days later groups of mice including naïve mice and survivor vector-treated mice (previously presented in FIG. 20) were challenged with 5LD$_{50}$ of B/Lee/40 (FIGS. 21A and 21B).

FIG. 21A is a line graph showing percent (%) change in weight for Rag KO mice challenged with 5LD$_{50}$ B/Lee/40. Mice were weighed daily, as represented by the x axis. Percentage weight loss was calculated based on weight at day of infection influenza challenge. Any mice showing signs of distress or ≥30% weight loss were euthanized. Surviving mice were sacrificed 42 days post-challenge. FIG. 21B graphs the percent survival following the B/Lee/40 challenge. Mice receiving AAVhu68.CB7.CI.JAb210a.rBG vector in the absence of a prior influenza infection survived the challenge with 5LD$_{50}$ of B/Lee/40. However, there was an impact on the survival of the group of mice that were previously exposed to a PR8 challenge. We observed an 80% survival rate for Rag KO mice given AAVhu68.CB7.CI.JAb210a.rBG vector and challenged with PR8.

Example 18

Toxicity and Tolerability of AAVhu68.CB7.CI.JAb210a.rBG; Non-Clinical Pharmacology/Toxicity and Biodistribution Study of AAVhu68.CB7.CI.JAb210a.rBG in Rhesus Macaques A. Overview For this non-clinical pharmacology/toxicology study, rhesus macaques receive a nasal delivery of one of two doses of AAVhu68.CB7.CI.JAb210a.rBG or vehicle (FFB) only as a control. The vector is diluted in sterile 1×DPBS+0.001% Pluronic F-68. The clinical vector formulation for the phase I clinical trial is PBS with final salt concentration of 200 mM, 0.001% (w/v) pluronic F68, and 5% glycerol. After vector administration, the nonhuman primates (NHPs) are monitored daily for general observations. The NHPs are monitored on a bi-weekly basis for comprehensive clinical pathology (cell counts with differentials, clinical chemistries and coagulation panel) and on a monthly basis for immune reactions to the gene transfer vector [neutralizing antibodies (NAb) to AAVhu68 capsid, and cytotoxic T lymphocyte (CTL) responses against both the capsid and the transgene are assessed by the IFN-γ ELISPOT assay].

Following completion of the in-life phase of this study at day 28 and day 90 post-vector administration, macaques are necropsied with tissues harvested for a comprehensive histopathological examination. DNA and RNA are extracted from samples of the nose, trachea and lung for genome copy and transgene expression analysis by qPCR and RT-PCR, respectively. JAb210a expression is also assessed in the nasal lavage and serum. At the time of necropsy, lymphocytes are harvested from the lung, spleen, and bone marrow to examine the presence of CTLs in these organs.

B. Vector

The test article, AAVhu68.CB7.CI.JAb210a.rBG, is manufactured as described in Example 16. The final product is diluted in FFB. Vector is stored at <−60° C. after production until the day of dosing. Vector preparations are performed on the day of dosing. Preparation and dilutions are verified. Diluted vector is kept on wet ice or at 2-8° C. until dosing for up to 6 hours. Control animals are administered with vehicle buffer containing no vector (control article). This serves as the vehicle control for this study. The control article is stored at room temperature upon receipt until the day of dosing. After dosing, the remaining vector preparations and control article are retained and refrozen at <−60° C.

The AAVhu68.CB7.CI.JAb210a.rBG vector is delivered non-invasively to each nostril using the LMA® MAD Nasal™ (MAD Nasal) device (Teleflex, Inc) as per SOP 7410. The MAD Nasal™ atomizes approved medications into a fine mist that can be administered IN. Similar studies in other species such as mice were performed using direct liquid instillation via the nasal airway. However, gene expression to the nasal airway of mice via liquid delivery does not equate to that of higher species in which the vector is delivered using the clinical device, MAD Nasal. Furthermore, certain toxicological and immune responses in the NHP closely represent that of a human.

TABLE 3

Comparison of Nose Surface Area and Dosing Volume between Rhesus Monkey and Human

| | Nose | |
| --- | --- | --- |
| | Human (adult) | Rhesus macaque (adult) (3-6 years) |
| Surface Area (m$^2$) | 0.0181* | 0.00616* |
| Delivery volume (µL) | 800 | 272 |

*Handbook of Toxicology, Third Edition, edited by Michael J. Derelanko, Carol S. Auletta.

The surface area of the human nose (0.0181 m$^2$) is approximately 2.94 times greater than the surface area of the rhesus macaque nose (0.00616 m$^2$) (Table 3). As such the volume proposed to be delivered into the NHP nose is 0.80 mL (the volume that vector is delivered in the human nose)÷2.94=0.272 mL. The highest clinical dose for use in humans is proposed to be 5×10$^{13}$ GC. When extrapolating this dose based on the surface area of the rhesus macaque nose the analogous dose for use in the rhesus macaque is $5 \times 10^{13}$ GC÷2.94=$1.7 \times 10^{13}$ GC. To allow for improved accuracy when delivering small volumes in the macaque nose, the volume is increased to 0.28 mL to allow for increased accuracy of delivering two aliquots of 70 μL instead of 68 μL per nostril; both nostrils treated.

C. Animals

Seven male and seven female rhesus macaques (3-6 years, 3-10 kg) are used in this study and two different doses of AAVhu68.CB7.CI.JAb210a.rBG are examined. One group (group 1) of NHPs receive $1.7 \times 10^{13}$ GC of AAVhu68.CB7.CI.JAb210a.rBG in a total volume of 0.28 mL (given as four aliquots of 70 μL) which, when extrapolated based on surface area of the human nose (Table 3), represents the highest vector dose of the clinical trial. The other group (group 2) of NHPs receive $4.25 \times 10^{13}$ GC of AAVhu68.CB7.CI.JAb210a.rBG, given as a total volume of 0.56 mL (given as eight aliquots of 0.07 mL). When extrapolated based on the surface area of the NHP nose, this dose is 2.5-fold higher than the highest vector dose of the clinical trial.

The vector is administered IN using the MAD nasal. Vector is delivered as 0.07 mL aliquots given in both the left and right nostrils; two aliquots per nostril are delivered for the $1.7 \times 10^{13}$ GC dose over 5 mins, and four aliquots per nostril are delivered for the $4.25 \times 10^{13}$ GC dose over 5 mins. The IN route via the nasal passages was selected for use because it is the most efficient route to target the nose, the clinical site of the disease target.

NHP of each sex is randomly assigned to one of the three cohorts by the online program Research Randomizer (www.randomizer.org/form.htm). Blood is collected from at least three time points prior to vector dosing and sent to Antech GLP for cell counts with differentials and clinical chemistries. NAB titers are determined at least twice prior to the initiation of the study and PBMCs are isolated to provide a baseline level of cellular immune response to vector capsid and transgene. All baseline assessments are performed within one month prior to initiation of the study.

The study room is maintained under conditions of positive airflow relative to the hallway. Rooms are independently supplied with a minimum of 10 air changes per hour of 100% fresh air passed through filters Animal holding rooms are maintained at a temperature range of 64-79° F. (18-26° C.) with a humidity range of 30-70%. Temperature, humidity, air changes are monitored by Edstrom Watchdog System, in accordance with SOP 8026.

Animals are individually housed under ABSL-2 conditions in stainless steel cages with a floor area of 4.3-6.0 square foot and a height of 30-32 inches, respectively. All cage sizes and housing conditions are in compliance with the Guide for the Care and Use of Laboratory Animals and in accordance with SOPs 7707 and 7710. The housing room and cages are kept locked at all times and are accessible only to authorized personnel. Animals are individually housed under an IACUC approved exemption to prevent seroconversion (development of AAV vector capsid-specific NABs) prior to vector administration. Animals can be pair housed from two weeks post-vector administration according to SOP 7709. Behavioral, emotional and social needs of the animal are provided via human and conspecific interaction (viz., auditory and visual stimuli), food reward, and manipulanda according to SOP 7701. Manipulanda is sanitized and rotated every two weeks. Entry into the facility is controlled through key and badge access. An automatically-controlled light cycle of 12-hours light: 12-hours dark is maintained and is controlled by the building automation system and monitored by the Edstrom Watchdog System. The dark period begins at 1900 hours(±30 minutes). Cages are cleaned daily and changed and sanitized every two weeks, in accordance with SOPs 7710 and 7711. Cages and racks are sanitized using cage wash equipment once every two weeks and as often as necessary to prevent excessive accumulation of dirt, debris, waste, feces, or disease hazard. Animals are fed Certified Primate Diet 5048 by PMI Feeds Inc., Brentwood, Mo., ad libitum, in accordance with SOP 7710. Analyses are routinely performed by the feed supplier. Water is provided ad libitum via an automatic watering system. The water supply is drawn from the City of Philadelphia and is filtered via reverse osmosis. Processed water is analyzed twice annually for possible chemical contamination (Lancaster Laboratories, Lancaster, Pa.) and quarterly for bacterial contamination (QC Laboratories, Southampton, Pa.). Certified enrichment devices are added to the cage of each study animal throughout the course of the study. Analysis for contamination are performed by the manufacturer and analysis data are available. Food enrichment such as fruits, vegetables, nuts and cereals are provided daily. Manipulanda such as kongs, mirrors, puzzle feeder and raisin balls are provided daily Animals also receive visual enrichment along with human interaction on a daily basis. Macaques are anesthetized, in accordance with SOP 7408.

Macaques are anesthetized, in accordance with SOP 7408. Vector is administered into the nose in a volume ranging from 0.28 mL to 0.56 mL as follows. AAV vector is delivered using the MAD nasal. Vector is delivered as 0.07 mL aliquots in each nostril. For the $1.7 \times 10^{13}$ GC dose, two aliquots in each nostril are delivered over 5 mins. For the $4.25 \times 10^{13}$ GC, four aliquots in each nostril are delivered over 5 mins. After vector administration, the animals are monitored daily for general observations. All observations are recorded in accordance with SOP 7404.

The animals are monitored by daily visual observation for general appearance, signs of toxicity, distress and changes in behaviour. All animals are physically examined each time they are anesthetized for blood draw. At the time of necropsy, the animals are examined for gross abnormalities.

D. Study Schedule

Table 4 Study Schedule

Red Top (RC): No anti-coagulant; Lavender Top (LT): Potassium EDTA; Green Top (GT): Heparin; Blue Top (BT): Sodium Citrate.

| | NHP Pharmacology/Toxicity and Biodistribution Study Schedule | | | |
|---|---|---|---|---|
| Study Timepoint | Sample/Procedure | Group 1 A, B, C, D, E, F* | Group 2 G, H, I, J, K, L* | Group 3 M, N* |
| -X Days | Body Weight, Temperature, Respiratory Rate, Heart Rate | 6 | 6 | 2 |
| | Clin path (baseline) (LT, RC) | 6 | 6 | 2 |
| | Coagulation panel (baseline) (BT) | 6 | 6 | 2 |

NHP Pharmacology/Toxicity and Biodistribution Study Schedule

| Study Timepoint | Sample/Procedure | Group 1 A, B, C, D, E, F* | Group 2 G, H, I, J, K, L* | Group 3 M, N* |
|---|---|---|---|---|
| | Vector shedding (urine and fecal sampling) | 6 | 6 | 2 |
| | Antibodies (baseline) (RC) | 6 | 6 | 2 |
| -Y Days (within one month of study start) | Body Weight, Temperature, Respiratory Rate, Heart Rate | 6 | 6 | 2 |
| | Immunology (baseline) (PBMC) (GT) | 6 | 6 | 2 |
| | Clin path (baseline) (LT, RC) | 6 | 6 | 2 |
| | Coagulation panel (baseline) (BT) | 6 | 6 | 2 |
| | PBMC isolation/ELISPOT | 6 | 6 | 2 |
| | Vector shedding (urine and fecal sampling) | 6 | 6 | 2 |
| | Antibodies (baseline) (RC) | 6 | 6 | 2 |
| | Nasal lavage fluid and serum for JAb210a protein expression | 6 | 6 | 2 |
| Day 0 | Body Weight, Temperature, Respiratory Rate, Heart Rate | 6 | 6 | 2 |
| | Clin path (baseline) (LT, RC) | 6 | 6 | 2 |
| | Coagulation panel (baseline) (BT) | 6 | 6 | 2 |
| | PBMC isolation/ELISPOT | 6 | 6 | 2 |
| | Vector shedding (urine and fecal sampling) | 6 | 6 | 2 |
| | Antibodies (baseline) (RC) | 6 | 6 | 2 |
| | Nasal lavage fluid and serum for JAb210a protein expression | 6 | 6 | 2 |
| | AAVhu68.CB7.CI.JAb210a.rBG, $1.7 \times 10^{13}$ GC in 0.28 mL, IN | 6 | — | — |
| | AAVhu68.CB7.CI.JAb210a.rBG, $4.25 \times 0^{13}$ GC in 0.56 mL, IN | — | 6 | — |
| | Vehicle control, 0.28 mL, IN | — | — | 2 |
| Day 7 | Body Weight, Temperature, Respiratory Rate, Heart Rate | 6 | 6 | 2 |
| | Clin path (LT, RC) | 6 | 6 | 2 |
| | Coagulation panel (BT) | 6 | 6 | 2 |
| | Vector shedding (urine and fecal sampling) | 6 | 6 | 2 |
| | Antibodies (RC) | 6 | 6 | 2 |
| | Nasal lavage fluid and serum for JAb210a protein expression | 6 | 6 | 2 |
| Day 14 | Body Weight, Temperature, Respiratory Rate, Heart Rate | 6 | 6 | 2 |
| | Immunology (PBMC) (GT) | 6 | 6 | 2 |
| | Clin path (LT, RC) | 6 | 6 | 2 |
| | Coagulation panel (BT) | 6 | 6 | 2 |
| | Vector shedding (urine and fecal sampling) | 6 | 6 | 2 |
| | Antibodies (RC) | 6 | 6 | 2 |
| | Nasal lavage fluid and serum for JAb210a protein expression | 6 | 6 | 2 |
| Day 21 | Body Weight, Temperature, Respiratory Rate, Heart Rate | 6 | 6 | 2 |
| | Clin path (LT, RC) | 6 | 6 | 2 |
| | Coagulation panel (BT) | 6 | 6 | 2 |
| | PBMC isolation/ELISPOT | 6 | 6 | 2 |
| | Antibodies (RC) | 6 | 6 | 2 |
| | Nasal lavage fluid and serum for JAb210a protein expression | 6 | 6 | 2 |
| Day 28 ± 3 | Body Weight, Temperature, Respiratory Rate, Heart Rate | 6 | 6 | 2 |
| | Immunology (PBMC) (GT) | 6 | 6 | 2 |
| | Clin path (LT, RC) | 6 | 6 | 2 |
| | Coagulation panel (BT) | 6 | 6 | 2 |
| | PBMC isolation/ELISPOT | 6 | 6 | 2 |
| | Lymphocyte isolation (lung, spleen)/ELISPOT | 3 | 3 | 2 |

| | NHP Pharmacology/Toxicity and Biodistribution Study Schedule | | | |
|---|---|---|---|---|
| Study Timepoint | Sample/Procedure | Group 1 A, B, C, D, E, F* | Group 2 G, H, I, J, K, L* | Group 3 M, N* |
| | Antibodies (RC) | 6 | 6 | 2 |
| | Nasal lavage fluid and serum for JAb210a protein expression | 6 | 6 | 2 |
| | Vector shedding (urine and fecal sampling) | 6 | 6 | 2 |
| | Necropsy | 3 | 3 | 2 |
| | Tissues to be harvested as described herein | 3 | 3 | 2 |
| Day 35 | Body Weight, Temperature, Respiratory Rate, Heart Rate | 3 | 3 | 0 |
| | Clin path (LT, RC) | 3 | 3 | 0 |
| | Coagulation panel (BT) | 3 | 3 | 0 |
| | PBMC isolation/ELISPOT | 3 | 3 | 0 |
| | Antibodies (RC) | 3 | 3 | 0 |
| | Nasal lavage fluid and serum for JAb210a protein expression | 3 | 3 | 0 |
| Day 42 | Body Weight, Temperature, Respiratory Rate, Heart Rate | 3 | 3 | 0 |
| | Immunology (PBMC) (GT) | 3 | 3 | 0 |
| | Clin path (LT, RC) | 3 | 3 | 0 |
| | Coagulation panel (BT) | 3 | 3 | 0 |
| | Vector shedding (urine and fecal sampling) | 3 | 3 | 0 |
| | Antibodies (RC) | 3 | 3 | 0 |
| | Nasal lavage fluid and serum for JAb210a protein expression | 3 | 3 | 0 |
| Day 49 | Body Weight, Temperature, Respiratory Rate, Heart Rate | 3 | 3 | 0 |
| | Clin path (LT, RC) | 3 | 3 | 0 |
| | Coagulation panel (BT) | 3 | 3 | 0 |
| | PBMC isolation/ELISPOT | 3 | 3 | 0 |
| | Antibodies (RC) | 3 | 3 | 0 |
| | Nasal lavage fluid and serum for JAb210a protein expression | 3 | 3 | 0 |
| Day 90 ± 3 | Body Weight, Temperature, Respiratory Rate, Heart Rate | 3 | 3 | 0 |
| | Immunology (PBMC) (GT) | 3 | 3 | 0 |
| | Clin path (LT, RC) | 3 | 3 | 0 |

The vector is administered IN using the MAD Nasal. Vector is delivered as 70 µL aliquots given in both the left and right nostrils; two aliquots per nostril are delivered for the $1.7 \times 10^{13}$ GC dose over 5 mins, and four aliquots per nostril are delivered for the $4.25 \times 10^{13}$ GC dose over 5 mins. Doses of $1.7 \times 10^{13}$ GC and $4.25 \times 10^{13}$ GC were chosen for this study. The highest dose that administers in the subjects of the clinical trial is $5 \times 10^{13}$ GC in 0.80 mL of PBS, given in 0.20 mL aliquots using the MAD Nasal. The doses selected for Group 1 ($1.7 \times 10^{13}$ GC) and Group 2 ($4.25 \times 10^{13}$ GC) reflect the highest dose planned for the clinical trial, $5 \times 10^{13}$ GC, and a dose that is 2.5-fold higher than the highest dose planned for the clinical trial, respectively.

Each vector treatment group includes six animals, a mixture of male and female rhesus macaques. The control group includes two animals and is sacrificed at day 28. Studies were performed in the nasal airways of rhesus macaques designed to evaluate the expression profile of AAV9, a serotype that closely resembles AAVhu68. Utilizing several transgenes, including rhesus AFP (rhAFP), the timeline of kinetics of expression in the nasal lavage fluid of NHPs was established when AAV is applied directly to the nose. Transgene expression was detected as early as day 14 following vector delivery and reached its peak between days 14-28. Transgene expression then stabilized and began to wane between days 56 and 84. The time points selected for the instant study described herein were chosen to capture the peak of gene expression (day 28) and also past the peak of vector expression (day 90). These time points allow collection of important information regarding vector safety and toxicity at early times (day 28) and long term as gene expression wanes (day 90).

On study day 0, macaques are dosed in the nose using the MAD Nasal™ with either $1.7 \times 10^{13}$ GC of AAVhu68.CB7.CI.JAb210a.rBG in a total volume of 0.28 mL (four aliquots of 70 µL) or $4.25 \times 10^{13}$ GC of AAVhu68.CB7.CI.JAb210a.rBG in a total volume of 0.56 mL (eight aliquots of 70 µL).

Daily viability checks are performed on all animals, in accordance with SOPs. Body weight, temperature, respiratory rate, and heart rate are monitored and recorded at all time points, in accordance with SOPs. NHPs are anesthetized and blood collected, in accordance with SOPs 7408 and 7411. Blood collected is used for CBC, clinical chemistries and coagulation panel examination. Clinical pathology, clinical chemistry, and coagulation panel are performed by Antech GLP. Changes in the blood chemistries and blood profiles of the animals are analyzed. Chemistries, complete blood counts (CBC) with differentials and platelet counts are evaluated on samples from the animals at indicated time points. The animals are anesthetized as per SOP 7408. A pediatric Foley catheter may be placed in one of the nostrils and, once in place, the balloon is inflated with air and the catheter pulled back until resistance is achieved. The head/body of the macaque is tilted to the respective side and up to 5 mL of PBS (per nostril) is then used to flush the nasal cavity; the fluid is collected as drops in a Falcon tube positioned right under the respective nostril. At the end of the process the catheter is removed and discarded and the procedure repeated for the adjacent nostril. The serum is separated and aliquoted into labeled microcentrifuge tubes. Humoral immune responses are examined on serum from indicated time points using the NAB assay, in accordance with SOPs. PBMCs are isolated and cryopreserved, in accordance with SOP 6003. T cell responses to AAVhu68 and JAb210a are analyzed by IFN-γ ELISPOT, in accordance with SOP 6002, where positive response criteria are spot forming units (SFU)/$10^6$ cells >55 and ×3 the medium negative control value (no stimulation). Serum NAB assay is done in accordance with SOP, IFN-γ ELISPOT in accordance with SOP 6002, and AAV vector shedding by TaqMan qPCR in accordance with SOP. Urine and fecal samples are collected at the indicated time points, frozen on dry ice and stored at <–60° C., in accordance with SOP 7428. DNA is extracted and TaqMan qPCR reactions were performed, in the spirit of SOP 3001 but modifications to the protocol may be necessary based on the sample.

At the scheduled necropsy time point points (day 28 and day 90 post-vector dosing), NHPs are euthanized in accordance with SOPs 7422 and 7600. Death is confirmed by absence of heartbeat and respiration, in accordance with SOP 7422. Animals are necropsied and tissues harvested for full pathology, in accordance with SOP 7600. Tissues are also harvested for biodistribution and stored at ≤–60° C.

Tissues collected for both biodistribution and histology include Cardiovascular System: Heart, Aorta (thoracic and abdominal); Digestive System: Liver (caudate, left, middle, and right lobes), Gallbladder, Esophagus, Stomach, Duodenum, Jejunum, Ileum, Cecum, Colon, Pancreas; Endocrine System: Pituitary gland, Thyroid gland left and right lobes, with parathyroid, Adrenal glands (left and right); Hematopoietic System: Spleen, Thymus, Lymph node (inguinal, left and right), Lymph node (mesenteric), Lymph node (axillary, left and right), Bone marrow (rib), Peyer's patches (collected with sections of intestine); Musculoskeletal System: Skeletal muscle (quadriceps); Respiratory System: Paranasal sinuses, Cribriform plate, Nasal septum, Pharynx, Larynx, Trachea, Lungs (4 lobes); Nervous System: Brain (including cerebrum [frontal & occipital] lobes), Midbrain, Optic nerve (left and right), Optic chiasm, Cerebellum, Medulla/pons, Eyes (left and right, collected in modified Davison's fixative); Spinal cord (cervical, midthoracic, lumbar), Sciatic nerve (left and right); Reproductive System (Male): Testes (left and right, collected in modified Davison's fixative), Epididymis (left and right), Prostate; Reproductive System (Female): Ovaries (left and right), Uterus, Mammary gland (left and right); Urinary System: Kidneys (left and right), Urinary Bladder; and Miscellaneous: Chest tattoo, Skin, Gross observations (made at necropsy for which histopathology is not appropriate (e.g., fluid, matter air, missing anatomic parts) are not collected).

All tissues are fixed in 10% NBF or modified Davidson's fixative and processed according to SOPs 4003, 4004, 4006, and 4007. Any gross lesions observed during necropsy are collected and preserved in 10% NBF. Tissue processing, histopathological evaluations, T-cell response, and RNA preparation are carried out by following respective SOPs. Histopathology slides are evaluated.

At the time of necropsy, lung, liver, spleen, and bone marrow are collected and lymphocytes isolated from each tissue, in accordance with SOPs 6004, 6005, and 6006, respectively. T cell responses to AAVhu68 and JAb210a are analyzed by IFN-γ ELISPOT, in accordance with SOP 6002, in which positive response criteria were spot forming units (SFU)/$10^6$ cells >55 and ×3 the medium negative control value (no stimulation). At the time of necropsy tissues are collected for biodistribution, frozen on dry ice, and stored at ≤–60° C. If requested, DNA is extracted from tissues and TaqMan qPCR reactions were performed, in accordance with SOP 3001. Additionally, at the time of necropsy tissues are collected for RNA expression, frozen on dry ice and stored at ≤–60° C. DNase treated total RNA is isolated from 100 mg of nose, trachea and several areas of the various lobes of the lungs. RNA is quantified by spectrophotometry and aliquots reverse transcribed to cDNA using random primers. cDNA containing the vector-derived message is quantified by qPCR detecting vector specific sequence, the region spanning the transgene and poly A signal.

Statistical analyses are performed on blood chemistry values. Ranges of normal values for wild type rhesus macaques are generated by taking the mean of all values collected for the study animals pre-vector dosing (a minimum of two baselines) and by calculating the standard deviation (SD). The range is presented as the mean±SD. Values outside of two SDs of the mean are considered to be extreme values.

The following clinical chemistry parameters are determined: Albumin, Alkaline Phosphatase (ALP), Alanine Aminotransferase (ALT), Aspartate Aminotransferase (AST), Amylase, Bilirubin (Direct), Bilirubin (Total), Calcium, Chloride, Cholesterol, Creatine Phosphokinase (CPK), Creatinine, Gamma Glutamyl Transferase (GGT), Glucose, Lactate Dehydrogenase (LD), Lipase, Magnesium, Phosphorus, Potassium, Sodium, Triglycerides, Total Protein, and Urea Nitrogen.

Blood for CBC and platelet count are collected and stored at 2-8° C. until overnight shipment to Antech GLP. The following Hematological parameters are determined: Complete Blood Count, Mean Platelet Volume (stable 8 hours), Red Cell Count, Red Cell Distribution Width, Haemoglobin, Haematocrit, Mean Corpuscular Volume (MCV), Mean Corpuscular Haemoglobin (MCH), Mean Corpuscular Haemoglobin Concentration (MCHC), Platelet Count, Leukocyte Count, Leukocyte Differential, and RBC Morphology.

Example 19

Clinical Development—Safety and Tolerability of AAV Vector for Delivery of Anti-Flu Antibody A. Overview Phase 1 clinical trial is under investigation to determine the appropriate dose of AAV2/hu68-expressed transgenes for subsequent phase 2 efficacy assessments. Clinical development is initiated with a phase 1 dose escalation trial evaluating a single administration of an AAV2/hu68 vector, delivering the JAB210a MDAb, with expansion for safety assessments at the optimal dose. If the vector has acceptable safety and PK profile in the initial phase 1 trial, subsequent phase 2 development may include evaluation of the vector for safety, PK, and preliminary efficacy in a controlled influenza challenge model. The elderly population (65 years and over) is the target population for this clinical product development plan. The vector is envisioned as having two potential roles: a countermeasure against a pandemic and an alternative to the traditional seasonal vaccine. Its use as a pandemic countermeasure could be in the context of a stockpile or a manufacturing campaign during the emergence of an influenza pandemic. The phase 1 trials commence in the United States with possible expansion to the phase 2 efficacy trials (i.e., challenge study) at a qualified CRO. If safety and preliminary efficacy are demonstrated in healthy volunteers, subsequent trials in an expanded population groups are considered for further development.

Provided that the phase 1 trial demonstrates acceptable safety (including full 6-month safety data and required preclinical safety data), pharmacokinetic (PK) and initial immunologic (e.g., influenza neutralization activity, level and duration of transgene expression, immune responses to capsid and transgenes) profiles, a phase 2 trial is conducted. The doses are chosen from the phase 1 trial and are tested in a controlled influenza challenge model. The goal of the phase 2 trial would be to evaluate preliminary efficacy and to establish an efficacious dose of the vector.

Vector is manufactured as described in Example 16. The vector is formulated as a solution containing in phosphate-buffered saline (PBS) with total salt concentration of 200 mM, 0.001% (w/v) pluronic F68 and 5% glycerol (Final Formulation Buffer, FFB). AAVhu68.CB7.CI.JAb210a.rBG is administered intranasally after dilution into FFB at four dose levels. The initial dose levels were chosen based on preclinical efficacy data, and are refined based on nonclinical safety assessments, with the highest dose limited by the concentration that can be achieved without AAV vector particle aggregation. Doses range from $6.25 \times 10^{12}$ genome copies (GC) to $5 \times 10^{13}$ GC administered as two aliquots of 0.2 ml per nostril via the commercially approved LMA intranasal mucosal atomization device (IMAD) by Teleflex Medical (MAD300) (MAD Nasal™) for a total volume delivered in each subject of 0.8 ml. The goal would be to achieve a concentration of 5-20 ng/ml of the JAb210a MDAb as measured in a nasal wash solution two weeks after administration of the vector. A single dose of the vector at one of the four dose cohorts ($6.25 \times 10^{12}$ GC, $1.25 \times 10^{13}$ GC, $2.5 \times 10^{13}$ GC or $5 \times 10^{13}$ GC) is administered on Day 0. Subjects in each dosing regimen are monitored for safety and immunogenicity parameters through to Study Day 180 (±2).

B. Objectives

Primary Objectives are safety and tolerability of the vector in elderly subjects was assessed by the occurrence of adverse events based on CBC, chemistries, urinalysis, local immune responses confined to the nose, and clinical findings. Adverse events are graded according to a modified version of the Toxicity Grading Scale for Healthy Adult and Adolescent Volunteers Enrolled in Preventative Vaccine Clinical Trials which was published by FDA September 2007.

Secondary Objectives are to assess the level and duration of influenza neutralization activity in nasal wash and serum, e.g., anti-idiotype ELISA and anti-HA ELISA—based assays; to assess the level and duration of JAb210a MDAb expression in nasal wash and serum; to assess the level of neutralizing antibodies to transgene and capsid; to assess the level of cellular responses to transgene, JAb210a MDAb and capsid as measured by the IFNγ ELISPOT assay and shedding of vectors in nasal, pharyngeal, urine, rectal and blood samples.

C. Study Design

To evaluate preliminary safety and tolerability, to understand the pharmacokinetics of the vector in healthy volunteers, and to select a dose level for further development, an open label, dose-escalation trial with the dose levels based on preclinical data is performed. The study enrolls up to five cohorts, with four subjects per cohort. Subjects are screened 4-12 weeks prior to treatment and are followed for up for 6 months.

Healthy volunteers are treated IN with the vector. Study goals are to evaluate safety and tolerability, and to understand pharmacokinetics of the vector, and to select optimal dose for future development.

Open label trial using single ascending vector dose with a formal safety assessment of each dose group prior to dose escalation. Four cohorts with four subjects per cohort, and adaptive expansion to eight for the optimal dose defined as that resulting in production of 5-20 ng/ml of MDAb in the nasal lavage fluid.

a. Administration

Each volunteer receives one 0.8 ml dose of the vector IN via two sequential applications of 0.2 ml per nostril into each nostril using the approved MAD Nasal. Up to twenty four volunteers are enrolled in five cohorts. Cohorts 1-4 receive increasing dosage levels of vector with the final cohort (cohort 5) expanded to 8 volunteers at the optimal dose level (defined by safety and pharmacokinetic parameters in cohorts 1-4).

The vector is administered using the MAD Nasal™ on Day 0.

Cohort 1: Dose $6.25\times10^{12}$ GC;

Cohort 2: Dose $1.25\times10^{13}$ GC;

Cohort 3: Dose $2.50\times10^{13}$ GC;

Cohort 4: Dose $5.00\times10^{13}$ GC;

Cohort 5: expansion cohort at the optimal dose level.

One week of observation is required between dosing of subjects within cohorts. A total of four weeks between cohorts are used to evaluate safety data before escalating to the next dose.

Subjects are admitted to a research inpatient unit the night before vector administration. In the morning, fasting blood is obtained, and then subjects are administered IN. Vital signs are monitored frequently for first 24 hours. Blood, nasal wash, urine and rectal swabs are collected for safety testing on days 1, 3, 7, 14 and 28 and months 2, 4 and 6 which represent the end of the study. Samples are used for safety labs, detection of shedding of vectors, assessment of transgene expression, and immunogenicity of transgene and vector capsid.

Study duration is 6 months (180 days) after vector administration.

Stopping rules are based on the occurrence of dose-limiting toxicity. Dose-limiting toxicity is defined as the occurrence of any one treatment related Grade 4 or any two Grade 3 treatment-related adverse events within a cohort. All adverse events are carefully reviewed prior to any decisions regarding dose-escalation, cohort expansion, or stopping.

TABLE 5

| Cohort | N active | AAVhu68.CB7.CI.JAb210a.rBG Dosage Level (GC) | Total volume to be administered (ml) | Administration Route |
|---|---|---|---|---|
| 1 | 4 | $6.25 \times 10^{12}$ | 0.2 ml in each nostril; two sets of applications, 0.8 ml total dose per subject | IN |
| 2 | 4 | $1.25 \times 10^{13}$ | | IN |
| 3 | 4 | $2.50 \times 10^{13}$ | | IN |
| 4 | 4 | $5.00 \times 10^{13}$ | | IN |
| 5 | 8 | Optimal dose | 0.2 ml in each nostril; two sets of applications, 0.8 ml total dose per subject | IN |
| Total | 24 | | | | b. Target Population, Inclusion/Exclusion Criteria

Diagnosis and main inclusion criteria is healthy male or female subjects aged 65 years and over with a body mass index ≥19 to ≥30 kg/m², and weight of ≥50 to ≤100 kg. Females of childbearing potential are eligible for enrollment if they have a negative serum pregnancy test before study entry, and they are using an effective method of contraception (hormonal, IUD).

Inclusion criteria are: Male or female subjects aged 65 years and over; Able to give written informed consent to participate; Healthy, as determined by medical history, physical examination, vital signs, and clinical safety laboratory examinations at baseline; Non-habitual smoker (habitual smokers are persons who smoke more than 4 cigarettes or other tobacco products on a weekly basis) and agree to not use tobacco products during participation; and Females should fulfill one of the following criteria: at least one year post-menopausal or surgically sterile.

Exclusion criteria are: Significant history of seasonal hay fever or a seasonal allergic rhinitis or perennial allergic rhinitis or chronic or nasal or sinus condition; History of asthma requiring treatment for up to 1 year prior to administration of the vector; Subjects with abnormal nasal structure including septal deviation and nasal polyps, chronic sinusitis, asthma, or COPD; Current use of intranasal steroids; Presence of significant uncontrolled medical or psychiatric illness (acute or chronic) as assessed by the Investigator (This includes, but is not limited to, institution of new medical or surgical treatment, or a significant dose alteration for uncontrolled symptoms or drug toxicity within 3 months of screening and reconfirmed on Day 0 prior to challenge); Positive serology for HIV-1 or HIV-2, or HBsAg or HCV antibodies; Cancer, or treatment for cancer, within 3 years, excluding basal cell carcinoma or squamous cell carcinoma, which is allowed; Presence of immunosuppression or any medical condition that may be associated with impaired immune responsiveness, including, but not limited to, diabetes mellitus; Presently receiving (or history of receiving), during the preceding 3-month period, any medications or other treatments that may adversely affect the immune system such as allergy injections, immune globulin, interferon, immunomodulators, cytotoxic drugs or other drugs known to be frequently associated with significant major organ toxicity, or systemic corticosteroids (oral or injectable) (Topical corticosteroids will be allowed); History of drug or chemical abuse in the year before the study; Receipt of any investigational product or nonregistered drug within the 30 days prior to administration of the vector or currently enrolled in any investigational drug study or intends to enroll in such a study within the ensuing study period; Receipt of blood or blood products six months prior to the vector administration or planned administration during the study period; Acute disease within 72 hours prior to the vector administration, defined as the presence of a moderate or severe illness with or without fever (as determined by the Investigator through medical history and physical examination), or presence of a fever >38° C. orally; Pregnant and/or lactating females; Serum circulating neutralizing antibodies to the AAV2/hu68 of >1:80; and Any condition that, in the opinion of the Investigator, might interfere with the primary study objectives and assessments.

c. Dose Level Determination

The initial dose levels were chosen based on preclinical efficacy data, and are refined based on nonclinical safety assessments, with the highest dose limited by the aggregation properties of AAV. Doses range from $6.25 \times 10^{12}$ to $5 \times 10^{13}$ GC/dose administered in 2×0.2 ml per nostril via the MAD Nasal™. The goal would be to have a target of 5-20 ng/ml of JAb210a MDAb in nasal wash at two weeks after administering the vector. These doses are substantially lower than those given to monkeys, mice and ferrets when adjusted for total body mass. No substantial toxicity was observed in any nonclinical studies conducted in these species at any dose with the vector or versions of the AAV vector similar in structure to the vector for the clinical trial.

d. Dosage Administration and Duration

Each dose group receive the vector in 0.4 ml per each nostril via MAD Nasal™. Subjects are dosed one by one. Treatment intervals within the same dose group would be determined by the nonclinical studies (e.g., 1 week). Once all subjects in one cohort have passed study day 14, preliminary safety data is reviewed. If no safety issues are identified, dose escalation to the next dose commences. After completion of cohort 4 and preliminary safety for the highest dose is demonstrated, a fifth and final cohort is enrolled for expansion for a total of eight subjects (i.e., four additional subjects) at the optimal dose which is the Maximally Tolerated Dose or the highest dose that can be administered. The maximum number of subjects is 24.

e. Duration of Proposed Clinical Investigation

Informed consent/HIPAA, demographic assessment/medical history and Inclusion/exclusion Screening are conducted during visit 0 (Screen) in weeks −12 to −4.

Medication history and Safety Labs (including: Comprehensive Metabolic panel [sodium, potassium, chloride, carbon dioxide, glucose, blood urea nitrogen, lactate dehydrogenase, creatinine, creatinine phosphokinase, calcium, total protein, albumin, AST, ALT, alkaline phosphatase, and total bilirubin]; CBC [white blood cell count, hemoglobin, hematocrit, platelet count, red cell distribution width, mean corpuscular volume, mean corpuscular hemoglobin, and mean corpuscular hemoglobin concentration]; Urinalysis [urinary color, turbidity, pH, glucose, bilirubin, ketones, blood, protein, WBCs]; Coagulation [PT, INR, PTT]; Serology (HIVAb, HBsAg, HepCAb, RPR)) are checked across the visits, including visit 0 (Screen) in weeks −12 to −4, visit 1 (Screen) in weeks −4 to −1, visit 2 on day 0, visit 3 on day 7, visit 4 on day 14, visit 5 on day 28, visit 6 in month 2, visit 7 in month 4 and visit 8 in month 6.

Urine pregnancy test (females of childbearing potential only), Pregnancy avoidance counseling, Electrocardiogram (Changes in QT and QTC from each visit are analyzed based on the most recent FDA guidance) and pulmonary function testing (Spirometry (including vital capacity, forced vital capacity, forced expiratory volume (FEV) at timed intervals of 0.5, 1, 2, and 3 seconds, forced expiratory flow 25-75% (FEF 25-27) and maximal voluntary ventilation (MVV)), Physical exam (weight, height (only be measured at visit 1), BMI), Chest x-ray (Chest x-ray does not have to be repeated if performed within 3 months of screening and was found to be normal and the subject does not ongoing pulmonary signs or symptoms), Vitals (Vital signs during infusion day: prior to infusion, at 15(±5), 30(±5) minutes and at 1(±10 min), 3(±10 min), and 6 hrs(±10 min) post-dosing. Includes blood pressure, heart rate, temperature, respirations), Research blood (T cell responses to capsid and transgene), Research nasal wash (Ab levels by a cell-based neutralization assay), Research serum (NAB to capsid and transgene, Ab levels), Peak nasal expiratory flow (performed using a portable inspiratory flow meter. After exhalation, the meter with a small mask attached is held horizontally to form an air-tight seal around the nose. The subject is then instructed to forcibly and sharply inhale (for about 1 second). The flow rate is noted by the position of the cursor on the calibrated scale after completion of each test), and SNOT-22 Questionnaire (a 22-point questionnaire that asks patients a range of health and quality of life questions where they grade their symptoms from 0 (no symptoms) to 5 (as bad as it can be). The score is the addition of all the numbers selected (Max 110). Patients are also allowed to mark up to 5 problems/concerns that are most important to them.) are assessed at visit 1 (Screen) in weeks −4 to −1, visit 2 on day 0, visit 3 on day 7, visit 4 on day 14, visit 5 on day 28, visit 6 in month 2, visit 7 in month 4 and visit 8 in month 6.

Vector Administration and Admission for 24 hour stay are performed at visit 2 on day 0.

Adverse Events are monitored at visit 2 on day 0, visit 3 on day 7, visit 4 on day 14, visit 5 on day 28, visit 6 in month 2, visit 7 in month 4 and visit 8 in month 6.

Local and systemic reactogenicity assessment is performed at visit 2 on day 0, visit 3 on day 7, visit 4 on day 14, and visit 5 on day 28.

f. Observations and Measurement Methodology

Primary objectives are safety and tolerability of single escalating dose of the vector solution as defined by the occurrence of the adverse events and by the changes in laboratory parameters and in vital signs, from baseline and up to six months post-treatment. Safety evaluation also includes reactogenicity assessment in nasal mucosa and lungs for the acute period of 14 days following the vector solution administration.

Secondary objectives are assessment of PK, including concentration of transgene in nasal wash, in serum concentration, maximal concentration, clearance, elimination half time; and assessment of immunogenicity of single escalating doses by measuring antibody binding and T-cell responses to all components of the IP (AAV2/hu68 capsid, JAb210a MDAb).

Assessments include Blood chemistry (liver function tests [LFTs], creatinine), hematology (complete blood count [CBC] with differential, platelets, prothrombin time/partial thromboplastin time (PT/PTT), creatinine phosphokinase (CPK), troponin, and urinalysis are evaluated throughout the course of the trial with more frequent monitoring in the acute/subacute period following the vector solution administration. Serum, nasal lavage and PBMCs sampling is conducted throughout the trial for monitoring transgene expression and for evaluations of antibodies and cellular responses to the transgene and the AAV2/hu68 capsid. Urinary human chorionic gonadotropin (HCG) testing is performed for all female volunteers prior to the vector solution administration.

Adverse events (AEs) and serious adverse events (SAEs) are collected for the duration of the study (i.e., 6 months).

Pharmacokinetics (PK) are evaluated routinely throughout the course of the trial to determine the kinetics of expression of the JAb210a MDAb. Nasal wash and serum are sampled at regular intervals and Ab level determined by mass spectroscopy and ELISAs using the assays.

Mass spectrometry, Anti-idiotype assays, Transgene Expression (ELISA), Assessment of vector shedding were developed according to conventional methods.

g. Administration of the Vector Solution

Administration of the vector solution occurs in two sequential 0.2 ml doses into each nostril (i.e., total of 0.8 ml of the vector solution). The vector solution is administered using a commercially approved device manufactured by Teleflex Medical (Teleflex.com). The device is called the LMA MAD Nasal™ (Intranasal Mucosal Atomization Device). Details as to how best use the device to deliver IP to nasal mucosa are provided in the company's Procedure Guide. Basically, the subject is placed in a recumbent position and the tip of the device is placed at the orifice of each nasal passage (one at a time) after which the vector solution is delivered by pushing the fluid through the atomizer via a syringe.

h. Study Design and Sample Size Determination

The primary endpoint, on which the dose-escalation scheme is based, is safety. Safety monitoring includes both clinical observations and the results of laboratory testing and is graded according to a modification of Toxicity Grading Scale for Healthy Adult and Adolescent Volunteers Enrolled in Preventative Vaccine Clinical Trials published by the FDA September 2007. The only revision is related to an assessment of clinical abnormalities which in the guidance document are focused on findings related to an injection site. Criteria related to clinical findings in the proximal and distal respiratory systems is established.

The maximum tolerated dose (MTD) is defined as the dose below the dose at which the subjects demonstrate dose-limiting toxicity (DLT), defined as any treatment related Grade 3 in two subjects or one treatment related Grade 4 event. It is recognized that the MTD may not be reached within the range of doses proposed. In this case the highest dose used is the recommended dose for future trials. A minimum of eight subjects are treated at the MTD, or in the event the MTD is not reached, at the highest dose. Thus, it may be necessary to add four additional subjects in order to ensure that eight subjects are treated at the recommended dose.

The design is a standard "4+4" phase I dose-escalating trial with 4 patients per dose level, expanding to 8 patients per level in the event of dose-limiting toxicity (DLT) at any level, and with provision to expand to 4 additional patients at the recommended dose to better characterize the optimal dose and rate of toxicity at that level. A minimum of 7 days between patients within a dose cohort and 2 weeks between cohorts is used to ensure adequate assessment of potential short-term toxicity. Subjects are observed for 6 months after dosing although the period of observation used to determine whether the MTD has been reached and/or to escalate to the next dose is the total body of data from the cohort including a minimum of 14 days after the final subject in the cohort.

If 0/4 subjects in a cohort experience Grade 3 or 4 toxicities, the dose is escalated and the next four subjects are treated at the next higher dose; If 1/4 subjects experience a treatment related Grade 3 toxicity, four additional subjects are treated at the same dose. If none of the additional subjects experience a treatment related Grade 3 or 4 toxicities (total of $1/8$), the dose is escalated and the next four subjects are treated at the next higher dose. If any of the additional subjects experience a Grade 3 or 4 toxicity (total of >1/8), an additional four subjects are enrolled in the lower dose cohort and if clean it is considered the MTD; If any subject experiences a treatment related Grade 4 toxicity, no more subjects are enrolled at this dose and an additional four subjects are enrolled in the cohort receiving a dose below that which the Grade 4 toxicity occurred to establish the MTD.

i. Safety and Adverse Events

Unanticipated problems involving risk to subjects or others are defined as any incident, experience, or outcome that meets all of the following criteria: Unexpected in nature, severity, or frequency (i.e. not described in study-related documents such as the IRB-approved protocol or consent form, the investigators brochure, etc.); Related or possibly related to participation in the research (i.e., possibly related means there is a reasonable possibility that the incident experience, or outcome may have been caused by the procedures involved in the research); and Suggests that the research places subjects or others at greater risk of harm (including physical, psychological, economic, or social harm).

An adverse event (AE) is any symptom, sign, illness or experience that develops or worsens in severity during the course of the study. Intercurrent illnesses or injuries should be regarded as adverse events. Abnormal results of diagnostic procedures are considered to be adverse events if the abnormality: results in study withdrawal; is associated with a serious adverse event; is associated with clinical signs or symptoms; leads to additional treatment or to further diagnostic tests; is considered by the investigator to be of clinical significance.

Adverse events are classified as serious or non-serious. A serious adverse event is any AE that is: fatal, life-threatening, requires or prolongs hospital stay, results in persistent or significant disability or incapacity, a congenital anomaly or birth defect, an important medical event.

Important medical events are those that may not be immediately life threatening, but are clearly of major clinical significance. They may jeopardize the subject, and may require intervention to prevent one of the other serious outcomes noted above. For example, drug overdose or abuse, a seizure that did not result in in-patient hospitalization, or intensive treatment of bronchospasm in an emergency department would typically be considered serious.

All adverse events that do not meet any of the criteria for serious should be regarded as nonserious adverse events.

A preexisting condition is one that is present at the start of the study. A preexisting condition should be recorded as an adverse event if the frequency, intensity, or the character of the condition worsens during the study period.

At screening, any clinically significant abnormality should be recorded as a preexisting condition. At the end of the study, any new clinically significant findings/abnormalities that meet the definition of an adverse event must also be recorded and documented as an adverse event.

All unresolved adverse events are followed by the investigator until the events are resolved, the subject is lost to follow-up, or the adverse event is otherwise explained. At the last scheduled visit, the investigator should instruct each subject to report any subsequent event(s) that the subject, or the subject's personal physician, believes might reasonably be related to participation in this study. The investigator should notify the study sponsor of any death or adverse event occurring at any time after a subject has discontinued or terminated study participation that may reasonably be related to this study. The sponsor should also be notified if the investigator should become aware of the development of cancer or of a congenital anomaly in a subsequently conceived offspring of a subject that has participated in this study.

A clinical laboratory abnormality is documented as an adverse event if any one of the following conditions is met: The laboratory abnormality is not otherwise refuted by a repeat test to confirm the abnormality; The abnormality suggests a disease and/or organ toxicity; The abnormality is of a degree that requires active management; e.g. change of dose, discontinuation of drug, more frequent follow-up assessments, further diagnostic investigation, etc.

Any adverse event that results in hospitalization or prolonged hospitalization is documented and reported as a serious adverse event unless specifically instructed otherwise. Any condition responsible for surgery is documented as an adverse event if the condition meets the criteria for and adverse event. Neither the condition, hospitalization, prolonged hospitalization, nor surgery are reported as an adverse event in the following circumstances: Hospitalization or prolonged hospitalization for diagnostic or elective surgical procedures for a preexisting condition. Surgery should not be reported as an outcome of an adverse event if the purpose of the surgery was elective or diagnostic and the outcome was uneventful; Hospitalization or prolonged hospitalization required to allow efficacy measurement for the study.

The investigator is responsible for ensuring that AEs are documented on the appropriate page of the CRF according to the following descriptors: Mild: associated with no limitation of usual activities or only slight discomfort; Moderate: associated with limitation of usual activities or significant discomfort; Severe: associated with inability to carry out usual activities or very marked discomfort Relationship to Study Drug.

The relationship of AEs to the study drug is determined by the investigator according to the following definitions:

Probable: a reaction that follows a reasonable temporal sequence from administration of the vector solution that follows a known or expected response pattern to the suspected study tracer; and that could not be reasonably explained by the known characteristics of that subject/patient's clinical state;

Possible: a reaction that follows a reasonable temporal sequence from administration of the study tracer; that follows a known or expected response pattern to the suspected study tracer; but that could readily have been produced by a number of other factors;

Unlikely: a reaction that does not follow a reasonable temporal sequence from administration of the study tracer. However, causality from the vector solution cannot be ruled out.

None: a reaction for which sufficient data exist to indicate that the etiology is unrelated to the study tracer.

To ensure that risks to subjects are minimized, subjects are enrolled into the study in separate cohorts of four to eight subjects each. Following the vector solution administration to all subjects within a cohort, dosing of subjects in other cohorts does not occur until the last subject within the cohort has completed at least 2 weeks of follow-up and the primary safety evaluation is done for the entire cohort and examined Dosing between members of a cohort occurs at intervals no less than 1 week apart. In this study, dose-limiting toxicity (DLT) is defined as two Grade 3 toxicities within a cohort or a Grade 4 event, in which they are deemed to be treatment-related. As described above, one subject within a cohort who experiences a Grade 3 treatment related toxicity triggers the dosing of four additional subjects at that dose for up to 8 subjects within that cohort. A second subject with treatment related Grade 3 toxicity at that dose triggers a dose reduction, with four additional subjects treated at the lower dose if needed to ensure a total of 8 subjects treated; if there are no more than two Grade 3 and no Grade 4 toxicities at this lower dose it is considered the MTD. Any treatment related Grade 4 toxicity stops accrual at that dose and triggers accrual of an additional 4 subjects at the lower dose to help establish the MTD. Any serious adverse event is immediately reported and assessed for its relationship to study treatment. If an SAE is deemed treatment-related, it serves as a stopping criterion for the study.

j. Statistical Analysis

Various descriptive statistics, including graphical methods, are used to summarize efficacy endpoints. Means, standard deviations, medians, and ranges are computed for measured continuous variables. Confidence intervals are produced for summary statistics as appropriate. Hypothesis tests are done using a two-sided significance level (Type I error) of $\alpha=0.05$ although actual p-values are reported. For measured continuous variables, two group comparisons (such as between dose cohorts) generally employ Wilcoxon rank-sum tests; Wilcoxon signed-rank tests are used for paired data such as change from baseline in lung function parameters. Categorical variables are compared between groups using Fisher's exact test and within patients using McNemar's test.

All patents, patent publications, and other publications listed in this specification, as well as the sequence listing labeled "17-7987PCT_ST25.txt" and priority applications, U.S. Provisional Patent Application No. 62/618,443, filed Jan. 17, 2018, Application No. 62/560,834, filed Sep. 20, 2017, Application No. 62/504,293, filed May 10, 2017 and Application No. 62/464,753, filed Feb. 2, 2017, which are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A non-replicating recombinant adeno-associated virus (rAAV) comprising an AAV capsid and a vector genome packaged in the AAV capsid, wherein the vector genome comprises AAV inverted terminal repeat sequences and an expression cassette comprising a nucleic acid sequence encoding an anti-influenza fusion protein having the amino acid sequence of SEQ ID NO: 27.

2. The rAAV according to claim 1, wherein the vector genome further comprises a 5' UTR which comprises is-a fragment of human c-myc 5' UTR.

3. The rAAV according to claim 1, wherein the vector genome comprises a single-stranded AAV 5' inverted terminal repeat and an AAV 3' inverted terminal repeat.

4. The rAAV according to claim 1, wherein the nucleic acid sequence encoding the anti-influenza fusion protein is of: SEQ ID NO: 21, or SEQ ID NO: 26.

5. The rAAV according to claim 1, wherein the rAAV has an AAVhu68 capsid, wherein the AAVhu68 capsid comprises:

(a) a heterogenous population of AAVhu68 vp1 proteins selected from one or more of: vp1 proteins produced by expression from a nucleic acid sequence which encodes the predicted amino acid sequence of 1 to 736 of SEQ ID NO:16, vp1 proteins produced from SEQ ID NO: 18, or vp1 proteins produced from a nucleic acid sequence at least 70% identical to SEQ ID NO:18 which encodes the predicted amino acid sequence of 1 to 736 of SEQ ID NO:16;

(b) a heterogenous population of AAVhu68 vp2 proteins selected from one or more of: vp2 proteins produced by expression from a nucleic acid sequence which encodes the predicted amino acid sequence of at least about amino acids 138 to 736 of SEQ ID NO:16, vp2 proteins produced from a sequence comprising at least nucleotides 412 to 2211 of SEQ ID NO:18, or vp2 proteins produced from a nucleic acid sequence at least 70% identical to at least nucleotides 412 to 2211 of SEQ ID NO:18 which encodes the predicted amino acid sequence of at least about amino acids 138 to 736 of SEQ ID NO:16; and (c) a heterogenous population of AAVhu68 vp3 proteins selected from one or more of: vp3 proteins produced by expression from a nucleic acid sequence which encodes the predicted amino acid sequence of at least about amino acids 203 to 736 of SEQ ID NO:16, vp3 proteins produced from a sequence comprising at least nucleotides 607 to 2211 of SEQ ID NO:18, or vp3 proteins produced from a nucleic acid sequence at least 70% identical to at least nucleotides 607 to 2211 of SEQ ID NO:18 which encodes the predicted amino acid sequence of at least about amino acids 203 to 736 of SEQ ID NO:16.

6. The rAAV according to claim 5, wherein the nucleic acid sequence encoding the vp1 proteins, vp2 proteins, and vp3 proteins is SEQ ID NO: 18, or a sequence at least 80% to at least 99% identical to SEQ ID NO: 18 which encodes the amino acid sequence of SEQ ID NO:16.

7. The rAAV according to claim 6, wherein the sequence is at least 80% to 97% identical to SEQ ID NO: 18.

8. The rAAV according to claim 1, wherein the rAAV has an AAV9 capsid, wherein said AAV9 capsid comprises vp1 capsid proteins having an amino acid sequence of SEQ ID NO: 17 or an amino acid sequence encoded by SEQ ID NO: 36.

9. A composition comprising a carrier, diluent or excipient and a stock of at least the non-replicating rAAV according to claim 1.

10. The composition according to claim 9, wherein the composition is formulated for intranasal administration.

11. The composition according to claim 9, wherein the composition is formulated for intramuscular or intravenous administration.

12. The A method for immunizing a human against influenza, wherein the method comprises intranasally administering to a human in need thereof about $10^9$ genome copies (GC) to about $10^{14}$ GC of the rAAV according to claim 1.

13. A product which comprises a container comprising the rAAV according to claim 1, optional diluent, and instructions for administration.

14. The rAAV according to claim 1, wherein the expression cassette comprises a nucleic acid sequence of SEQ ID NO: 26.

15. The rAAV according to claim 1, wherein the expression cassette further comprises a chicken beta actin promoter.

16. The rAAV according to claim 1, wherein the expression cassette further comprises a rabbit beta globin polyA.

17. The rAAV according to claim 1, wherein the expression cassette comprises the sequence of nucleotides 1992 to 4298 of SEQ ID NO: 5.

18. The composition according to claim 9, wherein the composition is formulated for delivery to the lung.

* * * * *

SEQUENCE LISTING

```
<160> NUMBER OF SEQ ID NOS: 39

<210> SEQ ID NO 1
<211> LENGTH: 124
<212> TYPE: PRT
<213> ORGANISM: Artificial Sequence
<220> FEATURE:
<223> OTHER INFORMATION: Amino acid sequence of the first immunoglobulin
      region

<400> SEQUENCE: 1

Gln Val Gln Leu Val Glu Ser Gly Gly Gly Val Val Gln Pro Gly Gly
1               5                   10                  15

Ser Leu Arg Leu Ser Cys Ala Ala Ser Ile Ser Ile Phe Asp Ile Tyr
            20                  25                  30

Ala Met Asp Trp Tyr Arg Gln Ala Pro Gly Lys Gln Arg Glu Leu Val
        35                  40                  45

Ala Val Ser Phe Arg Asp Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys His
                85                  90                  95

Val Ser Leu Tyr Arg Asp Pro Leu Gly Val Ala Gly Gly Ile Gly Val
                100                 105                 110

Tyr Trp Gly Gln Gly Thr Leu Val Thr Val Ser Ser
            115                 120
```

```
<210> SEQ ID NO 2
<211> LENGTH: 123
<212> TYPE: PRT
<213> ORGANISM: Artificial Sequence
<220> FEATURE:
<223> OTHER INFORMATION: Amino acid sequence of the second
      immunoglobulin region

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Tyr Ala Met Gly
            20                  25                  30

Trp Phe Arg Gln Ala Pro Gly Lys Glu Arg Glu Phe Val Ala Ala Ile
        35                  40                  45

Asn Ala Leu Gly Thr Arg Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Thr Ala Gln
                85                  90                  95

Gly Gln Trp Arg Ala Ala Pro Val Ala Val Ala Ala Glu Tyr Glu Phe
            100                 105                 110

Trp Gly Gln Gly Thr Leu Val Thr Val Ser Ser
        115                 120

<210> SEQ ID NO 3
<211> LENGTH: 129
<212> TYPE: PRT
<213> ORGANISM: Artificial Sequence
<220> FEATURE:
<223> OTHER INFORMATION: Amino acid sequence of the third immunoglobulin
      region

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Glu Asn Lys
            20                  25                  30

Ala Ile Gly Trp Phe Arg Gln Ala Pro Gly Lys Glu Arg Glu Gly Val
        35                  40                  45

Leu Cys Ile Ser Lys Ser Gly Ser Trp Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Thr Thr Ala Gly Gly Gly Leu Cys Trp Asp Gly Thr Thr Phe
            100                 105                 110

Ser Arg Leu Ala Ser Ser Trp Gly Gln Gly Thr Leu Val Thr Val Ser
        115                 120                 125

Ser

<210> SEQ ID NO 4
<211> LENGTH: 116
<212> TYPE: PRT
<213> ORGANISM: Artificial Sequence
<220> FEATURE:
<223> OTHER INFORMATION: Amino acid sequence of the fourth
      immunoglobulin region
```

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ser
            20                  25                  30

Trp Met Tyr Trp Leu Arg Gln Ala Pro Gly Lys Gly Leu Glu Trp Val
        35                  40                  45

Ser Val Ile Asn Thr Asp Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Trp Gly Gly Pro Glu Pro Thr Arg Gly Gln Gly Thr Leu Val
            100                 105                 110

Thr Val Ser Ser
        115

<210> SEQ ID NO 5
<211> LENGTH: 4718
<212> TYPE: DNA
<213> ORGANISM: Artificial Sequence
<220> FEATURE:
<223> OTHER INFORMATION: J210a Vector Genome with CB7 promoter and rBG
      polyA
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: chicken b-actin (CB) promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1938)..(1985)
<223> OTHER INFORMATION: c-myc 5'UTR
<220> FEATURE:
<221> NAME/KEY: misc_feature
<222> LOCATION: (1986)..(1991)
<223> OTHER INFORMATION: kozak
<220> FEATURE:
<221> NAME/KEY: misc_feature
<222> LOCATION: (1992)..(2051)
<223> OTHER INFORMATION: hmIL2 leader
<220> FEATURE:
<221> NAME/KEY: misc_feature
<222> LOCATION: (2052)..(2423)
<223> OTHER INFORMATION: The first immunoglobulin region
<220> FEATURE:
<221> NAME/KEY: misc_feature
<222> LOCATION: (2424)..(2453)
<223> OTHER INFORMATION: L1
<220> FEATURE:

<220> FEATURE:
<221> NAME/KEY: misc_feature
<222> LOCATION: (2454)..(2822)
<223> OTHER INFORMATION: The second immunoglobulin region
<220> FEATURE:
<221> NAME/KEY: misc_feature
<222> LOCATION: (2823)..(2852)
<223> OTHER INFORMATION: L2
<220> FEATURE:
<221> NAME/KEY: misc_feature
<222> LOCATION: (2853)..(3239)
<223> OTHER INFORMATION: The third immunoglobulin region
<220> FEATURE:
<221> NAME/KEY: misc_feature
<222> LOCATION: (3240)..(3269)
<223> OTHER INFORMATION: L3
<220> FEATURE:
<221> NAME/KEY: misc_feature
<222> LOCATION: (3270)..(3617)
<223> OTHER INFORMATION: The fourth immunoglobulin region
<220> FEATURE:
<221> NAME/KEY: misc_feature
<222> LOCATION: (3618)..(3632)
<223> OTHER INFORMATION: hinge
<220> FEATURE:
<221> NAME/KEY: misc_feature
<222> LOCATION: (3633)..(4298)
<223> OTHER INFORMATION: Fc
<220> FEATURE:
<221> NAME/KEY: polyA_signal
<222> LOCATION: (4374)..(4500)
<223> OTHER INFORMATION: rabbit globin polyA
<220> FEATURE:
<221> NAME/KEY: repeat_region
<222> LOCATION: (4589)..(4718)
<223> OTHER INFORMATION: 3' ITR

<400> SEQUENCE: 5

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggagt atttacggta     420
aactgcccac ttggcagtac atcaagtgta tcatatgcca gtacgccccc tattgacgt     480
caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctcccccc ctccccaccc caattttgt atttatttat     660
tttttaatta ttttgtgcag cgatggggc ggggggggg gggggcgcg cgccaggcgg     720
ggcggggcgg ggcgaggggc ggggcgggc gaggcggaga ggtgcggcgg cagccaatca     780
gagcggcgcg ctccgaaagt tcctttttat ggcgaggcgg cggcggcggc ggccctataa     840
aaagcgaagc gcgcggcggg cgggagtcgc tgcgcgctgc cttcgccccg tgccccgctc     900
cgccgccgcc tcgcgccgcc cgccccggct ctgactgacc gcgttactcc cacaggtgag     960
cgggcgggac ggcccttctc ctccgggctg taattagcgc ttggtttaat gacggcttgt    1020
ttcttttctg tggctgcgtg aaagccttga ggggctccgg gagggccctt tgtgcggggg    1080
gagcggctcg gggggtgcgt gcgtgtgtgt gtgcgtgggg agcgccgcgt gcggctccgc    1140
gctgcccggc ggctgtgagc gctgcgggcg cggcgcgggg ctttgtgcgc tccgcagtgt    1200
gcgcgagggg agcgcggccg ggggcggtgc cccgcggtgc gggggggct gcgaggggaa    1260
```

```
caaaggctgc gtgcggggtg tgtgcgtggg ggggtgagca gggggtgtgg gcgcgtcggt   1320
cgggctgcaa ccccccctgc accccctcc ccgagttgct gagcacggcc cggcttcggg    1380
tgcggggctc cgtacggggc gtggcgcggg gctcgccgtg ccgggcgggg ggtggcggca   1440
ggtgggggtg ccggcggggg cggggccgcc tcggccgggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca cccctctag cgggcgcggg gcgaagcggt gcggcgccgg    1680
caggaaggaa atgggcgggg agggccttcg tgcgtcgccg cgccgccgtc ccttctccc    1740 tctccagcct cggggctgtc cgcgggggga cggctgcctt cgggggggac ggggcagggc   1800
ggggttcggg ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctaggg cactttgcac tggaacttac aacacccgag caaggacgcg   1980
actctgccac catgtaccga atgcagctgc tgagctgtat cgcactgagc ctggcactgg   2040
tgaccaacag ccaggtgcag ctggtggaga gcggaggagg agtggtgcag ccaggaggaa   2100
gcctgcgact gagctgtgca gcaagcatca gcatcttcga catctacgca atggactggt   2160
accgacaggc accaggaaag cagcgagagc tggtggcagt gagcttccga gacgaagca    2220 cctactacgc agacagcgtg aagggacgat tcaccatcag ccgagacaac agcaagaaca   2280
ccctgtacct gcagatgaac agcctgcgag cagaggacac cgcagtgtac tactgtcatg   2340
tgagcctgta ccgggaccca ctgggagtgg caggaggaat cggagtgtac tggggacagg   2400
gaaccctggt gaccgtgagc agcggaggag gaggaagcgg aggaggagga agcgaagtgc   2460
agctgctgga aagcggcggc ggcctggtgc agcccgcgg cagcctgcgg ctgagctgtg    2520
ctgctagcgg ccggacctac gctatgggct ggtttcggca ggctcccggc aaggaacggg   2580
aatttgtggc tgctattaac gctctgggca cccggaccta ttatgctgac agcgtgaagg   2640
gccggtttac cattagccgg gacaacagca agaacaccct gtatctgcag atgaacagcc   2700
tgcgggctga agacaccgct gtgtattatt gtaccgctca gggccagtgg cgggctgctc   2760
ccgtggctgt ggctgctgaa tacgaatttt ggggccaggg caccctggtg accgtgagca   2820
gcggaggagg aggatctgga ggaggaggat ctgaggtgca gctgctggag agcggaggag   2880
gactggtgca gccaggagga agcctgcggc tgagctgcgc cgccagcgga ttcacccgg    2940 agaacaaggc catcggctgg ttccggcagg ccccaggaaa ggagcgggag ggagtgctgt   3000
gcatcagcaa gagcggaagc tggacctact acgccgatag cgtgaaggga cggttcacca   3060
tcagcccgga taacagcaag aacaccgtgt acctgcagat gaacagcctg cggccagagg   3120
ataccgccgt gtactactgc gccaccacca ccgccggagg aggactgtgc tgggacggaa   3180
ccaccttcag ccggctggcc agcagctggg acagggaac cctggtgacc gtgagcagcg   3240
gaggaggagg atccggagga ggaggatccg aggtgcagct ggtggagtca ggaggaggac   3300
tggtgcagcc cggaggatca ctgagactgt cctgcgctgc ttcaggattc accttctcaa   3360
cctcctggat gtattggctg agacaggctc ccggaaaagg actggagtgg gtgtcagtga   3420
tcaacaccga cggaggaacc tattatgctg attcagtgaa aggaagattc accatctcaa   3480
gagataactc aaaaaacacc ctgtatctgc agatgaactc actgagagct gaggataccg   3540
ctgtgtatta ttgcgctaaa gattgggag gacccgagcc caccagagga cagggaaccc    3600
```

```
tggtgaccgt gtcatcagac aagacccata cctgtccacc ttgtccagca ccagagctgc    3660
tgggaggacc aagcgtgttc ctgttcccac caaagccaaa ggacaccctg atgatcagcc    3720
gaaccccaga ggtgacctgt gtggtggtgg acgtgagcca tgaggaccca gaggtgaagt    3780
tcaactggta cgtggacgga gtggaggtgc ataacgcaaa gaccaagcca cgagaggagc    3840
agtacaacag cacctaccga gtggtgagcg tgctgaccgt gctgcatcag gactggctga    3900
acggaaagga gtacaagtgt aaggtgagca acaaggcact gccagcacca atcgagaaga    3960
ccatcagcaa ggcaaaggga cagccacgag agccacaggt gtacaccctg ccaccaagcc    4020
gagacgagct gaccaagaac caggtgagcc tgacctgtct ggtgaaggga ttctacccaa    4080
gcgacatcgc agtggagtgg gagagcaacg gacagccaga gaacaactac aagaccaccc    4140
caccagtgct ggacagcgac ggaagcttct tcctgtacag caagctgacc gtggacaaga    4200
gccggtggca gcagggaaac gtgttcagct gtagcgtgat gcacgaggca ctgcataacc    4260
attacaccca gaagagcctg agcctgagcc caggaaagtg ataaagcggc cgcggtacct    4320
ctagagtcga cccgggcggc ctcgaggacg gggtgaacta cgcctgagga tccgatcttt    4380
ttccctctgc caaaaattat ggggacatca tgaagcccct tgagcatctg acttctggct    4440
aataaaggaa atttattttc attgcaatag tgtgttggaa ttttttgtgt ctctcactcg    4500
gaagcaattc gttgatctga atttcgacca cccataatac ccattaccct ggtagataag    4560
tagcatggcg ggttaatcat taactacaag gaacccctag tgatggagtt ggccactccc    4620
tctctgcgcg ctcgctcgct cactgaggcc gggcgaccaa aggtcgcccg acgcccgggc    4680
tttgcccggg cggcctcagt gagcgagcga gcgcgcag                            4718
```

<210> SEQ ID NO 6
<211> LENGTH: 20
<212> TYPE: PRT
<213> ORGANISM: Artificial Sequence
<220> FEATURE:
<223> OTHER INFORMATION: Amino acid sequence of human IL2 (hmIL2) leader

<400> SEQUENCE: 6

Met Tyr Arg Met Gln Leu Leu Ser Cys Ile Ala Leu Ser Leu Ala Leu
1               5                   10                  15

Val Thr Asn Ser
            20

<210> SEQ ID NO 7
<211> LENGTH: 10
<212> TYPE: PRT
<213> ORGANISM: Artificial Sequence
<220> FEATURE:
<223> OTHER INFORMATION: Amino acid sequence of linker 1 (L1)

<400> SEQUENCE: 7

Gly Gly Gly Gly Ser Gly Gly Gly Gly Ser
1               5                   10

<210> SEQ ID NO 8
<211> LENGTH: 15
<212> TYPE: DNA
<213> ORGANISM: Artificial Sequence
<220> FEATURE:
<223> OTHER INFORMATION: hinge
<220> FEATURE:
<221> NAME/KEY: CDS
<222> LOCATION: (1)..(15)
<223> OTHER INFORMATION: hinge

<400> SEQUENCE: 8

```
gac aag acc cat acc                                                  15
Asp Lys Thr His Thr
1               5
```

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

```
Asp Lys Thr His Thr
1               5
```

<210> SEQ ID NO 10
<211> LENGTH: 666
<212> TYPE: DNA
<213> ORGANISM: Artificial Sequence
<220> FEATURE:
<223> OTHER INFORMATION: Fc
<220> FEATURE:
<221> NAME/KEY: CDS
<222> LOCATION: (1)..(666)

<400> SEQUENCE: 10

```
tgt cca cct tgt cca gca cca gag ctg ctg gga gga cca agc gtg ttc      48
Cys Pro Pro Cys Pro Ala Pro Glu Leu Leu Gly Gly Pro Ser Val Phe
1               5                   10                  15 ctg ttc cca cca aag cca aag gac acc ctg atg atc agc cga acc cca      96
Leu Phe Pro Pro Lys Pro Lys Asp Thr Leu Met Ile Ser Arg Thr Pro
            20                  25                  30 gag gtg acc tgt gtg gtg gtg gac gtg agc cat gag gac cca gag gtg     144
Glu Val Thr Cys Val Val Val Asp Val Ser His Glu Asp Pro Glu Val
        35                  40                  45 aag ttc aac tgg tac gtg gac gga gtg gag gtg cat aac gca aag acc     192
Lys Phe Asn Trp Tyr Val Asp Gly Val Glu Val His Asn Ala Lys Thr
    50                  55                  60 aag cca cga gag gag cag tac aac agc acc tac cga gtg gtg agc gtg     240
Lys Pro Arg Glu Glu Gln Tyr Asn Ser Thr Tyr Arg Val Val Ser Val
65                  70                  75                  80 ctg acc gtg ctg cat cag gac tgg ctg aac gga aag gag tac aag tgt     288
Leu Thr Val Leu His Gln Asp Trp Leu Asn Gly Lys Glu Tyr Lys Cys
                85                  90                  95 aag gtg agc aac aag gca ctg cca gca cca atc gag aag acc atc agc     336
Lys Val Ser Asn Lys Ala Leu Pro Ala Pro Ile Glu Lys Thr Ile Ser
            100                 105                 110 aag gca aag gga cag cca cga gag cca cag gtg tac acc ctg cca cca     384
Lys Ala Lys Gly Gln Pro Arg Glu Pro Gln Val Tyr Thr Leu Pro Pro
        115                 120                 125 agc cga gac gag ctg acc aag aac cag gtg agc ctg acc tgt ctg gtg     432
Ser Arg Asp Glu Leu Thr Lys Asn Gln Val Ser Leu Thr Cys Leu Val
    130                 135                 140 aag gga ttc tac cca agc gac atc gca gtg gag tgg gag agc aac gga     480
Lys Gly Phe Tyr Pro Ser Asp Ile Ala Val Glu Trp Glu Ser Asn Gly
145                 150                 155                 160 cag cca gag aac aac tac aag acc acc cca gtg ctg gac agc gac         528
Gln Pro Glu Asn Asn Tyr Lys Thr Thr Pro Val Leu Asp Ser Asp
                165                 170                 175 gga agc ttc ttc ctg tac agc aag ctg acc gtg gac aag agc cgg tgg     576
Gly Ser Phe Phe Leu Tyr Ser Lys Leu Thr Val Asp Lys Ser Arg Trp
            180                 185                 190
```

```
cag cag gga aac gtg ttc agc tgt agc gtg atg cac gag gca ctg cat    624
Gln Gln Gly Asn Val Phe Ser Cys Ser Val Met His Glu Ala Leu His
        195                 200                 205 aac cat tac acc cag aag agc ctg agc ctg agc cca gga aag            666
Asn His Tyr Thr Gln Lys Ser Leu Ser Leu Ser Pro Gly Lys
    210                 215                 220

<210> SEQ ID NO 11
<211> LENGTH: 222
<212> TYPE: PRT
<213> ORGANISM: Artificial Sequence
<220> FEATURE:
<223> OTHER INFORMATION: Synthetic Construct

<400> SEQUENCE: 11

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 12
<211> LENGTH: 746
<212> TYPE: PRT
<213> ORGANISM: Artificial Sequence
<220> FEATURE:
<223> OTHER INFORMATION: humanized FM1W3

<400> SEQUENCE: 12

Gln Val Gln Leu Val Glu Ser Gly Gly Gly Trp Gln Pro Gly Gly Ser
1               5                   10                  15

Leu Arg Leu Ser Cys Ala Ala Ser Ile Ser Ile Phe Asp Ile Tyr Ala
            20                  25                  30

Met Asp Trp Tyr Arg Gln Ala Pro Gly Lys Gln Arg Glu Leu Val Ala
        35                  40                  45
```

-continued

```
Val Ser Phe Arg Asp Gly Ser Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys His Val
                    85                  90                  95

Ser Leu Tyr Arg Asp Pro Leu Gly Val Ala Gly Ile Gly Val Tyr
                100                 105                 110

Trp Gly Gln Gly Thr Leu Val Thr Val Ser Ser Gly Gly Gly Gly Ser
                115                 120                 125

Gly Gly Gly Gly Ser Glu Val Gln Leu Leu Glu Ser Gly Gly Gly Leu
            130                 135                 140

Val Gln Pro Gly Gly Ser Leu Arg Leu Ser Cys Ala Ala Ser Gly Arg
145                 150                 155                 160

Thr Tyr Ala Met Gly Trp Phe Arg Gln Ala Pro Gly Lys Glu Arg Glu
                165                 170                 175

Phe Val Ala Ala Ile Asn Ala Leu Gly Thr Arg Thr Tyr Tyr Ala Asp
                180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
        210                 215                 220

Tyr Cys Thr Ala Gln Gly Gln Trp Arg Ala Ala Pro Val Ala Val Ala
225                 230                 235                 240

Ala Glu Tyr Glu Phe Trp Gly Gln Gly Thr Leu Val Thr Val Ser Ser
                245                 250                 255

Gly Gly Gly Gly Ser Gly Gly Gly Gly Ser Glu Val Gln Leu Leu Glu
            260                 265                 270

Ser Gly Gly Gly Leu Val Gln Pro Gly Gly Ser Leu Arg Leu Ser Cys
        275                 280                 285

Ala Ala Ser Gly Phe Thr Leu Glu Asn Lys Ala Ile Gly Trp Phe Arg
        290                 295                 300

Gln Ala Pro Gly Lys Glu Arg Glu Gly Val Leu Cys Ile Ser Lys Ser
305                 310                 315                 320

Gly Ser Trp Thr Tyr Tyr Ala Asp Ser Val Lys Gly Arg Phe Thr Ile
                325                 330                 335

Ser Arg Asp Asn Ser Lys Asn Thr Val Tyr Leu Gln Met Asn Ser Leu
                340                 345                 350

Arg Pro Glu Asp Thr Ala Val Tyr Tyr Cys Ala Thr Thr Ala Gly
            355                 360                 365

Gly Gly Leu Cys Trp Asp Gly Thr Thr Phe Ser Arg Leu Ala Ser Ser
        370                 375                 380

Trp Gly Gln Gly Thr Leu Val Thr Val Ser Ser Gly Gly Gly Gly Ser
385                 390                 395                 400

Gly Gly Gly Gly Ser Glu Val Gln Leu Val Glu Ser Gly Gly Gly Leu
            405                 410                 415

Val Gln Pro Gly Gly Ser Leu Arg Leu Ser Cys Ala Ala Ser Gly Phe
            420                 425                 430

Thr Phe Ser Thr Ser Trp Met Tyr Trp Leu Arg Gln Ala Pro Gly Lys
        435                 440                 445

Gly Leu Glu Trp Val Ser Val Ile Asn Thr Asp Gly Gly Thr Tyr Tyr
        450                 455                 460
```

-continued

```
Ala Asp Ser Val Lys Gly Arg Phe Thr Ile Ser Arg Asp Asn Ser Lys
465                 470                 475                 480

Asn Thr Leu Tyr Leu Gln Met Asn Ser Leu Arg Ala Glu Asp Thr Ala
            485                 490                 495

Val Tyr Tyr Cys Ala Lys Asp Trp Gly Gly Pro Glu Pro Thr Arg Gly
        500                 505                 510

Gln Gly Thr Leu Val Thr Val Ser Ser Asp Lys Thr His Thr Cys Pro
    515                 520                 525

Pro Cys Pro Ala Pro Glu Leu Leu Gly Gly Pro Ser Val Phe Leu Phe
530                 535                 540

Pro Pro Lys Pro Lys Asp Thr Leu Met Ile Ser Arg Thr Pro Glu Val
545                 550                 555                 560

Thr Cys Val Trp Asp Val Ser His Glu Asp Pro Glu Val Lys Phe Asn
                565                 570                 575

Trp Tyr Val Asp Gly Val Glu Val His Asn Ala Lys Thr Lys Pro Arg
            580                 585                 590

Glu Glu Gln Tyr Asn Ser Thr Tyr Arg Trp Ser Val Leu Thr Val Leu
        595                 600                 605

His Gln Asp Trp Leu Asn Gly Lys Glu Tyr Lys Cys Lys Val Ser Asn
610                 615                 620

Lys Ala Leu Pro Ala Pro Ile Glu Lys Thr Ile Ser Lys Ala Lys Gly
625                 630                 635                 640

Gln Pro Arg Glu Pro Gln Val Tyr Thr Leu Pro Pro Ser Arg Glu Glu
                645                 650                 655

Met Thr Lys Asn Gln Val Ser Leu Thr Cys Leu Val Lys Gly Phe Tyr
            660                 665                 670

Pro Ser Asp Ile Ala Val Glu Trp Glu Ser Asn Gly Gln Pro Glu Asn
        675                 680                 685

Asn Tyr Lys Thr Thr Pro Pro Val Leu Asp Ser Asp Gly Ser Phe Phe
    690                 695                 700

Leu Tyr Ser Lys Leu Thr Val Asp Lys Ser Arg Trp Gln Gln Gly Asn
705                 710                 715                 720

Val Phe Ser Cys Ser Val Met His Glu Ala Leu His Asn His Tyr Thr
                725                 730                 735

Gln Lys Ser Leu Ser Leu Ser Pro Gly Lys
            740                 745
```

```
<210> SEQ ID NO 13
<211> LENGTH: 4544
<212> TYPE: DNA
<213> ORGANISM: Artificial Sequence
<220> FEATURE:
<223> OTHER INFORMATION: humanized sdAb multimer J310a
<220> FEATURE:
<221> NAME/KEY: repeat_region
<222> LOCATION: (17)..(146)
<223> OTHER INFORMATION: 5' ITR
<220> FEATURE:
<221> NAME/KEY: promoter
<222> LOCATION: (207)..(1433)
<223> OTHER INFORMATION: UbC
<220> FEATURE:
<221> NAME/KEY: Intron
<222> LOCATION: (1527)..(1659)
<223> OTHER INFORMATION: Promega chimeric intron
<220> FEATURE:
<221> NAME/KEY: 5'UTR
<222> LOCATION: (1726)..(1773)
<223> OTHER INFORMATION: c-myc 5'UTR
<220> FEATURE:
<221> NAME/KEY: misc_feature
```

```
<222> LOCATION: (1774)..(1779)
<223> OTHER INFORMATION: kozak
<220> FEATURE:
<221> NAME/KEY: misc_feature
<222> LOCATION: (1780)..(1839)
<223> OTHER INFORMATION: hmIL2 leader
<220> FEATURE:
<221> NAME/KEY: misc_feature
<222> LOCATION: (1840)..(2211)
<223> OTHER INFORMATION: The first immunoglobulin region
<220> FEATURE:
<221> NAME/KEY: misc_binding
<222> LOCATION: (2212)..(2241)
<223> OTHER INFORMATION: L1
<220> FEATURE:
<221> NAME/KEY: misc_feature
<222> LOCATION: (2242)..(2610)
<223> OTHER INFORMATION: The second immunoglobulin region
<220> FEATURE:
<221> NAME/KEY: misc_binding
<222> LOCATION: (2611)..(2640)
<223> OTHER INFORMATION: L2
<220> FEATURE:
<221> NAME/KEY: misc_feature
<222> LOCATION: (2641)..(3027)
<223> OTHER INFORMATION: The third immunoglobulin region
<220> FEATURE:
<221> NAME/KEY: misc_binding
<222> LOCATION: (3028)..(3057)
<223> OTHER INFORMATION: L3
<220> FEATURE:
<221> NAME/KEY: misc_feature
<222> LOCATION: (3058)..(3405)
<223> OTHER INFORMATION: The fourth immunoglobulin region
<220> FEATURE:
<221> NAME/KEY: misc_binding
<222> LOCATION: (3406)..(3435)
<223> OTHER INFORMATION: L4
<220> FEATURE:
<221> NAME/KEY: misc_feature
<222> LOCATION: (3436)..(4101)
<223> OTHER INFORMATION: Fc
<220> FEATURE:
<221> NAME/KEY: polyA_signal
<222> LOCATION: (4119)..(4350)
<223> OTHER INFORMATION: SV40 late polyA signal
<220> FEATURE:
<221> NAME/KEY: repeat_region
<222> LOCATION: (4415)..(4544)
<223> OTHER INFORMATION: 3' ITR

<400> SEQUENCE: 13
taaggcctta attaggctgc gcgctcgctc gctcactgag gccgcccggg caaagcccgg      60
gcgtcgggcg acctttggtc gcccggcctc agtgagcgag cgagcgcgca gagagggagt     120
ggccaactcc atcactaggg gttccttgta gttaatgatt aacccgccat gctacttatc     180
tacgtagcca tgctctagga agatctggcc tccgcgccgg gttttggcgc ctcccgcggg     240
cgcccccctc ctcacggcga gcgctgccac gtcagacgaa gggcgcagga gcgtcctgat     300
ccttccgccc ggacgctcag gacagcggcc cgctgctcat aagactcggc cttagaaccc     360
cagtatcagc agaaggacat tttaggacgg gacttgggtg actctagggc actggttttc     420
tttccagaga gcggaacagg cgaggaaaag tagtcccttc tcggcgattc tgcggaggga     480
tctccgtggg gcggtgaacg ccgatgatta tataaggacg cgccgggtgt ggcacagcta     540
gttccgtcgc agccgggatt tgggtcgcgg ttcttgtttg tggatcgctg tgatcgtcac     600
ttggtgagta gcgggctgct gggctggccg gggctttcgt ggccgccggg ccgctcggtg     660
ggacggaagc gtgtggagag accgccaagg gctgtagtct gggtccgcga gcaaggttgc     720
cctgaactgg gggttggggg gagcgcagca aaatggcggc tgttcccgag tcttgaatgg     780
```

```
aagacgcttg tgaggcgggc tgtgaggtcg ttgaaacaag gtgggggca tggtgggcgg      840 caagaaccca aggtcttgag gccttcgcta atgcggaaa gctcttattc gggtgagatg      900
ggctggggca ccatctgggg accctgacgt gaagtttgtc actgactgga gaactcggtt     960
tgtcgtctgt tgcgggggcg gcagttatgc ggtgccgttg ggcagtgcac ccgtaccttt    1020
gggagcgcgc gccctcgtcg tgtcgtgacg tcacccgttc tgttggctta taatgcaggg    1080
tggggccacc tgccggtagg tgtgcggtag gcttttctcc gtcgcaggac gcagggttcg    1140
ggcctagggt aggctctcct gaatcgacag gcgccggacc tctggtgagg ggagggataa    1200
gtgaggcgtc agtttctttg gtcggtttta tgtacctatc ttcttaagta gctgaagctc    1260
cggttttgaa ctatgcgctc ggggttggcg agtgtgtttt gtgaagtttt ttaggcacct    1320
tttgaaatgt aatcatttgg gtcaatatgt aattttcagt gttagactag taaattgtcc    1380
gctaaattct ggccgttttt ggcttttttg ttagacgaag ctttattgcg gtagtttatc    1440
acagttaaat tgctaacgca gtcagtgctt ctgacacaac agtctcgaac ttaagctgca    1500
gaagttggtc gtgaggcact gggcaggtaa gtatcaaggt tacaagacag gtttaaggag    1560
accaatagaa actgggcttg tcgagacaga gaagactctt gcgtttctga taggcaccta    1620
ttggtcttac tgacatccac tttgcctttc tctccacagg tgtccactcc cagttcaatt    1680
acagctctta aggctagagt acttaatacg actcactata ggctagggca ctttgcactg    1740
gaacttacaa caccgagca aggacgcgac tctgccacca tgtaccgaat gcagctgctg    1800
agctgtatcg cactgagcct ggcactggtg accaacagcc aggtgcagct ggtggagagc    1860
ggaggaggag tggtgcagcc aggaggaagc ctgcgactga gctgtgcagc aagcatcagc    1920
atcttcgaca tctacgcaat ggactggtac cgacaggcac caggaaagca gcgagagctg    1980
gtggcagtga gcttccgaga cggaagcacc tactacgcag acagcgtgaa gggacgattc    2040
accatcagcc gagacaacag caagaacacc ctgtacctgc agatgaacag cctgcgagca    2100
gaggacaccg cagtgtacta ctgtcatgtg agcctgtacc gggacccact gggagtggca    2160
ggaggaatcg gagtgtactg gggacaggga accctggtga ccgtgagcag cggaggagga    2220
ggaagcggag gaggaggaag cgaagtgcag ctgctggaaa gcggcggcgg cctggtgcag    2280
cccggcggca gcctgcggct gagctgtgct gctagcggcc ggacctacgc tatgggctgg    2340
tttcggcagg ctcccggcaa ggaacgggaa tttgtggctg ctattaacgc tctgggcacc    2400
cggacctatt atgctgacag cgtgaagggc cggtttacca ttagccggga caacagcaag    2460
aacaccctgt atctgcagat gaacagcctg cgggctgaag acaccgctgt gtattattgt    2520
accgctcagg gccagtggcg ggctgctccc gtggctgtgg ctgctgaata cgaattttgg    2580
ggccagggca ccctggtgac cgtgagcagc ggaggaggag gatctggagg aggaggatct    2640
gaggtgcagc tgctggagag cggaggagga ctggtgcagc caggaggaag cctgcggctg    2700
agctgcgccg ccagcggatt caccctggag aacaaggcca tcggctggtt ccggcaggcc    2760
ccaggaaagg agcgggaggg agtgctgtgc atcagcaaga gcggaagctg gacctactac    2820
gccgatagcg tgaagggacg gttcaccatc agccgggata acagcaagaa caccgtgtac    2880
ctgcagatga cagcctgcg gccagaggat accgccgtgt actactgcgc caccaccacc    2940
gccggaggag gactgtgctg gacggaacc accttcagcc ggctggccag cagctgggga    3000
cagggaaccc tggtgaccgt gagcagcgga ggaggaggat ccggaggagg aggatccgag    3060
gtgcagctgt ggagtcagg aggaggactg gtgcagcccg aggatcact gagactgtcc    3120 tgcgctgctt caggattcac cttctcaacc tcctggatgt attggctgag acaggctccc    3180
```

```
ggaaaaggac tggagtgggt gtcagtgatc aacaccgacg gaggaaccta ttatgctgat    3240
tcagtgaaag gaagattcac catctcaaga gataactcaa aaaacaccct gtatctgcag    3300
atgaactcac tgagagctga ggataccgct gtgtattatt gcgctaaaga ttggggagga    3360
cccgagccca ccagaggaca gggaaccctg gtgaccgtgt catcaggagg aggaggatca    3420
ggaggaggag gatcctgtcc accttgtcca gcaccagagc tgctgggagg accaagcgtg    3480
ttcctgttcc caccaaagcc aaaggacacc ctgatgatca gccgaacccc agaggtgacc    3540
tgtgtggtgg tggacgtgag ccatgaggac ccagaggtga agttcaactg gtacgtggac    3600
ggagtggagg tgcataacgc aaagaccaag ccacagagg agcagtacaa cagcacctac    3660
cgagtggtga gcgtgctgac cgtgctgcat caggactggc tgaacggaaa ggagtacaag    3720
tgtaaggtga gcaacaaggc actgccagca ccaatcgaga agaccatcag caaggcaaag    3780
ggacagccac gagagccaca ggtgtacacc ctgccaccaa gccgagacga gctgaccaag    3840
aaccaggtga gcctgacctg tctggtgaag ggattctacc caagcgacat cgcagtggag    3900
tgggagagca acggacagcc agagaacaac tacaagacca ccccaccagt gctggacagc    3960
gacggaagct tcttcctgta cagcaagctg accgtggaca gagcggtg gcagcaggga    4020 aacgtgttca gctgtagcgt gatgcacgag gcactgcata accattacac ccagaagagc    4080
ctgagcctga gcccaggaaa gtgataaagc ggccgcttcg agcagacatg ataagataca    4140
ttgatgagtt tggacaaacc acaactagaa tgcagtgaaa aaaatgcttt atttgtgaaa    4200
tttgtgatgc tattgcttta tttgtaacca ttataagctg caataaacaa gttaacaaca    4260
acaattgcat tcattttatg tttcaggttc agggggagat gtgggaggtt ttttaaagca    4320
agtaaaacct ctacaaatgt ggtaaaatcg ataaggatct tcctagagca tggctacgta    4380
gataagtagc atggcgggtt aatcattaac tacaaggaac ccctagtgat ggagttggcc    4440
actccctctc tgcgcgctcg ctcgctcact gaggccgggc gaccaaaggt cgcccgacgc    4500
ccgggctttg cccgggcggc ctcagtgagc gagcgagcgc gcag                    4544
```

```
<210> SEQ ID NO 14
<211> LENGTH: 4733
<212> TYPE: DNA
<213> ORGANISM: Artificial Sequence
<220> FEATURE:
<223> OTHER INFORMATION: CB7_J310a
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<223> OTHER INFORMATION: TATA
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1938)..(1985)
<223> OTHER INFORMATION: c-myc 5'UTR
<220> FEATURE:
```

```
<221> NAME/KEY: misc_feature
<222> LOCATION: (1986)..(1991)
<223> OTHER INFORMATION: kozak
<220> FEATURE:
<221> NAME/KEY: misc_feature
<222> LOCATION: (1992)..(2051)
<223> OTHER INFORMATION: hmIL2 leader
<220> FEATURE:
<221> NAME/KEY: misc_feature
<222> LOCATION: (2052)..(2423)
<223> OTHER INFORMATION: The first immunoglobulin region
<220> FEATURE:
<221> NAME/KEY: misc_binding
<222> LOCATION: (2424)..(2453)
<223> OTHER INFORMATION: L1
<220> FEATURE:
<221> NAME/KEY: misc_feature
<222> LOCATION: (2454)..(2822)
<223> OTHER INFORMATION: The second immunoglobulin region
<220> FEATURE:
<221> NAME/KEY: misc_binding
<222> LOCATION: (2823)..(2852)
<223> OTHER INFORMATION: L2
<220> FEATURE:
<221> NAME/KEY: misc_feature
<222> LOCATION: (2853)..(3239)
<223> OTHER INFORMATION: The third immunoglobulin region
<220> FEATURE:
<221> NAME/KEY: misc_binding
<222> LOCATION: (3240)..(3269)
<223> OTHER INFORMATION: L3
<220> FEATURE:
<221> NAME/KEY: misc_feature
<222> LOCATION: (3270)..(3617)
<223> OTHER INFORMATION: The fourth immunoglobulin region
<220> FEATURE:
<221> NAME/KEY: misc_binding
<222> LOCATION: (3618)..(3647)
<223> OTHER INFORMATION: L4
<220> FEATURE:
<221> NAME/KEY: misc_feature
<222> LOCATION: (3648)..(4313)
<223> OTHER INFORMATION: Fc
<220> FEATURE:
<221> NAME/KEY: polyA_signal
<222> LOCATION: (4389)..(4515)
<223> OTHER INFORMATION: rabbit globin polyA
<220> FEATURE:
<221> NAME/KEY: repeat_region
<222> LOCATION: (4604)..(4733)
<223> OTHER INFORMATION: 3' ITR

<400> SEQUENCE: 14
ctgcgcgctc gctcgctcac tgaggccgcc cgggcaaagc ccgggcgtcg ggcgaccttt      60
ggtcgcccgg cctcagtgag cgagcgagcg cgcagagagg gagtgggccaa ctccatcact    120 aggggttcct tgtagttaat gattaacccg ccatgctact tatctaccag ggtaatgggg    180
atcctctaga actatagcta gtcgacattg attattgact agttattaat agtaatcaat    240 tacgggtca ttagttcata gcccatatat ggagttccgc gttacataac ttacggtaaa     300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctcccccccc ctccccaccc ccaatttgt atttatttat     660 ttttaatta ttttgtgcag cgatggggggc ggggggggg ggggggcgcg cgccaggcgg    720
ggcggggcgg ggcgaggggc ggggcggggc gaggcggaga ggtgcggcgg cagccaatca    780
```

```
gagcggcgcg ctccgaaagt ttccttttat ggcgaggcgg cggcggcggc ggccctataa      840
aaagcgaagc gcgcggcggg cgggagtcgc tgcgcgctgc cttcgccccg tgccccgctc      900
cgccgccgcc tcgcgccgcc cgccccggct ctgactgacc gcgttactcc cacaggtgag      960
cgggcgggac ggcccttctc ctccgggctg taattagcgc ttggtttaat gacggcttgt     1020
ttcttttctg tggctgcgtg aaagccttga ggggctccgg agggcccctt tgtgcggggg     1080
gagcggctcg gggggtgcgt gcgtgtgtgt gtgcgtgggg agcgccgcgt gcggctccgc     1140
gctgcccggc ggctgtgagc gctgcgggcg cggcgcgggg ctttgtgcgc tccgcagtgt     1200
gcgcgagggg agcgcggccg ggggcggtgc cccgcggtgc ggggggggct gcgaggggaa     1260
caaaggctgc gtgcggggtg tgtgcgtggg ggggtgagca gggggtgtgg gcgcgtcggt     1320
cgggctgcaa ccccccctgc accccctcc ccgagttgct gagcacggcc cggcttcggg      1380
tgcggggctc cgtacggggc gtggcgcggg gctcgccgtg ccgggcgggg ggtggcggca     1440
ggtgggggtg ccgggcgggg cggggccgcc tcggccgggg gagggctcgg gggaggggcg     1500
cggcggcccc cggagcgccg gcggctgtcg aggcgcggcg agccgcagcc attgcctttt     1560
atggtaatcg tgcgagaggg cgcagggact tcctttgtcc caaatctgtg cggagccgaa     1620
atctgggagg cgccgccgca ccccctctag cgggcgcggg gcgaagcggt gcggcgccgg     1680
caggaaggaa atgggcgggg agggccttcg tgcgtcgccg cgccgccgtc cccttctccc     1740
tctccagcct cggggctgtc cgcgggggga cggctgcctt cggggggggac ggggcagggc     1800 ggggttcggc ttctggcgtg tgaccggcgg ctctagagcc tctgctaacc atgttcatgc     1860
cttcttcttt ttcctacagc tcctgggcaa cgtgctggtt attgtgctgt ctcatcattt     1920
tggcaaagaa ttcgctaggg cactttgcac tggaacttac aacacccgag caaggacgcg     1980
actctgccac catgtaccga atgcagctgc tgagctgtat cgcactgagc ctggcactgg     2040
tgaccaacag ccaggtgcag ctggtggaga gcggaggagg agtggtgcag ccaggaggaa     2100
gcctgcgact gagctgtgca gcaagcatca gcatcttcga catctacgca atggactggt     2160
accgacaggc accaggaaag cagcgagagc tggtggcagt gagcttccga gacgaagcaa     2220
cctactacgc agacagcgtg aagggacgat tcaccatcag ccgagacaac agcaagaaca     2280
ccctgtacct gcagatgaac agcctgcgag cagaggacac cgcagtgtac tactgtcatg     2340
tgagcctgta ccgggaccca ctgggagtgg caggaggaat cggagtgtac tggggacagg     2400
gaaccctggt gaccgtgagc agcggaggag gaggaagcgg aggaggagga agcgaagtgc     2460
agctgctgga aagcggcggc ggcctggtgc agcccggcgg cagcctgcgg ctgagctgtg     2520
ctgctagcgg ccggacctac gctatgggct ggtttcggca ggctcccggc aaggaacggg     2580
aatttgtggc tgctattaac gctctgggca cccggaccta ttatgctgac agcgtgaagg     2640
gccggtttac cattagccgg acaacagcha agaacaccct gtatctgcag atgaacagcc     2700
tgcgggctga agacaccgct gtgtattatt gtaccgctca gggccagtgg cgggctgctc     2760
ccgtggctgt ggctgctgaa tacgaatttt ggggccaggg caccctggtg accgtgagca     2820
gcggaggagg aggatctgga ggaggaggat ctgaggtgca gctgctggag agcggaggag     2880
gactggtgca gccaggagga agcctgcggc tgagctgcgc cgccagcgga ttcaccctgg     2940
agaacaaggc catcggctgg ttccggcagg ccccaggaaa ggagcgggag ggagtgctgt     3000
gcatcagcaa gagcggaagc tggacctact acgccgatag cgtgaaggga cggttccacca     3060 tcagccggga taacagcaag aacaccgtgt acctgcagat gaacagcctg cggccagagg     3120
```

-continued

| | |
|---|---|
| ataccgccgt gtactactgc gccaccacca ccgccggagg aggactgtgc tgggacggaa | 3180 |
| ccaccttcag ccggctggcc agcagctggg acagggaac cctggtgacc gtgagcagcg | 3240 |
| gaggaggagg atccggagga ggaggatccg aggtgcagct ggtggagtca ggaggaggac | 3300 |
| tggtgcagcc cggaggatca ctgagactgt cctgcgctgc ttcaggattc accttctcaa | 3360 |
| cctcctggat gtattggctg agacaggctc ccggaaaagg actggagtgg gtgtcagtga | 3420 |
| tcaacaccga cggaggaacc tattatgctg attcagtgaa aggaagattc accatctcaa | 3480 |
| gagataactc aaaaaacacc ctgtatctgc agatgaactc actgagagct gaggataccg | 3540 |
| ctgtgtatta ttgcgctaaa gattggggag accccgagcc caccagagga cagggaaccc | 3600 |
| tggtgaccgt gtcatcagga ggaggaggat caggaggagg aggatcctgt ccaccttgtc | 3660 |
| cagcaccaga gctgctggga ggaccaagcg tgttcctgtt cccaccaaag ccaaaggaca | 3720 |
| ccctgatgat cagccgaacc ccagaggtga cctgtgtggg ggtggacgtg agccatgagg | 3780 |
| acccagaggt gaagttcaac tggtacgtgg acggagtgga ggtgcataac gcaaagacca | 3840 |
| agccacgaga ggagcagtac aacagcacct accgagtggt gagcgtgctg accgtgctgc | 3900 |
| atcaggactg gctgaacgga aaggagtaca agtgtaaggt gagcaacaag gcactgccag | 3960 |
| caccaatcga gaagaccatc agcaaggcaa agggacagcc acgagagcca caggtgtaca | 4020 |
| ccctgccacc aagccgagac gagctgacca gaaccaggt gagcctgacc tgtctggtga | 4080 |
| agggattcta cccaagcgac atcgcagtgg agtgggagag caacgacag ccagagaaca | 4140 |
| actacaagac caccccacca gtgctggaca gcgacggaag cttcttcctg tacagcaagc | 4200 |
| tgaccgtgga caagagccgg tggcagcagg gaaacgtgtt cagctgtagc gtgatgcacg | 4260 |
| aggcactgca taaccattac acccagaaga gcctgagcct gagcccagga aagtgataaa | 4320 |
| gcggccgcgg tacctctaga gtcgacccgg gcggcctcga ggacggggtg aactacgcct | 4380 |
| gaggatccga tcttttttccc tctgccaaaa attatgggga catcatgaag ccccttgagc | 4440 |
| atctgacttc tggctaataa aggaaattta ttttcattgc aatagtgtgt tggaattttt | 4500 |
| tgtgtctctc actcggaagc aattcgttga tctgaatttc gaccacccat aatacccatt | 4560 |
| accctggtag ataagtagca tggcgggtta atcattaact acaaggaacc cctagtgatg | 4620 |
| gagttggcca ctccctctct gcgcgctcgc tcgctcactg aggccgggcg accaaaggtc | 4680 |
| gcccgacgcc cgggctttgc ccgggcggcc tcagtgagcg agcgagcgcg cag | 4733 |

```
<210> SEQ ID NO 15
<211> LENGTH: 4718
<212> TYPE: DNA
<213> ORGANISM: Artificial Sequence
<220> FEATURE:
<223> OTHER INFORMATION: CB7 J2201
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
```

```
<223> OTHER INFORMATION: chicken beta-acin intron
<220> FEATURE:
<221> NAME/KEY: 5'UTR
<222> LOCATION: (1938)..(1985)
<223> OTHER INFORMATION: c-myc 5'UTR
<220> FEATURE:
<221> NAME/KEY: misc_feature
<222> LOCATION: (1986)..(1991)
<223> OTHER INFORMATION: kozak
<220> FEATURE:
<221> NAME/KEY: misc_feature
<222> LOCATION: (1992)..(2051)
<223> OTHER INFORMATION: hmIL2 leader
<220> FEATURE:
<221> NAME/KEY: misc_feature
<222> LOCATION: (2052)..(2423)
<223> OTHER INFORMATION: The first immunoglobulin region
<220> FEATURE:
<221> NAME/KEY: misc_binding
<222> LOCATION: (2424)..(2453)
<223> OTHER INFORMATION: L1
<220> FEATURE:
<221> NAME/KEY: misc_feature
<222> LOCATION: (2454)..(2822)
<223> OTHER INFORMATION: The second immunoglobulin region
<220> FEATURE:
<221> NAME/KEY: misc_binding
<222> LOCATION: (2823)..(2852)
<223> OTHER INFORMATION: L2
<220> FEATURE:
<221> NAME/KEY: misc_feature
<222> LOCATION: (2853)..(3239)
<223> OTHER INFORMATION: The third immunoglobulin region
<220> FEATURE:
<221> NAME/KEY: misc_binding
<222> LOCATION: (3240)..(3269)
<223> OTHER INFORMATION: L3
<220> FEATURE:
<221> NAME/KEY: misc_feature
<222> LOCATION: (3270)..(3617)
<223> OTHER INFORMATION: The fourth immunoglobulin region
<220> FEATURE:
<221> NAME/KEY: misc_binding
<222> LOCATION: (3618)..(3632)
<223> OTHER INFORMATION: hinge
<220> FEATURE:
<221> NAME/KEY: misc_feature
<222> LOCATION: (3633)..(4298)
<223> OTHER INFORMATION: Fc
<220> FEATURE:
<221> NAME/KEY: polyA_signal
<222> LOCATION: (4374)..(4500)
<223> OTHER INFORMATION: Rabbit globin poly A
<220> FEATURE:
<221> NAME/KEY: repeat_region
<222> LOCATION: (4589)..(4718)
<223> OTHER INFORMATION: 3' ITR

<400> SEQUENCE: 15
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctaccag ggtaatgggg    180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca gtacgcccc ctattgacgt    480 caatgacggt aaatggcccg cctggcatta tgcccagtac atgaccttat gggactttcc    540
tacttggcag tacatctacg tattagtcat cgctattacc atggtcgagg tgagccccac    600
```

```
gttctgcttc actctcccca tctccccccc ctccccaccc ccaattttgt atttatttat    660
tttttaatta ttttgtgcag cgatggggggc gggggggggg ggggggcgcg cgccaggcgg    720
ggcggggcgg ggcgagggggc ggggcggggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagcccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc gggggggggct gcgaggggaa   1260
caaaggctgc gtgcgggtg tgtgcgtggg ggggtgagca ggggtgtgg gcgcgtcggt   1320
cgggctgcaa cccccctgc accccctcc ccgagttgct gagcacggcc cggcttcggg   1380
tgcgggctc cgtacggggc gtggcgcggg gctcgccgtg ccgggcggg ggtggcggca   1440
ggtgggggtg ccggggcggg cggggccgcc tcggccgggg gagggctcgg gggagggggcg   1500
cggcggcccc cggagcgccg gcggctgtcg aggcgcggcg agccgcagcc attgccttt    1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgccttt cggggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctaggg cactttgcac tggaacttac aacacccgag caaggacgcg   1980
actctgccac catgtaccgg atgcagctgc tgagctgcat cgccctgagc ctggccctgg   2040
tgaccaacag ccaggtgcag ctggtggaga gcggaggagg agtggtgcag ccaggaggaa   2100
gcctgcggct gagctgcgcc gccagcatca gcatcttcga tatctacgcc atggattggt   2160
accggcaggc cccaggaaag cagcgggagc tggtggccgt gagcttccgg gacggaagca   2220
cctactacgc cgatagcgtg aagggacggt tcaccatcag ccgggataac agcaagaaca   2280
ccctgtacct gcagatgaac agcctgcggg ccgaggatac cgccgtgtac tactgccacg   2340
tgagcctgta ccgggatcca ctgggagtgg ccggaggaat cggagtgtac tggggacagg   2400
gaaccctggt gaccgtgagc agcggaggag gaggaagcgg aggaggagga agcgaggtgc   2460
agctgctgga gagcggagga ggactggtgc agccaggagg aagcctgcga ctgagctgtg   2520
cagcaagcgg acgaacctac gcaatgggct ggttccgaca ggcaccagga aaggagcgag   2580
agttcgtggc agcaatcaac gcactgggaa cccgaaccta ctacgcagac agcgtgaagg   2640
gacgattcac catcagccga gacaacagca agaacaccct gtacctgcag atgaacagcc   2700
tgcgagcaga ggacaccgca gtgtactact gtaccgcaca gggacagtgg cgagcagcac   2760
cagtggcagt ggcagcagag tacgagttct ggggacaggg aaccctggtg accgtgagca   2820
gcggaggagg aggatctgga ggaggaggat ctgaagtgca gctgctggaa agcggcggcg   2880
gcctggtgca gccggcggc agcctgcggc tgagctgtgc tgctagcggc tttaccctgg   2940
```

| | |
|---|---|
| aaaacaaggc tattggctgg tttcggcagg ctcccggcaa ggaacgggaa ggcgtgctgt | 3000 |
| gtattagcaa gagcggcagc tggacctatt atgctgacag cgtgaagggc cggtttacca | 3060 |
| ttagccggga caacagcaag aacaccgtgt atctgcagat gaacagcctg cggcccgaag | 3120 |
| acaccgctgt gtattattgt gctaccacca ccgctggcgg cggcctgtgt tgggacggca | 3180 |
| ccaccttag ccggctggct agcagctggg gccagggcac cctggtgacc gtgagcagcg | 3240 |
| gaggaggagg atccggagga ggaggatccg aggtgcagct ggtggagtca ggaggaggac | 3300 |
| tggtgcagcc cggaggatca ctgagactgt cctgcgctgc ttcaggattc accttctcaa | 3360 |
| cctcctggat gtattggctg agacaggctc ccggaaaagg actggagtgg gtgtcagtga | 3420 |
| tcaacaccga cggaggaacc tattatgctg attcagtgaa aggaagattc accatctcaa | 3480 |
| gagataactc aaaaaacacc ctgtatctgc agatgaactc actgagagct gaggataccg | 3540 |
| ctgtgtatta ttgcgctaaa gattggggag acccgagcc caccagagga cagggaaccc | 3600 |
| tggtgaccgt gtcatcagat aagacccaca cttgcccacc ttgcccagcc ccagagctgc | 3660 |
| tgggaggacc aagcgtgttc ctgttcccac caaagccaaa ggatacctg atgatcagcc | 3720 |
| ggacccccaga ggtgacctgc gtggtggtgg atgtgagcca cgaggatcca gaggtgaagt | 3780 |
| tcaactggta cgtggacgga gtggaggtgc acaacgccaa gaccaagcca cgggaggagc | 3840 |
| agtacaacag cacctaccgg gtggtgagcg tgctgaccgt gctgcaccag gattggctga | 3900 |
| acggaaagga gtacaagtgc aaggtgagca acaaggccct gccagcccca atcgagaaga | 3960 |
| ccatcagcaa ggccaaggga cagccacggg agccacaggt gtacaccctg ccaccaagcc | 4020 |
| gggatgagct gaccaagaac caggtgagcc tgacctgcct ggtgaaggga ttctacccaa | 4080 |
| gcgatatcgc cgtggagtgg gagagcaacg gacagccaga gaacaactac aagaccaccc | 4140 |
| caccagtgct ggatagcgac ggaagcttct tcctgtacag caagctgacc gtggataaga | 4200 |
| gccggtggca gcaggaaac gtgttcagct gcagcgtgat gcacgaggcc ctgcacaacc | 4260 |
| actacaccca gaagagcctg agcctgagcc caggaaagtg ataaagcggc cgcggtacct | 4320 |
| ctagagtcga cccgggcggc ctcgaggacg gggtgaacta cgcctgagga tccgatcttt | 4380 |
| ttccctctgc caaaaattat ggggacatca tgaagcccct tgagcatctg acttctggct | 4440 |
| aataaaggaa atttatttc attgcaatag tgtgttggaa ttttttgtgt ctctcactcg | 4500 |
| gaagcaattc gttgatctga atttcgacca cccataatac ccattaccct ggtagataag | 4560 |
| tagcatggcg ggttaatcat taactacaag gaaccctag tgatggagtt ggccactccc | 4620 |
| tctctgcgcg ctcgctcgct cactgaggcc gggcgaccaa aggtcgcccg acgcccgggc | 4680 |
| tttgcccggg cggcctcagt gagcgagcga gcgcgcag | 4718 |

<210> SEQ ID NO 16
<211> LENGTH: 736
<212> TYPE: PRT
<213> ORGANISM: Artificial Sequence
<220> FEATURE:
<223> OTHER INFORMATION: AAV hu68 vp1

<400> SEQUENCE: 16

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

-continued

```
Gly Tyr Lys Tyr Leu Gly Pro Gly Asn Gly Leu Asp Lys Gly Glu Pro
         50                  55                  60

Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
```

```
                465               470               475               480
Gly Pro Ser Tyr Arg Gln Gln Arg Val Ser Thr Thr Val Thr Gln Asn
                485               490               495
Asn Asn Ser Glu Phe Ala Trp Pro Gly Ala Ser Ser Trp Ala Leu Asn
                500               505               510
Gly Arg Asn Ser Leu Met Asn Pro Gly Pro Ala Met Ala Ser His Lys
                515               520               525
Glu Gly Glu Asp Arg Phe Phe Pro Leu Ser Gly Ser Leu Ile Phe Gly
                530               535               540
Lys Gln Gly Thr Gly Arg Asp Asn Val Asp Ala Asp Lys Val Met Ile
545               550               555               560
Thr Asn Glu Glu Glu Ile Lys Thr Thr Asn Pro Val Ala Thr Glu Ser
                565               570               575
Tyr Gly Gln Val Ala Thr Asn His Gln Ser Ala Gln Ala Gln Ala Gln
                580               585               590
Thr Gly Trp Val Gln Asn Gln Gly Ile Leu Pro Gly Met Val Trp Gln
                595               600               605
Asp Arg Asp Val Tyr Leu Gln Gly Pro Ile Trp Ala Lys Ile Pro His
                610               615               620
Thr Asp Gly Asn Phe His Pro Ser Pro Leu Met Gly Gly Phe Gly Met
625               630               635               640
Lys His Pro Pro Gln Ile Leu Ile Lys Asn Thr Pro Val Pro Ala
                645               650               655
Asp Pro Pro Thr Ala Phe Asn Lys Asp Lys Leu Asn Ser Phe Ile Thr
                660               665               670
Gln Tyr Ser Thr Gly Gln Val Ser Val Glu Ile Glu Trp Glu Leu Gln
                675               680               685
Lys Glu Asn Ser Lys Arg Trp Asn Pro Glu Ile Gln Tyr Thr Ser Asn
                690               695               700
Tyr Tyr Lys Ser Asn Asn Val Glu Phe Ala Val Asn Thr Glu Gly Val
705               710               715               720
Tyr Ser Glu Pro Arg Pro Ile Gly Thr Arg Tyr Leu Thr Arg Asn Leu
                725               730               735

<210> SEQ ID NO 17
<211> LENGTH: 736
<212> TYPE: PRT
<213> ORGANISM: Artificial Sequence
<220> FEATURE:
<223> OTHER INFORMATION: human adeno-associated virus 9 vp1

<400> SEQUENCE: 17

Met Ala Ala Asp Gly Tyr Leu Pro Asp Trp Leu Glu Asp Asn Leu Ser
1               5                 10                15
Glu Gly Ile Arg Glu Trp Trp Ala Leu Lys Pro Gly Ala Pro Gln Pro
                20                25                30
Lys Ala Asn Gln Gln His Gln Asp Asn Ala Arg Gly Leu Val Leu Pro
                35                40                45
Gly Tyr Lys Tyr Leu Gly Pro Gly Asn Gly Leu Asp Lys Gly Glu Pro
                50                55                60
Val Asn Ala Ala Asp Ala Ala Ala Leu Glu His Asp Lys Ala Tyr Asp
65                70                75                80
Gln Gln Leu Lys Ala Gly Asp Asn Pro Tyr Leu Lys Tyr Asn His Ala
                85                90                95
Asp Ala Glu Phe Gln Glu Arg Leu Lys Glu Asp Thr Ser Phe Gly Gly
```

```
            100                 105                 110
Asn Leu Gly Arg Ala Val Phe Gln Ala Lys Lys Arg Leu Leu Glu Pro
            115                 120                 125

Leu Gly Leu Val Glu Ala Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525
```

| | | | | | | | | | | | |
|---|---|---|---|---|---|---|---|---|---|---|---|
Glu | Gly | Glu | Asp | Arg | Phe | Phe | Pro | Leu | Ser | Gly | Ser | Leu | Ile | Phe | Gly
    |     | 530 |     |     |     | 535 |     |     |     | 540 |     |     |     |     |

```
Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 18
<211> LENGTH: 2211
<212> TYPE: DNA
<213> ORGANISM: Artificial Sequence
<220> FEATURE:
<223> OTHER INFORMATION: AAVhu68 vp1 coding sequence

<400> SEQUENCE: 18

```
atggctgccg atggttatct tccagattgg ctcgaggaca acctcagtga aggcattcgc    60
gagtggtggg ctttgaaacc tggagcccct caacccaagg caaatcaaca acatcaagac   120
aacgctcggg gtcttgtgct tccgggttac aaataccttg acccggcaa cggactcgac    180
aaggggagc cggtcaacga agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgt gggtattggc   480
aaatcgggtg cacagcccgc taaaaagaga ctcaatttcg gtcagactgg cgacacagag   540
tcagtccccg accctcaacc aatcggagaa cctcccgcag cccctcagg tgtgggatct   600
cttacaatgg cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca tcacctcta caagcaaatc   780
tccaacagca catctggagg atcttcaaat gacaacgcct acttcggcta cagcaccccc   840
tgggggtatt ttgacttcaa cagattccac tgccactttc caccacgtga ctggcaaaga   900
```

```
ctcatcaaca acaactgggg attccggcct aagcgactca acttcaagct cttcaacatt    960
caggtcaaag aggttacgga caacaatgga gtcaagacca tcgctaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatcta   1140
acgcttaatg atggaagcca agccgtgggt cgttcgtcct tttactgcct ggaatatttc   1200
ccgtcgcaaa tgctaagaac gggtaacaac ttccagttca gctacgagtt tgagaacgta   1260
cctttccata gcagctatgc tcacagccaa agcctggacc gactcatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgcacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaaggaa gaggaccgtt tctttccttt gtctggatct   1620
ttaattttg gcaaacaagg aactggaaga gacaacgtgg atgcggacaa agtcatgata   1680
accaacgaag aagaaattaa aactaccaac ccagtagcaa cggagtccta tggacaagtg   1740
gccacaaacc accagagtgc ccaagcacag cgcagaccg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gctttcaaca aggacaagct gaactctttc atcacccagt attctactgg ccaagtcagc   2040
gtggagattg agtgggagct gcagaaggaa aacagcaagc gctggaaccc ggagatccag   2100
tacacttcca actattacaa gtctaataat gttgaatttg ctgttaatac tgaaggtgtt   2160
tattctgaac cccgccccat tggcaccaga tacctgactc gtaatctgta a            2211
```

```
<210> SEQ ID NO 19
<211> LENGTH: 5351
<212> TYPE: DNA
<213> ORGANISM: Artificial Sequence
<220> FEATURE:
<223> OTHER INFORMATION: Vector genome encoding four immunolobobulin
      domains with UbC promoter and SV40 polyA
<220> FEATURE:
<221> NAME/KEY: repeat_region
<222> LOCATION: (17)..(146)
<223> OTHER INFORMATION: AAV2-5' ITR
<220> FEATURE:
<221> NAME/KEY: promoter
<222> LOCATION: (207)..(1433)
<223> OTHER INFORMATION: UbC promoter, including UB fow priming site
<220> FEATURE:
<221> NAME/KEY: Intron
<222> LOCATION: (1527)..(1659)
<223> OTHER INFORMATION: chimeric intron
<220> FEATURE:
<221> NAME/KEY: 5'UTR
<222> LOCATION: (1726)..(1773)
<223> OTHER INFORMATION: c-myc 5'UTR
<220> FEATURE:
<221> NAME/KEY: misc_feature
<222> LOCATION: (1774)..(1779)
<223> OTHER INFORMATION: kozak
<220> FEATURE:
<221> NAME/KEY: misc_feature
<222> LOCATION: (1780)..(1839)
<223> OTHER INFORMATION: hm IL2 leader
<220> FEATURE:
<221> NAME/KEY: misc_feature
```

```
<222> LOCATION: (1840)..(2111)
<223> OTHER INFORMATION: coding region for the first immunoglobulin
      region
<220> FEATURE:
<221> NAME/KEY: misc_binding
<222> LOCATION: (2212)..(2241)
<223> OTHER INFORMATION: linker L1
<220> FEATURE:
<221> NAME/KEY: misc_feature
<222> LOCATION: (2242)..(2610)
<223> OTHER INFORMATION: coding sequence for the second immunoglobulin
      region
<220> FEATURE:
<221> NAME/KEY: misc_binding
<222> LOCATION: (2611)..(2640)
<223> OTHER INFORMATION: linker L2
<220> FEATURE:
<221> NAME/KEY: misc_feature
<222> LOCATION: (2641)..(3303)
<223> OTHER INFORMATION: Fc1
<220> FEATURE:
<221> NAME/KEY: misc_binding
<222> LOCATION: (3304)..(3315)
<223> OTHER INFORMATION: furin
<220> FEATURE:
<221> NAME/KEY: misc_binding
<222> LOCATION: (3316)..(3387)
<223> OTHER INFORMATION: 2A
<220> FEATURE:
<221> NAME/KEY: misc_feature
<222> LOCATION: (3388)..(3447)
<223> OTHER INFORMATION: hm1 IL2 leader
<220> FEATURE:
<221> NAME/KEY: misc_feature
<222> LOCATION: (3448)..(3834)
<223> OTHER INFORMATION: coding sequence for the third immunoglobulin
      region
<220> FEATURE:
<221> NAME/KEY: misc_binding
<222> LOCATION: (3835)..(3864)
<223> OTHER INFORMATION: linker sequence L3
<220> FEATURE:
<221> NAME/KEY: misc_feature
<222> LOCATION: (3865)..(4212)
<223> OTHER INFORMATION: coding sequence for the fourth immunoglobulin
      region
<220> FEATURE:
<221> NAME/KEY: misc_binding
<222> LOCATION: (4213)..(4242)
<223> OTHER INFORMATION: linker L4
<220> FEATURE:
<221> NAME/KEY: misc_feature
<222> LOCATION: (4243)..(4908)
<223> OTHER INFORMATION: Fc2
<220> FEATURE:
<221> NAME/KEY: polyA_signal
<222> LOCATION: (4926)..(5157)
<223> OTHER INFORMATION: SV40 late polyA signal
<220> FEATURE:
<221> NAME/KEY: repeat_region
<222> LOCATION: (5222)..(5351)
<223> OTHER INFORMATION: AAV2 - 3' ITR

<400> SEQUENCE: 19
taaggcctta attaggctgc gcgctcgctc gctcactgag gccgcccggg caaagcccgg      60
gcgtcgggcg acctttggtc gcccggcctc agtgagcgag cgagcgcgca gagagggagt     120
ggccaactcc atcactaggg gttccttgta gttaatgatt aacccgccat gctacttatc     180
tacgtagcca tgctctagga agatctggcc tccgcgccgg gttttggcgc ctcccgcggg     240
cgcccccctc ctcacggcga gcgctgccac gtcagacgaa gggcgcagga gcgtcctgat     300
ccttccgccc ggacgctcag gacagcggcc cgctgctcat aagactcggc cttagaaccc     360
cagtatcagc agaaggacat tttaggacgg gacttgggtg actctagggc actggttttc     420
```

```
tttccagaga gcggaacagg cgaggaaaag tagtcccttc tcggcgattc tgcggaggga    480
tctccgtggg gcggtgaacg ccgatgatta tataaggacg cgccgggtgt ggcacagcta    540
gttccgtcgc agccgggatt tgggtcgcgg ttcttgtttg tggatcgctg tgatcgtcac    600
ttggtgagta gcgggctgct gggctggccg gggctttcgt ggccgccggg ccgctcggtg    660
ggacggaagc gtgtggagag accgccaagg gctgtagtct gggtccgcga gcaaggttgc    720
cctgaactgg gggttggggg gagcgcagca aaatggcggc tgttcccgag tcttgaatgg    780
aagacgcttg tgaggcgggc tgtgaggtcg ttgaaacaag gtgggggca tggtgggcgg     840
caagaaccca aggtcttgag gccttcgcta atgcgggaaa gctcttattc gggtgagatg    900
ggctggggca ccatctgggg accctgacgt gaagtttgtc actgactgga gaactcggtt    960
tgtcgtctgt tgcgggggcg gcagttatgc ggtgccgttg ggcagtgcac ccgtaccttt   1020
gggagcgcgc gccctcgtcg tgtcgtgacg tcacccgttc tgttggctta taatgcaggg   1080
tggggccacc tgccggtagg tgtgcggtag gcttttctcc gtcgcaggac gcagggttcg   1140
ggcctagggt aggctctcct gaatcgacag gcgccggacc tctggtgagg ggagggataa   1200
gtgaggcgtc agtttctttg gtcggtttta tgtacctatc ttcttaagta gctgaagctc   1260
cggttttgaa ctatgcgctc ggggttggcg agtgtgtttt tgaagttttt ttaggcacct   1320
tttgaaatgt aatcatttgg gtcaatatgt aattttcagt gttagactag taaattgtcc   1380
gctaaattct ggccgttttt ggcttttttg ttagacgaag ctttattgcg gtagtttatc   1440
acagttaaat tgctaacgca gtcagtgctt ctgacacaac agtctcgaac ttaagctgca   1500
gaagttggtc gtgaggcact gggcaggtaa gtatcaaggt tacaagacag gtttaaggag   1560
accaatagaa actgggcttg tcgagacaga gaagactctt gcgtttctga taggcaccta   1620
ttggtcttac tgacatccac tttgcctttc tctccacagg tgtccactcc cagttcaatt   1680
acagctctta aggctagagt acttaatacg actcactata ggctagggca cttgtgcactg   1740
gaacttacaa cacccgagca aggacgcgac tctgccacca tgtaccggat gcagctgctg   1800
agctgcatcg ccctgagcct ggccctggtg accaacagcc aggtgcagct ggtggagagc   1860
ggaggaggag tggtgcagcc aggaggaagc ctgcggctga gctgcgccgc cagcatcagc   1920
atcttcgata tctacgccat ggattggtac cggcaggccc caggaaagca gcgggagctg   1980
gtggccgtga gcttccggga cggaagcacc tactacgccg atagcgtgaa gggacggttc   2040
accatcagcc gggataacag caagaacacc ctgtacctgc agatgaacag cctgcgggcc   2100
gaggataccg ccgtgtacta ctgccacgtg agcctgtacc gggatccact gggagtggcc   2160
ggaggaatcg gagtgtactg gggacaggga accctggtga ccgtgagcag cggaggagga   2220
ggaagcggag gaggaggaag cgaggtgcag ctgctggaga gcggaggagg actggtgcag   2280
ccaggaggaa gcctgcgact gagctgtgca gcaagcggac gaacctacgc aatgggctgg   2340
ttccgacagg caccaggaaa ggagcgagag ttcgtggcag caatcaacgc actgggaacc   2400
cgaacctact acgcagacag cgtgaaggga cgattcacca tcagccgaga caacagcaag   2460
aacaccctgt acctgcagat gaacagcctg cgagcagagg acaccgcagt gtactactgt   2520
accgcacagg acagtggcg agcagcacca gtggcagtgg cagcagagta cgagttctgg   2580
ggacagggaa ccctggtgac cgtgagcagc ggaggaggag gatctggagg aggaggatct   2640
tgtccacctt gtccagcacc agagctgctg ggaggaccaa gcgtgttcct gttcccacca   2700
aagccaaagg acacccctga tgatcagccg aaccccagagg tgacctgtgt ggtggtggac   2760
gtgagccatg aggacccaga ggtgaagttc aactggtacg tggacggagt ggaggtgcat   2820
```

```
aacgcaaaga ccaagccacg agaggagcag tacaacagca cctaccgagt ggtgagcgtg   2880
ctgaccgtgc tgcatcagga ctggctgaac ggaaaggagt acaagtgtaa ggtgagcaac   2940
aaggcactgc cagcaccaat cgagaagacc atcagcaagg caaagggaca gccacgagag   3000
ccacaggtgt acaccctgcc accaagccga gacgagctga ccaagaacca ggtgagcctg   3060
acctgtctgg tgaagggatt ctacccaagc gacatcgcag tggagtggga gagcaacgga   3120
cagccagaga caaactacaa gaccaccccca ccagtgctgg acagcgacgg aagcttcttc   3180
ctgtacagca agctgaccgt ggacaagagc cggtggcagc agggaaacgt gttcagctgt   3240
agcgtgatgc acgaggcact gcataaccat tacacccaga gagcctgag cctgagccca   3300
ggacggaagc ggcgggcccc agtgaagcag accctgaact tcgatctgct gaagctggcc   3360
ggagacgtgg agagcaaccc aggaccaatg taccggatgc agctgctgct gctgatcgcc   3420
ctgagcctgg ccctggtgac aacagcgaa gtgcagctgc tggaaagcgg cggcggcctg   3480
gtgcagcccg gcggcagcct gcggctgagc tgtgctgcta gcggctttac cctggaaaac   3540
aaggctattg gctggtttcg gcaggctccc ggcaaggaac gggaaggcgt gctgtgtatt   3600
agcaagagcg gcagctggac ctattatgct gacagcgtga agggccggtt taccattagc   3660
cgggacaaca gcaagaacac cgtgtatctg cagatgaaca gcctgcggcc cgaagacacc   3720
gctgtgtatt attgtgctac caccaccgct ggcggcggcc tgtgttggga cggcaccacc   3780
tttagccggc tggctagcag ctggggccag ggcaccctgg tgaccgtgag cagcggagga   3840
ggaggatccg gaggaggagg atccgaggtg cagctggtgg agtcaggagg aggactggtg   3900
cagcccggag gatcactgag actgtcctgc gctgcttcag gattcacctt ctcaacctcc   3960
tggatgtatt ggctgagaca ggctcccgga aaaggactgg agtgggtgtc agtgatcaac   4020
accgacggag gaacctatta tgctgattca gtgaaaggaa gattcaccat ctcaagagat   4080
aactcaaaaa acaccctgta tctgcagatg aactcactga gagctgagga taccgctgtg   4140
tattattgcg ctaaagattg gggaggaccc gagcccacca gggacagggg aaccctggtg   4200
accgtgtcat caggaggagg aggatcagga ggaggaggat cctgcccacc ttgcccagcc   4260
ccagagctgc tgggaggacc aagcgtgttc ctgttcccac caaagccaaa ggatacccctg   4320
atgatcagcc ggaccccaga ggtgacctgc gtggtggtgg atgtgagcca cgaggatcca   4380
gaggtgaagt tcaactggta cgtggacgga gtggaggtgc acaacgccaa gaccaagcca   4440
cgggaggagc agtacaacag cacctaccgg gtggtgagcg tgctgaccgt gctgcaccag   4500
gattggctga acggaaagga gtacaagtgc aaggtgagca caaggccct gccagcccca   4560
atcgagaaga ccatcagcaa ggccaaggga cagccacggg agccacaggt gtacaccctg   4620
ccaccaagcc gggatgagct gaccaagaac caggtgagcc tgacctgcct ggtgaaggga   4680
ttctacccaa gcgatatcgc cgtggagtgg gagagcaacg gacagccaga gaacaactac   4740
aagaccaccc caccagtgct ggatagcgac ggaagcttct tcctgtacag caagctgacc   4800
gtggataaga gccggtggca gcagggaaac gtgttcagct gcagcgtgat gcacgaggcc   4860
ctgcacaacc actacaccca gaagagcctg agcctgagcc caggaaagtg ataaagcggc   4920
cgcttcgagc agacatgata agatacattg atgagtttgg acaaaccaca actagaatgc   4980
agtgaaaaaa atgctttatt tgtgaaattt gtgatgctat tgctttattt gtaaccatta   5040
taagctgcaa taaacaagtt aacaacaaca attgcattca ttttatgttt caggttcagg   5100
gggagatgtg gaggttttt taaagcaagt aaaacctcta caaatgtggt aaaatcgata   5160
```

-continued

```
aggatcttcc tagagcatgg ctacgtagat aagtagcatg gcgggttaat cattaactac    5220
aaggaacccc tagtgatgga gttggccact ccctctctgc gcgctcgctc gctcactgag    5280
gccgggcgac caaaggtcgc ccgacgcccg ggctttgccc gggcggcctc agtgagcgag    5340
cgagcgcgca g                                                        5351
```

```
<210> SEQ ID NO 20
<211> LENGTH: 4808
<212> TYPE: DNA
<213> ORGANISM: Artificial Sequence
<220> FEATURE:
<223> OTHER INFORMATION: vector genome with TBG promoter, BGH polyA
<220> FEATURE:
<221> NAME/KEY: repeat_region
<222> LOCATION: (1)..(130)
<223> OTHER INFORMATION: AAV2 - 5' ITR
<220> FEATURE:
<221> NAME/KEY: promoter
<222> LOCATION: (205)..(913)
<223> OTHER INFORMATION: thyroxine binding globlulin (TBG) promoter
<220> FEATURE:
<221> NAME/KEY: TATA_signal
<222> LOCATION: (875)..(878)
<220> FEATURE:
<221> NAME/KEY: Intron
<222> LOCATION: (939)..(1071)
<223> OTHER INFORMATION: SV40 misc intron
<220> FEATURE:
<221> NAME/KEY: 5'UTR
<222> LOCATION: (1096)..(1143)
<223> OTHER INFORMATION: c-myc 5'UTR
<220> FEATURE:
<221> NAME/KEY: misc_feature
<222> LOCATION: (1144)..(1149)
<223> OTHER INFORMATION: kozak
<220> FEATURE:
<221> NAME/KEY: misc_feature
<222> LOCATION: (1150)..(1209)
<223> OTHER INFORMATION: hmIL2 linker
<220> FEATURE:
<221> NAME/KEY: misc_feature
<222> LOCATION: (1210)..(1581)
<223> OTHER INFORMATION: coding sequence for the first immunoglobulin
      region
<220> FEATURE:
<221> NAME/KEY: misc_binding
<222> LOCATION: (1582)..(1611)
<223> OTHER INFORMATION: linker L1
<220> FEATURE:
<221> NAME/KEY: misc_feature
<222> LOCATION: (1612)..(1980)
<223> OTHER INFORMATION: coding sequence for the second immunoglobulin
      region
<220> FEATURE:
<221> NAME/KEY: misc_binding
<222> LOCATION: (1981)..(1995)
<223> OTHER INFORMATION: hinge
<220> FEATURE:
<221> NAME/KEY: misc_feature
<222> LOCATION: (1996)..(2658)
<223> OTHER INFORMATION: Fc1
<220> FEATURE:
<221> NAME/KEY: misc_binding
<222> LOCATION: (2659)..(2670)
<223> OTHER INFORMATION: furin
<220> FEATURE:
<221> NAME/KEY: misc_binding
<222> LOCATION: (2671)..(2742)
<223> OTHER INFORMATION: 2A
<220> FEATURE:
<221> NAME/KEY: misc_feature
<222> LOCATION: (2743)..(2802)
<223> OTHER INFORMATION: hm IL2 leader
<220> FEATURE:
<221> NAME/KEY: misc_feature
<222> LOCATION: (2803)..(3189)
```

```
<223> OTHER INFORMATION: coding sequence for the third immunoglobulin
      region
<220> FEATURE:
<221> NAME/KEY: misc_binding
<222> LOCATION: (3190)..(3219)
<223> OTHER INFORMATION: linker sequence L3
<220> FEATURE:
<221> NAME/KEY: misc_feature
<222> LOCATION: (3220)..(3567)
<223> OTHER INFORMATION: coding sequence for the fourth immunoglobulin
      region
<220> FEATURE:
<221> NAME/KEY: misc_binding
<222> LOCATION: (3568)..(3582)
<223> OTHER INFORMATION: hinge
<220> FEATURE:
<221> NAME/KEY: misc_feature
<222> LOCATION: (3583)..(4248)
<223> OTHER INFORMATION: Fc2
<220> FEATURE:
<221> NAME/KEY: polyA_signal
<222> LOCATION: (4377)..(4591)
<223> OTHER INFORMATION: bovine growth hormone (BGH) polyA
<220> FEATURE:
<221> NAME/KEY: repeat_region
<222> LOCATION: (4679)..(4808)
<223> OTHER INFORMATION: AAV2 - 3'ITR

<400> SEQUENCE: 20
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tgtagttaat gattaacccg ccatgctact tatctacgta gccatgctct      180
aggaagatcg gaattcgccc ttaagctagc aggttaattt ttaaaaagca gtcaaaagtc      240
caagtggccc ttggcagcat ttactctctc tgtttgctct ggttaataat ctcaggagca      300
caaacattcc agatccaggt taattttttaa aaagcagtca aaagtccaag tggcccttgg      360
cagcatttac tctctctgtt tgctctggtt aataatctca ggagcacaaa cattccagat      420
ccggcgcgcc agggctggaa gctacctttg acatcatttc ctctgcgaat gcatgtataa      480
tttctacaga acctattaga aaggatcacc cagcctctgc ttttgtacaa ctttccctta      540
aaaaactgcc aattccactg ctgtttggcc caatagtgag aacttttttcc tgctgcctct      600 tggtgctttt gcctatggcc cctattctgc ctgctgaaga cactcttgcc agcatggact      660
taaacccctc cagctctgac aatcctcttt ctcttttgtt ttacatgaag ggtctggcag      720
ccaaagcaat cactcaaagt tcaaacctta tcattttttg ctttgttcct cttggccttg      780
gttttgtaca tcagctttga aaataccatc ccagggttaa tgctgggggtt aatttataac      840 taagagtgct ctagttttgc aatacaggac atgctataaa aatggaaaga tgttgctttc      900
tgagagactg cagaagttgg tcgtgaggca ctgggcaggt aagtatcaag gttacaagac      960
aggtttaagg agaccaatag aaactgggct tgtcgagaca gagaagactc ttgcgtttct     1020
gataggcacc tattggtctt actgacatcc actttgcctt tctctccaca ggtgtccagg     1080
cggccaattc gtctagggca ctttgcactg gaacttacaa caccccgagca aggacgcgac     1140 tctgccacca tgtatcggat gcagctgctg agctgtattg ctctgagcct ggctctggtg     1200
accaacagcc aggtgcagct ggtggaaagc ggcggcggcg tggtgcagcc cggcggcagc     1260
ctgcggctga gctgtgctgc tagcattagc attttttgaca tttacgctat ggactggtat     1320
cggcaggctc ccggcaagca gcgggaactg gtgctgtga gctttcggga cggcagcacc     1380
tattatgctg acagcgtgaa gggccggttt accattagcc gggacaacag caagaacacc     1440
ctgtatctgc agatgaacag cctgcgggct gaagacaccg ctgtgtatta ttgtcatgtg     1500
```

```
agcctgtatc gggaccccct gggcgtggct ggcggcattg gcgtgtattg gggccagggc   1560
accctggtga ccgtgagcag cggaggagga ggaagcggag gaggaggaag cgaggtgcag   1620
ctgctggaga gcggaggagg actggtgcag ccaggaggaa gcctgcgact gagctgtgca   1680
gcaagcggac gaacctacgc aatgggctgg ttccgacagg caccaggaaa ggagcgagag   1740
ttcgtggcag caatcaacgc actgggaacc cgaacctact acgcagacag cgtgaaggga   1800
cgattcacca tcagccgaga caacagcaag aacaccctgt acctgcagat gaacagcctg   1860
cgagcagagg acaccgcagt gtactactgt accgcacagg acagtggcg agcagcacca   1920 gtggcagtgg cagcagagta cgagttctgg ggacagggaa ccctggtgac cgtgagcagc   1980
gacaagaccc ataccttgtcc accttgtcca gcaccagagc tgctgggagg accaagcgtg   2040
ttcctgttcc caccaaagcc aaaggacacc ctgatgatca gccgaacccc agaggtgacc   2100
tgtgtggtgg tggacgtgag ccatgaggac ccagaggtga agttcaactg gtacgtggac   2160
ggagtggagg tgcataacgc aaagaccaag ccacgagagg agcagtacaa cagcacctac   2220
cgagtggtga gcgtgctgac cgtgctgcat caggactggc tgaacggaaa ggagtacaag   2280
tgtaaggtga gcaacaaggc actgccagca ccaatcgaga agaccatcag caaggcaaag   2340
ggacagccac gagagccaca ggtgtacacc ctgccaccaa gccgagacga gctgaccaag   2400
aaccaggtga gcctgacctg tctggtgaag ggattctacc caagcgacat cgcagtggag   2460
tgggagagca acggacagcc agagaacaac tacaagacca ccccaccagt gctggacagc   2520
gacggaagct tctttctgta cagcaagctg accgtggaca gagccggtg gcagcaggga   2580 aacgtgttca gctgtagcgt gatgcacgag gcactgcata accattacac ccagaagagc   2640
ctgagcctga gcccaggacg gaagcggcgg gctcccgtga agcagaccct gaactttgac   2700
ctgctgaagc tggctggcga cgtggaaagc aaccccggcc ccatgtatcg gatgcagctg   2760
ctgctgctga ttgctctgag cctggctctg gtgaccaaca gcgaggtgca gctgctggag   2820
agcggaggag gactggtgca gccaggagga agcctgcggc tgagctgcgc cgccagcgga   2880
ttcaccctgg agaacaaggc catcggctgg ttccggcagg ccccaggaaa ggagcgggag   2940
ggagtgctgt gcatcagcaa gagcggaagc tggacctact acgccgatag cgtgaaggga   3000
cggttcacca tcagccggga taacagcaag aacaccgtgt acctgcagat gaacagcctg   3060
cggccagagg ataccgccgt gtactactgc gccaccacca cgccggagg aggactgtgc   3120 tgggacggaa ccaccttcag ccggctggcc agcagctggg acagggaac cctggtgacc   3180 gtgagcagcg gaggaggagg atccggagga ggaggatccg aggtgcagct ggtggagtca   3240
ggaggaggac tggtgcagcc cggaggatca ctgagactgt cctgcgctgc ttcaggattc   3300
accttctcaa cctcctggat gtattggctg agacaggctc ccggaaaagg actggagtgg   3360
gtgtcagtga tcaacaccga cggaggaacc tattatgctg attcagtgaa aggaagattc   3420
accatctcaa gagataactc aaaaaacacc ctgtatctgc agatgaactc actgagagct   3480
gaggataccg ctgtgtatta ttgcgctaaa gattgggag acccgagcc accagagga   3540 cagggaaccc tggtgaccgt gtcatcagac aagacccata cctgtccccc ctgtcccgct   3600
cccgaactgc tgggcggccc cagcgtgttt ctgtttcccc caagcccaa ggacaccctg   3660 atgattagcc ggaccccga agtgacctgt gtggtggtgg acgtgagcca tgaagacccc   3720
gaagtgaagt ttaactggta cgtggacggc gtggaagtgc ataacgctaa gaccaagccc   3780
cgggaagaac agtataacag cacctatcgg gtggtgagcg tgctgaccgt gctgcatcag   3840
```

-continued

```
gactggctga acggcaagga atataagtgt aaggtgagca acaaggctct gcccgctccc    3900
attgaaaaga ccattagcaa ggctaagggc cagccccggg aacccaggt gtataccctg     3960 cccccagcc gggacgaact gaccaagaac caggtgagcc tgacctgtct ggtgaagggc     4020
ttttatccca gcgacattgc tgtggagtgg gaaagcaacg gccagcccga aaacaactat    4080
aagaccaccc ccccgtgct ggacagcgac ggcagctttt ttctgtatag caagctgacc     4140
gtggacaaga gccggtggca gcagggcaac gtgtttagct gtagcgtgat gcacgaagct    4200
ctgcataacc attatacca gaagagcctg agcctgagcc ccggcaagtg ataaagcggc     4260
cgcagcttat ggggattggt ggcgacgact cctggagccc gtcagtatcg gcggaattcc    4320
agctgagcgc cggtcgctac cattaccagt tggtctggtg tcaaaaataa ggatctgcct    4380
cgactgtgcc ttctagttgc cagccatctg ttgtttgccc ctcccccgtg ccttccttga    4440
ccctggaagg tgccactccc actgtccttt cctaataaaa tgaggaaatt gcatcgcatt    4500
gtctgagtag gtgtcattct attctggggg gtggggtggg gcaggacagc aaggggagg    4560 attgggaaga caatagcagg catgctgggg actcgagtta agggcgaatt cccgataagg    4620
atcttcctag agcatggcta cgtagataag tagcatggcg ggttaatcat taactacaag    4680 gaaccctag tgatggagtt ggccactccc tctctgcgcg ctcgctcgct cactgaggcc     4740
gggcgaccaa aggtcgcccg acgcccgggc tttgcccggg cggcctcagt gagcgagcga    4800
gcgcgcag                                                             4808
```

```
<210> SEQ ID NO 21
<211> LENGTH: 2361
<212> TYPE: DNA
<213> ORGANISM: Artificial Sequence
<220> FEATURE:
<223> OTHER INFORMATION: J211 coding sequence for fusion protein
<220> FEATURE:
<221> NAME/KEY: 5'UTR
<222> LOCATION: (1)..(48)
<223> OTHER INFORMATION: c-myc 5'UTR
<220> FEATURE:
<221> NAME/KEY: misc_feature
<222> LOCATION: (49)..(54)
<223> OTHER INFORMATION: kozak
<220> FEATURE:
<221> NAME/KEY: misc_feature
<222> LOCATION: (55)..(114)
<223> OTHER INFORMATION: hmIL2 leader
<220> FEATURE:
<221> NAME/KEY: misc_feature
<222> LOCATION: (115)..(486)
<223> OTHER INFORMATION: coding sequence for the first immunoglobulin
      region
<220> FEATURE:
<221> NAME/KEY: misc_binding
<222> LOCATION: (487)..(516)
<223> OTHER INFORMATION: linker sequence L1
<220> FEATURE:
<221> NAME/KEY: misc_feature
<222> LOCATION: (517)..(885)
<223> OTHER INFORMATION: coding sequence for the second immunoglobulin
      region
<220> FEATURE:
<221> NAME/KEY: misc_binding
<222> LOCATION: (886)..(915)
<223> OTHER INFORMATION: leader sequence L2
<220> FEATURE:
<221> NAME/KEY: misc_feature
<222> LOCATION: (916)..(1302)
<223> OTHER INFORMATION: coding sequence for the third immunoglobulin
      region
<220> FEATURE:
<221> NAME/KEY: misc_binding
<222> LOCATION: (1303)..(1332)
```

```
<223> OTHER INFORMATION: linker sequence L3
<220> FEATURE:
<221> NAME/KEY: misc_feature
<222> LOCATION: (1333)..(1680)
<223> OTHER INFORMATION: coding sequence for the fourth immunoglobulin
      region
<220> FEATURE:
<221> NAME/KEY: misc_binding
<222> LOCATION: (1681)..(1695)
<223> OTHER INFORMATION: hinge
<220> FEATURE:
<221> NAME/KEY: misc_feature
<222> LOCATION: (1696)..(2361)
<223> OTHER INFORMATION: Fc

<400> SEQUENCE: 21
gggcactttg cactggaact tacaacaccc gagcaaggac gcgactctgc caccatgtat      60
cggatgcagc tgctgagctg tattgctctg agcctggctc tggtgaccaa cagccaggtg     120
cagctggtgg aaagcggcgg cggcgtggtg cagcccggcg gcagcctgcg gctgagctgt     180
gctgctagca ttagcatttt tgacatttac gctatggact ggtatcggca ggctcccggc     240
aagcagcggg aactggtggc tgtgagcttt cgggacggca gcacctatta tgctgacagc     300
gtgaagggcc ggtttaccat tagccgggac aacagcaaga cacccctgta tctgcagatg     360
aacagcctgc gggctgaaga caccgctgtg tattattgtc atgtgagcct gtatcgggac     420
cccctgggcg tggctggcgg cattggcgtg tattggggcc agggcaccct ggtgaccgtg     480
agcagcggag gaggaggaag cggaggagga ggaagcgagg tgcagctgct ggagagcgga     540
ggaggactgg tgcagccagg aggaagcctg cgactgagct gtgcagcaag cggacgaacc     600
tacgcaatgg gctggttccg acaggcacca ggaaaggagc gagagttcgt ggcagcaatc     660
aacgcactgg gaacccgaac ctactacgca gacagcgtga agggacgatt caccatcagc     720
cgagacaaca gcaagaacac cctgtacctg cagatgaaca gcctgcgagc agaggacacc     780
gcagtgtact actgtaccgc acagggacag tggcgagcag caccagtggc agtggcagca     840
gagtacgagt tctggggaca gggaaccctg gtgaccgtga gcagcggagg aggaggatct     900
ggaggaggag gatctgaggt gcagctgctg gagagcggag gaggactggt gcagccagga     960
ggaagcctgc ggctgagctg cgccgccagc ggattcaccc tggagaacaa ggccatcggc    1020
tggttccggc aggcccccagg aaaggagcgg gagggagtgc tgtgcatcag caagagcgga    1080
agctggacct actacgccga tagcgtgaag gacggttca ccatcagccg ggataacagc      1140
aagaacaccg tgtacctgca gatgaacagc ctgcggccag aggataccgc cgtgtactac    1200
tgcgccacca ccaccgccgg aggagctg tgctgggacg aaccaccttc agccggctg       1260 gccagcagct ggggacaggg aaccctggtg accgtgagca gcggaggagg aggatccga    1320 ggaggaggat ccgaggtgca gctggtggag tcaggaggag gactggtgca gcccggagga    1380
tcactgagac tgtcctgcgc tgcttcagga ttcaccttct caacctcctg gatgtattgg    1440
ctgagacagg ctcccggaaa aggactggag tgggtgtcag tgatcaacac cgacggagga    1500
acctattatg ctgattcagt gaaaggaaga ttcaccatct caagagataa ctcaaaaaac    1560
accctgtatc tgcagatgaa ctcactgaga gctgaggata ccgctgtgta ttattgcgct    1620
aaagattggg gaggacccga gcccaccaga ggacagggaa ccctggtgac cgtgtcatca    1680
gacaagaccc atacctgtcc ccctgtccc gctcccgaac tgctgggcgg cccccagcgtg    1740 tttctgtttc cccccaagcc caaggacacc ctgatgatta gcggaccccc gaagtgacc    1800 tgtgtggtgg tggacgtgag ccatgaagac cccgaagtga agtttaactg gtacgtggac    1860
```

```
ggcgtggaag tgcataacgc taagaccaag ccccgggaag aacagtataa cagcacctat    1920
cgggtggtga gcgtgctgac cgtgctgcat caggactggc tgaacggcaa ggaatataag    1980
tgtaaggtga gcaacaaggc tctgcccgct cccattgaaa agaccattag caaggctaag    2040
ggccagcccc gggaacccca ggtgtatacc ctgccccccca gccggacga actgaccaag    2100 aaccaggtga gcctgacctg tctggtgaag ggcttttatc ccagcgacat tgctgtggag    2160
tgggaaagca acggccagcc cgaaaacaac tataagacca ccccccccgt gctggacagc    2220
gacggcagct ttttctgta tagcaagctg accgtggaca agagccggtg gcagcagggc    2280
aacgtgttta gctgtagcgt gatgcacgaa gctctgcata accattatac ccagaagagc    2340
ctgagcctga gccccggcaa g                                              2361
```

```
<210> SEQ ID NO 22
<211> LENGTH: 38
<212> TYPE: PRT
<213> ORGANISM: Artificial Sequence
<220> FEATURE:
<223> OTHER INFORMATION: Linker

<400> SEQUENCE: 22

Ala Ala Ala Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser
        35

<210> SEQ ID NO 23
<211> LENGTH: 15
<212> TYPE: PRT
<213> ORGANISM: Artificial Sequence
<220> FEATURE:
<223> OTHER INFORMATION: Linker

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 35
<212> TYPE: PRT
<213> ORGANISM: Artificial Sequence
<220> FEATURE:
<223> OTHER INFORMATION: Linker

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 25
<211> LENGTH: 57
<212> TYPE: PRT
<213> ORGANISM: Artificial Sequence
<220> FEATURE:
<223> OTHER INFORMATION: Linker

<400> SEQUENCE: 25
```

```
Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser
            20              25              30

Gly Gly Gly Gly Ser Gly Gly Gly Ser Gly Gly Gly Ser Gly
        35                  40              45

Gly Gly Gly Ser Gly Gly Gly Ser
    50              55

<210> SEQ ID NO 26
<211> LENGTH: 2307
<212> TYPE: DNA
<213> ORGANISM: Artificial Sequence
<220> FEATURE:
<223> OTHER INFORMATION: J210a coding sequence
<220> FEATURE:
<221> NAME/KEY: CDS
<222> LOCATION: (1)..(2307)

<400> SEQUENCE: 26 atg tac cga atg cag ctg ctg agc tgt atc gca ctg agc ctg gca ctg      48
Met Tyr Arg Met Gln Leu Leu Ser Cys Ile Ala Leu Ser Leu Ala Leu
1               5                   10                  15 gtg acc aac agc cag gtg cag ctg gtg gag agc gga gga gga gtg gtg      96
Val Thr Asn Ser Gln Val Gln Leu Val Glu Ser Gly Gly Gly Val Val
            20                  25                  30 cag cca gga gga agc ctg cga ctg agc tgt gca gca agc atc agc atc     144
Gln Pro Gly Gly Ser Leu Arg Leu Ser Cys Ala Ala Ser Ile Ser Ile
        35                  40                  45 ttc gac atc tac gca atg gac tgg tac cga cag gca cca gga aag cag     192
Phe Asp Ile Tyr Ala Met Asp Trp Tyr Arg Gln Ala Pro Gly Lys Gln
    50                  55                  60 cga gag ctg gtg gca gtg agc ttc cga gac gga agc acc tac tac gca     240
Arg Glu Leu Val Ala Val Ser Phe Arg Asp Gly Ser Thr Tyr Tyr Ala
65                  70                  75                  80 gac agc gtg aag gga cga ttc acc atc agc cga gac aac agc aag aac     288
Asp Ser Val Lys Gly Arg Phe Thr Ile Ser Arg Asp Asn Ser Lys Asn
                85                  90                  95 acc ctg tac ctg cag atg aac agc ctg cga gca gag gac acc gca gtg     336
Thr Leu Tyr Leu Gln Met Asn Ser Leu Arg Ala Glu Asp Thr Ala Val
            100                 105                 110 tac tac tgt cat gtg agc ctg tac cgg gac cca ctg gga gtg gca gga     384
Tyr Tyr Cys His Val Ser Leu Tyr Arg Asp Pro Leu Gly Val Ala Gly
        115                 120                 125 gga atc gga gtg tac tgg gga cag gga acc ctg gtg acc gtg agc agc     432
Gly Ile Gly Val Tyr Trp Gly Gln Gly Thr Leu Val Thr Val Ser Ser
    130                 135                 140 gga gga gga gga agc gga gga gga gga agc gaa gtg cag ctg ctg gaa     480
Gly Gly Gly Gly Ser Gly Gly Gly Gly Ser Glu Val Gln Leu Leu Glu
145                 150                 155                 160 agc ggc ggc ggc ctg gtg cag ccc ggc ggc agc ctg cgg ctg agc tgt     528
Ser Gly Gly Gly Leu Val Gln Pro Gly Gly Ser Leu Arg Leu Ser Cys
                165                 170                 175 gct gct agc ggc cgg acc tac gct atg ggc tgg ttt cgg cag gct ccc     576
Ala Ala Ser Gly Arg Thr Tyr Ala Met Gly Trp Phe Arg Gln Ala Pro
            180                 185                 190 ggc aag gaa cgg gaa ttt gtg gct gct att aac gct ctg ggc acc cgg     624
Gly Lys Glu Arg Glu Phe Val Ala Ala Ile Asn Ala Leu Gly Thr Arg
        195                 200                 205 acc tat tat gct gac agc gtg aag ggc cgg ttt acc att agc cgg gac     672
Thr Tyr Tyr Ala Asp Ser Val Lys Gly Arg Phe Thr Ile Ser Arg Asp
```

-continued

```
              210                 215                 220
aac agc aag aac acc ctg tat ctg cag atg aac agc ctg cgg gct gaa      720
Asn Ser Lys Asn Thr Leu Tyr Leu Gln Met Asn Ser Leu Arg Ala Glu
225                 230                 235                 240 gac acc gct gtg tat tat tgt acc gct cag ggc cag tgg cgg gct gct      768
Asp Thr Ala Val Tyr Tyr Cys Thr Ala Gln Gly Gln Trp Arg Ala Ala
                245                 250                 255 ccc gtg gct gtg gct gct gaa tac gaa ttt tgg ggc cag ggc acc ctg      816
Pro Val Ala Val Ala Ala Glu Tyr Glu Phe Trp Gly Gln Gly Thr Leu
            260                 265                 270 gtg acc gtg agc agc gga gga gga gga tct gga gga gga tct gag          864
Val Thr Val Ser Ser Gly Gly Gly Gly Ser Gly Gly Gly Ser Glu
        275                 280                 285 gtg cag ctg ctg gag agc gga gga gga ctg gtg cag cca gga gga agc      912
Val Gln Leu Leu Glu Ser Gly Gly Gly Leu Val Gln Pro Gly Gly Ser
290                 295                 300 ctg cgg ctg agc tgc gcc gcc agc gga ttc acc ctg gag aac aag gcc      960
Leu Arg Leu Ser Cys Ala Ala Ser Gly Phe Thr Leu Glu Asn Lys Ala
305                 310                 315                 320 atc ggc tgg ttc cgg cag gcc cca gga aag gag cgg gag gga gtg ctg     1008
Ile Gly Trp Phe Arg Gln Ala Pro Gly Lys Glu Arg Glu Gly Val Leu
                325                 330                 335 tgc atc agc aag agc gga agc tgg acc tac tac gcc gat agc gtg aag     1056
Cys Ile Ser Lys Ser Gly Ser Trp Thr Tyr Tyr Ala Asp Ser Val Lys
            340                 345                 350 gga cgg ttc acc atc agc cgg gat aac agc aag aac acc gtg tac ctg     1104
Gly Arg Phe Thr Ile Ser Arg Asp Asn Ser Lys Asn Thr Val Tyr Leu
        355                 360                 365 cag atg aac agc ctg cgg cca gag gat acc gcc gtg tac tac tgc gcc     1152
Gln Met Asn Ser Leu Arg Pro Glu Asp Thr Ala Val Tyr Tyr Cys Ala
370                 375                 380 acc acc acc gcc gga gga gga ctg tgc tgg gac gga acc acc ttc agc     1200
Thr Thr Thr Ala Gly Gly Gly Leu Cys Trp Asp Gly Thr Thr Phe Ser
385                 390                 395                 400 cgg ctg gcc agc agc tgg gga cag gga acc ctg gtg acc gtg agc agc     1248
Arg Leu Ala Ser Ser Trp Gly Gln Gly Thr Leu Val Thr Val Ser Ser
                405                 410                 415 gga gga gga gga tcc gga gga gga gga tcc gag gtg cag ctg gtg gag     1296
Gly Gly Gly Gly Ser Gly Gly Gly Gly Ser Glu Val Gln Leu Val Glu
            420                 425                 430 tca gga gga gga ctg gtg cag ccc gga gga tca ctg aga ctg tcc tgc     1344
Ser Gly Gly Gly Leu Val Gln Pro Gly Gly Ser Leu Arg Leu Ser Cys
        435                 440                 445 gct gct tca gga ttc acc ttc tca acc tcc tgg atg tat tgg ctg aga     1392
Ala Ala Ser Gly Phe Thr Phe Ser Thr Ser Trp Met Tyr Trp Leu Arg
450                 455                 460 cag gct ccc gga aaa gga ctg gag tgg gtg tca gtg atc aac acc gac     1440
Gln Ala Pro Gly Lys Gly Leu Glu Trp Val Ser Val Ile Asn Thr Asp
465                 470                 475                 480 gga gga acc tat tat gct gat tca gtg aaa gga aga ttc acc atc tca     1488
Gly Gly Thr Tyr Tyr Ala Asp Ser Val Lys Gly Arg Phe Thr Ile Ser
                485                 490                 495 aga gat aac tca aaa aac acc ctg tat ctg cag atg aac tca ctg aga     1536
Arg Asp Asn Ser Lys Asn Thr Leu Tyr Leu Gln Met Asn Ser Leu Arg
            500                 505                 510 gct gag gat acc gct gtg tat tat tgc gct aaa gat tgg gga gga ccc     1584
Ala Glu Asp Thr Ala Val Tyr Tyr Cys Ala Lys Asp Trp Gly Gly Pro
        515                 520                 525 gag ccc acc aga gga cag gga acc ctg gtg acc gtg tca tca gac aag     1632
```

| | | | | | | | | | | | | | | |
|---|---|---|---|---|---|---|---|---|---|---|---|---|---|---|
| Glu | Pro | Thr | Arg | Gly | Gln | Gly | Thr | Leu | Val | Thr | Val | Ser | Ser | Asp | Lys |
| | 530 | | | | 535 | | | | | 540 | | | | | |

```
acc cat acc tgt cca cct tgt cca gca cca gag ctg ctg gga gga cca      1680
Thr His Thr Cys Pro Pro Cys Pro Ala Pro Glu Leu Leu Gly Gly Pro
545                 550                 555                 560 agc gtg ttc ctg ttc cca cca aag cca aag gac acc ctg atg atc agc      1728
Ser Val Phe Leu Phe Pro Pro Lys Pro Lys Asp Thr Leu Met Ile Ser
                565                 570                 575 cga acc cca gag gtg acc tgt gtg gtg gtg gac gtg agc cat gag gac      1776
Arg Thr Pro Glu Val Thr Cys Val Val Val Asp Val Ser His Glu Asp
                580                 585                 590 cca gag gtg aag ttc aac tgg tac gtg gac gga gtg gag gtg cat aac      1824
Pro Glu Val Lys Phe Asn Trp Tyr Val Asp Gly Val Glu Val His Asn
                595                 600                 605 gca aag acc aag cca cga gag gag cag tac aac agc acc tac cga gtg      1872
Ala Lys Thr Lys Pro Arg Glu Glu Gln Tyr Asn Ser Thr Tyr Arg Val
610                 615                 620 gtg agc gtg ctg acc gtg ctg cat cag gac tgg ctg aac gga aag gag      1920
Val Ser Val Leu Thr Val Leu His Gln Asp Trp Leu Asn Gly Lys Glu
625                 630                 635                 640 tac aag tgt aag gtg agc aac aag gca ctg cca gca cca atc gag aag      1968
Tyr Lys Cys Lys Val Ser Asn Lys Ala Leu Pro Ala Pro Ile Glu Lys
                645                 650                 655 acc atc agc aag gca aag gga cag cca cga gag cca cag gtg tac acc      2016
Thr Ile Ser Lys Ala Lys Gly Gln Pro Arg Glu Pro Gln Val Tyr Thr
                660                 665                 670 ctg cca cca agc cga gac gag ctg acc aag aac cag gtg agc ctg acc      2064
Leu Pro Pro Ser Arg Asp Glu Leu Thr Lys Asn Gln Val Ser Leu Thr
                675                 680                 685 tgt ctg gtg aag gga ttc tac cca agc gac atc gca gtg gag tgg gag      2112
Cys Leu Val Lys Gly Phe Tyr Pro Ser Asp Ile Ala Val Glu Trp Glu
690                 695                 700 agc aac gga cag cca gag aac aac tac aag acc acc cca cca gtg ctg      2160
Ser Asn Gly Gln Pro Glu Asn Asn Tyr Lys Thr Thr Pro Pro Val Leu
705                 710                 715                 720 gac agc gac gga agc ttc ttc ctg tac agc aag ctg acc gtg gac aag      2208
Asp Ser Asp Gly Ser Phe Phe Leu Tyr Ser Lys Leu Thr Val Asp Lys
                725                 730                 735 agc cgg tgg cag cag gga aac gtg ttc agc tgt agc gtg atg cac gag      2256
Ser Arg Trp Gln Gln Gly Asn Val Phe Ser Cys Ser Val Met His Glu
                740                 745                 750 gca ctg cat aac cat tac acc cag aag agc ctg agc ctg agc cca gga      2304
Ala Leu His Asn His Tyr Thr Gln Lys Ser Leu Ser Leu Ser Pro Gly
                755                 760                 765 aag                                                                   2307
Lys

<210> SEQ ID NO 27
<211> LENGTH: 769
<212> TYPE: PRT
<213> ORGANISM: Artificial Sequence
<220> FEATURE:
<223> OTHER INFORMATION: Synthetic Construct

<400> SEQUENCE: 27

Met Tyr Arg Met Gln Leu Leu Ser Cys Ile Ala Leu Ser Leu Ala Leu
1               5                   10                  15

Val Thr Asn Ser Gln Val Gln Leu Val Glu Ser Gly Gly Gly Val Val
                20                  25                  30

Gln Pro Gly Gly Ser Leu Arg Leu Ser Cys Ala Ala Ser Ile Ser Ile
```

```
              35                  40                  45
Phe Asp Ile Tyr Ala Met Asp Trp Tyr Arg Gln Ala Pro Gly Lys Gln
 50                  55                  60

Arg Glu Leu Val Ala Val Ser Phe Arg Asp Gly Ser Thr Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys His Val Ser Leu Tyr Arg Asp Pro Leu Gly Val Ala Gly
                115                 120                 125

Gly Ile Gly Val Tyr Trp Gly Gln Gly Thr Leu Val Thr Val Ser Ser
                130                 135                 140

Gly Gly Gly Gly Ser Gly Gly Gly Ser Glu Val Gln Leu Leu Glu
145                 150                 155                 160

Ser Gly Gly Gly Leu Val Gln Pro Gly Gly Ser Leu Arg Leu Ser Cys
                165                 170                 175

Ala Ala Ser Gly Arg Thr Tyr Ala Met Gly Trp Phe Arg Gln Ala Pro
                180                 185                 190

Gly Lys Glu Arg Glu Phe Val Ala Ala Ile Asn Ala Leu Gly Thr Arg
                195                 200                 205

Thr Tyr Tyr Ala Asp Ser Val Lys Gly Arg Phe Thr Ile Ser Arg Asp
                210                 215                 220

Asn Ser Lys Asn Thr Leu Tyr Leu Gln Met Asn Ser Leu Arg Ala Glu
225                 230                 235                 240

Asp Thr Ala Val Tyr Tyr Cys Thr Ala Gln Gly Gln Trp Arg Ala Ala
                245                 250                 255

Pro Val Ala Val Ala Ala Glu Tyr Glu Phe Trp Gly Gln Gly Thr Leu
                260                 265                 270

Val Thr Val Ser Ser Gly Gly Gly Gly Ser Gly Gly Gly Gly Ser Glu
                275                 280                 285

Val Gln Leu Leu Glu Ser Gly Gly Gly Leu Val Gln Pro Gly Gly Ser
                290                 295                 300

Leu Arg Leu Ser Cys Ala Ala Ser Gly Phe Thr Leu Glu Asn Lys Ala
305                 310                 315                 320

Ile Gly Trp Phe Arg Gln Ala Pro Gly Lys Glu Arg Glu Gly Val Leu
                325                 330                 335

Cys Ile Ser Lys Ser Gly Ser Trp Thr Tyr Tyr Ala Asp Ser Val Lys
                340                 345                 350

Gly Arg Phe Thr Ile Ser Arg Asp Asn Ser Lys Asn Thr Val Tyr Leu
                355                 360                 365

Gln Met Asn Ser Leu Arg Pro Glu Asp Thr Ala Val Tyr Tyr Cys Ala
                370                 375                 380

Thr Thr Thr Ala Gly Gly Gly Leu Cys Trp Asp Gly Thr Thr Phe Ser
385                 390                 395                 400

Arg Leu Ala Ser Ser Trp Gly Gln Gly Thr Leu Val Thr Val Ser Ser
                405                 410                 415

Gly Gly Gly Gly Ser Gly Gly Gly Ser Glu Val Gln Leu Val Glu
                420                 425                 430

Ser Gly Gly Gly Leu Val Gln Pro Gly Gly Ser Leu Arg Leu Ser Cys
                435                 440                 445

Ala Ala Ser Gly Phe Thr Phe Ser Thr Ser Trp Met Tyr Trp Leu Arg
                450                 455                 460
```

-continued

Gln Ala Pro Gly Lys Gly Leu Glu Trp Val Ser Val Ile Asn Thr Asp
465                 470                 475                 480

Gly Gly Thr Tyr Tyr Ala Asp Ser Val Lys Gly Arg Phe Thr Ile Ser
            485                 490                 495

Arg Asp Asn Ser Lys Asn Thr Leu Tyr Leu Gln Met Asn Ser Leu Arg
        500                 505                 510

Ala Glu Asp Thr Ala Val Tyr Tyr Cys Ala Lys Asp Trp Gly Gly Pro
    515                 520                 525

Glu Pro Thr Arg Gly Gln Gly Thr Leu Val Thr Val Ser Ser Asp Lys
530                 535                 540

Thr His Thr Cys Pro Pro Cys Pro Ala Pro Glu Leu Leu Gly Gly Pro
545                 550                 555                 560

Ser Val Phe Leu Phe Pro Pro Lys Pro Lys Asp Thr Leu Met Ile Ser
            565                 570                 575

Arg Thr Pro Glu Val Thr Cys Val Val Val Asp Val Ser His Glu Asp
        580                 585                 590

Pro Glu Val Lys Phe Asn Trp Tyr Val Asp Gly Val Glu Val His Asn
    595                 600                 605

Ala Lys Thr Lys Pro Arg Glu Glu Gln Tyr Asn Ser Thr Tyr Arg Val
610                 615                 620

Val Ser Val Leu Thr Val Leu His Gln Asp Trp Leu Asn Gly Lys Glu
625                 630                 635                 640

Tyr Lys Cys Lys Val Ser Asn Lys Ala Leu Pro Ala Pro Ile Glu Lys
            645                 650                 655

Thr Ile Ser Lys Ala Lys Gly Gln Pro Arg Glu Pro Gln Val Tyr Thr
        660                 665                 670

Leu Pro Pro Ser Arg Asp Glu Leu Thr Lys Asn Gln Val Ser Leu Thr
    675                 680                 685

Cys Leu Val Lys Gly Phe Tyr Pro Ser Asp Ile Ala Val Glu Trp Glu
690                 695                 700

Ser Asn Gly Gln Pro Glu Asn Asn Tyr Lys Thr Thr Pro Pro Val Leu
705                 710                 715                 720

Asp Ser Asp Gly Ser Phe Phe Leu Tyr Ser Lys Leu Thr Val Asp Lys
            725                 730                 735

Ser Arg Trp Gln Gln Gly Asn Val Phe Ser Cys Ser Val Met His Glu
        740                 745                 750

Ala Leu His Asn His Tyr Thr Gln Lys Ser Leu Ser Leu Ser Pro Gly
    755                 760                 765

Lys

<210> SEQ ID NO 28
<211> LENGTH: 26
<212> TYPE: DNA
<213> ORGANISM: Artificial Sequence
<220> FEATURE:
<223> OTHER INFORMATION: primer prm504

<400> SEQUENCE: 28
gctgcgycaa ctggaccaat gagaac                                    26

<210> SEQ ID NO 29
<211> LENGTH: 28
<212> TYPE: DNA
<213> ORGANISM: Artificial Sequence
<220> FEATURE:
<223> OTHER INFORMATION: primer prm505

<400> SEQUENCE: 29
cgcagagacc aaagttcaac tgaaacga                                              28

<210> SEQ ID NO 30
<211> LENGTH: 772
<212> TYPE: PRT
<213> ORGANISM: Artificial Sequence
<220> FEATURE:
<223> OTHER INFORMATION: amino acid sequence of MD3606
<220> FEATURE:
<221> NAME/KEY: MISC_FEATURE
<222> LOCATION: (24)..(147)
<223> OTHER INFORMATION: The first immunoglobulin region with I110M
<220> FEATURE:
<221> NAME/KEY: MISC_FEATURE
<222> LOCATION: (158)..(280)
<223> OTHER INFORMATION: The second immunoglobulin region
<220> FEATURE:
<221> NAME/KEY: MISC_FEATURE
<222> LOCATION: (291)..(419)
<223> OTHER INFORMATION: The third immunoglobulin region
<220> FEATURE:
<221> NAME/KEY: MISC_FEATURE
<222> LOCATION: (430)..(485)
<223> OTHER INFORMATION: The fourth immunoglobulin region
<220> FEATURE:
<221> NAME/KEY: MISC_FEATURE
<222> LOCATION: (551)..(772)
<223> OTHER INFORMATION: Fc

<400> SEQUENCE: 30

Glu Phe Ala Thr Met Ala Trp Val Trp Thr Leu Leu Phe Leu Met Ala
1               5                   10                  15

Ala Ala Gln Ser Ile Gln Ala Gln Val Gln Leu Val Glu Ser Gly Gly
            20                  25                  30

Gly Val Val Gln Pro Gly Gly Ser Leu Arg Leu Ser Cys Ala Ala Ser
        35                  40                  45

Ile Ser Ile Phe Asp Ile Tyr Ala Met Asp Trp Tyr Arg Gln Ala Pro
    50                  55                  60

Gly Lys Gln Arg Glu Leu Val Ala Val Ser Phe Arg Asp Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys His Val Ser Leu Tyr Arg Asp Pro Leu Gly
        115                 120                 125

Val Ala Gly Gly Met Gly Val Tyr Trp Gly Gln Gly Thr Leu Val Thr
    130                 135                 140

Val Ser Ser Gly Gly Gly Gly Ser Gly Gly Gly Gly Ser Glu Val Gln
145                 150                 155                 160

Leu Leu Glu Ser Gly Gly Gly Leu Val Gln Pro Gly Gly Ser Leu Arg
                165                 170                 175

Leu Ser Cys Ala Ala Ser Gly Arg Thr Tyr Ala Met Gly Trp Phe Arg
            180                 185                 190

Gln Ala Pro Gly Lys Glu Arg Glu Phe Val Ala Ala Ile Asn Ala Leu
        195                 200                 205

Gly Thr Arg Thr Tyr Tyr Ala Asp Ser Val Lys Gly Arg Phe Thr Ile
    210                 215                 220

Ser Arg Asp Asn Ser Lys Asn Thr Leu Tyr Leu Gln Met Asn Ser Leu
225                 230                 235                 240

```
Arg Ala Glu Asp Thr Ala Val Tyr Tyr Cys Thr Ala Gln Gly Gln Trp
                245                 250                 255

Arg Ala Ala Pro Val Ala Val Ala Ala Glu Tyr Glu Phe Trp Gly Gln
                260                 265                 270

Gly Thr Leu Val Thr Val Ser Ser Gly Gly Gly Gly Ser Gly Gly Gly
                275                 280                 285

Gly Ser Glu Val Gln Leu Leu Glu Ser Gly Gly Gly Leu Val Gln Pro
            290                 295                 300

Gly Gly Ser Leu Arg Leu Ser Cys Ala Ala Ser Gly Phe Thr Leu Glu
305                 310                 315                 320

Asn Lys Ala Ile Gly Trp Phe Arg Gln Ala Pro Gly Lys Glu Arg Glu
                325                 330                 335

Gly Val Leu Cys Ile Ser Lys Ser Gly Ser Trp Thr Tyr Tyr Ala Asp
                340                 345                 350

Ser Val Lys Gly Arg Phe Thr Ile Ser Arg Asp Asn Ser Lys Asn Thr
                355                 360                 365

Val Tyr Leu Gln Met Asn Ser Leu Arg Pro Glu Asp Thr Ala Val Tyr
            370                 375                 380

Tyr Cys Ala Thr Thr Ala Gly Gly Leu Cys Trp Asp Gly Thr
385                 390                 395                 400

Thr Phe Ser Arg Leu Ala Ser Ser Trp Gly Gln Gly Thr Leu Val Thr
                405                 410                 415

Val Ser Ser Gly Gly Gly Gly Ser Gly Gly Gly Gly Ser Glu Val Gln
                420                 425                 430

Leu Val Glu Ser Gly Gly Gly Leu Val Gln Pro Gly Gly Ser Leu Arg
            435                 440                 445

Leu Ser Cys Ala Ala Ser Gly Phe Thr Phe Ser Thr Ser Trp Met Tyr
450                 455                 460

Trp Leu Arg Gln Ala Pro Gly Lys Gly Leu Glu Trp Val Ser Val Ile
465                 470                 475                 480

Asn Thr Asp Gly Gly Thr Tyr Tyr Ala Asp Ser Val Lys Gly Arg Phe
                485                 490                 495

Thr Ile Ser Arg Asp Asn Ser Lys Asn Thr Leu Tyr Leu Gln Met Asn
                500                 505                 510

Ser Leu Arg Ala Glu Asp Thr Ala Val Tyr Tyr Cys Ala Lys Asp Trp
                515                 520                 525

Gly Gly Pro Glu Pro Thr Arg Gly Gln Gly Thr Leu Val Thr Val Ser
            530                 535                 540

Ser Asp Lys Thr His Thr Cys Pro Pro Cys Pro Ala Pro Glu Leu Leu
545                 550                 555                 560

Gly Gly Pro Ser Val Phe Leu Phe Pro Pro Lys Pro Lys Asp Thr Leu
                565                 570                 575

Met Ile Ser Arg Thr Pro Glu Val Thr Cys Val Val Val Asp Val Ser
                580                 585                 590

His Glu Asp Pro Glu Val Lys Phe Asn Trp Tyr Val Asp Gly Val Glu
            595                 600                 605

Val His Asn Ala Lys Thr Lys Pro Arg Glu Glu Gln Tyr Asn Ser Thr
                610                 615                 620

Tyr Arg Val Val Ser Val Leu Thr Val Leu His Gln Asp Trp Leu Asn
625                 630                 635                 640

Gly Lys Glu Tyr Lys Cys Lys Val Ser Asn Lys Ala Leu Pro Ala Pro
                645                 650                 655
```

```
Ile Glu Lys Thr Ile Ser Lys Ala Lys Gly Gln Pro Arg Glu Pro Gln
            660                 665                 670

Val Tyr Thr Leu Pro Pro Ser Arg Asp Glu Leu Thr Lys Asn Gln Val
        675                 680                 685

Ser Leu Thr Cys Leu Val Lys Gly Phe Tyr Pro Ser Asp Ile Ala Val
    690                 695                 700

Glu Trp Glu Ser Asn Gly Gln Pro Glu Asn Asn Tyr Lys Thr Thr Pro
705                 710                 715                 720

Pro Val Leu Asp Ser Asp Gly Ser Phe Phe Leu Tyr Ser Lys Leu Thr
                725                 730                 735

Val Asp Lys Ser Arg Trp Gln Gln Gly Asn Val Phe Ser Cys Ser Val
            740                 745                 750

Met His Glu Ala Leu His Asn His Tyr Thr Gln Lys Ser Leu Ser Leu
        755                 760                 765

Ser Pro Gly Lys
    770

<210> SEQ ID NO 31
<211> LENGTH: 4690
<212> TYPE: DNA
<213> ORGANISM: Artificial Sequence
<220> FEATURE:
<223> OTHER INFORMATION: AAV vector genome AAV.CB7.hJAB Fc
<220> FEATURE:
<221> NAME/KEY: repeat_region
<222> LOCATION: (1)..(130)
<223> OTHER INFORMATION: 5' IRT
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<223> OTHER INFORMATION: TATA
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: misc_feature
<222> LOCATION: (1941)..(4259)
<223> OTHER INFORMATION: coding sequence for MD3606
<220> FEATURE:
<221> NAME/KEY: polyA_signal
<222> LOCATION: (4346)..(4472)
<223> OTHER INFORMATION: Rabbit globin poly A
<220> FEATURE:
<221> NAME/KEY: repeat_region
<222> LOCATION: (4561)..(4690)
<223> OTHER INFORMATION: 3' ITR

<400> SEQUENCE: 31
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120 agggggttcct tgtagttaat gattaacccg ccatgctact tatctaccag ggtaatgggg   180
atcctctaga actatagcta gtcgacattg attattgact agttattaat agtaatcaat   240
tacggggtca ttagttcata gcccatatat ggagttccgc gttacataac ttacggtaaa   300
```

```
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctcccccc ctccccaccc ccaattttgt atttatttat    660
tttttaatta ttttgtgcag cgatggggg ggggggggg gggggggcgcg cgccaggcgg    720 ggcggggcgg ggcgagggc ggggcgggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggttaaat gacggcttgt   1020 ttctttttctg tggctgcgtg aaagccttga ggggctccgg gagggcccttt tgtgcggggg   1080 gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc gggggggggct gcgaggggaa   1260 caaaggctgc gtgcggggtg tgtgcgtggg ggggtgagca ggggggtgtgg gcgcgtcggt   1320 cgggctgcaa ccccccctgc accccctcc ccgagttgct gagcacggcc cggcttcggg   1380
tgcggggctc cgtacggggc gtggcgcggg gctcgccgtg ccggcgggg ggtggcggca   1440 ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagat gaattcgcca ccatggcttg ggtgtggacc ttgctattcc   1980
tgatggcagc tgcccaaagt atacaggccc aggtgcagct ggtggagagc ggcggcggcg   2040
tggtgcagcc cggcggcagc ctgcgcctga gctgcgccgc cagcatcagc atcttcgaca   2100
tctacgccat ggactggtac cgccaggccc ccggcaagca gcgcgagctg gtggccgtga   2160
gcttccgcga cggcagcacc tactacgccg acagcgtgaa gggccgcttc accatcagcc   2220
gcgacaacag caagaacacc ctgtacctgc agatgaacag cctgcgcgcc gaggacaccg   2280
ccgtgtacta ctgccacgtg agcctgtacc gcgaccccct gggcgtggcc ggcggcatgg   2340
gcgtgtactg gggccagggc accctggtga ccgtgagcag cggcggcggc ggcagcggcg   2400
gcggcggcag cgaggtgcag ctgctggaga gcggcggcgg cctggtgcag cccggcggca   2460
gcctgcgcct gagctgcgcc gccagcggcc gcacctacgc catgggctgg ttccgccagg   2520
cccccggcaa ggagcgcgag ttcgtggccg ccatcaacgc cctgggcacc cgcacctact   2580
acgccgacag cgtgaagggc cgcttcacca tcagccgcga caacagcaag aacaccctgt   2640
```

-continued

```
acctgcagat gaacagcctg cgcgccgagg acaccgccgt gtactactgc accgcccagg    2700
gccagtggcg cgccgccccc gtggccgtgg ccgccgagta cgagttctgg ggccagggca    2760
ccctggtgac cgtgagcagc ggcggcggcg gcagcggcgg cggcggcagc gaggtgcagc    2820
tgctggagag cggcggcggc ctggtgcagc ccggcggcag cctgcgcctg agctgcgccg    2880
ccagcggctt caccctggag aacaaggcca tcggctggtt ccgccaggcc cccggcaagg    2940
agcgcgaggg cgtgctgtgc atcagcaaga gcggcagctg gacctactac gccgacagcg    3000
tgaagggccg cttcaccatc agccgcgaca acagcaagaa caccgtgtac ctgcagatga    3060
acagcctgcg ccccgaggac accgccgtgt actactgcgc caccaccacc gccggcggcg    3120
gcctgtgctg ggacggcacc accttcagcc gcctggccag cagctggggc cagggcaccc    3180
tggtgaccgt gagcagcggc ggcggcggca gcggcggcgg cggcagcgag gtgcagctgg    3240
tggagagcgg cggcggcctg gtgcagcccg gcggcagcct gcgcctgagc tgcgccgcca    3300
gcggcttcac cttcagcacc agctggatgt actggctgcg ccaggccccc ggcaagggcc    3360
tggagtgggt gagcgtgatc aacaccgacg gcggcaccta ctacgccgac agcgtgaagg    3420
gccgcttcac catcagccgc gacaacagca gaacaccct gtacctgcag atgaacagcc    3480
tgcgcgccga ggacaccgcc gtgtactact gcgccaagga ctggggcggc cccgagccca    3540
cccgcggcca gggcaccctg gtgaccgtga gcagcgacaa aactcacaca tgcccaccgt    3600
gcccagcacc tgaactcctg ggggaccgt cagtcttcct cttcccccca aaacccaagg    3660
acaccctcat gatctcccgg acccctgagg tcacatgcgt ggtggtggac gtgagccacg    3720
aagaccctga ggtcaagttc aactggtacg tggacggcgt ggaggtgcat aatgccaaga    3780
caaagccgcg ggaggagcag tacaacagca cgtaccgggt ggtcagcgtc ctcaccgtcc    3840
tgcaccagga ctggctgaat ggcaaggagt acaagtgcaa ggtctccaac aaagccctcc    3900 cagccccat cgagaaaacc atctccaaag ccaagggca gccccgagaa ccacaggtgt    3960
acaccctgcc cccatcccgg gatgagctga ccaagaacca ggtcagcctg acctgcctgg    4020
tcaaaggctt ctatcccagc gacatcgccg tggagtggga gagcaatggg cagccggaga    4080
acaactacaa gaccacgcct cccgtgctgg actccgacgg ctccttcttc ctctacagca    4140
agctcaccgt ggacaagagc aggtggcagc aggggaacgt cttctcatgc tccgtgatgc    4200
atgaggctct gcacaaccac tacacgcaga agagcctctc cctgtctccg ggtaaatgag    4260
aattcatcgg atcccgggcc gtcgactgc agaggcctgc atgcaagctt ggctcgagga    4320
cggggtgaac tacgcctgag gatccgatct ttttccctct gccaaaaatt atggggacat    4380
catgaagccc cttgagcatc tgacttctgg ctaataaagg aaatttattt tcattgcaat    4440
agtgtgttgg aattttttgt gtctctcact cggaagcaat tcgttgatct gaatttcgac    4500
cacccataat acccattacc ctggtagata agtagcatgg cgggttaatc attaactaca    4560
aggaacccct agtgatggag ttggccactc cctctctgcg cgctcgctcg ctcactgagg    4620
ccgggcgacc aaaggtcgcc cgacgcccgg gctttgcccg gcggcctcca gtgagcgagc    4680
gagcgcgcag                                                          4690
```

<210> SEQ ID NO 32
<211> LENGTH: 2319
<212> TYPE: DNA
<213> ORGANISM: Artificial Sequence
<220> FEATURE:
<223> OTHER INFORMATION: coding sequence of MD3606

<400> SEQUENCE: 32

-continued

```
gaattcgcca ccatggcttg ggtgtggacc ttgctattcc tgatggcagc tgcccaaagt      60
atacaggccc aggtgcagct ggtggagagc ggcggcggcg tggtgcagcc cggcggcagc     120
ctgcgcctga gctgcgccgc cagcatcagc atcttcgaca tctacgccat ggactggtac     180
cgccaggccc ccggcaagca gcgcgagctg gtggccgtga gcttccgcga cggcagcacc     240
tactacgccg acagcgtgaa gggccgcttc accatcagcc gcgacaacag caagaacacc     300
ctgtacctgc agatgaacag cctgcgcgcc gaggacaccg ccgtgtacta ctgccacgtg     360
agcctgtacc gcgacccct gggcgtggcc ggcggcatgg gcgtgtactg gggccagggc     420
accctggtga ccgtgagcag cggcggcggc ggcagcggcg gcggcggcag cgaggtgcag     480
ctgctggaga gcggcggcgg cctggtgcag cccggcggca gcctgcgcct gagctgcgcc     540
gccagcggcc gcacctacgc catgggctgg ttccgccagg cccccggcaa ggagcgcgag     600
ttcgtggccg ccatcaacgc cctgggcacc cgcacctact acgccgacag cgtgaagggc     660
cgcttcacca tcagccgcga caacagcaag aacaccctgt acctgcagat gaacagcctg     720
cgcgccgagg acaccgccgt gtactactgc accgcccagg ccagtggccg cccgcccccc     780
gtggccgtgg ccgccgagta cgagttctgg ggccagggca ccctggtgac cgtgagcagc     840
ggcggcggcg gcagcggcgg cggcggcagc gaggtgcagc tgctggagag cggcggcggc     900
ctggtgcagc ccgcggcag cctgcgcctg agctgcgccg ccagcggctt caccctggag     960
aacaaggcca tcggctggtt ccgccaggcc cccggcaagg agcgcgaggg cgtgctgtgc    1020
atcagcaaga gcggcagctg gacctactac gccgacagcg tgaagggccg cttcaccatc    1080
agccgcgaca acagcaagaa caccgtgtac ctgcagatga acagcctgcg ccccgaggac    1140
accgccgtgt actactgcgc caccaccacc gccggcggcg gcctgtgctg ggacggcacc    1200
accttcagcc gcctggccag cagctggggc cagggcaccc tggtgaccgt gagcagcggc    1260
ggcggcggca gcggcggcgg cggcagcgag gtgcagctgg tggagagcgg cggcggcctg    1320
gtgcagcccg gcggcagcct gcgcctgagc tgcgccgcca gcggcttcac cttcagcacc    1380
agctggatgt actggctgcg ccaggccccc ggcaagggcc tggagtgggt gagcgtgatc    1440
aacaccgacg gcggcaccta ctacgccgac agcgtgaagg gccgcttcac catcagccgc    1500
gacaacagca gaacaccct gtacctgcag atgaacagcc tgcgcgccga ggacaccgcc    1560
gtgtactact gcgccaagga ctggggcggc cccgagccca ccgcggcca gggcaccctg    1620
gtgaccgtga gcagcgacaa aactcacaca tgcccaccgt gcccagcacc tgaactcctg    1680
gggggaccgt cagtcttcct cttccccca aacccaagg acaccctcat gatctcccgg    1740
acccctgagg tcacatgcgt ggtggtggac gtgagccacg aagaccctga ggtcaagttc    1800
aactggtacg tggacggcgt ggaggtgcat aatgccaaga caaagccgcg ggaggagcag    1860
tacaacagca cgtaccgggt ggtcagcgtc ctcaccgtcc tgcaccagga ctggctgaat    1920
ggcaaggagt acaagtgcaa ggtctccaac aaagccctcc cagcccccat cgagaaaacc    1980
atctccaaag ccaaagggca gccccgagaa ccacaggtgt acaccctgcc cccatcccgg    2040
gatgagctga ccaagaacca ggtcagcctg acctgcctgg tcaaaggctt ctatcccagc    2100
gacatcgccg tggagtggga gagcaatggg cagccggaga caactacaa gaccacgcct    2160
cccgtgctgg actccgacgg ctccttcttc ctctacagca agctcaccgt ggacaagagc    2220
aggtggcagc aggggaacgt cttctcatgc tccgtgatgc atgaggctct gcacaaccac    2280
tacacgcaga agagcctctc cctgtctccg ggtaaatga                          2319
```

<210> SEQ ID NO 33
<211> LENGTH: 16
<212> TYPE: DNA
<213> ORGANISM: Artificial Sequence
<220> FEATURE:
<223> OTHER INFORMATION: Spacer

<400> SEQUENCE: 33
atgacttaaa ccaggt                                                          16

<210> SEQ ID NO 34
<211> LENGTH: 736
<212> TYPE: PRT
<213> ORGANISM: Artificial Sequence
<220> FEATURE:
<223> OTHER INFORMATION: human AAVhu31 vp1

<400> SEQUENCE: 34

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Ser Thr Glu Gly Val
705                 710                 715                 720

Tyr Ser Glu Pro Arg Pro Ile Gly Thr Arg Tyr Leu Thr Arg Asn Leu
```

-continued

```
                725                 730                 735

<210> SEQ ID NO 35
<211> LENGTH: 736
<212> TYPE: PRT
<213> ORGANISM: Artificial Sequence
<220> FEATURE:
<223> OTHER INFORMATION: human AAVhu32 vp1

<400> SEQUENCE: 35

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
```

355                 360                 365
Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 36
<211> LENGTH: 2211
<212> TYPE: DNA
<213> ORGANISM: Artificial Sequence
<220> FEATURE:
<223> OTHER INFORMATION: AAV9 capsid vp1 coding sequence

<400> SEQUENCE: 36

```
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaataccttg acccggcaa cggactcgac      180
aaggggagc cggtcaacgc agcagacgcg gcggccctcg agcacgacaa ggcctacgac      240
cagcagctca aggccggaga caacccgtac ctcaagtaca accacgccga cgccgagttc     300
caggagcggc tcaaagaaga tacgtctttt gggggcaacc tcgggcgagc agtcttccag     360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
tcagtcccag accctcaacc aatcggagaa cctcccgcag cccctcagg tgtgggatct      600
cttacaatgg cttcaggtgg tggcgcacca gtggcagaca taacgaagg tgccgatgga      660
gtgggtagtt cctcgggaaa ttggcattgc gattcccaat ggctggggga cagagtcatc     720
accaccagca cccgaacctg ggccctgccc acctacaaca atcacctcta caagcaaatc     780
tccaacagca catctggagg atcttcaaat gacaacgcct acttcggcta cagcaccccc     840
tgggggtatt ttgacttcaa cagattccac tgccacttct caccacgtga ctggcagcga     900
ctcatcaaca caactgggg attccggcct aagcgactca acttcaagct cttcaacatt     960
caggtcaaag aggttacgga caacaatgga gtcaagacca cgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgcagaccg gctgggttca aaaccaagga    1800
atacttccgg gtatggttttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a            2211
```

<210> SEQ ID NO 37
<211> LENGTH: 2211

```
<212> TYPE: DNA
<213> ORGANISM: Artificial sequence
<220> FEATURE:
<223> OTHER INFORMATION: AAVhu31 coding sequence

<400> SEQUENCE: 37
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagagac tcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca tcacctcta caagcaaatc   780
tccaacagca catctggagg atcttcaaat gacaacgcct acttcggcta cagcacccc    840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac   1080
gagggctgcc tcccgccgtt cccagcgac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact gtactatctc tcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttcctt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc caagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccccg ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa acagcaagc gctggaaccc ggagatccag  2100
tacacttcca actattacaa gtctaataat gttgaatttg ctgttaatac tgaaggtgta  2160
```

| tatagtgaac cccgccccat tggcaccaga tacctgactc gtaatctgta a | 2211 |

<210> SEQ ID NO 38
<211> LENGTH: 2211
<212> TYPE: DNA
<213> ORGANISM: Artificial sequence
<220> FEATURE:
<223> OTHER INFORMATION: AAVhu32 VP1 coding sequence

<400> SEQUENCE: 38

| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg acccggcaa cggactcgac | 180 |
| aaggggagc cggtcaacgc agcagacgcg gcggccctcg agcacgacaa ggcctacgac | 240 |
| cagcagctca aggccggaga caacccgtac ctcaagtaca accacgccga cgccgagttc | 300 |
| caggagcggc tcaaagaaga tacgtctttt ggggggcaacc tcgggcgagc agtcttccag | 360 |
| gccaaaaaga ggcttcttga acctcttggt ctggttgagg aagcggctaa gacggctcct | 420 |
| ggaaagaaga ggcctgtaga gcagtctcct caggaaccgg actcctccgc gggtattggc | 480 |
| aaatcgggtt cacagcccgc taaaaagaaa ctcaatttcg gtcagactgg cgacacagag | 540 |
| tcagtccccg accctcaacc aatcggagaa cctcccgcag cccccctcagg tgtgggatct | 600 |
| cttacaatgg cttcaggtgg tgccgcacca gtggcagaca taacgaagg tgccgatgga | 660 |
| gtgggtagtt cctcgggaaa ttggcattgc gattcccaat ggctggggga cagagtcatc | 720 |
| accaccagca cccgaacctg ggccctgccc acctacaaca tcacctcta caagcaaatc | 780 |
| tccaacagca catctggagg atcttcaaat gacaacgcct acttcggcta cagcacccc | 840 |
| tgggggtatt ttgacttcaa cagattccac tgccacttct caccacgtga ctggcagcga | 900 |
| ctcatcaaca caaactgggg attccggcct aagcgactca acttcaagct cttcaacatt | 960 |
| caggtcaaag aggttacgga caacaatgga gtcaagacca tcgccaataa ccttaccagc | 1020 |
| acggtccagg tcttcacgga ctcagactat cagctcccgt acgtgctcgg tcggctcac | 1080 |
| gagggctgcc tcccgccgtt cccagcgac gttttcatga ttcctcagta cgggtatctg | 1140 |
| acgcttaatg atgggagcca ggccgtgggt cgttcgtcct tttactgcct ggaatatttc | 1200 |
| ccgtcgcaaa tgctaagaac gggtaacaac ttccagttca gctacgagtt tgagaacgta | 1260 |
| cctttccata gcagctacgc tcacagccaa agcctggacc gactaatgaa tccactcatc | 1320 |
| gaccaatact tgtactatct ctcaaagact attaacggtt ctggacagaa tcaacaaacg | 1380 |
| ctaaaattca gcgtggccgg acccagcaac atggctgtcc agggaagaaa ctacatacct | 1440 |
| ggacccagct accgacaaca acgtgtctca accactgtga ctcaaaacaa caacagcgaa | 1500 |
| tttgcttggc ctggagcttc ttcttgggct ctcaatggac gtaatagctt gatgaatcct | 1560 |
| ggacctgcta tggccagcca caagaaggga gaggaccgtt tctttcctt gtctggatct | 1620 |
| ttaatttttg gcaaacaagg aactggaaga gacaacgtgg atgcggacaa agtcatgata | 1680 |
| accaacgaag aagaaattaa aactactaac ccggtagcaa cggagtccta tggacaagtg | 1740 |
| gccacaaacc accagagtgc ccaagcacag gcgcagaccg gctgggttca aaaccaagga | 1800 |
| atacttccgg gtatggtttg caggacaga gatgtgtacc tgcaaggacc catttgggcc | 1860 |
| aaaattcctc acacggacgg caactttcac ccttctccgc taatgggagg gtttggaatg | 1920 |
| aagcacccgc ctcctcagat cctcatcaaa aacacacctg tacctgcgga tcctccaacg | 1980 |
| gctttcaata aggacaagct gaactctttc atcacccagt attctactgg ccaagtcagc | 2040 |

```
gtggagattg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a              2211
```

<210> SEQ ID NO 39
<211> LENGTH: 736
<212> TYPE: PRT
<213> ORGANISM: Artificial Sequence
<220> FEATURE:
<223> OTHER INFORMATION: modified hu68vp1
<220> FEATURE:
<221> NAME/KEY: MISC_FEATURE
<222> LOCATION: (23)..(23)
<223> OTHER INFORMATION: Xaa may be W (Trp, tryptophan), or oxidated W.
<220> FEATURE:
<221> NAME/KEY: MISC_FEATURE
<222> LOCATION: (35)..(35)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (57)..(57)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (66)..(66)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (94)..(94)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (97)..(97)
<223> OTHER INFORMATION: Xaa may be D (asp, aspartic acid), or
      isomerized D.
<220> FEATURE:
<221> NAME/KEY: MISC_FEATURE
<222> LOCATION: (107)..(107)
<223> OTHER INFORMATION: Xaa may be D (asp, aspartic acid), or
      isomerized D.
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: MISC_FEATURE
<222> LOCATION: (149)..(149)
<223> OTHER INFORMATION: Xaa may be S (Ser, serine), or Phosphorilated S
<220> FEATURE:
<221> NAME/KEY: MISC_FEATURE
<222> LOCATION: (149)..(149)
<223> OTHER INFORMATION: Xaa may be S (Ser, serine), or Phosphorylated S
<220> FEATURE:
<221> NAME/KEY: MISC_FEATURE
<222> LOCATION: (247)..(247)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (253)..(253)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (259)..(259)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (270)..(270)

```
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (297)..(297)
<223> OTHER INFORMATION: Xaa represents D (Asp, aspartic acid) or
      amindated D to N (Asn, asparagine)
<220> FEATURE:
<221> NAME/KEY: MISC_FEATURE
<222> LOCATION: (304)..(304)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (306)..(306)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (314)..(314)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (319)..(319)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (329)..(329)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (332)..(332)
<223> OTHER INFORMATION: Xaa may be K (lys, lysine), or acetylated K
<220> FEATURE:
<221> NAME/KEY: MISC_FEATURE
<222> LOCATION: (336)..(336)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (384)..(384)
<223> OTHER INFORMATION: Xaa may be D (asp, aspartic acid), or
      isomerized D.
<220> FEATURE:
<221> NAME/KEY: MISC_FEATURE
<222> LOCATION: (404)..(404)
<223> OTHER INFORMATION: Xaa may be M (Met, Methionine), or oxidated M.
<220> FEATURE:
<221> NAME/KEY: MISC_FEATURE
<222> LOCATION: (409)..(409)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (436)..(436)
<223> OTHER INFORMATION: Xaa may be M (Met, Methionine), or oxidated M.
<220> FEATURE:
<221> NAME/KEY: MISC_FEATURE
<222> LOCATION: (452)..(452)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (477)..(477)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (499)..(499)
<223> OTHER INFORMATION: Xaa may be S (Ser, serine), or Phosphorylated S
<220> FEATURE:
<221> NAME/KEY: MISC_FEATURE
<222> LOCATION: (512)..(512)
<223> OTHER INFORMATION: Xaa may be Asn, or deamidated to Asp, isoAsp,
      or Asp/isoAsp
<220> FEATURE:
```

```
<221> NAME/KEY: MISC_FEATURE
<222> LOCATION: (515)..(515)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (518)..(518)
<223> OTHER INFORMATION: Xaa may be M (Met, Methionine), or oxidated M.
<220> FEATURE:
<221> NAME/KEY: MISC_FEATURE
<222> LOCATION: (524)..(524)
<223> OTHER INFORMATION: Xaa may be M (Met, Methionine), or oxidated M.
<220> FEATURE:
<221> NAME/KEY: MISC_FEATURE
<222> LOCATION: (559)..(559)
<223> OTHER INFORMATION: Xaa may be M (Met, Methionine), or oxidated M.
<220> FEATURE:
<221> NAME/KEY: MISC_FEATURE
<222> LOCATION: (569)..(569)
<223> OTHER INFORMATION: Xaa may be T (Thr, threonine), or
      Phosphorylated T
<220> FEATURE:
<221> NAME/KEY: MISC_FEATURE
<222> LOCATION: (586)..(586)
<223> OTHER INFORMATION: Xaa may be S (Ser, serine), or Phosphorylated S
<220> FEATURE:
<221> NAME/KEY: MISC_FEATURE
<222> LOCATION: (599)..(599)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (605)..(605)
<223> OTHER INFORMATION: Xaa may be M (Met, Methionine), or oxidated M.
<220> FEATURE:
<221> NAME/KEY: MISC_FEATURE
<222> LOCATION: (619)..(619)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (628)..(628)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (640)..(640)
<223> OTHER INFORMATION: Xaa may be M (Met, Methionine), or oxidated M.
<220> FEATURE:
<221> NAME/KEY: MISC_FEATURE
<222> LOCATION: (651)..(651)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (663)..(663)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (666)..(666)
<223> OTHER INFORMATION: Xaa may be K (lys, lysine), or acetylated K
<220> FEATURE:
<221> NAME/KEY: MISC_FEATURE
<222> LOCATION: (689)..(689)
<223> OTHER INFORMATION: Xaa may be K (lys, lysine), or acetylated K
<220> FEATURE:
<221> NAME/KEY: MISC_FEATURE
<222> LOCATION: (693)..(693)
<223> OTHER INFORMATION: Xaa may be K (lys, lysine), or acetylated K
<220> FEATURE:
<221> NAME/KEY: MISC_FEATURE
<222> LOCATION: (695)..(695)
<223> OTHER INFORMATION: Xaa may be W (Trp, tryptophan), or oxidated W.
<220> FEATURE:
<221> NAME/KEY: MISC_FEATURE
<222> LOCATION: (709)..(709)
<223> OTHER INFORMATION: Xaa may be Asn, or deamidated to Asp, isoAsp,
``` or Asp/isoAsp
<220> FEATURE:
<221> NAME/KEY: MISC_FEATURE
<222> LOCATION: (735)..(735)
<223> OTHER INFORMATION: Xaa may be Asn, or deamidated to Asp, isoAsp,
      or Asp/isoAsp

<400> SEQUENCE: 39

Met Ala Ala Asp Gly Tyr Leu Pro Asp Trp Leu Glu Asp Asn Leu Ser
1               5                   10                  15

Glu Gly Ile Arg Glu Trp Xaa Ala Leu Lys Pro Gly Ala Pro Gln Pro
            20                  25                  30

Lys Ala Xaa Gln Gln His Gln Asp Asn Ala Arg Gly Leu Val Leu Pro
        35                  40                  45

Gly Tyr Lys Tyr Leu Gly Pro Gly Xaa Gly Leu Asp Lys Gly Glu Pro
    50                  55                  60

Val Xaa Glu Ala Asp Ala Ala Leu Glu His Asp Lys Ala Tyr Asp
65              70                  75                  80

Gln Gln Leu Lys Ala Gly Asp Asn Pro Tyr Leu Lys Tyr Xaa His Ala
                85                  90                  95

Xaa Ala Glu Phe Gln Glu Arg Leu Lys Glu Xaa Thr Ser Phe Gly Gly
            100                 105                 110

Xaa Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Xaa Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Xaa Ala Leu Pro Thr Tyr Xaa Asn His Leu
                245                 250                 255

Tyr Lys Xaa Ile Ser Asn Ser Thr Ser Gly Gly Ser Ser Xaa Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Xaa Trp Gln Arg Leu Ile Asn Xaa
    290                 295                 300

Asn Xaa Gly Phe Arg Pro Lys Arg Leu Xaa Phe Lys Leu Phe Xaa Ile
305                 310                 315                 320

Gln Val Lys Glu Val Thr Asp Asn Xaa Gly Val Xaa Thr Ile Ala Xaa
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Xaa

```
                370             375             380
Gly Ser Gln Ala Val Gly Arg Ser Phe Tyr Cys Leu Glu Tyr Phe
385             390             395             400

Pro Ser Gln Xaa Leu Arg Thr Gly Xaa Asn Phe Gln Phe Ser Tyr Glu
            405             410             415

Phe Glu Asn Val Pro Phe His Ser Ser Tyr Ala His Ser Gln Ser Leu
            420             425             430

Asp Arg Leu Xaa Asn Pro Leu Ile Asp Gln Tyr Leu Tyr Tyr Leu Ser
            435             440             445

Lys Thr Ile Xaa Gly Ser Gly Gln Asn Gln Gln Thr Leu Lys Phe Ser
450             455             460

Val Ala Gly Pro Ser Asn Met Ala Val Gln Gly Arg Xaa Tyr Ile Pro
465             470             475             480

Gly Pro Ser Tyr Arg Gln Gln Arg Val Ser Thr Thr Val Thr Gln Asn
            485             490             495

Asn Asn Xaa Glu Phe Ala Trp Pro Gly Ala Ser Ser Trp Ala Leu Xaa
            500             505             510

Gly Arg Xaa Ser Leu Xaa Asn Pro Gly Pro Ala Xaa Ala Ser His Lys
            515             520             525

Glu Gly Glu Asp Arg Phe Phe Pro Leu Ser Gly Ser Leu Ile Phe Gly
530             535             540

Lys Gln Gly Thr Gly Arg Asp Asn Val Asp Ala Asp Lys Val Xaa Ile
545             550             555             560

Thr Asn Glu Glu Glu Ile Lys Thr Xaa Asn Pro Val Ala Thr Glu Ser
            565             570             575

Tyr Gly Gln Val Ala Thr Asn His Gln Xaa Ala Gln Ala Gln Ala Gln
            580             585             590

Thr Gly Trp Val Gln Asn Gln Gly Ile Leu Pro Gly Xaa Val Trp Gln
            595             600             605

Asp Arg Asp Val Tyr Leu Gln Gly Pro Ile Xaa Ala Lys Ile Pro His
610             615             620

Thr Asp Gly Xaa Phe His Pro Ser Pro Leu Met Gly Gly Phe Gly Xaa
625             630             635             640

Lys His Pro Pro Pro Gln Ile Leu Ile Lys Xaa Thr Pro Val Pro Ala
            645             650             655

Asp Pro Pro Thr Ala Phe Xaa Lys Asp Xaa Leu Asn Ser Phe Ile Thr
            660             665             670

Gln Tyr Ser Thr Gly Gln Val Ser Val Glu Ile Glu Trp Glu Leu Gln
            675             680             685

Xaa Glu Asn Ser Xaa Arg Xaa Asn Pro Glu Ile Gln Tyr Thr Ser Asn
            690             695             700

Tyr Tyr Lys Ser Xaa Asn Val Glu Phe Ala Val Asn Thr Glu Gly Val
705             710             715             720

Tyr Ser Glu Pro Arg Pro Ile Gly Thr Arg Tyr Leu Thr Arg Xaa Leu
            725             730             735
```